(12) United States Patent
Yu et al.

(10) Patent No.: US 9,861,620 B2
(45) Date of Patent: Jan. 9, 2018

(54) SUBSTITUTED QUINOLIZINE DERIVATIVES USEFUL AS HIV INTEGRASE INHIBITORS

(71) Applicant: MERCK SHARP & DOHME CORP., Rahway, NJ (US)

(72) Inventors: Tao Yu, Edison, NJ (US); Yonglian Zhang, Metuchen, NJ (US); Sherman Tim Waddell, Westfield, NJ (US); Andrew Stamford, Chatham, NJ (US); John S. Wai, Harleysville, PA (US); Paul J. Coleman, Harleysville, PA (US); John M. Sanders, Collegeville, PA (US); Ronald Ferguson, Scotch Plains, NJ (US); Thomas H. Graham, Quincy, MA (US); Hong Li, Edison, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/025,038

(22) PCT Filed: Sep. 26, 2014

(86) PCT No.: PCT/US2014/057572
§ 371 (c)(1),
(2) Date: Mar. 25, 2016

(87) PCT Pub. No.: WO2015/048363
PCT Pub. Date: Apr. 2, 2015

(65) Prior Publication Data
US 2016/0228419 A1    Aug. 11, 2016

Related U.S. Application Data

(60) Provisional application No. 61/883,463, filed on Sep. 27, 2013.

(51) Int. Cl.

| | | |
|---|---|---|
| *A61K 31/44* | (2006.01) | |
| *C07D 491/02* | (2006.01) | |
| *C07D 491/00* | (2006.01) | |
| *C07D 221/00* | (2006.01) | |
| *C07D 453/00* | (2006.01) | |
| *A61K 31/4375* | (2006.01) | |
| *C07D 455/02* | (2006.01) | |
| *A61K 31/427* | (2006.01) | |
| *A61K 31/4402* | (2006.01) | |
| *A61K 31/444* | (2006.01) | |
| *A61K 31/4745* | (2006.01) | |
| *A61K 31/505* | (2006.01) | |
| *A61K 31/513* | (2006.01) | |

(Continued)

(52) U.S. Cl.
CPC ........ *A61K 31/4375* (2013.01); *A61K 31/427* (2013.01); *A61K 31/4402* (2013.01); *A61K 31/444* (2013.01); *A61K 31/4745* (2013.01);

*A61K 31/505* (2013.01); *A61K 31/513* (2013.01); *A61K 31/52* (2013.01); *A61K 31/635* (2013.01); *A61K 31/675* (2013.01); *A61K 45/06* (2013.01); *C07D 455/00* (2013.01); *C07D 455/02* (2013.01); *C07D 455/04* (2013.01); *C07D 471/14* (2013.01); *C07D 491/147* (2013.01); *C07D 519/00* (2013.01)

(58) Field of Classification Search
CPC .. C07D 455/02; C07D 455/03; C07D 519/00; A61K 31/4375
USPC .......... 546/121, 94, 83, 84, 89, 93; 514/306, 514/290, 291, 292, 293, 294
See application file for complete search history.

(56) References Cited

U.S. PATENT DOCUMENTS 6,630,488 B1    10/2003    Lamothe et al.
7,037,908 B2    5/2006    Naidu et al.
(Continued)

FOREIGN PATENT DOCUMENTS

EP    1852434 B1    7/2011
JP    2006342115 A    12/2006
(Continued)

OTHER PUBLICATIONS

JP 2006-342115A Machine translation English 2006.*
(Continued)

*Primary Examiner* — Shengjun Wang

(74) *Attorney, Agent, or Firm* — Nicole M. Beeler; Catherine D. Fitch

(57) ABSTRACT

The present invention relates to Substituted Quinolizine Derivatives of Formula (I): and pharmaceutically acceptable salts or prodrug thereof, wherein X, Y, $R^1$, $R^2$, $R^3$, $R^4$, $R^5$, $R^9$ and $R^{10}$ are as defined herein. The present invention also relates to compositions comprising at least one Substituted Quinolizine Derivative, and methods of using the Substituted Quinolizine Derivatives for treating or preventing HIV infection in a subject.

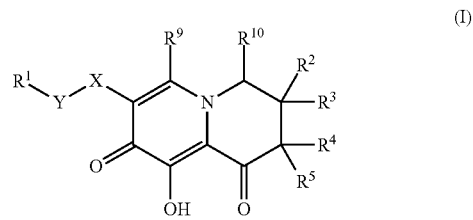

(I)

27 Claims, No Drawings

(51) Int. Cl.

| | | |
|---|---|---|
| A61K 31/52 | (2006.01) | |
| A61K 31/635 | (2006.01) | |
| A61K 31/675 | (2006.01) | |
| C07D 455/00 | (2006.01) | |
| C07D 455/04 | (2006.01) | |
| C07D 471/14 | (2006.01) | |
| C07D 491/147 | (2006.01) | |
| A61K 45/06 | (2006.01) | |
| C07D 519/00 | (2006.01) | |

(56) References Cited

U.S. PATENT DOCUMENTS

| | | |
|---|---|---|
| 7,115,601 B2 | 10/2006 | Naidu et al. |
| 7,135,467 B2 | 11/2006 | Walker et al. |
| 7,157,447 B2 | 1/2007 | Naidu et al. |
| 7,169,780 B2 | 1/2007 | Crescenzi et al. |
| 7,173,022 B2 | 2/2007 | Naidu et al. |
| 7,176,196 B2 | 2/2007 | Naidu et al. |
| 7,192,948 B2 | 3/2007 | Banville et al. |
| 7,211,572 B2 | 5/2007 | Miyazaki et al. |
| 7,232,819 B2 | 6/2007 | Di Francesco et al. |
| 7,273,859 B2 | 9/2007 | Naidu |
| 7,279,487 B2 | 10/2007 | Egbertson et al. |
| 7,414,045 B2 | 8/2008 | Crescenzi et al. |
| 7,419,969 B2 | 9/2008 | Naidu et al. |
| 2004/0229909 A1 | 11/2004 | Kiyama et al. |
| 2007/0049606 A1 | 3/2007 | Banville et al. |
| 2007/0111984 A1 | 5/2007 | Naidu et al. |
| 2007/0111985 A1 | 5/2007 | Naidu et al. |
| 2007/0112190 A1 | 5/2007 | Naidu |
| 2007/0149556 A1 | 6/2007 | Mikamiyama et al. |
| 2007/0281917 A1 | 12/2007 | Naidu et al. |
| 2008/0004265 A1 | 1/2008 | Walker et al. |
| 2012/0220571 A1 | 8/2012 | Wai et al. |

FOREIGN PATENT DOCUMENTS

| | | |
|---|---|---|
| WO | 02089780 A2 | 11/2002 |
| WO | 2006066414 A1 | 6/2006 |
| WO | 2006103399 A1 | 10/2006 |
| WO | WO2006116764 A1 | 11/2006 |
| WO | 2011045330 A1 | 4/2011 |
| WO | WO2011094150 A1 | 8/2011 |
| WO | 2011121105 A1 | 10/2011 |

OTHER PUBLICATIONS

Liu, P. S.; et al, Synthesis of Ptent Ani-HIV Agents: Esters of Castamospermine, Tetrahedron Letters, 1990, pp. 2829-2832, vol. 31, No. 20.
Berge et al., Pharmaceutical Salts, J. Pharm Sci., 1977, pp. 1-19, 66(1).
Bingham et al., Over one hundred solvates of sulfathiazole, Chem. Commun., 2001, 603-604.
Caira et al., Preparation and Crystal Characterization of a Polymorph,a Monohydrate, and an Ethyl Acetate Solvate of the Antifungal Fluconazole, J. Pharmaceutical Sci, 2004, 601-611, 93(3).
Ester Muraglia, et al, Design and Synthesis of Bicyclic Pyrimidinones as Potent and Orally Bioavailable HIV-1 Integrase Inhibits, J. Med. Chem., 2008, pp. 861-874, vol. 51, US.
Gould, Salt selection for basic drugs, International J. of Pharmaceutics, 1986, 201-217, 33.
Green & Wuts, Protective Groups in Organic Synthesis, 2nd Edition, 1991.
Hiroyuki Toh, et al, Close Structural Resemblance Between Putative Polymerase of a *Drosophila* Transposable Genetic Element 17.5 and Pol Gene Product of Moloney Murine Leukaemia Virus, The EMBO Journal, 1985, pp. 1267-1272, vol. 4, No. 5, US.
Laurence H. Pearl, et al, A Structural Model for the Retroviral Proteases, Nature, 1987, pp. 351-354, vol. 329, US.
Lee Ratner, et al, Complete Nucleotide Sequence of AIDS Virus, HTLV-III, Nature, 1985, pp. 277-284, vol. 313, US.
Marco Ferrara, et al, Synthesis of a Hexahydropyrimido[1,2-a]Azepine-2-Carboxamide Derivative Useful as an HIV Integrase Inhibitor, Tetrahedron Letters, Jul. 2007, pp. 8379-8382, vol. 48, No. 37, US.
Michael D. Power, et al, Nucleotide Sequence of SRV-1, a Type D Simian, Science, 1986, pp. -1572, vol. 231, US.
Olaf D. Kinzel et al, The Syntheis of Tetahydopyridopyrmdones as a New Scafod for HIV-1 Integrase Inhibitors, Tetrahedron Letters, 2007, pp. 6552-6555, vol. 48, No. 37, US.
T. Higuchi and V. Stella, Pro-drugs as NovelDelivery Systems (1987) 14 of the A.C.S. Symposium Series.
Van Tonder, et al, Preparation and Physicochemical Characterization of 5 Niclosamide Solvates and 1 Hemisolvate, AAPS Pharmscitech, 2004, pp. 1-10, 5(1), US.
Clayton, et al., Chemoselectivity and protecting groups, Organic Chemistry, 2012, 529-530, 2nd ed., Oxford University Press.
Extended European Search Report for 14849935.3, mailed Jan. 20, 2017.
Search Report and Written Opinion for Brunei Darussalam Patent Application No. BN/N/2016/0027, dated Apr. 5, 2017, 23 pages.
Liao, et al, Authentic HIV-1 integrase inhibitors, Future Med Chem, 2010, 1107-1122, 2(7).

* cited by examiner

SUBSTITUTED QUINOLIZINE DERIVATIVES USEFUL AS HIV INTEGRASE INHIBITORS

CROSS-REFERENCE TO RELATED APPLICATIONS

This application is the national stage application under 35 U.S.C. 371 of International Patent Application No. PCT/US2014/057572, filed Sep. 26, 2014, which claims priority to U.S. Provisional Patent Application No. 61/883,463, filed Sep. 27, 2013. Each of the aforementioned provisional and PCT applications is incorporated by reference in its entirety.

FIELD OF THE INVENTION

The present invention relates to Substituted Quinolizine Derivatives, compositions comprising at least one Substituted Quinolizine Derivative, and methods of using the Substituted Quinolizine Derivatives for treating or preventing HIV infection in a subject.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

The following references may be of interest as background:

International Publication Nos. WO 11/045330 and WO 11/121105 disclose macrocyclic compounds having HIV integrase inhibitory activity.

Kinzel et al., *Tet. Letters* 2007, 48(37): pp. 6552-6555 discloses the synthesis of tetrahydropyridopyrimidones as a scaffold for HIV-1 integrase inhibitors.

Ferrara et al., *Tet. Letters* 2007, 48(37), pp. 8379-8382 discloses the synthesis of a hexahydropyrimido[1,2-a]azepine-2-carboxamide derivative useful as an HIV integrase inhibitor.

Muraglia et al., *J. Med. Chem.* 2008, 51: 861-874 discloses the design and synthesis of bicyclic pyrimidinones as potent and orally bioavailable HIV-1 integrase inhibitors.

US2004/229909 discloses certain compounds having integrase inhibitory activity.

U.S. Pat. No. 7,232,819 and US 2007/0083045 disclose certain 5,6-dihydroxypyrimidine-4-carboxamides as HIV integrase inhibitors.

U.S. Pat. No. 7,169,780, U.S. Pat. No. 7,217,713, and US 2007/0123524 disclose certain N-substituted 5-hydroxy-6-oxo-1,6-dihydropyrimidine-4-carboxamides as HIV integrase inhibitors.

U.S. Pat. No. 7,279,487 discloses certain hydroxynaphthyridinone carboxamides that are useful as HIV integrase inhibitors.

U.S. Pat. No. 7,135,467 and U.S. Pat. No. 7,037,908 disclose certain pyrimidine carboxamides that are useful as HIV integrase inhibitors.

U.S. Pat. No. 7,211,572 discloses certain nitrogenous condensed ring compounds that are HIV integrase inhibitors.

U.S. Pat. No. 7,414,045 discloses certain tetrahydro-4H-pyrido[1,2-a]pyrimidine carboxamides, hexahydropyrimido[1,2-a]azepine carboxamides, and related compounds that are useful as HIV integrase inhibitors.

U.S. Pat. No. 8,129,385 discloses certain hexahydro-2H-pyrido[1',2':4,5]pyrazino[2,1-b][1,3]oxazine-9-carboxamides, and related compounds that are useful as HIV integrase inhibitors.

WO 2006/103399 discloses certain tetrahydro-4H-pyrimidooxazepine carboxamides, tetrahydropyrazinopyrimidine carboxamides, hexahydropyrimidodiazepine carboxamides, and related compounds that are useful as HIV integrase inhibitors.

US 2007/0142635 discloses processes for preparing hexahydropyrimido[1,2-a]azepine-2-carboxylates and related compounds.

US 2007/0149556 discloses certain hydroxypyrimidinone derivatives having HIV integrase inhibitory activity.

Various pyrimidinone compounds useful as HIV integrase inhibitors are also disclosed in U.S. Pat. No. 7,115,601, U.S. Pat. No. 7,157,447, U.S. Pat. No. 7,173,022, U.S. Pat. No. 7,176,196, U.S. Pat. No. 7,192,948, U.S. Pat. No. 7,273,859, and U.S. Pat. No. 7,419,969.

US 2007/0111984 discloses a series of bicyclic pyrimidinone compounds useful as HIV integrase inhibitors.

US 2006/0276466, US 2007/0049606, US 2007/0111985, US 2007/0112190, US 2007/0281917, US 2008/0004265 each disclose a series of bicyclic pyrimidinone compounds useful as HIV integrase inhibitors.

SUMMARY OF THE INVENTION

In one aspect, the present invention provides Compounds of Formula (I):

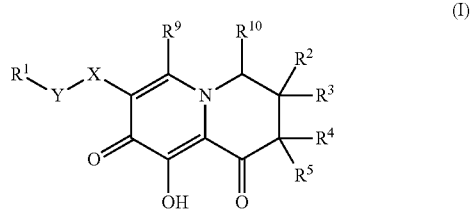

or a pharmaceutically acceptable salt thereof, wherein:

X is selected from a single bond, 5 or 6-membered monocyclic heteroaryl and —N(R$^6$)C(O)—;

Y is a single bond or C$_1$-C$_3$ alkylene;

R$^1$ is selected from C$_6$-C$_{10}$ aryl, 5 or 6-membered monocyclic heteroaryl and 9 or 10-membered bicyclic heteroaryl, wherein said C$_6$-C$_{10}$ aryl group, said 5 or 6-membered monocyclic heteroaryl group and said 9 or 10-membered bicyclic heteroaryl group can each be optionally substituted with up to three R$^8$ groups;

R$^2$ is H, C$_1$-C$_6$ alkyl, —N(R$^{11}$)$_2$, or —OR$^7$ or R$^2$ and R$^4$, together with the carbon atoms to which they are attached, can join to form a 5 to 8-membered monocyclic cycloalkyl group, 5 to 8-membered monocyclic heterocycloalkyl group, 5 to 8-membered monocyclic heterocycloalkenyl group or a 8 to 11-membered bicyclic heterocycloalkyl, wherein said 5 to 8-membered monocyclic cycloalkyl group, said 5 to 8-membered monocyclic heterocycloalkyl group, said 5 to 8-membered monocyclic heterocycloalkenyl group and said 8 to 11-membered bicyclic heterocycloalkyl group can be optionally substituted with up to three R$^8$ groups, which can be the same or different;

R$^3$ is H, C$_1$-C$_6$ alkyl, —N(R$^{11}$)$_2$ or —OR$^7$;

R$^4$ is selected from H, C$_1$-C$_6$ alkyl, —(C$_1$-C$_6$ alkylene)-O—(C$_1$-C$_6$ alkyl), —N(R$^{11}$)$_2$ and —OR$^7$, such that when R$^2$ and/or R$^3$ are —N(R$^{11}$)$_2$, then R$^4$ is other than H;

R$^5$ is selected from H, C$_1$-C$_6$ alkyl, —(C$_1$-C$_6$ alkylene)-O—(C$_1$-C$_6$ alkyl), —N(R$^{11}$)$_2$ and —OR$^7$, such that when R$^2$ and/or R$^3$ are —N(R$^{11}$)$_2$, then R$^5$ is other than H;

each occurrence of R$^6$ is independently H or C$_1$-C$_6$ alkyl;

each occurrence of R$^7$ is independently selected from H, C$_1$-C$_6$ alkyl, —(C$_1$-C$_6$ alkylene)-O—(C$_1$-C$_6$ alkyl) and C$_3$-C$_7$ cycloalkyl;

each occurrence of R$^8$ is independently selected from C$_1$-C$_6$ alkyl, halo, —OR$^6$, —SR$^6$, C$_1$-C$_6$ haloalkyl, C$_1$-C$_6$ hydroxyalkyl, —O—(C$_1$-C$_6$ haloalkyl), —CN, —NO$_2$, —N(R$^6$)$_2$, —C(O)OR$^7$, —C(O)N(R$^7$)$_2$ and —NHC(O)R$^7$;

R$^9$ is selected from H, C$_1$-C$_6$ alkyl, —C$_1$-C$_6$ alkyl-O—C$_1$-C$_6$ alkyl, —C$_1$-C$_6$ alkyl-NR$^6$—C$_1$-C$_6$ alkyl, —C$_1$-C$_6$ haloalkyl, —C$_1$-C$_6$ hydroxyalkyl;

R$^{10}$ is selected from H, C$_1$-C$_6$ alkyl, —C$_1$-C$_6$ alkyl-O—C$_1$-C$_6$ alkyl, —C$_1$-C$_6$ alkyl-NR$^6$—C$_1$-C$_6$ alkyl, —C$_1$-C$_6$ haloalkyl, —C$_1$-C$_6$ hydroxyalkyl;

each occurrence of R$^{11}$ is independently selected from H, C$_1$-C$_6$ alkyl, —S(O)$_2$R$_{12}$ and —C(O)R$^{12}$; and each occurrence of R$^{12}$ is independently selected from C$_1$-C$_6$ alkyl, C$_3$-C$_7$ cycloalkyl, C$_6$-C$_{10}$ aryl, 4 to 7-membered monocyclic heterocycloalkyl, 8 to 11-membered bicyclic heterocycloalkyl, 5 or 6-membered monocyclic heteroaryl and 9 or 10-membered bicyclic heteroaryl, wherein said C$_3$-C$_7$ cycloalkyl group, said C$_6$-C$_{10}$ aryl group, 4 to 7-membered monocyclic heterocycloalkyl, said 8 to 11-membered bicyclic heterocycloalkyl group, said 5 or 6-membered monocyclic heteroaryl group and said 9 or 10-membered bicyclic heteroaryl group can each be optionally substituted with up to three R$^8$ groups.

The Compounds of Formula (I) (also referred to herein as the "Substituted Quinolizine Derivatives") and pharmaceutically acceptable salts or prodrugs thereof can be useful, for example, for inhibiting HIV viral replication or replicon activity, or for treating or preventing HIV infection in a subject. Without being bound by any specific theory, it is believed that the Substituted Quinolizine Derivatives inhibit HIV viral replication by inhibiting HIV Integrase.

Accordingly, the present invention provides methods for treating or preventing HIV infection in a subject, comprising administering to the subject an effective amount of at least one Substituted Quinolizine Derivative.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention includes Substituted Quinolizine Derivatives, compositions comprising at least one Substituted Quinolizine Derivative, and methods of using the Substituted Quinolizine Derivatives for treating or preventing HIV infection in a subject.

DEFINITIONS AND ABBREVIATIONS

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . . .

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of Substituted Quinolizine Derivative and/or an additional therapeutic agent, or a composition thereof that is effective in inhibiting HIV replication and in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms (C$_1$-C$_6$ alkyl) or from about 1 to about 4 carbon atoms (C$_1$-C$_4$ alkyl).

Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)—alkyl, —O—C(O)-aryl, —O—C(O)-cycloalkyl, —C(O)OH and —C(O)O-alkyl. The term "C$_2$-C$_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group has from about 3 to about 5 carbon atoms. In another embodiment, an alkylene group is branched. In another embodiment, an alkylene group is linear. In one embodiment, an alkylene group is —CH$_2$—. The term "C$_1$-C$_6$ alkylene" refers to an alkylene group having from 1 to 6 carbon atoms. The term "C$_2$-C$_4$ alkylene" refers to an alkylene group having from 2 to 4 carbon atoms.

The term "alkenylene," as used herein, refers to an alkenyl group, as defined above, wherein one of the alkenyl group's hydrogen atoms has been replaced with a bond. Non-limiting examples of alkenylene groups include —CH═CH—, —CH═CHCH$_2$—, —CH$_2$CH═CH—, —CH$_2$CH═CHCH$_2$—, —CH═CHCH$_2$CH$_2$—, —CH$_2$CH$_2$CH═CH— and —CH(CH$_3$)CH═CH—. In one embodiment, an alkenylene group has from 2 to about 6 carbon atoms. In another embodiment, an alkenylene group has from about 3 to about 5 carbon atoms. In another embodiment, an alkenylene group is branched. In another embodiment, an alkenylene group is linear. The term "C$_2$-C$_6$ alkylene" refers to an alkenylene group having from 2 to 6 carbon atoms. The term "C$_3$-C$_5$ alkenylene" refers to an alkenylene group having from 3 to 5 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group can be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group can be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

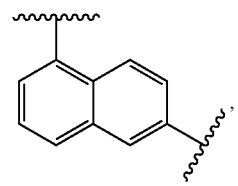 [SMILES: *c1ccc2c(*)cccc2c1]

is understood to represent both:

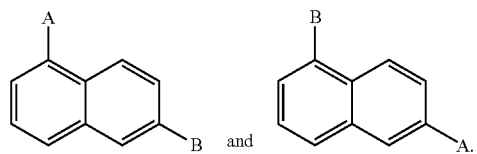

In one embodiment, an arylene group can be optionally fused to a cycloalkyl or cycloalkanoyl group. Non-limiting examples of arylene groups include phenylene and naphthalene. In one embodiment, an arylene group is unsubstituted. In another embodiment, an arylene group is:

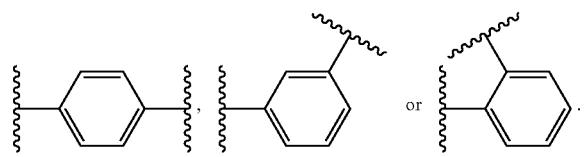

Unless otherwise indicated, an arylene group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

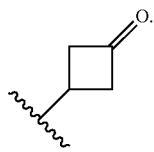 [SMILES: *C1CC(=O)C1]

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an —OH group. In one embodiment, a hydroxyalkyl group has from 1 to 6 carbon atoms. Non-limiting examples of hydroxyalkyl groups include —$CH_2OH$, —$CH_2CH_2OH$, —$CH_2CH_2CH_2OH$ and —$CH_2CH(OH)CH_3$. The term "$C_1$-$C_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. In another embodiment, a heteroaryl group is bicyclic and has 9 or 10 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered monocyclic heteroaryl. In another embodiment, a heteroaryl group comprises a 5- to 6-membered monocyclic heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 5 to about 8 ring atoms. In another embodiment, a heterocycloalkyl group is bicyclic and has from about 8 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

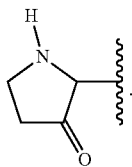 [SMILES: *C1NCCC1=O]

In one embodiment, a heterocycloalkyl group is a 5-membered monocyclic heterocycloalkyl. In another embodiment, a heterocycloalkyl group is a 6-membered monocyclic heterocycloalkyl. The term "4 to 7-membered monocyclic heterocycloalkyl" refers to a monocyclic heterocycloalkyl group having from 4 to 7 ring atoms. The term "5 to 8-membered monocyclic heterocycloalkyl" refers to a monocyclic heterocycloalkyl group having from 5 to 8 ring atoms. The term "8 to 11-membered bicyclic heterocycloalkyl" refers to a bicyclic heterocycloalkyl group having from 8 to 11 ring atoms. Unless otherwise indicated, a heterocycloalkyl group is unsubstituted.

The term "heterocycloalkenyl," as used herein, refers to an heterocycloalkyl group, as defined above, which is non-aromatic and contains at least one endocyclic double bond between two adjacent ring atoms. A heterocycloalkenyl group can be joined via a ring carbon, ring silicon atom or ring nitrogen atom. In one embodiment, a heterocycloalkenyl group is monocyclic and has from about 3 to about 7 ring atoms. In another embodiment, a heterocycloalkenyl group is monocyclic has from about 5 to about 8 ring atoms. In another embodiment, a heterocycloalkenyl group is bicyclic and has from about 8 to about 11 ring atoms. In still another embodiment, a heterocycloalkenyl group is monocyclic and has 5 or 6 ring atoms. In one embodiment, a heterocycloalkenyl group is monocyclic. In another embodiment, a heterocycloalkenyl group is bicyclic. There are no adjacent oxygen and/or sulfur atoms present in the ring system. Any —NH group in a heterocycloalkenyl ring may be substituted or may exist protected such as, for example, as an —N(BOC), —N(Cbz), —N(Tos) group and the like; such protected heterocycloalkenyl groups are considered part of this invention. The term "heterocycloalkenyl" also encompasses a heterocycloalkenyl group, as defined above, which is fused to an aryl (e.g., benzene) or heteroaryl ring. A heterocycloalkenyl group can be optionally substituted by one or more "ring system substituents" which may be the same or different, and are as defined herein below. The nitrogen or sulfur atom of the heterocycloalkenyl can be optionally oxidized to the corresponding N-oxide, S-oxide or S,S-dioxide.

A ring carbon atom of a heterocycloalkenyl group may be functionalized as a carbonyl group. An illustrative example of such a heterocycloalkenyl group is:

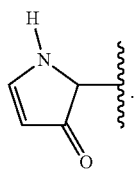

In one embodiment, a heterocycloalkenyl group is a 5-membered monocyclic heterocycloalkenyl. In another embodiment, a heterocycloalkenyl group is a 6-membered monocyclic heterocycloalkenyl. The term "4 to 7-membered monocyclic heterocycloalkenyl" refers to a monocyclic heterocycloalkenyl group having from 4 to 7 ring atoms. The term "5 to 8-membered monocyclic heterocycloalkenyl" refers to a monocyclic heterocycloalkenyl group having from 5 to 8 ring atoms. The term "8 to 11-membered bicyclic heterocycloalkenyl" refers to a bicyclic heterocycloalkenyl group having from 8 to 11 ring atoms. Unless otherwise indicated, a heterocycloalkenyl group is unsubstituted.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si (alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$) (Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

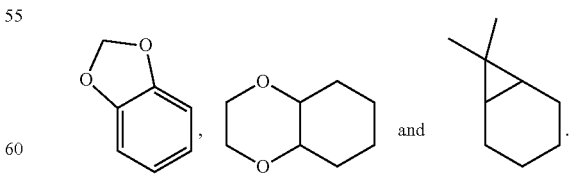

The term "substituted" means that one or more hydrogens on the designated atom is replaced with a selection from the indicated group, provided that the designated atom's normal valency under the existing circumstances is not exceeded, and that the substitution results in a stable compound.

Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., alkyl, $R^1$, $R^7$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Substituted Quinolizine Derivative or a pharmaceutically acceptable salt of the compound. The transformation may occur by various mechanisms (e.g., by metabolic or chemical processes), such as, for example, through hydrolysis in blood. For example, if a Substituted Quinolizine Derivative or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl, and the like.

Similarly, if a Substituted Quinolizine Derivative contains an alcohol functional group, a prodrug can be formed by the replacement of one or more of the hydrogen atoms of the alcohol groups with a group such as, for example, ($C_1$-$C_6$) alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkyl, α-amino ($C_1$-$C_4$)alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a Substituted Quinolizine Derivative incorporates an amine functional group, a prodrug can be formed by the replacement of a hydrogen atom in the amine group with a group such as, for example, R-carbonyl-, RO-carbonyl-, NRR'-carbonyl- wherein R and R' are each independently ($C_1$-$C_{10}$)alkyl, ($C_3$-$C_7$)cycloalkyl, benzyl, a natural α-aminoacyl, —C(OH)C(O)O$Y^1$ wherein $Y^1$ is H, ($C_1$-$C_6$) alkyl or benzyl, —C(O$Y^2$)$Y^3$ wherein $Y^2$ is ($C_1$-$C_4$)alkyl and $Y^3$ is ($C_1$-$C_6$)alkyl; carboxy ($C_1$-$C_6$)alkyl; amino($C_1$-$C_4$)alkyl or mono-N— or di-N,N—($C_1$-$C_6$)alkylaminoalkyl; —C($Y^4$)$Y^5$ wherein $Y^4$ is H or methyl and $Y^5$ is mono-N— or di-N,N—($C_1$-$C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters, including those corresponding to both natural and non-natural amino acids (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvates, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Substituted Quinolizine Derivatives can form salts which are also within the scope of this invention. Reference to a Substituted Quinolizine Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Substituted Quinolizine Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Substituted Quinolizine Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), arylalkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Substituted Quinolizine Derivatives may be atropisomers (e.g., substituted biaryls) and are considered as part of this invention. Enantiomers can also be directly separated using chiral chromatographic techniques.

It is also possible that the Substituted Quinolizine Derivatives may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Substituted Quinolizine Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

The Substituted Quinolizine Derivatives are useful in human and veterinary medicine for treating or preventing HIV infection in a subject. In one embodiment, the Substituted Quinolizine Derivatives can be inhibitors of HIV viral replication. In a specific embodiment, the Substituted Quinolizine Derivatives are inhibitors of HIV-1. Accordingly, the Substituted Quinolizine Derivatives are useful for treating HIV infections and AIDS. In accordance with the invention, the Substituted Quinolizine Derivatives can be administered to a subject in need of treatment or prevention of HIV infection.

Accordingly, in one embodiment, the invention provides methods for treating HIV infection in a subject comprising administering to the subject an effective amount of at least one Substituted Quinolizine Derivative or a pharmaceutically acceptable salt thereof. In a specific embodiment, the present invention provides methods for treating AIDS in a subject comprising administering to the subject an effective amount of at least one Substituted Quinolizine Derivative or a pharmaceutically acceptable salt thereof.

LIST OF ABBREVIATIONS

Anal.=analytical
ACN=acetonitrile
AcOH=acetic acid
n-BuLi=n-butyl lithium
BnBr=benzyl bromide
br=broad
calc.=calculated
m-CPBA=3-chloroperoxybenzoic acid
d=doublet
DBU=1,8-diazabicycloundec-7-ene
DCM=dichloromethane
DEA=diethylamine
DIPEA or DIEA=N,N-diisopropylethylamine
DMF=dimethylformamide
DMSO=dimethyl sulfoxide
ESI=electrospray ionization
$Et_2O$=diethylether
$Et_3N$=triethylamine
EtOAc=ethyl acetate
EtOH=ethanol
HCl=hydrochloric acid
HPLC=high-pressure liquid chromatography
IPA=iso-propyl alcohol
IPAc=iso-propyl acetate
KF=Karl-Fischer titration (to determine water content)
KOt-Bu=potassium tert-butoxide
LCMS=liquid chromatography-mass spectrometry
LiHMDS=lithium hexamethyl silazane
m=multiplet
MeCN=acetonitrile
MeOH=methyl alcohol
MPa=millipascal
MS=mass spectroscopy
MTBE=methyl tert-butyl ether
$NaHCO_3$=sodium bicarbonate
NBS=N-bromosuccinimide
NHS=normal human serum
NMP=N-methylpyrrolidine
NMR=nuclear magnetic resonance spectroscopy Piv=pivalate, 2,2-dimethylpropanoyl
Pd/C=palladium on carbon
rt=room temperature
s=singlet
SFC=supercritical fluid chromatography
$SiO_2$=silical gel
t=triplet
TFA=trifluoroacetic acid
THF=tetrahydrofuran
TLC=thin-layer chromatography
$TMSN_3$=trimethylsilyl azide
p-TsOH=para-toluene sulfonic acid
wt %=percentage by weight The Compounds of Formula (I)

The present invention provides Substituted Quinolizine Derivatives of Formula

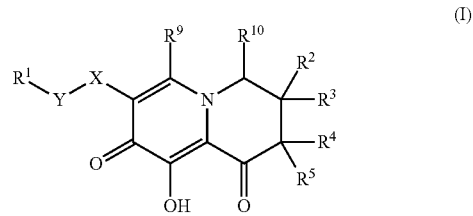

(I)

and pharmaceutically acceptable salts thereof, wherein X, Y, $R^1$, $R^2$, $R^3$, $R^4$, $R^5$, $R^9$ and $R^{10}$ are defined above for the Compounds of Formula (I).

In one embodiment, X is a single bond.
In another embodiment, X is —NHC(O)—.
In another embodiment, X is 5 or 6-membered heteroaryl.
In still another embodiment, X is 5-membered heteroaryl.
In another embodiment, X is 1,3,4-thiadiazole.
In one embodiment, Y is a single bond.
In another embodiment, Y is $C_1$-$C_3$ alkylene.
In another embodiment, Y is $CH_2$.
In one embodiment, X is —NHC(O)— and Y is $CH_2$.
In another embodiment, X is 5-membered heteroaryl and Y is $CH_2$.

In one embodiment, $R^1$ is optionally substituted $C_6$-$C_{10}$ aryl or optionally substituted 9 or 10-membered bicyclic heteroaryl.

In another embodiment, $R^1$ is optionally substituted $C_6$-$C_{10}$ aryl.

In another embodiment, $R^1$ is optionally substituted phenyl.

In one embodiment, $R^1$ is selected from:

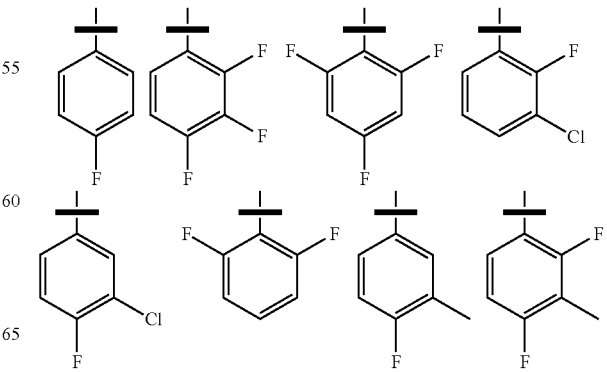

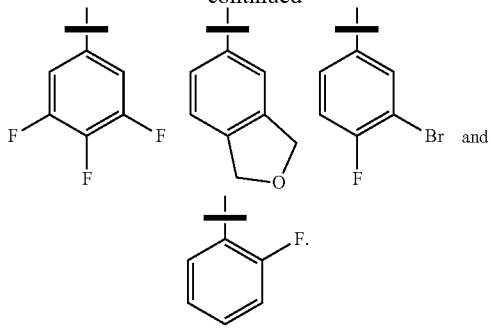

In another embodiment, R¹ is phenyl with is substituted with one or more halo groups.

In another embodiment, R¹ is phenyl with is substituted with 1-3 halo groups.

In still another embodiment, R¹ is phenyl with is substituted with one or two F groups.

In another embodiment, R¹ is 4-fluorophenyl.

In yet another embodiment, R¹ is 2,4-difluorophenyl.

In another embodiment, R¹ is 3-chloro-2-fluorophenyl.

In one embodiment, the group R¹—Y— is phenyl-CH₂—, wherein said phenyl group is substituted with 1-3 groups, independently selected from F and Cl.

In another embodiment, the group R¹—Y— is phenyl-CH₂—, wherein said phenyl group is substituted with one or two F groups.

In one embodiment, R² is H.

In another embodiment, R² is —O—($C_1$-$C_6$ alkylene)-O—($C_1$-$C_6$ alkyl).

In one embodiment, R³ is H.

In another embodiment, R³ is —OH.

In one embodiment, R³ is —O—($C_1$-$C_6$ alkyl).

In another embodiment, R³ is methoxy.

In one embodiment, R² and R³ are each independently H, —OH or —O—($C_1$-$C_6$ alkyl).

In another embodiment, R² is H and R³ is —OH or —O—($C_1$-$C_6$ alkyl).

In another embodiment, R² is H and R³ is methoxy.

In one embodiment, R⁴ is H.

In another embodiment, R⁴ is $C_1$-$C_6$ alkyl.

In another embodiment, R⁴ is —($C_1$-$C_6$ alkylene)-O—($C_1$-$C_6$ alkyl).

In still another embodiment, R⁴ is methyl.

In another embodiment, R⁴ is —CH₂CH₂OCH₃.

In one embodiment, R⁵ is H.

In another embodiment, R⁵ is $C_1$-$C_6$ alkyl.

In another embodiment, R⁵ is —($C_1$-$C_6$ alkylene)-O—($C_1$-$C_6$ alkyl).

In another embodiment, R⁵ is methyl.

In still another embodiment, R⁵ is —CH₂CH₂OCH₃.

In one embodiment, R⁴ and R⁵ are each independently H, $C_1$-$C_6$ alkyl or —($C_1$-$C_6$ alkylene)-O—($C_1$-$C_6$ alkyl).

In another embodiment, R⁴ and R⁵ are each $C_1$-$C_6$ alkyl.

In still another embodiment, R⁴ and R⁵ are each methyl.

In one embodiment, R² and R⁴, together with the carbon atoms to which they are attached, join to form a 5 to 8-membered monocyclic heterocycloalkyl group.

In one embodiment, R³ is —O—($C_1$-$C_6$ alkyl) and R⁴ is —($C_1$-$C_6$ alkylene)-O—($C_1$-$C_6$ alkyl).

In one embodiment, R⁹ is H.

In another embodiment, R¹⁰ is H.

In another embodiment, R⁹ and R¹⁰ are each H.

In one embodiment, the compounds of formula (I) have the formula (Ia):

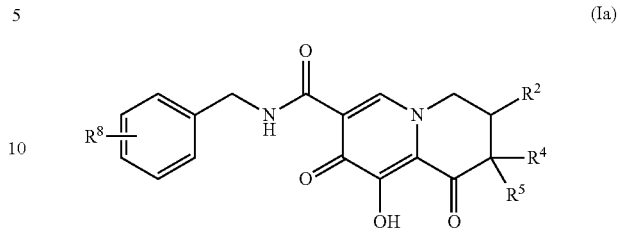

or a pharmaceutically acceptable salt thereof,
wherein:

R² and R⁴, together with the carbon atoms to which they are attached, join to form a 5 to 8-membered monocyclic heterocycloalkyl group;

R⁵ is H or $C_1$-$C_6$ alkyl; and

R⁸ represents 1 or 2 phenyl group substituents, each independently selected from halo.

In one embodiment, for the compounds of formulas (I) and (Ia), R² and R⁴, together with the carbon atoms to which they are attached, can join to form a 5 to 8-membered monocyclic heterocycloalkyl group, 5 to 8-membered monocyclic heterocycloalkenyl group or a 8 to 11-membered bicyclic heterocycloalkyl, wherein said 5 to 8-membered monocyclic heterocycloalkyl group, said 5 to 8-membered monocyclic heterocycloalkenyl group and said 8 to 11-membered bicyclic heterocycloalkyl group can be optionally substituted with up to three R⁸ groups, which can be the same or different;

In one embodiment, for the compounds of formulas (I) and (Ia), R² and R⁴, together with the carbon atoms to which they are attached, join to form a 5 to 8-membered monocyclic heterocycloalkyl group, R³ is H and R⁵ is H.

In another embodiment, for the compounds of formulas (I) and (Ia), R² and R⁴, together with the carbon atoms to which they are attached, join to form a 5 to 8-membered monocyclic heterocycloalkyl group, R³ is H and R⁵ is methyl.

In another embodiment, for the compounds of formulas (I) and (Ia), R² and R⁴, together with the carbon atoms to which they are attached, join to form a 6-membered monocyclic heterocycloalkyl group.

In still another embodiment, for the compounds of formulas (I) and (Ia), R² and R⁴, together with the carbon atoms to which they are attached, join to form a 5-membered monocyclic heterocycloalkyl group.

In another embodiment, for the compounds of formulas (I) and (Ia), R² and R⁴, together with the carbon atoms to which they are attached, join to form a 1,3-dioxane group or a 1,4-dioxane group.

In one embodiment, for the compounds of formulas (I) and (Ia), R² and R⁴, together with the carbon atoms to which they are attached, join to form a group selected from:

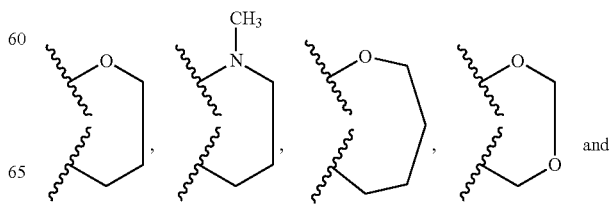

-continued

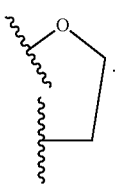

In another embodiment, for the compounds of formulas (I) and (Ia), $R^2$ and $R^4$, together with the carbon atoms to which they are attached, join to form a group selected from:

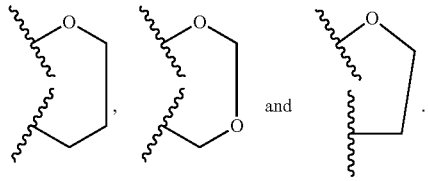

In another embodiment, for the compounds of formulas (I) and (Ia), $R^2$ and $R^4$, together with the carbon atoms to which they are attached, join to form the following group:

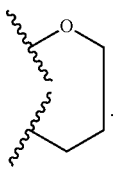 [SMILES: *CCCO*]

In one embodiment, for the compounds of formulas (I) and (Ia), $R^3$ is H; $R^5$ is H or methyl; and $R^2$ and $R^4$, together with the carbon atoms to which they are attached, join to form a group selected from:

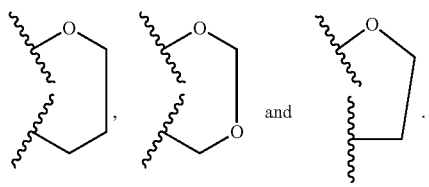

In another embodiment, for the compounds of formulas (I) and (Ia), $R^3$ is H; $R^5$ is methyl; and $R^2$ and $R^4$, together with the carbon atoms to which they are attached, join to form a group having the structure:

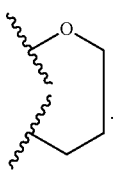 [SMILES: *CCCO*]

In one embodiment, the compounds of formula (I) have the formula (Ib):

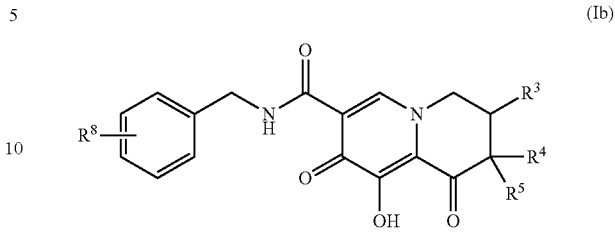

or a pharmaceutically acceptable salt thereof,
wherein:
$R^3$ is H or —O—$C_1$-$C_6$ alkyl;
$R^4$ is H, $C_1$-$C_6$ alkyl or —($C_1$-$C_6$ alkylene)-O—($C_1$-$C_6$ alkyl);
$R^5$ is H or $C_1$-$C_6$ alkyl; and
$R^8$ represents 1 or 2 phenyl group substituents, each independently selected from halo.

In one embodiment, for the compounds of formula (Ib), $R^3$ is H.

In one embodiment, for the compounds of formula (Ib), $R^3$ is —O—($C_1$-$C_6$ alkyl).

In another embodiment, for the compounds of formula (Ib), $R^3$ is methoxy.

In one embodiment, for the compounds of formula (Ib), $R^4$ is H.

In another embodiment, for the compounds of formula (Ib), $R^4$ is $C_1$-$C_6$ alkyl.

In another embodiment, for the compounds of formula (Ib), $R^4$ is —($C_1$-$C_6$ alkylene)-O—($C_1$-$C_6$ alkyl).

In another embodiment, for the compounds of formula (Ib), $R^4$ is methyl.

In another embodiment, for the compounds of formula (Ib), $R^4$ is —$CH_2CH_2OCH_3$.

In one embodiment, for the compounds of formula (Ib), $R^5$ is H.

In another embodiment, for the compounds of formula (Ib), $R^5$ is $C_1$-$C_6$ alkyl.

In another embodiment, for the compounds of formula (Ib), $R^5$ is —($C_1$-$C_6$ alkylene)-O—($C_1$-$C_6$ alkyl).

In another embodiment, for the compounds of formula (Ib), $R^5$ is methyl.

In one embodiment, for the compounds of formula (Ib), $R^4$ and $R^5$ are each independently H, $C_1$-$C_6$ alkyl or —($C_1$-$C_6$ alkylene)-O—($C_1$-$C_6$ alkyl).

In another embodiment, for the compounds of formula (Ib), $R^4$ and $R^5$ are each $C_1$-$C_6$ alkyl.

In still another embodiment, for the compounds of formula (Ib), $R^4$ and $R^5$ are each methyl.

In one embodiment, for the compounds of formula (Ib), $R^3$ is —O—($C_1$-$C_6$ alkyl) and $R^4$ is —($C_1$-$C_6$ alkylene)-O—($C_1$-$C_6$ alkyl).

In another embodiment, for the compounds of formula (Ib), $R^4$ is —($C_1$-$C_6$ alkylene)-O—($C_1$-$C_6$ alkyl) and $R^5$ is $C_1$-$C_6$ alkyl.

In another embodiment, for the compounds of formula (Ib), $R^4$ is —$CH_2CH_2OCH_3$ and $R^5$ is methyl.

In one embodiment, for the compounds of formula (Ib), $R^8$ represents a para fluoro substituent and an ortho fluoro substituent.

In one embodiment, variables X, Y, $R^1$, $R^2$, $R^3$, $R^4$, $R^5$, $R^9$ and $R^{10}$ for the Compounds of Formula (I) are selected independently of each other.

In another embodiment, the Compounds of Formula (I) are in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HIV antiviral agents, immunomodulators, and anti-infective agents.

(c) The pharmaceutical composition of (b), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(d) A pharmaceutical combination that is (i) a Compound of Formula (I) and (ii) a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(e) The combination of (d), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(f) A method of inhibiting HIV replication in a subject in need thereof which comprises administering to the subject an effective amount of a Compound of Formula (I).

(g) A method of treating HIV infection and/or reducing the likelihood or severity of symptoms of HIV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine, (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (k) above are understood to include all embodiments of the compounds, including such embodiments as result from combinations of embodiments.

The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

Non-limiting examples of the Compounds of Formula (I) include compounds 1-124 as set forth in the Examples below, compounds 125-137 as set forth immediately below, and pharmaceutically acceptable salts thereof.

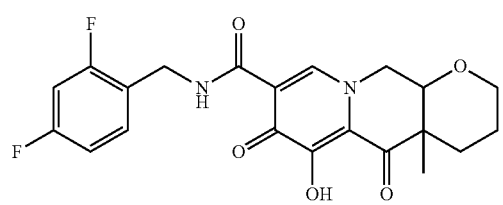

125

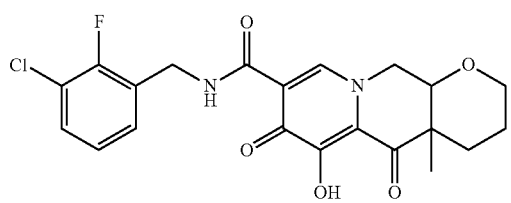

126

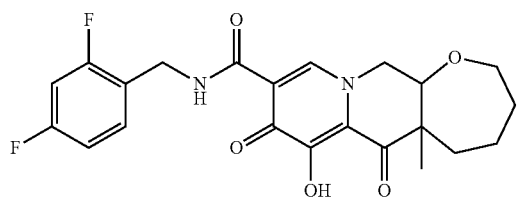

127

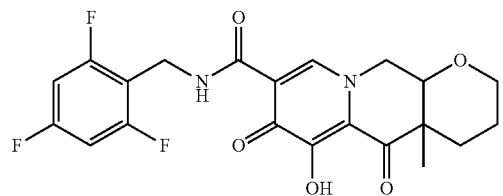

128

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes 1 and 2 below. Alternative synthetic pathways and analogous structures will be apparent to those skilled in the art of organic synthesis.

Scheme 1 describes a method for making the compounds of formula (I), which corresponds to the bridged tetracyclic 4-pyridinone compounds of Formula (I).

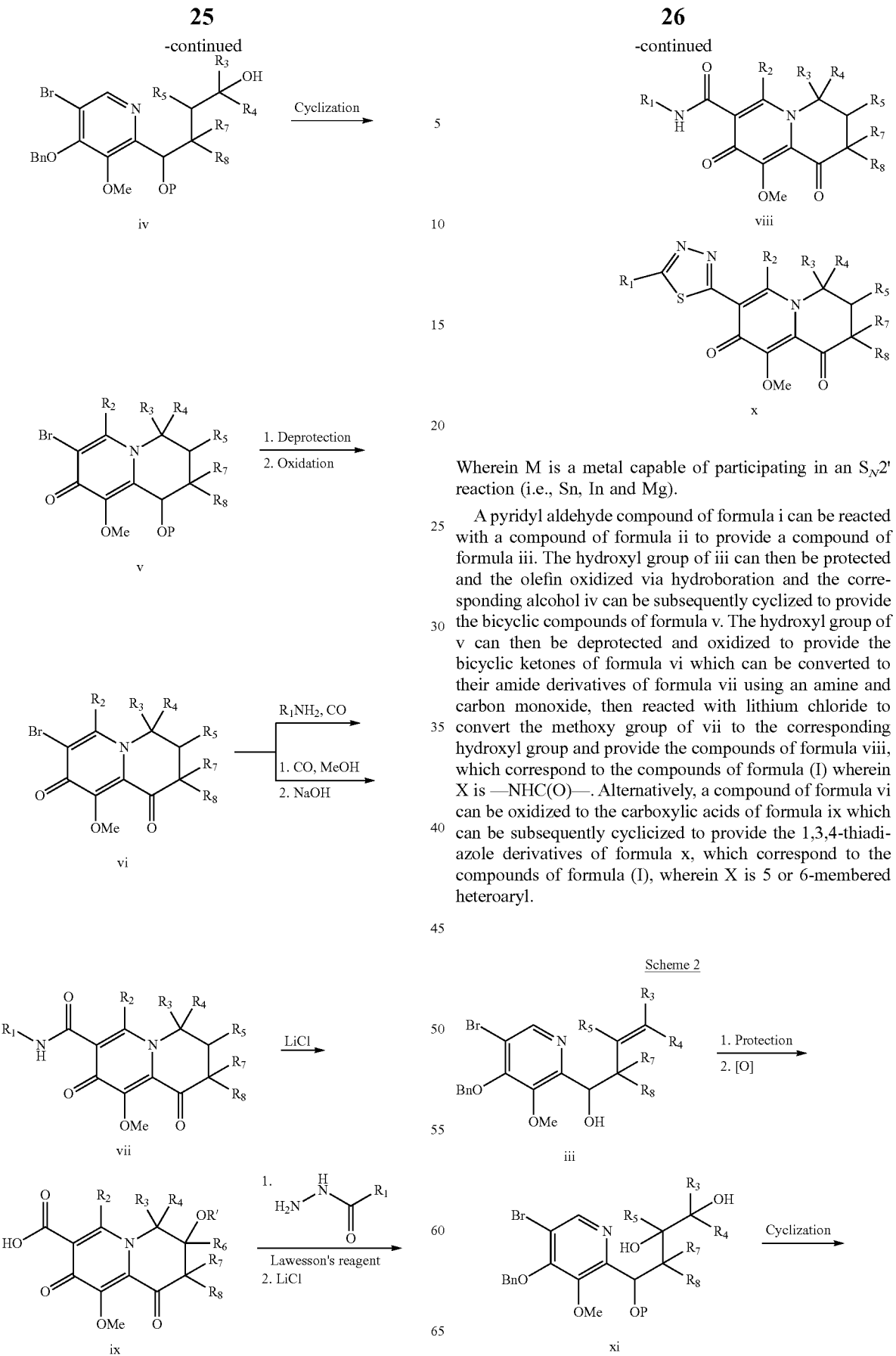

Wherein M is a metal capable of participating in an $S_N2'$ reaction (i.e., Sn, In and Mg).

A pyridyl aldehyde compound of formula i can be reacted with a compound of formula ii to provide a compound of formula iii. The hydroxyl group of iii can then be protected and the olefin oxidized via hydroboration and the corresponding alcohol iv can be subsequently cyclized to provide the bicyclic compounds of formula v. The hydroxyl group of v can then be deprotected and oxidized to provide the bicyclic ketones of formula vi which can be converted to their amide derivatives of formula vii using an amine and carbon monoxide, then reacted with lithium chloride to convert the methoxy group of vii to the corresponding hydroxyl group and provide the compounds of formula viii, which correspond to the compounds of formula (I) wherein X is —NHC(O)—. Alternatively, a compound of formula vi can be oxidized to the carboxylic acids of formula ix which can be subsequently cyclicized to provide the 1,3,4-thiadiazole derivatives of formula x, which correspond to the compounds of formula (I), wherein X is 5 or 6-membered heteroaryl.

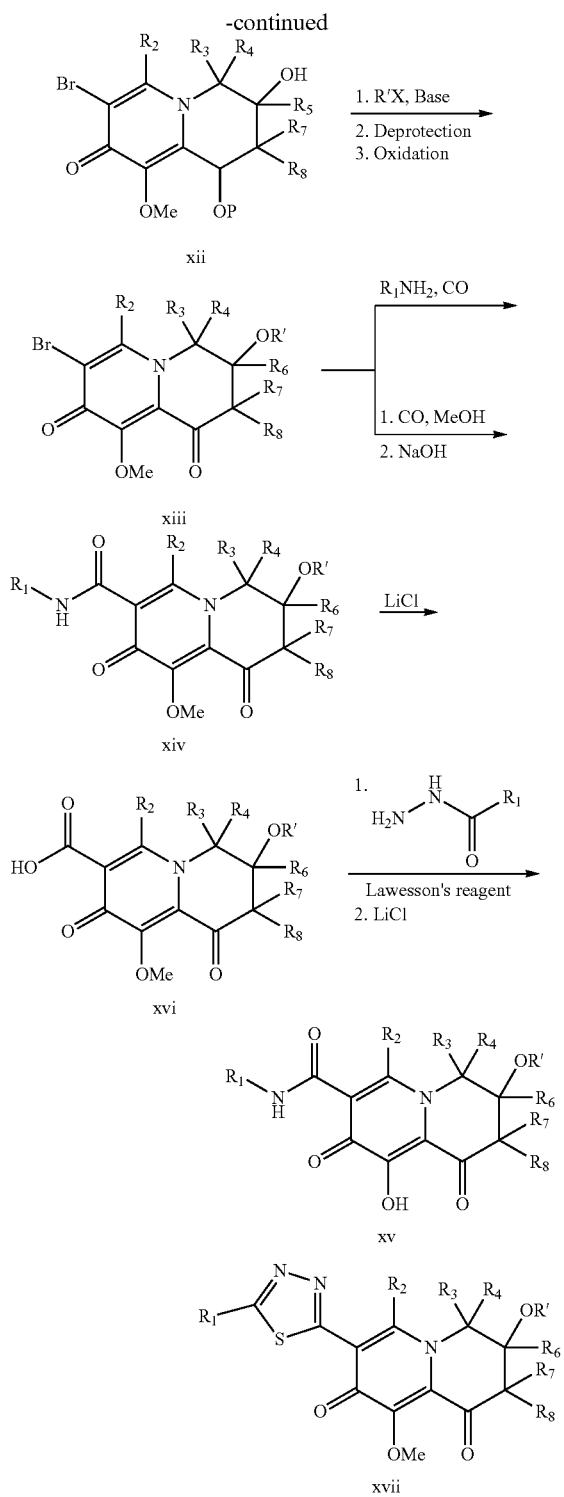

amide derivatives of formula xiv using an amine and carbon monoxide, then reacted with lithium chloride to convert the methoxy group of xiv to the corresponding hydroxyl group and provide the compounds of formula xv, which correspond to the compounds of formula (I) wherein X is —NHC(O)—. hydroxyl group of v can then be deprotected and oxidized to provide the bicyclic ketones of formula vii which can be reacted with lithium chloride to convert the methoxy group of vii to hydroxyl group and provide the compounds of formula viii, which correspond to the compounds of formula (I) wherein X is —NHC(O)— and $R^3$ is —$OR^7$. Alternatively, a compound of formula xii can be oxidized to the carboxylic acids of formula xvi which can be subsequently cyclicized to provide the 1,3,4-thiadiazole derivatives of formula xvii, which correspond to the compounds of formula (I), wherein X is 5 or 6-membered heteroaryl and $R^3$ is —$OR^7$.

In the methods for preparing compounds of the present invention set forth in the foregoing schemes, functional groups in various moieties and substituents (in addition to those already explicitly noted in the foregoing schemes) may be sensitive or reactive under the reaction conditions employed and/or in the presence of the reagents employed. Such sensitivity/reactivity can interfere with the progress of the desired reaction to reduce the yield of the desired product, or possibly even preclude its formation. Accordingly, it may be necessary or desirable to protect sensitive or reactive groups on any of the molecules concerned. Protection can be achieved by means of conventional protecting groups, such as those described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, $3^{rd}$ edition, 1999, and $2^{nd}$ edition, 1991. The protecting groups may be removed at a convenient subsequent stage using methods known in the art. Alternatively the interfering group can be introduced into the molecule subsequent to the reaction Step of concern.

One skilled in the art of organic synthesis will recognize that the synthesis of compounds with multiple reactive functional groups, such as —OH and $NH_2$, may require protection of certain functional groups (i.e., derivatization for the purpose of chemical compatibility with a particular reaction condition). Suitable protecting groups for the various functional groups of these compounds and methods for their installation and removal are well-known in the art of organic chemistry. A summary of many of these methods can be found in Greene & Wuts, *Protecting Groups in Organic Synthesis*, John Wiley & Sons, $3^{rd}$ edition (1999).

One skilled in the art of organic synthesis will also recognize that one route for the synthesis of the Compounds of Formula (I) may be more desirable depending on the choice of appendage substituents. Additionally, one skilled in the relevant art will recognize that in some cases the order of reactions may differ from that presented herein to avoid functional group incompatibilities and thus adjust the synthetic route accordingly.

Compounds of formula vii, x, xv and xvii may be further elaborated using methods that would be well-known to those skilled in the art of organic synthesis or, for example, the methods described in the Examples below, to make the full scope of the Compounds of Formula (I).

The starting materials used and the intermediates prepared using the methods set forth in Schemes 1 and 2 may be isolated and purified if desired using conventional techniques, including but not limited to filtration, distillation, crystallization, chromatography and alike. Such materials The hydroxyl group of an olefin of formula iii can be protected and the olefin oxidized via to provide the corresponding diols of formula xi, which can be subsequently cyclicized to provide the bicyclic compounds of formula xii. A compound of formula xii can then be reacted with an alkyl halide and base to derivatize the free hydroxy group of xii, followed by deprotection and oxidation of the other hydroxyl group to provide the bicyclic ketones of formula xiii. The compounds of formula xiii can be converted to their can be characterized using conventional means, including physical constants and spectral data.

EXAMPLES

General Methods

The following examples serve only to illustrate the invention and its practice. The examples are not to be construed as limitations on the scope or spirit of the invention. In these examples, all temperatures are degrees Celsius unless otherwise noted, and "room temperature" refers to a temperature in a range of from about 20° C. to about 25° C. Reactions sensitive to moisture or air were performed under nitrogen using anhydrous solvents and reagents. The progress of reactions was determined by either analytical thin layer chromatography (TLC) performed with E. Merck precoated TLC plates, silica gel 60F-254, layer thickness 0.25 mm or liquid chromatography-mass spectrum (LC-MS). For HPLC/MS data, the two HPLC conditions used were as follows: 1) LC2 (Waters C18 XTerra™ 3.5 μm 2.1×20 mm column with gradient 10:90-98:2 v/v CH$_3$CN/H$_2$O+v 0.05% TFA over 1.25 min then hold at 98:2 v/v CH$_3$CN/H$_2$O+v 0.05% TFA for 0.75 min; flow rate 1.5 mL/min, UV wavelength 254 nm); and 2) LC4 (Waters C18 XTerra 3.5 μm 2.1×20 mm column with gradient 10:90-98:2 v/v CH$_3$CN/H$_2$O+v 0.05% TFA over 3.25 min then hold at 98:2 v/v CH$_3$CN/H$_2$O+v 0.05% TFA for 0.75 min; flow rate 1.5 mL/min, UV wavelength 254 nm).

Mass analysis was performed with electrospray ionization in positive ion detection mode. $^1$H NMR spectra were recorded on Varian or Bruker instruments at 400-500 MHz. Concentration of solutions was carried out on a rotary evaporator under reduced pressure or by lyophilization. Flash chromatography was performed on pre-packed silica gel columns using a commercial MPLC system. Compounds described herein were synthesized as racemic mixtures unless otherwise stated in the experimental procedures.

Example 1

Preparation of Intermediate Compound Int-1

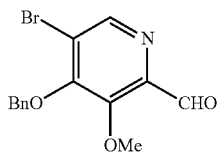

Compound Int-1 was prepared using the method described in U.S. Patent Publication No. US2006/066414.

Example 2

Preparation of Compound 1

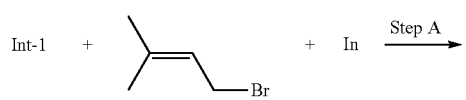

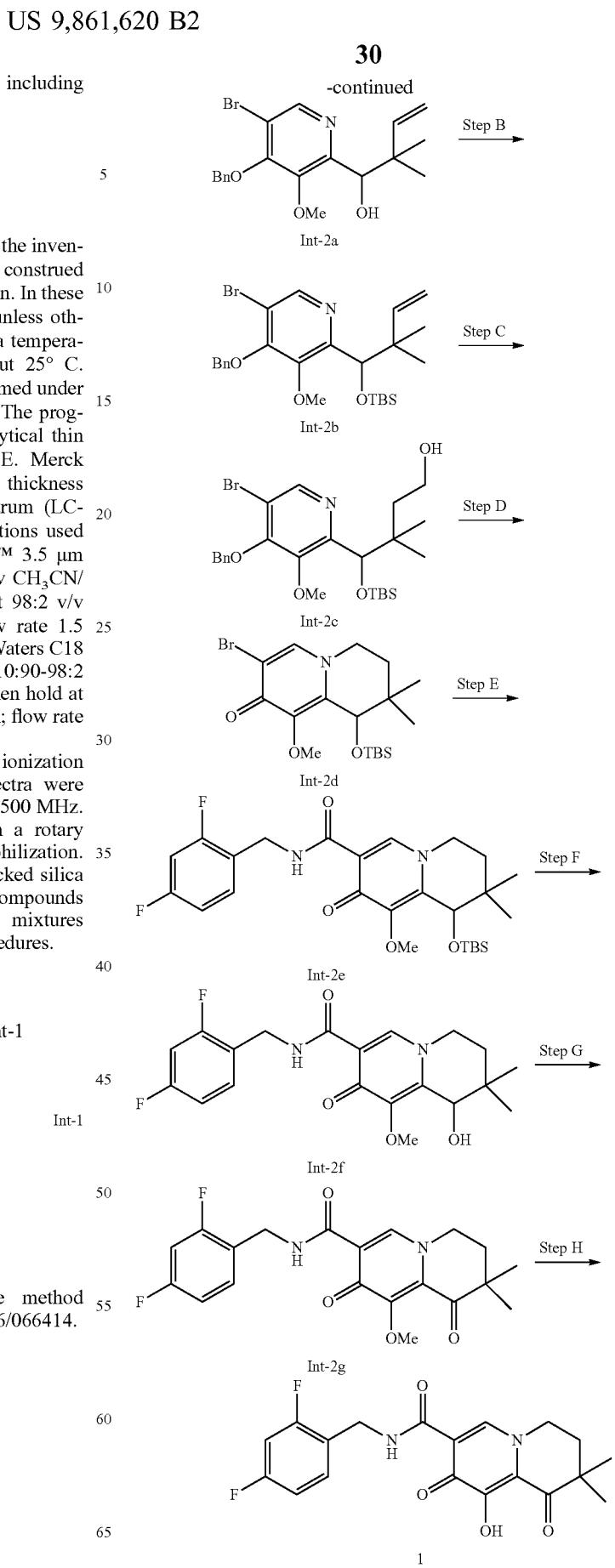

Step A—Synthesis of Compound Int-2a

To a mixed solution of NaI (279 mg, 1.862 mmol), indium powder (891 mg, 7.76 mmol) and phenylbromide (278 mg, 1.862 mmol) in 3 mL of DMF, was added 4-(benzyloxy)-5-bromo-3-methoxypicolinaldehyde (500 mg, 1.552 mmol). The mixture was allowed to stir at room temperature for 1 hour. The reaction was diluted with 100 mL of EtOAc. The organic phase was washed with water and brine and then dried over anhydrous sodium sulfate. After filtration, the organic solvent was removed in vacuo to provide a residue, which was purified using a preparative TLC plate eluting with 20% EtOAc/hexane to provide compound Int-2a as a colorless oil. LCMS anal. calcd. for $C_{19}H_{22}BrNO_3$: 391.08. Found: 392.07 (M+1)$^+$.

Step B—Synthesis of Compound Int-2b

A solution of compound Int-2a (380 mg, 0.969 mmol) in 0.1 mL of DMF was added TBSCl (292 mg, 1.937 mmol) and imidazole (198 mg, 2.91 mmol)). The mixture was allowed to stir at 60° C. overnight. It was diluted with 20 mL of EtOAc. The organic phase was washed with $H_2O$ and brine, dried over $Na_2SO_4$ and concentrated. The resulting residue was purified using a silica-gel column (40 g) eluting with 15% EtOAc/hexane to provide compound Int-2b as a colorless oil. LCMS anal. calcd. for $C_{25}H_{36}BrNO_3Si$: 505.16. Found: 506.14 (M+1)$^+$.

Step C—Synthesis of Compound Int-2c

To an ice-cold solution of 4-(benzyloxy)-5-bromo-2-(1-((tert-butyldimethylsilyl)oxy)-2,2-dimethylbut-3-en-1-yl)-3-methoxypyridine (200 mg, 0.395 mmol) in 4 mL of dry THF was added borane-tetrahydrofuran complex (1 M in THF) (0.592 ml, 0.592 mmol) under an atmosphere of nitrogen. The mixture was allowed to stir at room temperature for 1 h. After successive addition of water (2.0 mL), sodium hydroxide (aq) (1.974 ml, 3.95 mmol) and hydrogen peroxide in water (35% wt.) (448 mg, 3.95 mmol), the resulting mixture was stirred for an additional hour. The mixture was extracted with EtOAc (3×20 mL). The combined organic extracts were washed with 20 mL of brine and dried over anhydrous $MgSO_4$. After concentration, the resulting residue was purified using silica gel column chromatography eluting with 30% EtOAc/hexane to provide compound Int-2c as a clear oil. LCMS anal. calcd. for $C_{25}H_{38}BrNO_4Si$: 523.18. Found: 524.10 (M+1)$^+$.

Step D—Synthesis of Compound Int-2d

To a stirred solution of triphenylphosphine (255 mg, 0.972 mmol) in 4 mL of dichloromethane was added iodine (247 mg, 0.972 mmol). The mixture was allowed to stir at room temperature for 5 min, followed by adding 4-(4-(benzyloxy)-5-bromo-3-methoxypyridin-2-yl)-4-((tert-butyldimethylsilyl)oxy)-3,3-dimethylbutan-1-ol (170 mg, 0.324 mmol) and imidazole (66.2 mg, 0.972 mmol). The reaction was allowed to stir at room temperature for 2 h. At completion, it was concentrated to remove most of dichloromethane. The resulting residue was added 3 mL of 2:1 ACN/$H_2O$ and the resulting solution was directly purified using a C18 reverse phase column (40 mg, 12 run lengths, 5% ACN/$H_2O$-100% ACN/$H_2O$ with 0.1% TFA) to afford compound Int-2d as a colorless oil. LCMS anal. calcd. for $C_{18}H_{30}BrNO_3Si$: 415.12. Found: 416.10 (M+1)$^+$.

Step E—Synthesis of Compound Int-2e

A mixture of 7-bromo-1-((tert-butyldimethylsilyl)oxy)-9-methoxy-2,2-dimethyl-3,4-dihydro-1H-quinolizin-8(2H)-one (50 mg, 0.120 mmol), 2,4-difluorobenzylamine (25.8 mg, 0.180 mmol), diethylpropylethylamine (38.8 mg, 0.300 mmol) and Pd(PPh$_3$)$_4$ (13.87 mg, 0.012 mmol) in 1 mL of DMSO was degassed and heated at 90° C. under a CO balloon for 16 h. LC-mass showed partial completion of reaction. The above reaction was directly injected onto C18 reverse phase column (40 mg, 12 run lengths, 5% ACN/$H_2O$-100% ACN/$H_2O$ with 0.1% TFA) to afford compound Int-2e as a white solid. LCMS anal. calcd. for $C_{26}H_{36}F_2N_2O_4Si$: 506.24. Found: 507.30 (M+1)$^+$.

Step F—Synthesis of Compound Int-2f

The solution of 1-((tert-butyldimethylsilyl)oxy)-N-(2,4-difluorobenzyl)-9-methoxy-2,2-dimethyl-8-oxo-2,3,4,8-tetrahydro-1H-quinolizine-7-carboxamide (14.0 mg, 0.028 mmol) in 1 mL of THF was added a solution of tetrabutylammoniumfluoride (1 N in THF) (0.055 ml, 0.055 mmol). The mixture was allowed to stir at room temperature for 1.5 h. At completion, the reaction mixture was directly purified using a preparative TLC plate eluting with EtOAc to afford compound Int-2f as a white solid. LCMS anal. calcd. for $C_{20}H_{22}F_2N_2O_4$: 392.15. Found: 393.08 (M+1)$^+$.

Step G—Synthesis of Compound Int-2g

The solution of N-(2,4-difluorobenzyl)-1-hydroxy-9-methoxy-2,2-dimethyl-8-oxo-2,3,4,8-tetrahydro-1H-quinolizine-7-carboxamide (8.0 mg, 0.020 mmol) in 1 mL of dichloromethane was added Dess-Martin periodinane (17.29 mg, 0.041 mmol). The mixture was allowed to stir at room temperature for 30 min. The reaction was then directly purified using a preparative TLC plate eluting with EtOAc to afford compound Int-2g as a white solid. LCMS anal. calcd. for $C_{20}H_{20}F_2N_2O_4$: 390.14. Found: 391.07 (M+1)$^+$.

Step H—Synthesis of Compound 1

A mixture of N-(2,4-difluorobenzyl)-9-methoxy-2,2-dimethyl-1,8-dioxo-2,3,4,8-tetrahydro-1H-quinolizine-7-carboxamide (5.0 mg, 0.013 mmol) and lithium chloride (5.43 mg, 0.128 mmol) in 1 mL of DMF was heated at 100° C. for 4 h. It was cooled to room temperature. The mixture was directly purified using a reverse phase-HPLC (Gilson system with a Waters Sunfire C18 ODB, 5 uM, 19 mm×100 mm, Part No. 186002567, Ser. No. 20913930114, 10% to 75% MeCN/water+0.10% TFA over 10 min, 25 mL/min, UV 254 nM). The product containing fractions were lyophilized to afford compound 1 as a white solid. $^1$H NMR (400 MHz, CDCl$_3$): δ 10.41 (s, 1H); 8.47 (s, 1H); 7.40 (m, 1H); 6.81-6.86 (m, 2H); 4.67 (d, J=4.8 Hz, 2H); 4.27-4.29 (t, J=4.8 Hz, 2H); 2.20-2.22 (t, J=4.8 Hz, 2H); 1.40 (s, 6H). LCMS anal. calcd. for $C_{19}H_{18}F_2N_3O_5$: 376.12. Found: 377.12 (M+1)$^+$.

Example 3

Preparation of Compound 2

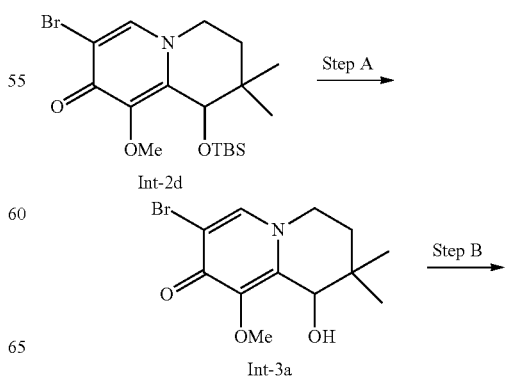

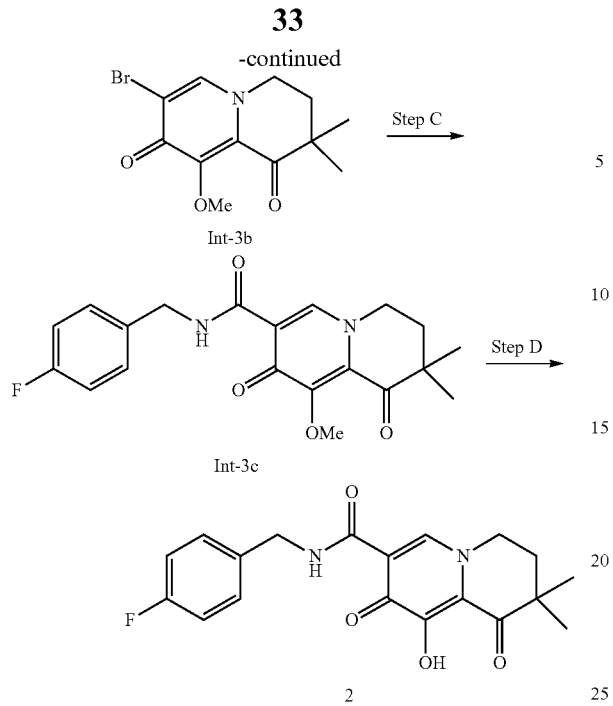

Int-3b

Step C →

Int-3c

Step D →

2

Step A—Synthesis of Compound Int-3a

To a solution of compound Int-2d (60 mg, 0.144 mmol) in THF (2.0 ml) was added tetrabutylammoniumfluoride (1 M in THF) (0.288 ml, 0.288 mmol). The mixture was allowed to stir at room temperature for 1.5 h. The reaction mixture was directly purified using a preparative TLC plate eluting with 10% MeOH/dichloromethane to afford crude compound Int-3a with some TBAF impurity. LCMS anal. calcd. for $C_{12}H_{16}BrNO_3$: 301.03. Found: 301.98 (M+1)$^+$.

Step B—Synthesis of Compound Int-3b

To a solution of 7-bromo-1-hydroxy-9-methoxy-2,2-dimethyl-3,4-dihydro-1H-quinolizin-8(2H)-one (43.0 mg, 0.142 mmol) in 2 mL of dichloromethane was added Dess-Martin periodinane (121 mg, 0.285 mmol). The mixture was allowed to stir at room temperature for 30 min. The reaction was then directly purified using a preparative TLC plate eluting with EtOAc to afford compound Int-3b as a white solid. LCMS anal. calcd. for $C_{12}H_{14}BrNO_3$: 299.02. Found: 300.00 (M+1)$^+$.

Step C—Synthesis of Compound Int-3c

A mixture of 7-bromo-9-methoxy-2,2-dimethyl-3,4-dihydro-1H-quinolizine-1,8(2H)-dione (20 mg, 0.067 mmol), 4-fluorobenzylamine (12.5 mg, 0.101 mmol), diisopropylethylamine (34.4 mg, 0.267 mmol) and Pd(PPh$_3$)$_4$ (7.70 mg, 6.66 μmol) in 2 mL of DMSO was degassed and heated at 90° C. under a CO balloon for 16 h. After cooled to room temperature, the reaction mixture was directly purified using a reverse phase C18 column (40 mg, 12 run lengths, 5% ACN/H$_2$O-100% ACN/H$_2$O with 0.1% TFA) to afford compound Int-3c. LCMS anal. calcd. for $C_{20}H_{21}FN_2O_4$: 372.15. Found: 373.16 (M+1)$^+$.

Step D—Synthesis of Compound 2

A mixture of N-(4-fluorobenzyl)-9-methoxy-2,2-dimethyl-1,8-dioxo-2,3,4,8-tetrahydro-1H-quinolizine-7-carboxamide (5.0 mg, 0.013 mmol) and lithium chloride (5.69 mg, 0.134 mmol) in 1 mL of DMF was heated at 100° C. for 2 h. It was cooled to room temperature and directly purified using a reverse phase-HPLC (Gilson system with a Waters Sunfire C18 ODB, 5 uM, 19 mm×100 mm, Part No. 186002567, Ser. No. 20913930114, 10% to 75% 0.1% TFA in MeCN/0.1% TFA in water over 10 min, 25 mL/min, UV 254 nM). The product containing fractions were lyophilized to afford compound 2 as a white solid. $^1$H NMR (400 MHz, CDCl$_3$): δ 10.41 (s, 1H); 8.46 (s, 1H); 7.35 (m, 2H); 7.01 (m, 2H); 5.3 (s, 2H); 4.64 (d, J=4.8 Hz, 2H); 4.28 (t, J=4.8 Hz, 2H); 2.21 (t, J=4.8 Hz, 2H); 1.40 (s, 6H). LCMS anal. calcd. for $C_{19}H_{19}FN_2O_4$: 358.13. Found: 359.12 (M+1)$^+$.

Example 4

Preparation of Compound 3

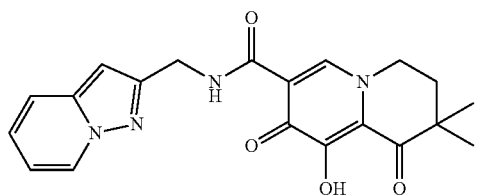

3

Compound 3 was prepared from compound Int-3b, using essentially the same method described in the Step C and Step D in Example 3, replacing 4-fluorobenzylamine with pyrazolo[1,5-a]pyridin-2-ylmethanamine in Step C. $^1$H NMR (400 MHz, CDCl$_3$): δ 10.60 (s, 1H); 8.53 (d, J=4.9 Hz, 1H); 8.52 (s, 1H); 7.48 (d, J=7.2 Hz, 1H); 7.15 (dd, J=7.2, 5.2 Hz, 1H); 6.78 (dd, J=5.2, 5.1 Hz, 1H); 6.54 (s, 1H); 4.90 (d, J=4.0 Hz, 1H); 4.30 (t, J=4.8 Hz, 2H); 2.21 (t, J=4.8 Hz, 2H); 1.40 (s, 6H). LCMS anal. calcd. for $C_{20}H_{20}N_4O_4$: 380.15. Found: 381.16 (M+1)$^+$.

Example 5

Preparation of Compound 4

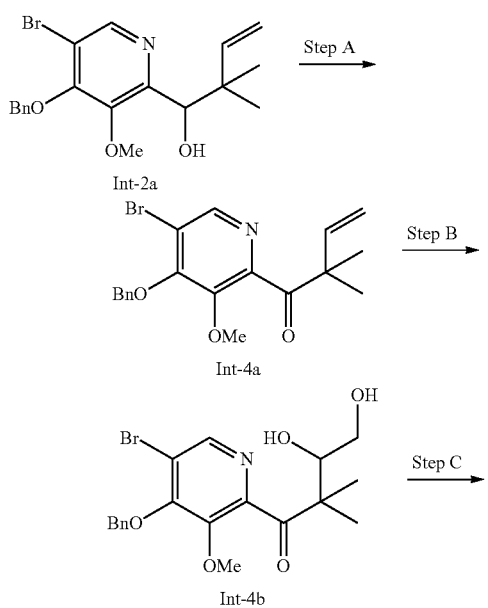

Int-2a

Step A →

Int-4a

Step B →

Int-4b

Step C →

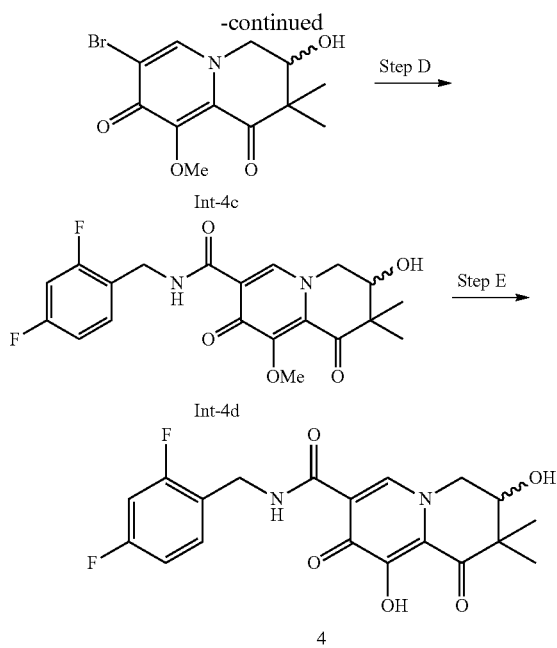

Step A—Synthesis of Compound Int-4a

To a solution of 1-(4-(benzyloxy)-5-bromo-3-methoxy-pyridin-2-yl)-2,2-dimethylbut-3-en-1-ol (230 mg, 0.586 mmol) in 10 mL of dichloromethane was added a drop of water, followed by adding Dess-Martin periodinane (497 mg, 1.173 mmol). The mixture was allowed to stir at room temperature for 2 h. It was diluted with 20 mL of dichloromethane. The organic phase was washed with 20 mL of $Na_2CO_3$ (aq), dried over $Na_2SO_4$ and then concentrated. The resulting residue was purified using a silica-gel column (40 g) eluting with 20% EtOAc/hexane to afford compound Int-4a as a colorless oil. LCMS anal. calcd. for $C_{19}H_{20}BrNO_3$: 389.06. Found: 390.09 $(M+1)^+$.

Step B—Synthesis of Compound Int-4b

To a solution of 1-(4-(benzyloxy)-5-bromo-3-methoxy-pyridin-2-yl)-2,2-dimethylbut-3-en-1-one (190 mg, 0.487 mmol) in 4 mL of THF and 1 mL of water, was added a solution of osmium tetroxide in t-BuOH (2.5% wt.) (0.122 ml, 9.74 µmol) and 4-methylmorpholine N-oxide (171 mg, 1.461 mmol). The mixture was allowed to stir at room temperature overnight. It was diluted with 20 mL of EtOAc. The organic phase was washed with $NaS_2O_3$ (aq) and brine, dried over anhydrous $Na_2SO_4$ and then concentrated. The resulting residue was purified using a silica-gel column eluting with EtOAc to afford compound Int-4b as light green oil. LCMS anal. calcd. For $C_{19}H_{22}BrNO_5$: 423.07. Found: 423.97 $(M+1)^+$.

Step C—Synthesis of Compound Int-4c

To a solution of 1-(4-(benzyloxy)-5-bromo-3-methoxy-pyridin-2-yl)-3,4-dihydroxy-2,2-dimethylbutan-1-one (170 mg, 0.401 mmol) in 3 mL of pyridine, was added p-toluenesulfonyl chloride (153 mg, 0.801 mmol). The reaction was allowed to stir at room temperature for 6 h. It was diluted with 10 mL of MeOH. The resulting solution was then concentrated in vacuo. The resulting residue was diluted with 2 mL of DMSO and purified using a reverse phase C18 column (40 g, 12 run lengths, 5% ACN/$H_2O$-100% ACN/$H_2O$ with 0.1% TFA) to provide the crude product which was further purified using a preparative TLC plate eluting with 10% MeOH/dichloromethane to afford compound Int-4c as a yellow oil. LCMS anal. calcd. For $C_{12}H_{14}BrNO_4$: 315.01. Found: 316.05 $(M+1)^+$.

Step D—Synthesis of Compound Int-4d

A mixture of 7-bromo-3-hydroxy-9-methoxy-2,2-dimethyl-3,4-dihydro-1H-quinolizine-1,8(2H)-dione (9 mg, 0.028 mmol), 2,4-difluorobenzylamine (6.11 mg, 0.043 mmol), diisopropylethylamine (9.20 mg, 0.071 mmol) and $Pd(PPh_3)_4$ (3.29 mg, 2.85 µmol) in 1 mL of DMSO was degassed by passing through a stream of CO gas for 5 min. It was then heated at 90° C. under a CO balloon for 16 h. After the reaction was cooled to room temperature, it was purified using a reverse phase C18 column (40 mg, 12 run lengths, 5% ACN/$H_2O$-100% ACN/$H_2O$ with 0.1% TFA) to afford compound Int-4d. LCMS anal. calcd. For $C_{20}H_{20}F_2N_2O_5$: 406.13. Found: 407.16 $(M+1)^+$.

Step E—Synthesis of Compound 4

A mixture of N-(2,4-difluorobenzyl)-3-hydroxy-9-methoxy-2,2-dimethyl-1,8-dioxo-2,3,4,8-tetrahydro-1H-quinolizine-7-carboxamide (5.0 mg, 0.012 mmol) and lithium chloride (5.22 mg, 0.123 mmol) in 1 mL of DMF was heated at 100° C. for 2 h. It was cooled to room temperature. The resulting solution was directly purified using a reverse phase HPLC (Gilson system with a Waters Sunfire C18 ODB, 5 uM, 19 mm×100 mm, Part No. 186002567, Ser. No. 20913930114, 10% to 75% MeCN/water with 0.10% TFA over 10 min, 25 mL/min, UV 254 nM). The product containing fractions were lyophilized to afford compound 4 as a white solid. $^1$H NMR (400 MHz, DMSO-$d_6$): δ 10.40 (s, 1H); 8.34 (s, 1H); 7.35 (m, 1H); 6.84 (m, 2H); 4.65 (d, J=3.0 Hz, 2H); 4.46-4.48 (apparent d, J=10.0 Hz, 1H); 4.23-4.27 (dd, J=11.6, 2.4 Hz, 1H); 4.11 (apparent brs, 1H); 1.48 (s, 1H); 1.35 (s, 1H). LCMS anal. calcd. for $C_{19}H_{18}F_2N_2O_5$: 392.12. Found: 393.14 $(M+1)^+$.

Example 6

Preparation of Compound Int-5e

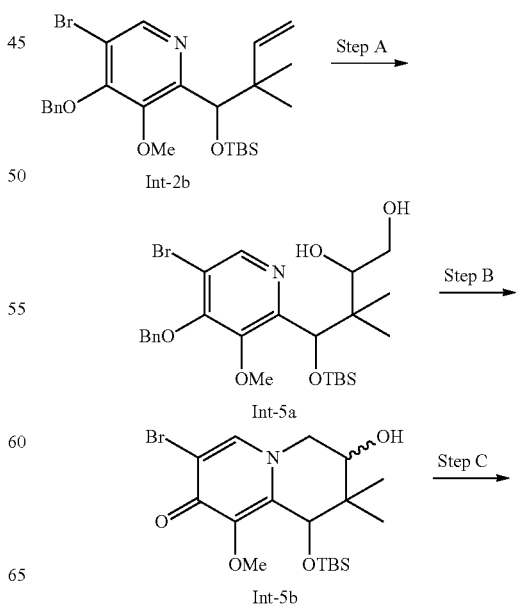

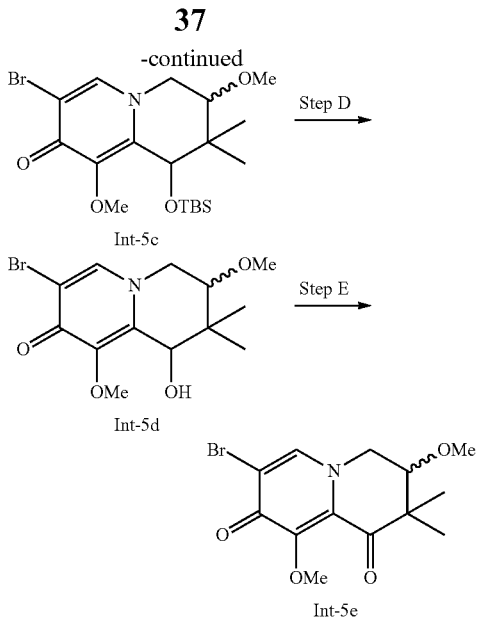

Step A—Synthesis of Compound Int-5a

To solution of 4-(benzyloxy)-5-bromo-2-(1-((tert-butyldimethylsilyl)oxy)-2,2-dimethylbut-3-en-1-yl)-3-methoxypyridine (430 mg, 0.849 mmol) in 5 mL of (4:1) THF/water, was added osmium tetroxide (2.5% wt.) in t-BuOH (0.213 ml, 0.017 mmol) and 4-methylmorpholine N-oxide (298 mg, 2.55 mmol). The mixture was allowed to stir at room temperature overnight. At completion, it was added 20 mL of EtOAc. The organic phase was washed with $Na_2S_2O_3$ aqueous solution and brine. It was dried over anhydrous $Na_2SO_4$ and concentrated. The resulting residue was purified using a silica-gel column eluting with 50% EtOAc to afford compound Int-5a as a light green oil. LCMS anal. calcd. for $C_{25}H_{38}BrNO_5Si$: 539.17. Found: 540.22 $(M+1)^+$.

Step B—Synthesis of Compound Int-5b

A mixture was 4-(4-(benzyloxy)-5-bromo-3-methoxypyridin-2-yl)-4-((tert-butyldimethylsilyl)oxy)-3,3-dimethylbutane-1,2-diol (650 mg, 1.202 mmol) and 4-methylbenzene-1-sulfonyl chloride (344 mg, 1.804 mmol) in 10 mL of pyridine was allowed to stir at room temperature overnight. At completion, it was concentrated in vacuo to remove most of pyridine. The resulting residue was then was added 2 mL of DMSO and the resulting solution was purified using a reverse phase C18 column (120 mg, 12 run lengths, 5% $ACN/H_2O$-100% $ACN/H_2O$ with 0.1% TFA) to afford compound Int-5b as a white solid. $C_{18}H_{30}BrNO_4Si$: 431.11. Found: 432.15 $(M+1)^+$.

Step C—Synthesis of Compound Int-5c

To a solution of 7-bromo-1-((tert-butyldimethylsilyl)oxy)-3-hydroxy-9-methoxy-2,2-dimethyl-3,4-dihydro-1H-quinolizin-8(2H)-one (160 mg, 0.370 mmol) in 4 mL of THF, was added iodomethane (158 mg, 1.11 mmol), followed by NaH (60% wt. in mineral oil) (44.4 mg, 1.11 mmol). The mixture was allowed to stir at room temperature for 2 h. It was quenched by adding 1 mL of water. The resulting mixture was directly purified using a preparative TLC plate eluting with 50% EtOAc/hexane to afford compound Int-5c as a light yellow oil. LCMS anal. calcd. for $C_{19}H_{32}BrNO_4Si$: 445.13. Found: 446.01 $(M+1)^+$.

Step D—Synthesis of Compound Int-5d

To a solution of 7-bromo-1-((tert-butyldimethylsilyl)oxy)-3,9-dimethoxy-2,2-dimethyl-3,4-dihydro-1H-quinolizin-8(2H)-one (105 mg, 0.235 mmol) in 2 mL of THF, was added tetrabutylammoniumfluoride (1 M in THF) (0.470 ml, 0.470 mmol). The mixture was allowed to stir at room temperature for 1.5 h. The reaction solution was directly purified using a preparative TLC plate eluting with 10% MeOH/dichloromethane to provide the crude compound Int-5d, which was used immediately in the following reaction. LCMS anal. calcd. for $C_{13}H_{18}BrNO_4$: 331.94. Found: 333.02 $(M+1)^+$.

Step E—Synthesis of Compound Int-5e

To a solution of 7-bromo-1-hydroxy-3,9-dimethoxy-2,2-dimethyl-3,4-dihydro-1H-quinolizin-8(2H)-one (78 mg, 0.235 mmol) in 2 mL of dichloromethane, was added Dess-Martin periodinane (199 mg, 0.470 mmol). The mixture was allowed to stir at room temperature for 1 h. The reaction mixture was then directly purified using a preparative TLC plate eluting with EtOAc to afford compound Int-5e as a light yellow solid. LCMS anal. calcd. for $C_{13}H_{16}BrNO_4$: 329.03. Found: 330.05 $(M+1)^+$.

Example 7

Preparation of Compound 5

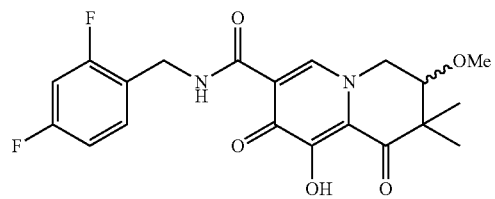

Compound 5 was prepared using essentially the same method described in the Step D and Step E in Example 5, and replacing compound Int-4c with compound Int-5e in Step D. $^1$H NMR (400 MHz, $CDCl_3$): 10.41 (s, 1H), 8.42 (s, 1H); 7.38 (m, 1H); 6.83-6.85 (m, 2H); 4.67 (m, 2H); 4.38 (dd, J=11.2, 1.6 Hz, 1H); 4.35 (dd, J=11.2, 2.8 Hz, 1H); 3.57 (dd, J=2.8, 1.6 Hz, 1H); 3.46 (s, 3H); 1.43 (s, 3H); 1.35 (s, 3H). LCMS anal. calcd. for $C_{20}H_{20}F_2N_2O_5$: 406.13. Found: 407.12 $(M+1)^+$.

Example 8

Preparation of Compound 6

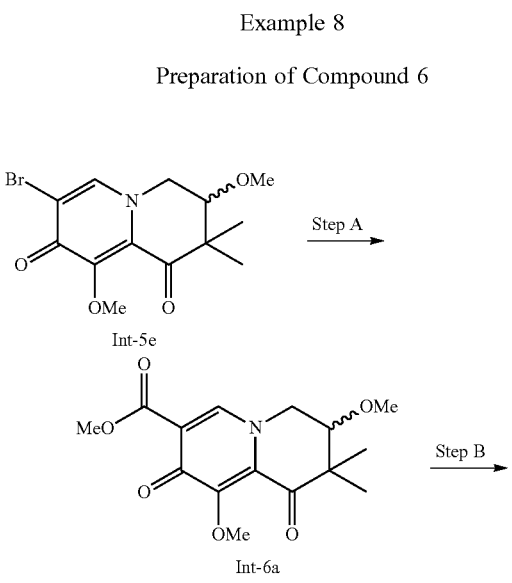

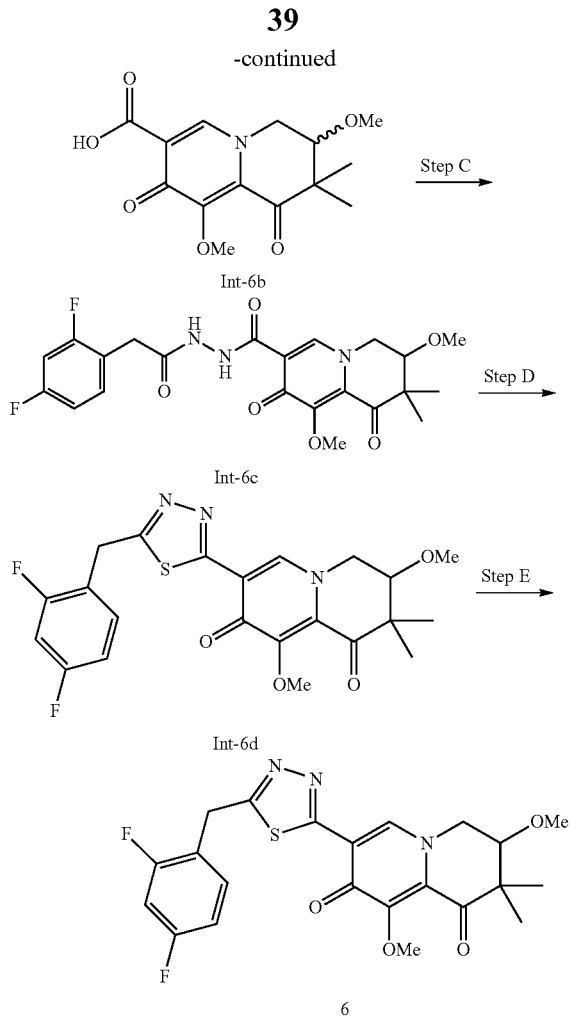

Step A—Synthesis of Compound Int-6a

A mixture of 7-bromo-3,9-dimethoxy-2,2-dimethyl-3,4-dihydro-1H-quinolizine-1,8(2H)-dione (120 mg, 0.363 mmol), methanol (58.2 mg, 1.817 mmol), diisopropylethylamine (235 mg, 1.817 mmol) and Pd(PPh$_3$)$_4$ (84 mg, 0.073 mmol) in 3 mL of DMSO, was degassed by passing through a stream of CO for 5 min. The reaction mixture was then heated at 90° C. under a CO balloon for 16 h. After the reaction was cooled to room temperature, it was directly purified using a reverse phase C18 column (40 mg, 12 run lengths, 5% ACN/H$_2$O-100% ACN/H$_2$O with 0.1% TFA) to afford compound Int-6a as a brown solid. LCMS anal. calcd. for C$_{15}$H$_{19}$NO$_6$: 309.12. Found: 310.12 (M+1)$^+$.

Step B—Synthesis of Compound Int-6b

To a solution of methyl 3,9-dimethoxy-2,2-dimethyl-1,8-dioxo-2,3,4,8-tetrahydro-1H-quinolizine-7-carboxylate (20.0 mg, 0.065 mmol) in 1 mL of MeOH, was added 2 N lithium hydroxide aqueous solution (0.323 ml, 0.647 mmol). The mixture was allowed to stir at room temperature for 2 h. It was concentrated to removed most of MeOH. To the resulting residue was added 2 mL of DMSO, and the resulting solution was directly purified using Gilson (10% ACN (0.1% TFA)/H$_2$O-90% ACN (0.1% TFA)/H$_2$O, 12 min) to afford compound Int-6b as a white solid. LCMS anal. calcd. for C$_{14}$H$_{12}$NO$_6$: 295.11. Found: 296.12 (M+1)$^+$.

Step C—Synthesis of Compound Int-6c

To a stirred solution of 3,9-dimethoxy-2,2-dimethyl-1,8-dioxo-2,3,4,8-tetrahydro-1H-quinolizine-7-carboxylic acid (14.0 mg, 0.047 mmol) in 1 mL of DMF, was added 2-(2,4-difluorophenyl)acetohydrazide (10.59 mg, 0.057 mmol), diisopropylethylamine (24.51 mg, 0.190 mmol) and ((1H-benzo[d][1,2,3]triazol-1-yl)oxy)tri(pyrrolidin-1-yl) phosphonium hexafluorophosphate(V) (29.6 mg, 0.057 mmol) sequentially. The mixture was allowed to stir at room temperature for 1 h. It was diluted with 1.0 mL of DMF and 0.3 mL of water. The clear solution was purified using a reverse phase Gilson HPLC (10% ACN (0.1% TFA)/H$_2$O-90% ACN (0.1% TFA)/H$_2$O, 12 min) to afford compound Int-6c as a light yellow solid. LCMS anal. calcd. for C$_{22}$H$_{23}$F$_2$N$_3$O$_6$: 463.16. Found: 464.25 (M+1)$^+$.

Step D—Synthesis of Compound Int-6d

A mixture of N'-(2-(2,4-difluorophenyl)acetyl)-3,9-dimethoxy-2,2-dimethyl-1,8-dioxo-2,3,4,8-tetrahydro-1H-quinolizine-7-carbohydrazide (12 mg, 0.026 mmol) and Lawesson's reagent (11.52 mg, 0.028 mmol) in 0.5 mL of THF was heated at 60° C. overnight. The solvent was removed in vacuo. The resulting residue was dissolved in 2 mL of DMSO. The resulting solution was purified using a reverse phase Gilson HPLC (10% ACN (0.1% TFA)/H$_2$O-90% ACN (0.1% TFA)/H$_2$O, 12 min) to afford compound Int-6d as a yellow solid. LCMS anal. calcd. for C$_{22}$H$_{21}$F$_2$N$_3$O$_4$S: 461.12. Found: 462.20 (M+1)$^+$.

Step E—Synthesis of Compound 6

A mixture of 7-(5-(2,4-difluorobenzyl)-1,3,4-thiadiazol-2-yl)-3,9-dimethoxy-2,2-dimethyl-3,4-dihydro-1H-quinolizine-1,8(2H)-dione (6.0 mg, 0.013 mmol) and lithium chloride (16.54 mg, 0.390 mmol) in 1 mL of DMF was heated at 100° C. for 1 h. It was cooled to room temperature, and the mixture was diluted with 1.0 mL of DMF and 0.3 mL of water. The resulting solution was purified by a reverse phase Gilson HPLC (10% ACN (0.1% TFA)/H$_2$O—90% ACN (0.1% TFA)/H$_2$O, 12 min) to afford compound 6 as a light yellow solid. $^1$H NMR (399 MHz, CDCl$_3$): 8.76 (s, 1H); 7.35 (m, 1H); 6.86-6.91 (m, 2H); 4.49 (dd, J=1.6, 11.2 Hz, 1H); 4.45 (dd, J=2.8, 11.2, Hz, 1H); 3.63 (dd, J=2.8, 1.6 Hz, 1H); 3.50 (s, 3H); 1.44 (s, 3H); 1.39 (s, 3H). LCMS anal. calcd. for C$_{21}$H$_{19}$F$_2$N$_3$O$_4$S: 447.11. Found: 448.01 (M+1)$^+$.

Example 9

Preparation of Compound Int-7b

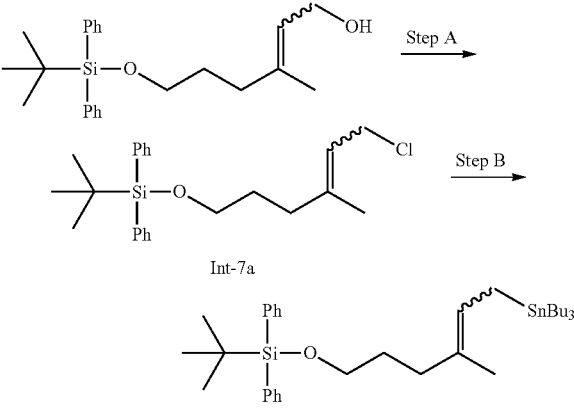

Step A—Synthesis of Compound Int-7a

To a solution of 6-((tert-butyldiphenylsilyl)oxy)-3-methylhex-2-en-1-ol (3 g, 8.14 mmol) in 60 mL of dichloromethanane, was added diisopropylethylamine (3.54 ml, 20.35 mmol) followed by methanesulfonyl chloride (1.029 ml, 13.02 mmol). The reaction was allowed to stir at room temperature for 2 h. It was diluted with 200 mL of dichloromethane and washed with 100 mL of 0.2 N HCl (aq.) solution, then with 100 mL of brine. The organic phase was concentrated, and the resulting residue was purified using a silica gel column (80 g) eluting with 5% EtOAc/hexanes to provide compound Int-7a as a mixture (2.5:1) of (E) and (Z) stereoisomers. $^1$H NMR (400 MHz, CDCl$_3$): δ 7.71-7.74 (m, 4H); 7.41-7.50 (m, 6H); 5.42-5.56 (m, 1H); 4.12 & 4.13 (d, J=8.0 Hz, 2H); 3.71 & 3.72 (t, J=6.4 Hz, 2H); 2.19 & 2.26 (dd, J=8.0, 7.7 Hz, 2H); 1.74 & 1.79 (s, 3H), 1.66-1.76 (m, 2H), 1.11 & 1.12 (s, 9H).

Step B—Synthesis of Compound Int-7b

To a solution of lithium diisopropylamide (7.17 ml, 14.34 mmol) in 20 mL of THF cooled at 0° C., was added tributyltinhydride (3.48 ml, 13.04 mmol). The reaction was allowed to stir at 0° C. for 15 min. It was then cooled to −78° C., and a solution of compound Int-7a (2523 mg, 6.52 mmol) in 10 mL of THF was added via syringe. The reaction was allowed to stir at −78° C. for 30 min. It was diluted with 150 mL of 20% EtOAc/hexanes, and washed 150 mL of water. The organic phase was concentrated in vacuo. The resulting residue was purified using a silica gel column (80 g) eluting initially with hexanes to removed tributyltinhydride, and then with 3% EtOAc/hexanes to provide compound Int-7b as a colorless oil. $^1$H NMR (400 MHz, CDCl$_3$): δ 7.69-7.73 (m, 4H); 7.38-7.47 (m, 6H); 5.28-5.37 (m, 1H); 3.64-3.75 (m, 2H); 2.01-2.13 (m, 2H); 1.63-1.70 (m, 5H); 1.46-1.59 (m, 8H); 1.28-1.36 (m, 6H), 1.08 (s, 9H), 0.84-0.94 (m, 15H).

Example 10

Preparation of Compounds 7 and 8

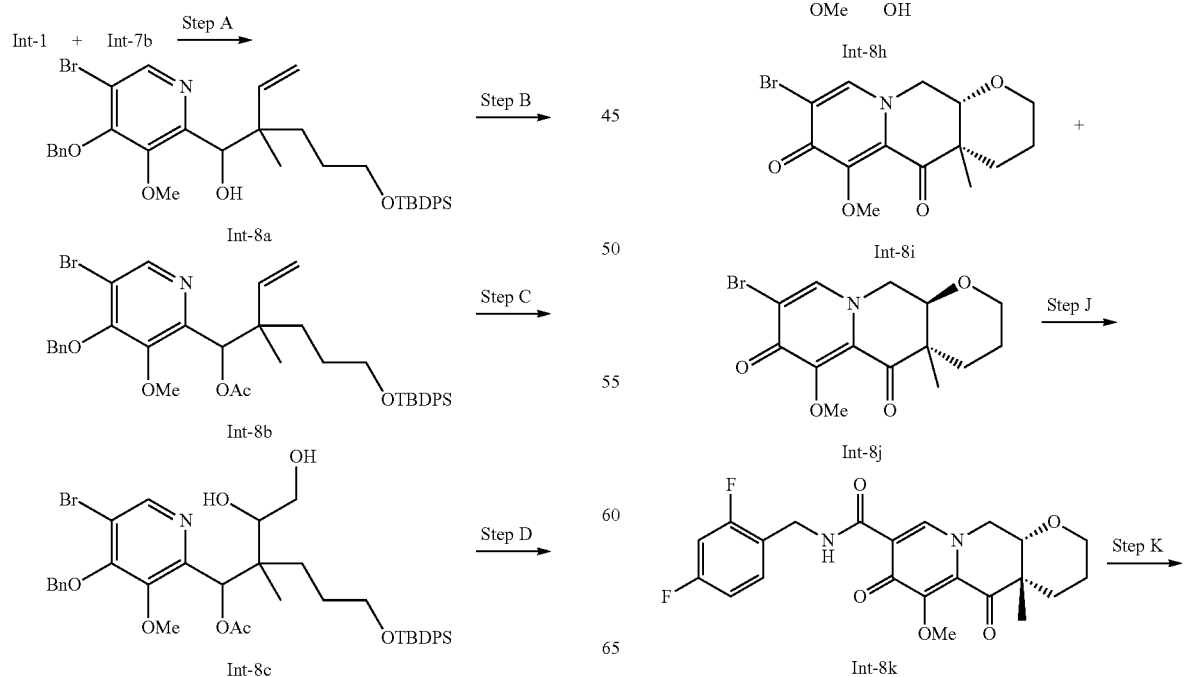

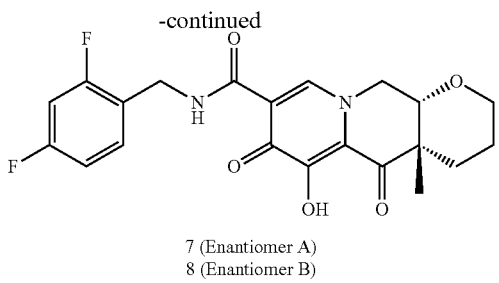

7 (Enantiomer A)
8 (Enantiomer B)

Step A—Synthesis of Compound Int-8a

To a solution of 4-(benzyloxy)-5-bromo-3-methoxypicolinaldehyde (390 mg, 1.21 mmol) and tert-butyl((4-methyl-6-(tributylstannyl)hex-4-en-1-yl)oxy)diphenylsilane (932 mg, 1.45 mmol) in 11 mL of ACN stirred at 0° C., was added Tin (II) $Cl_2$ (344 mg, 1.50 mmol). The reaction was then warmed to room temperature and stirred for 15 min. This was diluted with 100 mL of 30% EtOAc/hexanes, and 100 mL of (15% wt.) $NH_4F$ aqueous solution. The resulting mixture was allowed to stir at room temperature for 15 min. Solid was filtered off. The organic from the mother liquor was concentrated in vacuo and the resulting residue was purified using a silica gel column (80 g) eluting initially with dichloromethane to removed Tin reagent, and then with 3% EtOAc/dichloromethane to provide Compound Int-8a as a mixture of stereoisomers. LCMS anal. calcd. for $C_{37}H_{44}BrNO_4Si$: 675.22. Found: 676.18 (M+1)$^+$.

Step B—Synthesis of Compound Int-8b

To a solution of compound Int-8a (1200 mg, 1.78 mmol) in 8 mL of acetic anhydride was added triethylamine (2200 mg, 21.7 mmol) and DMAP (65.2 mg, 0.534 mmol). The reaction was allowed to stir at room temperature for 1 h. It was diluted with 50 mL of dichloromethane. The solution was cooled to 0° C. and added 10 mL of MeOH. It was stirred for 1 h at room temperature. The solvent was removed in vacuo. The resulting residue was purified using a silica gel column (120 g) eluting with 25% EtOAc/hexanes to provide compound Int-8b as a colorless film. LCMS anal. calcd. for $C_{39}H_{46}BrNO_5Si$: 717.23. Found: 718.35 (M+1)$^+$.

Step C—Synthesis of Compound Int-8c

To a solution of Int-8b (410 mg, 0.572 mmol) in 3.6 mL of THF/t-BuOH/water (5:5:1), was added 4-methylmorpholine 4-oxide (67 mg, 0.572 mmol) followed by osmium(VIII) oxide (2.5% wt. in t-BuOH) (1.06 ml, 0.086 mmol). The reaction was allowed to stir at room temperature for 16 h. To this was added 10 g of solid $Na_2S_2O_5$. The mixture was allowed to stir at room temperature for 1 h. The content was diluted with 70 mL of 50% EtOAc/hexanes. The brown solid was filtered off. The filtrated was washed with water and then concentrated. The resulting residue was purified using a silica gel column (40 g) eluting with 55% EtOAc/hexanes to provide compound Int-8c as a colorless oil. LCMS anal. calcd. for $C_{39}H_{48}BrNO_7Si$: 751.24. Found: 752.29 (M+1)$^+$.

Step D—Synthesis of Compound Int-8d

To a mixture of compound Int-8c (300 mg, 0.400 mmol) and 4-methylbenzene-1-sulfonyl chloride (137 mg, 0.719 mmol), was added 3 mL of pyridine. The reaction solution was allowed to stir at room temperature overnight. To this was added 10 mL of MeOH. It was allowed to stir at room temperature for 1 h. It was diluted with 80 mL of EtOAc, and washed with 100 mL of 0.4 N HCl (aq.). The organic phase was concentrated. The resulting residue was purified using a silica gel column (40 g) eluting with 5% MeOH/dichloromethane to provide Compound Int-8d as a colorless film.

LCMS anal. calcd. for $C_{32}H_{40}BrNO_6Si$: 643.18. Found: 644.05 (M+1)$^+$.

Step E—Synthesis of Compound Int-8e

To a solution of compound Int-8d (125 mg, 0.195 mmol) in 4 mL of dichloromethane was added Dess-Martin periodinane (165 mg, 0.389 mmol). The reaction was allowed to stir at room temperature for 30 min. It was diluted with 15 mL of EtOAc. The solid was filtered off. The liquid portion was washed with 15 mL of sat. $Na_2CO_3$ (aq.) solution and then 15 mL of brine. It was concentrated in vacuo and purified using a silica gel column (40 g) eluting with 4% MeOH/dichloromethane to provide compound Int-8e as a white solid. LCMS anal. calcd. for $C_{32}H_{38}BrNO_6Si$: 641.16. Found: 642.13 (M+1)$^+$.

Step F—Synthesis of Compound Int-8f

A solution of compound Int-8e (115 mg, 0.180 mmol) in 4 mL of 1.25 M HCl in MeOH (50 ml, 63.4 mmol) was allowed to stir at room temperature for 16 h. The solvent was removed in vacuo. To the resulting residue was added 5 mL of dichloromethane and 0.5 mL of diisopropylethylamine. The resulting solution was purified using a silica gel column (25 g) eluting with 6% MeOH/dichloromethane to provide compound Int-8f as a white solid. LCMS anal. calcd. for $C_{16}H_{20}BrNO_6$: 401.05. Found: 402.09 (M+1)$^+$.

Step G—Synthesis of Compound Int-8g

To a solution of Int-8f (66 mg, 0.164 mmol) in 2 mL of dichloromethane was added triethylsilane (382 mg, 3.28 mmol) followed by methanesulfonic acid (200 mg, 2.08 mmol). The reaction was allowed to stir at room temperature for 10 h. This was diluted with 15 mL of dichloromethane. Solid $NaHCO_3$ (2 g) was added. The resulting mixture was allowed to stir at room temperature until the color of the mixture turned light yellowish. It was filtered. The filtrate was purified using a preparative TLC plate eluting with 5% MeOH/dichloromethane to provide compound Int-8g as a colorless film. LCMS anal. calcd. for $C_{16}H_{20}BrNO_5$: 387.05. Found: 388.06 (M+1)$^+$.

Step H—Synthesis of Compound Int-8h

To a solution of compound Int-8g (57 mg, 0.148 mmol) in 5 mL of MeOH, was added $K_2CO_3$ (82 mg, 0.59 mmol). The reaction was then stirred at 60° C. for 1 h. Most of the solvent was removed in vacuo. To the resulting residue was added 50 mL of dichloromethane. The solvent was removed in vacuo. The resulting residue was purified using a silica gel column (25 g) eluting with 7% MeOH/dichloromethane to provide compound Int-8h as a white solid. LCMS anal. calcd. for $C_{14}H_{18}BrNO_4$: 343.04. Found: 344.05 (M+1)$^+$.

Step I—Synthesis of Compound Int-8i and Compound Int-8j

To a solution of Int-8h (46 mg, 0.134 mmol) in 4 mL of dichloromethane, was added Dess-Martin reagent (85 mg, 0.20 mmol). The reaction was allowed to stir at room temperature for 45 min. It was diluted with 15 mL of EtOAc. The solid was filtered off. The liquid portion was concentrated. The resulting residue was purified by a reverse phase C18 column (120 g) eluting with 0.05% TFA in water/0.05% TFA in ACN (from 0-90%) over 15 column length to provide the cis-fused isomer compound Int-8i and the trans-fused isomer compound Int-8j separately as white solids. LCMS anal. calcd. for $C_{14}H_{16}BrNO_4$: 341.03; Found: 342.04 (M+1)$^+$.

Step J—Synthesis of Compound Int-8k

To a solution of compound Int-8i (18 mg, 0.053 mmol) in 1 mL of DMSO, was added (2,4-difluorophenyl)methanamine (11.3 mg, 0.079 mmol), diisopropylethylamine (17.0 mg, 0.132 mmol) and $Pd(PPh_3)_4$ (12.2 mg, 10.5 μmol) sequentially. The reaction vessel was filled with CO gas. It was stirred under a balloon of CO at 90° C. for 8 h. It was cooled to room temperature. The content was purified using a reverse phase C18 column (40 mg) eluting with 0.05% TFA in water/0.05% TFA in ACN (from 5-100%) over 12 column length to provide a mixture of the crude compound Int-8k along with triphenylphosphine oxide. This material was further purified using a chiral preparative SFC (Chiral-Pak IA, 30×250 mm, 70 mL/min, 120 bar, 40% (2:1 MeOH:ACN)/CO$_2$, 35° C.) to provide enantiomer A of compound Int-8k (earlier eluting component) and enantiomer B of compound Int-8k (later eluting component). LCMS anal. calcd. for $C_{22}H_{22}F_2N_2O_5$: 432.15. Found: 433.18 $(M+1)^+$.

Step K—Synthesis of Compound 7 and Compound 8

To a solution of the earlier eluting Enantiomer A of compound Int-8k (5 mg, 0.012 mmol) in 1 mL of DMF, was added lithium chloride (4.90 mg, 0.116 mmol). The reaction was allowed to stir at 100° C. for 2 h. It was cooled to room temperature, and the content was purified using Gilson reverse phase HPLC eluting with 0.05% TFA in water/0.05% TFA in ACN (from 10% to 90%) to provide compound 7 as a white solid. $^1$H NMR (400 MHz, CDCl$_3$): δ 10.44 (brs, 1H); 8.46 (s, 1H); 7.35-7.40 (m, 1H); 6.80-6.86 (m, 2H); 4.67 (m, 2H); 4.50 (dd, J=11.2, 1.6 Hz, 1H); 4.24 (dd, J=11.2, 2.4 Hz, 1H); 4.00 (dd, J=9.2, 1.6 Hz, 1H); 3.82 (dd, J=2.4, 1.6 Hz, 1H), 3.51-3.56 (m, 1H); 2.69 (dd, J=9.2, 1.2 Hz, 1H); 1.56-1.58 (m, 2H); 1.43-1.50 (m, 1H); 1.30 (s, 3H). LCMS anal. calcd. for $C_{21}H_{20}F_2N_2O_5$: 418.13. Found: 419.18 $(M+1)^+$.

To a solution of the later eluting Enantiomer B of compound Int-8k (5 mg, 0.012 mmol) in 1 mL of DMF, was added lithium chloride (4.90 mg, 0.116 mmol). The reaction was allowed to stir at 100° C. for 2 h. It was cooled to room temperature, and the content was purified using Gilson reverse phase HPLC eluting with 0.05% TFA in water/0.05% TFA in ACN (from 10% to 90%) to provide compound 8 as a white solid. $^1$H NMR (400 MHz, CDCl$_3$): δ 10.46 (brs, 1H); 8.48 (s, 1H); 7.35-7.40 (m, 1H); 6.80-6.86 (m, 2H); 4.67 (m, 2H); 4.50 (dd, J=11.2, 1.6 Hz, 1H); 4.25 (dd, J=11.2, 2.4 Hz, 1H); 3.99 (dd, J=9.2, 1.6 Hz, 1H); 3.82 (dd, J=2.4, 1.6 Hz, 1H), 3.51-3.56 (m, 1H); 2.69 (dd, J=9.2, 1.2 Hz, 1H); 1.56-1.58 (m, 2H); 1.42-1.50 (m, 1H); 1.29 (s, 3H). LCMS anal. calcd. for $C_{21}H_{20}F_2N_2O_5$: 418.13. Found: 419.18 $(M+1)^+$.

Example 11

Preparation of Compound 14

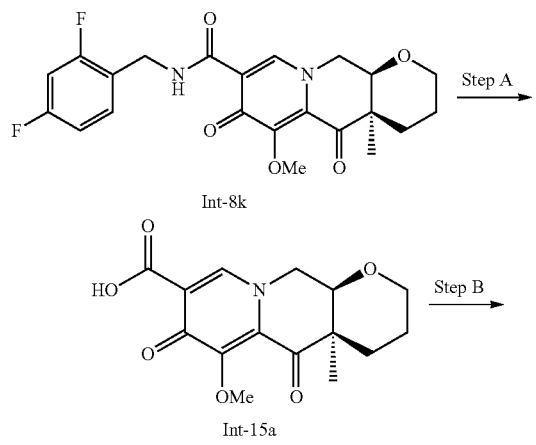

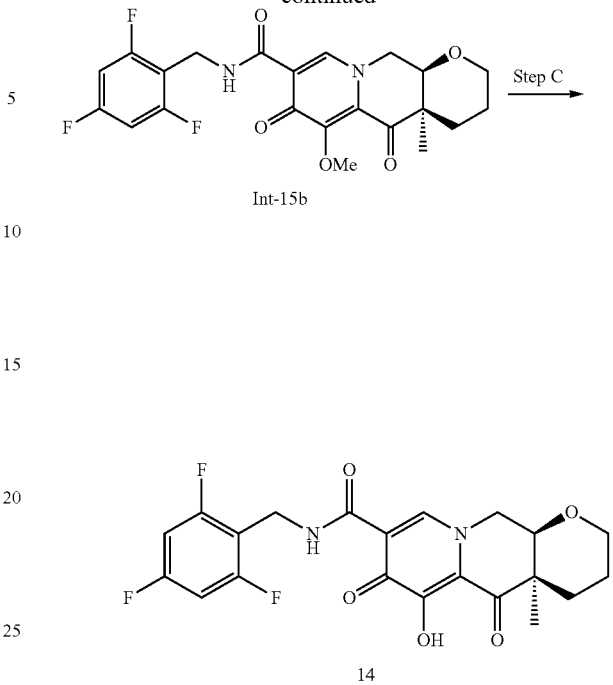

Step A—Synthesis of Compound Int-15a

To a solution of enantiomer A of compound Int-8k (61 mg, 0.141 mmol) in 1 mL of toluene, was added di-tert-butyl dicarbonate (123 mg, 0.564 mmol) followed by DMAP (51.7 mg, 0.423 mmol). The reaction was allowed to stir at 110° C. for 1 h. The solvent was removed in vacuo. The resulting residue was dissolved in 2 mL of MeOH. To the resulting solution was added potassium carbonate (78 mg, 0.564 mmol). The reaction was allowed to stir at room temperature for 2.5 h. To the resulting mixture was added 1.4 mL of 0.5 N LiOH aqueous solution. The reaction was allowed to stir at room temperature for 1 h. The solvent was removed in vacuo. The resulting residue was purified using a reverse phase Gilson (5-100% 0.05% TFA in ACN/0.05% TFA in water) to provide compound Int-15a as a white solid. $C_{15}H_{17}NO_6$: 307.11. Found: 308.02 $(M+1)^+$.

Step B—Synthesis of Compound Int-15b

To a solution of compound Int-15a (12 mg, 0.039 mmol) in 0.5 mL of DMF, was added (2,4,6-trifluorophenyl)methanamine (9.44 mg, 0.059 mmol), 4-methylmorpholine (15.80 mg, 0.156 mmol), and HATU (22.27 mg, 0.059 mmol) sequentially. The reaction was allowed to stir at room temperature for 16 h. The reaction solution was purified using Gilson reverse phase HPLC (0-100% 0.05% TFA in ACN/0.05% TFA in water) to provide compound Int-15b as a light yellow film. $C_{22}H_{21}F_3N_2O_5$: 450.14. Found: 451.01 $(M+1)^+$.

Step C—Synthesis of Compound 14

Using the method described in Step K in example 10, compound 14 was prepared from compound Int-15b. 1H NMR (500 MHz, CDCl$_3$): δ 10.40 (brs, 1H); 8.48 (s, 1H); 6.69 (t, J=8.2 Hz, 2H); 4.65-4.74 (m, 2H); 4.46-4.55 (m, 1H); 4.20-4.28 (m, 1H); 3.99 (dd, J=11.5, 2.0 Hz, 1H); 3.82 (m, 1H); 3.48-3.57 (m, 1H); 2.64-2.78 (m, 1H); 1.53-1.61 (m, 2H); 1.42-1.52 (m, 1H); 1.29 (s, 3H). LCMS anal. calcd. for $C_{21}H_{19}F_3N_2O_5$: 436.12. Found: 437.01 $(M+1)^+$.

Example 12

Preparation of Compound 15-18

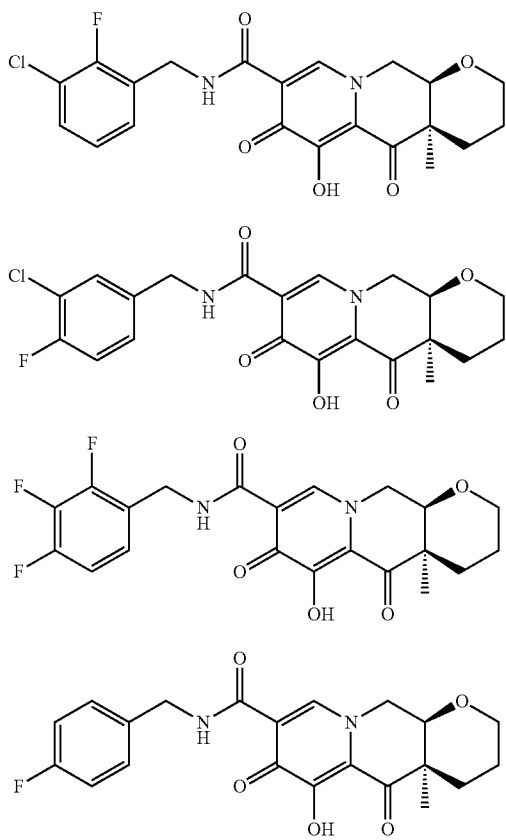

Starting from compound Int 15a, following essentially the same method described in Step B and Step C of Example 11, only replacing (2,4,6-trifluorophenyl)methanamine with appropriate amine in Step B, compounds 15-18 were prepared.

Compound 15: $^1$H NMR (500 MHz, CDCl$_3$): δ 10.50 (brs, 1H); 8.50 (s, 1H); 7.27-7.35 (m, 2H); 7.06 (t, J=7.9 Hz, 1H); 4.70-4.78 (m, 2H); 4.52 (dd, J=13.7, 1.4 Hz, 1H); 4.27 (dd, J=13.8, 2.4 Hz, 1H); 3.99 (dd, J=11.5, 2.4 Hz, 1H); 3.82 (m, 1H); 3.51-3.56 (m, 1H); 2.65-2.78 (m, 1H); 1.53-1.61 (m, 2H); 1.42-1.52 (m, 1H); 1.30 (s, 3H). LCMS anal. calcd. for C$_{21}$H$_{20}$ClFN$_2$O$_5$: 434.10. Found: 434.97 (M+1)$^+$.

Compound 16: $^1$H NMR (500 MHz, CDCl$_3$): δ 10.53 (brs, 1H); 8.51 (s, 1H); 7.40 (d, J=7.0 Hz, 1H); 7.19-7.27 (m, 1H); 7.11 (t, J=8.6 Hz, 1H); 4.57-4.66 (m, 2H); 4.48-4.55 (m, 1H); 4.28 (dd, J=13.6, 1.6 Hz, 1H); 4.00 (dd, J=11.5, 2.0 Hz, 1H); 3.83 (m, 1H); 3.50-3.58 (m, 1H); 2.66-2.79 (m, 1H); 1.53-1.61 (m, 2H); 1.22-1.52 (m, 1H); 1.30 (s, 3H). LCMS anal. calcd. for C$_{21}$H$_{20}$ClFN$_2$O$_5$: 434.10. Found: 434.97 (M+1)$^+$.

Compound 17: $^1$H NMR (400 MHz, CDCl$_3$): 10.46 (broad, 1H); 8.45 (s, 1H); 7.10-7.14 (m, 1H); 6.91-6.96 (m, 1H); 4.65-4.70 (m, 2H); 4.51 (dd, J=10.8 Hz, 1H); 4.24 (dd, J=1.6, 11.2 Hz, 1H); 3.99 (dd, J=8.8 Hz, 1H); 3.83 (m, 1H); 3.52-3.56 (m, 1H); 2.68-2.73 (m, 1H); 1.55-1.60 (m, 2H); 1.43-1.50 (m, 1H); 1.30 (s, 3H). LCMS anal. calcd. for C$_{21}$H$_{19}$F$_3$N$_2$O$_5$: 436.12. Found: 437.17 (M+1)$^+$.

Compound 18: $^1$H NMR (400 MHz, CDCl$_3$): 10.47 (broad, 1H); 8.48 (s, 1H); 7.33-7.36 (m, 2H); 7.01-7.05 (m, 2H); 4.60-4.68 (m, 2H); 4.51 (dd, J=10.8 Hz, 1H); 4.26 (dd, J=1.6, 11.2 Hz, 1H); 3.98 (dd, J=1.2, 8.8 Hz, 1H); 3.83 (m, 1H); 3.51-3.57 (m, 1H); 2.68-2.73 (m, 1H); 1.56-1.61 (m, 2H); 1.44-1.50 (m, 1H); 1.30 (s, 3H). LCMS anal. calcd. for C$_{21}$H$_{21}$FN$_2$O$_5$: 400.14. Found: 401.18 (M+1)$^+$.

Example 13

Preparation of Compounds 19-30

Starting from enantiomer B of compound Int 8k, using essentially the same method described in Step A to Step C in example 11 and only substituted with the appropriate amines in Step B, the following compounds were prepared:

| Compound # | Structure | Rt (min) | MS (M + H) |
|---|---|---|---|
| 19 | 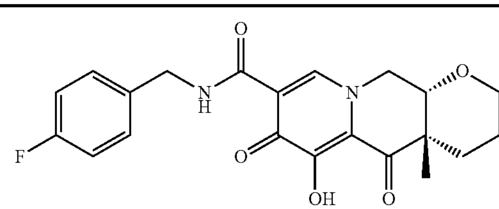 | 2.93 (LC5) | 401.1 |
| 20 | 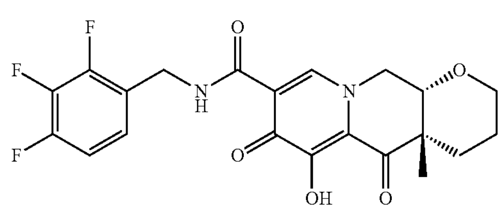 | 3.12 (LC5) | 437.1 |

-continued

| Compound # | Structure | Rt (min) | MS (M + H) |
|---|---|---|---|
| 21 | 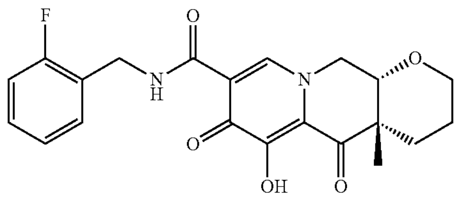 [SMILES: C[C@]12CCCO[C@H]1Cn1cc(C(=O)NCc3ccccc3F)c(=O)c(O)c1C2=O] | 1.78 (LC3) | 401.1 |
| 22 | 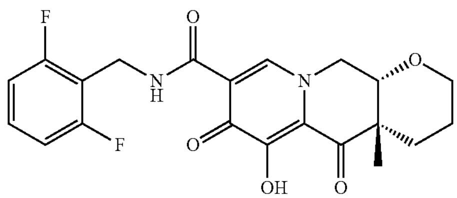 [SMILES: C[C@]12CCCO[C@H]1Cn1cc(C(=O)NCc3c(F)cccc3F)c(=O)c(O)c1C2=O] | 1.79 (LC3) | 419.1 |
| 23 | 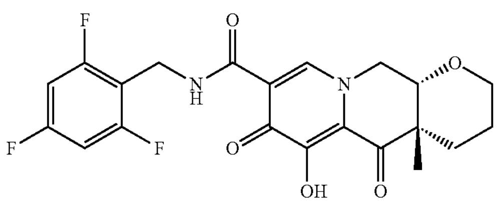 [SMILES: C[C@]12CCCO[C@H]1Cn1cc(C(=O)NCc3c(F)cc(F)cc3F)c(=O)c(O)c1C2=O] | 0.97 (LC2) | 437.1 |
| 24 | 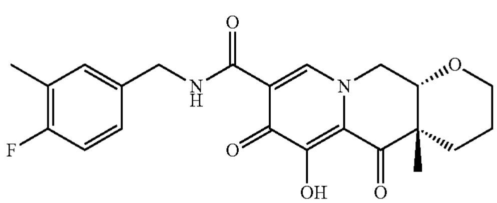 [SMILES: Cc1cc(CNC(=O)c2cn3c(c(O)c2=O)C(=O)[C@@]2(C)CCCO[C@H]2C3)ccc1F] | 1.02 (LC2) | 415.1 |
| 25 | 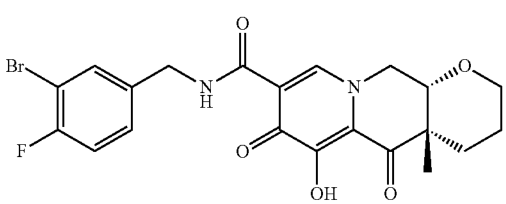 | 1.05 (LC2) | 480.9 |
| 26 | 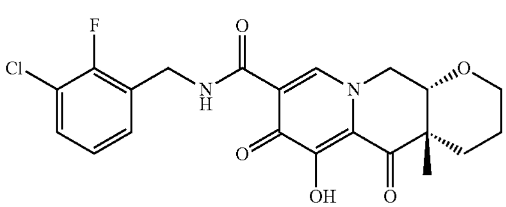 [SMILES: C[C@]12CCCO[C@H]1Cn1cc(C(=O)NCc3cccc(Cl)c3F)c(=O)c(O)c1C2=O] | 1.04 (LC2) | 435.1 |
| 27 | 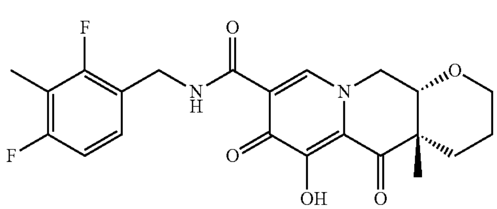 [SMILES: Cc1c(F)ccc(CNC(=O)c2cn3c(c(O)c2=O)C(=O)[C@@]2(C)CCCO[C@H]2C3)c1F] | 1.05 (LC2) | 433.2 |

-continued

| Compound # | Structure | Rt (min) | MS (M + H) |
|---|---|---|---|
| 28 | 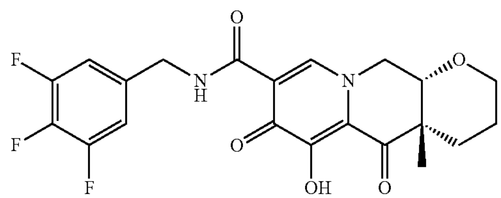 [SMILES: C[C@]12CCCO[C@H]1Cn1cc(C(=O)NCc3cc(F)c(F)c(F)c3)c(=O)c(O)c1C2=O] | 1.02 (LC2) | 437.1 |
| 29 | 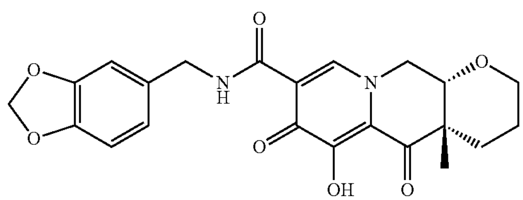 [SMILES: C[C@]12CCCO[C@H]1Cn1cc(C(=O)NCc3ccc4c(c3)OCO4)c(=O)c(O)c1C2=O] | 0.90 (LC2) | 427.0 |
| 30 | 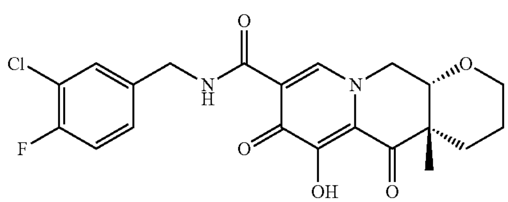 [SMILES: C[C@]12CCCO[C@H]1Cn1cc(C(=O)NCc3ccc(F)c(Cl)c3)c(=O)c(O)c1C2=O] | 1.04 (LC2) | 435.1 |
| 31 | 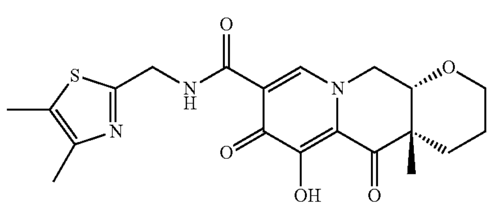 [SMILES: Cc1nc(CNC(=O)c2cn3c(c(O)c2=O)C(=O)[C@@]2(C)CCCO[C@H]2C3)sc1C] | 0.81 (LC2) | 419.1 |
| 32 | 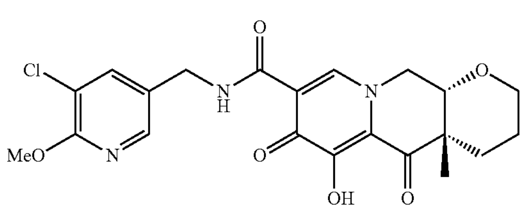 [SMILES: COc1ncc(CNC(=O)c2cn3c(c(O)c2=O)C(=O)[C@@]2(C)CCCO[C@H]2C3)cc1Cl] | 0.94 (LC2) | 448.2 |

Example 14

Preparation of Compound 9

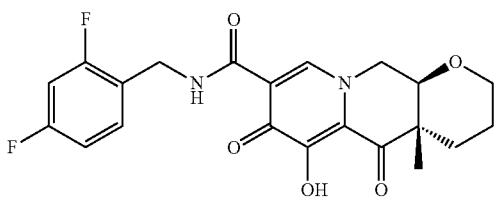

9

The trans-fused compound Int-8j (prepared in the Step I of Example 10) was converted into compound 9 using the method described in Step J and Step K of Example 10. $^1$H NMR (400 MHz, CDCl$_3$): δ 10.36 (brs, 1H); 8.49 (s, 1H); 7.35-7.41 (m, 1H); 6.82-6.88 (m, 2H); 4.68 (d, J=5.9 Hz, 2H); 4.12-4.24 (m, 3H); 3.92 (dd, J=11.3, 5.4 Hz, 1H); 3.52-3.59 (m, 1H); 2.25-2.31 (m, 1H); 1.96-2.03 (m, 1H); 1.68-1.79 (m, 2H); 1.37 (s, 3H). LCMS anal. calcd. for C$_{21}$H$_{20}$F$_2$N$_2$O$_5$: 418.13. Found: 419.18 (M+1)$^+$.

Example 15

Preparation of Compound 33 and Compound 34

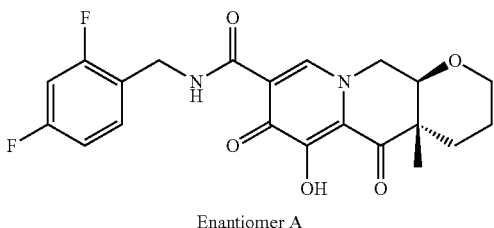

33

Enantiomer A

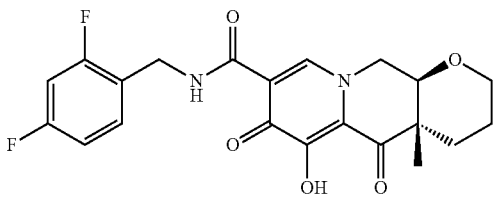

34

Enantiomer B

Using the methods described above for making compounds 7 and 8, and starting from compound Int-8j, compound 33 and 34 were prepared by chiral separation separation (IC column, 20×250 mm, 50% MeOH (0.2% NH$_4$OH)/CO$_2$, 50 ml/min, 100 bar) of the intermediate prior to the last step in the synthesis of compound 9. The earlier eluting compound was deprotected using the conditions described in Step K of Example 10 to provide compound 33, the later eluting compound was deprotected to provide compound 34.

Compound 33: $^1$H NMR (400 MHz, CDCl$_3$): δ 10.36 (brs, 1H); 8.49 (s, 1H); 7.35-7.41 (m, 1H); 6.82-6.88 (m, 2H); 4.68 (d, J=5.9 Hz, 2H); 4.12-4.24 (m, 3H); 3.92 (dd, J=11.3, 5.4 Hz, 1H); 3.52-3.59 (m, 1H); 2.25-2.31 (m, 1H); 1.96-2.03 (m, 1H); 1.68-1.79 (m, 2H); 1.37 (s, 3H). LCMS anal. calcd. for C$_{21}$H$_{20}$F$_2$N$_2$O$_5$: 418.13. Found: 419.18 (M+1)$^+$.

Compound 34: $^1$H NMR (400 MHz, CDCl$_3$): δ 10.36 (brs, 1H); 8.49 (s, 1H); 7.35-7.41 (m, 1H); 6.82-6.88 (m, 2H); 4.68 (d, J=5.9 Hz, 2H); 4.12-4.24 (m, 3H); 3.92 (dd, J=11.3, 5.4 Hz, 1H); 3.52-3.59 (m, 1H); 2.25-2.31 (m, 1H); 1.96-2.03 (m, 1H); 1.68-1.79 (m, 2H); 1.37 (s, 3H). LCMS anal. calcd. for C$_{21}$H$_{20}$F$_2$N$_2$O$_5$: 418.13. Found: 419.18 (M+1)$^+$.

Example 16

Preparation of Compound 35 and Compound 36

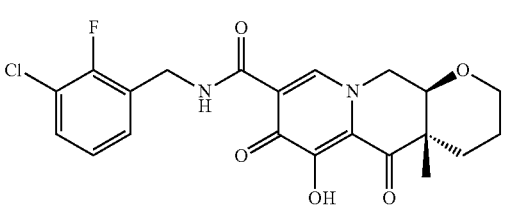

35

Enantiomer A

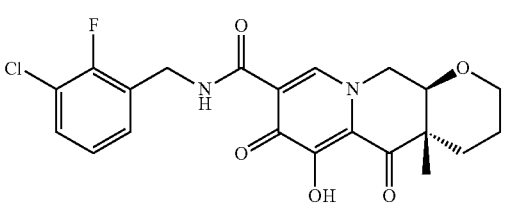

36

Enantiomer B

Starting from compound Int 8j, compound 35 and 36 were prepared by essentially the same method described in step J and K of Example 10, only replacing 2,4-difluorobenzylamine with 2-fluoro-3-chlorobenzylamine. The earlier eluting compound in the chiral separation process (IC column, 20×250 mm, 40% MeOH (0.2% NH$_4$OH)/CO$_2$, 55 ml/min, 100 bar) of step J was deprotected to provide compound 35, the later eluting compound was deprotected to provide compound 36.

Compound 35: $^1$H NMR (500 MHz, CDCl$_3$): δ 10.36 (brs, 1H), 8.49 (s, 1H), 7.34-7.27 (m, 2H), 7.05 (t, J=7.8 Hz, 1H), 4.73 (m, 2H), 4.20-4.28 (m, 1H), 4.09-4.19 (m, 2H), 3.88-3.96 (m, 1H), 3.48-3.59 (m, 1H), 2.21-2.32 (m, 1H), 1.96-2.06 (m, 1H), 1.68-1.78 (m, 2H), 1.36 (s, 3H). LCMS anal. calcd. for C$_{21}$H$_{20}$ClFN$_2$O$_5$: 434.10. Found: 435.04 (M+1)$^+$.

Compound 36: $^1$H NMR (500 MHz, CDCl$_3$): δ 10.36 (brs, 1H), 8.49 (s, 1H), 7.35-7.27 (m, 2H), 7.05 (t, J=7.8 Hz, 1H), 4.73 (m, 2H), 4.20-4.28 (m, 1H), 4.09-4.19 (m, 2H), 3.88-3.98 (m, 1H), 3.51-3.57 (m, 1H), 2.21-2.32 (m, 1H), 1.96-2.06 (m, 1H), 1.68-1.78 (m, 2H), 1.36 (s, 3H). LCMS anal. calcd. for C$_{21}$H$_{20}$ClFN$_2$O$_5$: 434.10. Found: 435.06 (M+1)$^+$.

Example 17

Preparation of Compound Int-9b

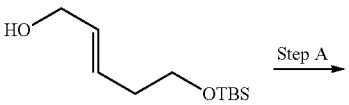

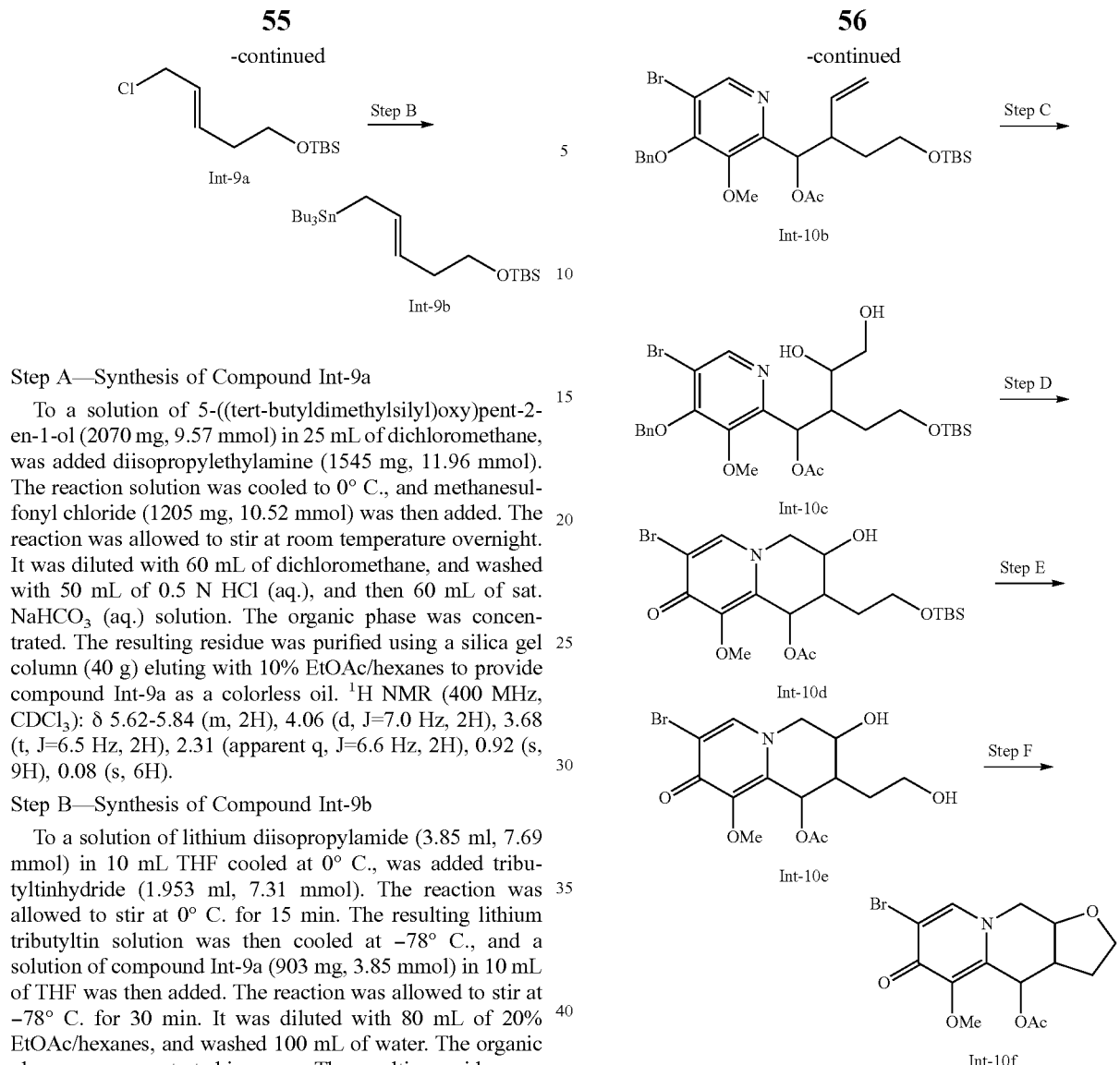

Step A—Synthesis of Compound Int-9a

To a solution of 5-((tert-butyldimethylsilyl)oxy)pent-2-en-1-ol (2070 mg, 9.57 mmol) in 25 mL of dichloromethane, was added diisopropylethylamine (1545 mg, 11.96 mmol). The reaction solution was cooled to 0° C., and methanesulfonyl chloride (1205 mg, 10.52 mmol) was then added. The reaction was allowed to stir at room temperature overnight. It was diluted with 60 mL of dichloromethane, and washed with 50 mL of 0.5 N HCl (aq.), and then 60 mL of sat. NaHCO$_3$ (aq.) solution. The organic phase was concentrated. The resulting residue was purified using a silica gel column (40 g) eluting with 10% EtOAc/hexanes to provide compound Int-9a as a colorless oil. $^1$H NMR (400 MHz, CDCl$_3$): δ 5.62-5.84 (m, 2H), 4.06 (d, J=7.0 Hz, 2H), 3.68 (t, J=6.5 Hz, 2H), 2.31 (apparent q, J=6.6 Hz, 2H), 0.92 (s, 9H), 0.08 (s, 6H).

Step B—Synthesis of Compound Int-9b

To a solution of lithium diisopropylamide (3.85 ml, 7.69 mmol) in 10 mL THF cooled at 0° C., was added tributyltinhydride (1.953 ml, 7.31 mmol). The reaction was allowed to stir at 0° C. for 15 min. The resulting lithium tributyltin solution was then cooled at −78° C., and a solution of compound Int-9a (903 mg, 3.85 mmol) in 10 mL of THF was then added. The reaction was allowed to stir at −78° C. for 30 min. It was diluted with 80 mL of 20% EtOAc/hexanes, and washed 100 mL of water. The organic phase was concentrated in vacuo. The resulting residue was purified using a silica gel column (80 g) eluting with hexanes to provide compound Int-9b as a colorless oil. $^1$H NMR (400 MHz, CDCl$_3$): δ 5.62 (dt, J=15.3, 8.4 Hz, 1H), 5.62 (dt, J=15.1, 7.0 Hz, 1H), 3.87 (t, J=7.3 Hz, 2H), 2.22 (apparent q, J=7.3 Hz, 2H), 1.72 (d, J=8.5 Hz, 2H), 1.42-1.58 (m, 6H), 1.28-1.36 (m, 6H), 0.79-1.06 (m, 24H), 0.08 (s, 6H).

Example 18

Preparation of Compound Int-10f

Step A—Synthesis of Compound Int-10a

To a solution of compound Int-1 (500 mg, 1.552 mmol) and compound Int-9b (912 mg, 1.862 mmol) in 15 mL of ACN stirred at 0° C., was added Tin (II) Cl$_2$ (441 mg, 2.328 mmol). The reaction was stirred for 30 min. The content was diluted with 100 mL of 30% EtOAc/hexanes, and washed with 100 mL of 15% wt. NH$_4$F in water. The organic phase was separated and filtered. The mother liquor was concentrated in vacuo and the resulting residue was purified using a silica gel column (80 g) eluting initially with dichloromethane to removed Tin reagent, and then with 5% EtOAc/dichloromethane to provide compound Int-10a as a mixture of stereoisomers. LCMS anal. calcd. for C$_{25}$H$_{36}$BrNO$_4$Si: 523.16. Found: 524.07 (M+1)$^+$.

Step B—Synthesis of Compound Int-10b

To a solution of compound Int-10a (610 mg, 1.167 mmol) in 8 mL of dichloromethane, was added acetic anhydride (2000 mg, 19.59 mmol), triethylamine (800 mg, 7.91 mmol), and DMAP (143 mg, 1.167 mmol) sequentially. The reaction was allowed to stir at room temperature for 1 h. It was further diluted with 20 mL of dichloromethane, and then added 3 mL of MeOH. It was allowed to stir at room temperature for 2 h to quench excess acetic anhydride. The solvent was removed in vacuo and the resulting residue was purified using a silica gel column (120 g) eluting with 15% EtOAc/hexanes to provide compound Int-10b as a colorless film. LCMS anal. calcd. for $C_{27}H_{38}BrNO_5Si$: 565.17. Found: 566.11 (M+1)$^+$.

Step C—Synthesis of Compound Int-10c

To a solution of compound Int-10b (293 mg, 0.519 mmol) in 4.5 mL of THF/t-BuOH/water (5:5:1), was added 4-methylmorpholine 4-oxide (66.9 mg, 0.571 mmol) followed by 4-methylmorpholine N-oxide (66.9 mg, 0.571 mmol). The reaction was allowed to stir at room temperature for 16 h. To this was added 5 g of solid $Na_2S_2O_5$. The mixture was allowed to stir at room temperature for 1 h. The content was diluted with 70 mL of 50% EtOAc/hexanes. The brown solid was filtered off. The filtrate was washed with water and then concentrated. The resulting residue was purified using a silica gel column (40 g) eluting with 5% MeOH/dichloromethane to provide compound Int-10c as a colorless oil. LCMS anal. calcd. for $C_{27}H_{40}BrNO_7Si$: 599.17. Found: 600.12 (M+1)$^+$.

Step D—Synthesis of Compound Int-10d

To a solution of compound Int-10c (272 mg, 0.454 mmol) in 3 mL of pyridine, was added 4-methylbenzene-1-sulfonyl chloride (130 mg, 0.682 mmol). The reaction was allowed to stir at room temperature for 36 h. To the reaction was added 1 mL of MeOH. It was allowed to stir at room temperature for 1 h. The content was diluted with 30 mL of dichloromethane, and washed with 20 mL for 0.5 N HCl (aq.) solution. The organic phase was concentrated. The resulting residue was purified using a silica gel column (80 g) eluting with EtOAc to provide compound Int-10d as a colorless film. LCMS anal. calcd. for $C_{20}H_{32}BrNO_6Si$: 491.12. Found: 492.02 (M+1)$^+$.

Step E—Synthesis of Compound Int-10e

To a solution of compound Int-10d (80 mg, 0.163 mmol) in 2 mL of MeOH, was added 1.25 N HCl in MeOH (0.5 ml, 0.625 mmol). The reaction was allowed to stir at room temperature for 2 h. The solvent was removed in vacuo. The resulting residue was purified using a silica gel column (40 g) eluting with 20% MeOH/dichloromethane to provide compound Int-10e as a colorless film. LCMS anal. calcd. for $C_{14}H_{18}BrNO_6$: 377.03. Found: 378.00 (M+1)$^+$.

Step F—Synthesis of Compound Int-10f

To a solution of compound Int-10e (18.64 mg, 0.090 mmol) in 1 mL of ACN, was added methanesulfonic anhydride (14.82 mg, 0.085 mmol). The reaction was allowed to stir at room temperature for 30 min. This solution was then added via syringe into a vial containing 7-bromo-3-hydroxy-2-(2-hydroxyethyl)-9-methoxy-8-oxo-2,3,4,8-tetrahydro-1H-quinolizin-1-yl acetate (20 mg, 0.053 mmol). The reaction was allowed to stir at 50° C. overnight. The solvent was removed in vacuo. The resulting residue was purified using Gilson reverse phase column eluting with 0.05% TFA in ACN/0.05% TFA in water (0 to 90%) to provide compound Int-10f as a colorless film. LCMS anal. calcd. for $C_{14}H_{16}BrNO_5$: 359.02. Found: 359.96 (M+1)$^+$.

Example 19

Preparation of Compound 10

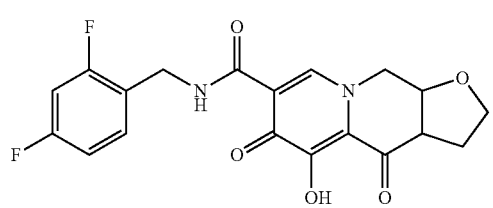

Compound 10 was prepared by following essentially the same reaction sequence from Step H to Step K in Example 10, and replacing compound Int-8g with compound Int-10f. $^1$H NMR (400 MHz, CDCl$_3$): δ 10.27 (b, 1H), 8.46 (s, 1H), 7.35-7.40 (m, 1H), 6.81-6.86 (m, 2H), 4.67 (m, 2H), 4.59 (m, 1H), 4.24 (dd, J=2.4, 11.2 Hz, 1H), 3.98 (dd, J=1.6, 9.2 Hz, 1H), 3.76 (m, 1H), 3.54 (m, 1H), 3.42 (m, 1H), 2.77 (m, 1H), 2.48 (m, 1H). LCMS anal. calcd. for $C_{19}H_{16}F2N2O5$: 390.10. Found: 391.12 (M+1)$^+$.

Example 20

Preparation of Compound Int-11

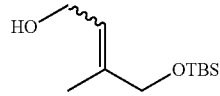

Compound Int-11 was prepared as a roughly 1:1 mixture of (E) and (Z) isomers using the method described in Baldwin et al, Chem. Commun. 22:2786 (2003).

Example 21

Preparation of Compound Int-12

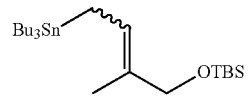

Compound Int-12 was prepared as a roughly 1:1 mixture of (E) and (Z) isomers by following essentially the same method described in Example 17, and replacing 5-((tert-butyldimethylsilyl)oxy)pent-2-en-1-ol with compound Int-11 in Step A. $^1$H NMR (400 MHz, CDCl$_3$): δ 5.60 & 5.40 (dt, J=9.0, 1.1 Hz, 1H), 4.16 & 4.03 (s, 2H), 1.70-1.84 (m, 2H), 1.61 & 1.59 (s, 3H), 1.42-1.58 (m, 6H), 1.28-1.36 (m, 6H), 0.79-1.02 (m, 24H), 0.11 & 0.08 (s, 6H).

Example 22

Preparation of Compound Int-13

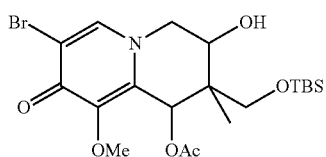

Int-13

Compound Int-13 was prepared using the method described in Steps A to D of Example 18, and replacing compound Int-9b with compound Int-12 in Step A. LCMS anal. calcd. for $C_{20}H_{32}BrNO_6Si$: 491.12. Found: 492.04 $(M+1)^+$.

Example 23

Preparation of Compounds 11 and 12

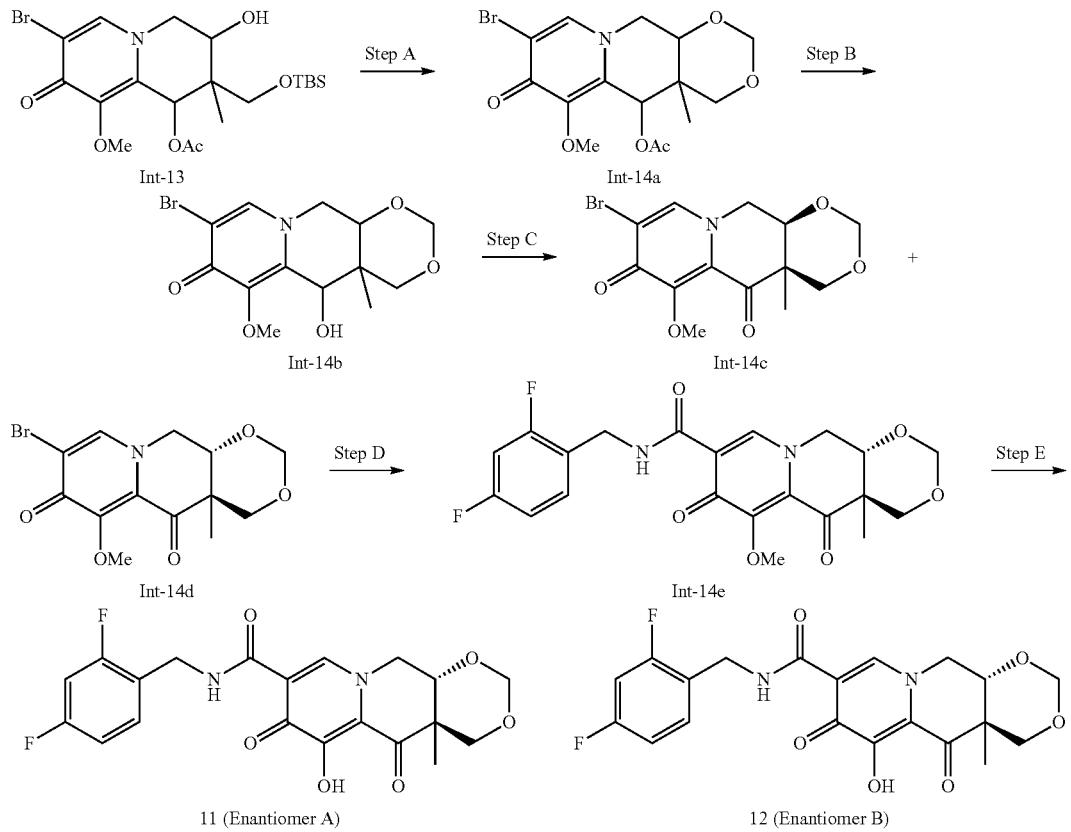

Step A—Synthesis of Compound Int-14a

To a solution of paraformaldehyde (93 mg, 3.09 mmol) in 4 mL of AcOH was added sulfuric acid (120 mg, 1.224 mmol). The reaction was allowed to stir at room temperature for 20 min before compound Int-13 (160 mg, 0.309 mmol) was added. The reaction was allowed to stir at room temperature for 1 h and then at 70° C. for 1 h. It was cooled to room temperature. To the content was added 1 g of NaHCO₃ solid portionwise. The mixture was diluted with 20 mL of EtOAc and then filtered. The filtrate was concentrated in vacuo and purified using a reverse phase column (120 g) eluting with 0.05% TFA in water and 0.05% TFA in ACN (from 0% to 90% over 10 column length) to provide compound Int-14a. LCMS anal. calcd. for $C_{15}H_{18}BrNO_6$: 389.03. Found: 390.02 $(M+1)^+$.

Step B—Synthesis of Compound Int-14b

To a solution of compound Int-14a, TFA salt (150 mg, 0.299 mmol) in 5 mL of MeOH, was added potassium carbonate (165 mg, 1.195 mmol). The reaction was allowed to stir at room temperature for 2 h. The solvent was removed in vacuo. The resulting residue was purified using a silica gel column (40 g) eluting with 8% MeOH/dichloromethane to provide compound Int-14b as a colorless film. LCMS anal. calcd. for $C_{13}H_{16}BrNO_5$: 347.02. Found: 348.11 $(M+1)^+$.

Step C—Synthesis of Compound Int-14c and Compound Int-14d

To a solution of compound Int-14b (88 mg, 0.254 mmol) in 5 mL of dichloromethane, was added Dess-Martin periodinane (162 mg, 0.381 mmol). The reaction was allowed to stir at room temperature for 45 min. It was diluted with 60 mL of EtOAc. The solid was filtered off. The liquid portion was concentrated. The resulting residue was purified by a silica gel column (40 g) eluting with EtOAc to provide cis-fused compound Int-14c and trans-fused compound Int-14d individually as a white solid. LCMS anal. calcd. for $C_{13}H_{14}BrNO_5$: 345.00. Found: 346.02 $(M+1)^+$.

Step D—Synthesis of Compound Int-14e

To a solution of compound Int-14d (42 mg, 0.122 mmol) in 2 mL of DMSO, was added (2,4-difluorophenyl)methanamine (34.9 mg, 0.244 mmol), diisopropylethylamine (39.4 mg, 0.305 mmol) and Pd(PPh$_3$)$_4$ (35.3 mg, 0.031 mmol) sequentially. The reaction vessel was filled with CO gas by doubling CO into the solution through a needle over 20 min. It was stirred under a balloon of CO at 90° C. for 6 h. It was cooled to room temperature. The content was purified using reverse phase Gilson eluting with 0.05% TFA in water/ 0.05% TFA in ACN (from 10-90%) to provide the crude compound Int-14e. This material was further purified using a chiral preparative SFC (Chiral AD 30×250 mm column, 40% 2:1 MeOH:ACN/CO$_2$, 70 mL/min, 100 bar, 4 mg/mL in MeOH/dichloromethane, 35° C., 254 nM) to provide enantiomer A of compound Int-14e (earlier eluting component) and enantiomer B of compound Int-14e (later eluting component). LCMS anal. calcd. for C$_{21}$H$_{20}$F$_2$N$_2$O$_6$: 434.13. Found: 435.04 (M+1)$^+$.

Step E—Synthesis of Compound 11 and 12

To a solution of the enantiomer A of compound Int-14e (4.0 mg, 9.21 µmol) in 4 mL of DMF, was added lithium chloride (7.81 mg, 0.184 mmol). The mixture was allowed to stir at 100° C. for 1 h. It was cooled to room temperature. The mixture was separated by reverse phase Gilson (10% ACN (0.05% TFA)/H$_2$O-90% ACN (0.05% TFA)/H$_2$O, 12 min) to afford compound 11 as a white solid. $^1$H NMR (400 MHz, CDCl$_3$): δ 10.25 (b, 1H), 8.51 (s, 1H), 7.35-7.40 (m, 1H), 6.81-6.87 (m, 2H), 5.19 (d, J=5.2 Hz, 1H), 4.80 (d, J=5.2 Hz, 1H), 4.67 (d, J=4.8 Hz, 2H), 4.28-4.34 (4H), 3.87 (d, J=9.2 Hz, 1H), 1.6 (brs, 1H), 1.57 (s, 3H). LCMS anal. calcd. for C$_{20}$H$_{18}$F$_2$N$_2$O$_6$: 420.11. Found: 421.04 (M+1)$^+$.

To a solution of the enantiomer B of compound Int-14e (4.0 mg, 9.21 µmol) in 4 mL of DMF, was added lithium chloride (7.81 mg, 0.184 mmol). The mixture was allowed to stir at 100° C. for 1 h. It was cooled to room temperature. The mixture was separated by reverse phase Gilson (10% ACN (0.05% TFA)/H$_2$O-90% ACN (0.05% TFA)/H$_2$O, 12 min) to afford compound 12 as a white solid. $^1$H NMR (400 MHz, CDCl$_3$) δ 10.29 (b, 1H); 8.53 (s, 1H), 7.35-7.40 (m, 1H), 6.81-6.87 (m, 2H), 5.19 (d, J=5.2 Hz, 1H), 4.80 (d, J=5.2 Hz, 1H), 4.67 (d, J=4.8 Hz, 2H), 4.27-4.34 (4H), 3.87 (d, J=9.2 Hz, 1H), 1.6 (brs, 1H); 1.61 (s, 3H). LCMS anal. calcd. for C$_{20}$H$_{18}$F$_2$N$_2$O$_6$: 420.11. Found: 421.04 (M+1)$^+$.

Example 24

Preparation of Compound 13

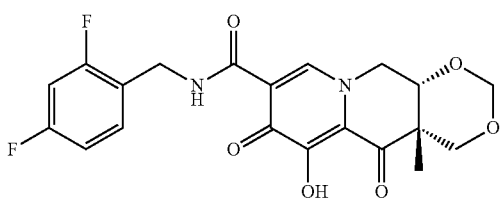

The cis-fused compound Int-14c prepared in the Step C of Example 23 was converted into compound 13 using the method described in Step D and Step E of Example 23. $^1$H NMR (400 MHz, CDCl$_3$) δ 10.38 (b, 1H); 8.47 (s, 1H); 7.35-7.42 (m, 1H); 6.81-6.88 (m, 2H), 5.07 (d, J=6.3 Hz, 1H), 4.82 (d, J=6.3 Hz, 1H), 4.78 (d, J=11.5 Hz, 1H), 4.62-4.73 (m, 2H), 4.51 (d, J=13.8 Hz, 1H), 4.31 (d, J=13.9 Hz, 1H), 4.16 (s, 1H), 3.45 (d, J=11.4 Hz, 1H), 1.21 (s, 3H). LCMS anal. calcd. for C$_{20}$H$_{18}$F$_2$N$_2$O$_6$: 420.11. Found: 421.06 (M+1)$^+$.

Example 25

Preparation of Compound 37 and 38

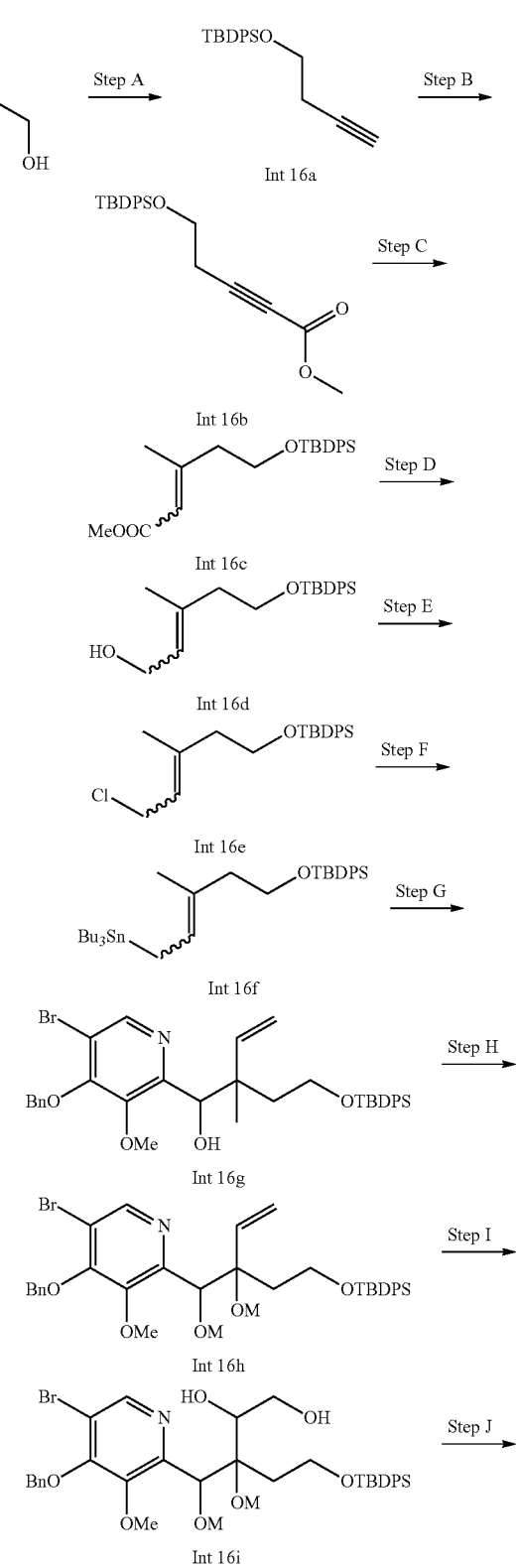

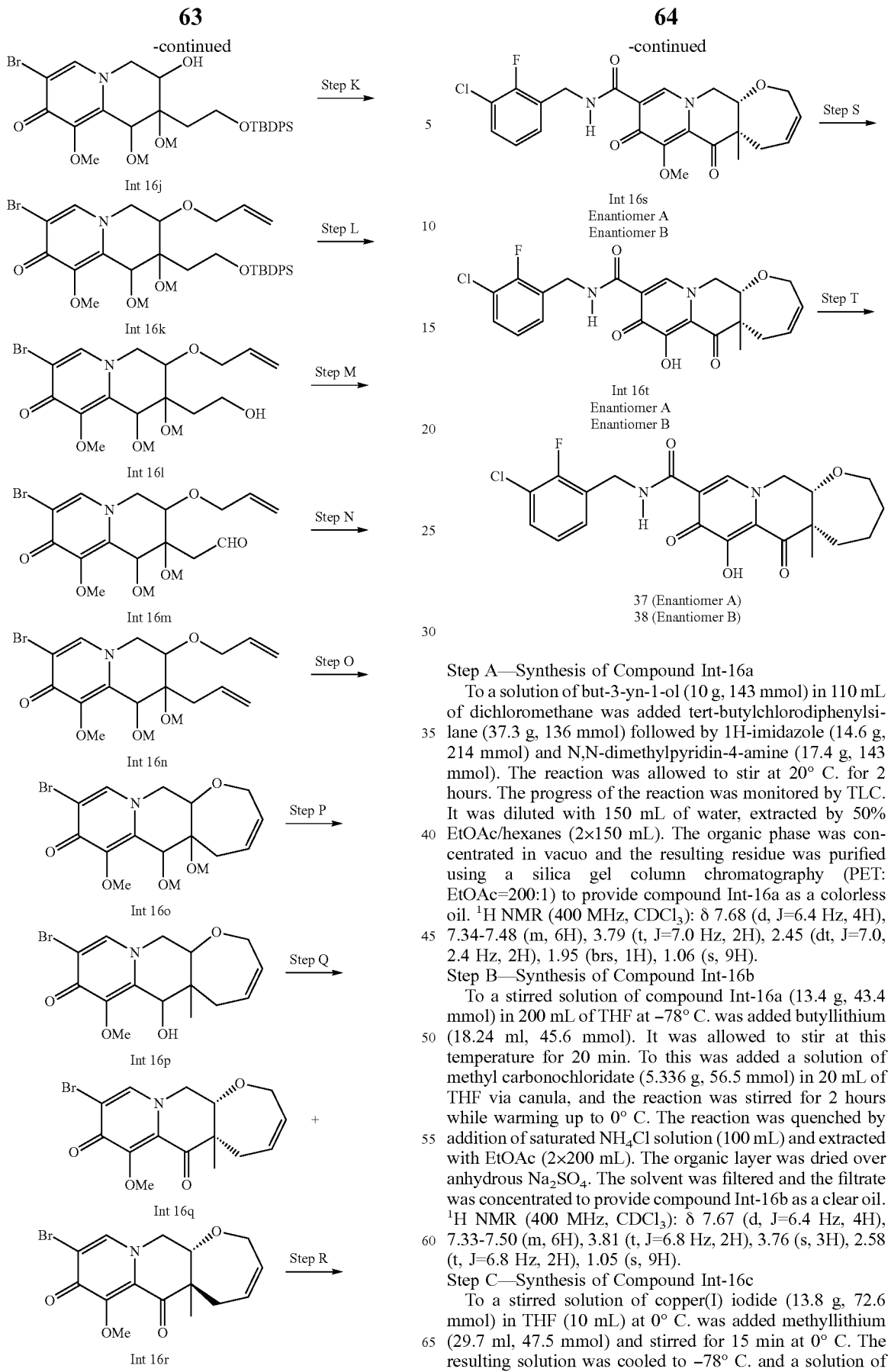

Step A—Synthesis of Compound Int-16a

To a solution of but-3-yn-1-ol (10 g, 143 mmol) in 110 mL of dichloromethane was added tert-butylchlorodiphenylsilane (37.3 g, 136 mmol) followed by 1H-imidazole (14.6 g, 214 mmol) and N,N-dimethylpyridin-4-amine (17.4 g, 143 mmol). The reaction was allowed to stir at 20° C. for 2 hours. The progress of the reaction was monitored by TLC. It was diluted with 150 mL of water, extracted by 50% EtOAc/hexanes (2×150 mL). The organic phase was concentrated in vacuo and the resulting residue was purified using a silica gel column chromatography (PET: EtOAc=200:1) to provide compound Int-16a as a colorless oil. $^1$H NMR (400 MHz, CDCl$_3$): δ 7.68 (d, J=6.4 Hz, 4H), 7.34-7.48 (m, 6H), 3.79 (t, J=7.0 Hz, 2H), 2.45 (dt, J=7.0, 2.4 Hz, 2H), 1.95 (brs, 1H), 1.06 (s, 9H).

Step B—Synthesis of Compound Int-16b

To a stirred solution of compound Int-16a (13.4 g, 43.4 mmol) in 200 mL of THF at −78° C. was added butyllithium (18.24 ml, 45.6 mmol). It was allowed to stir at this temperature for 20 min. To this was added a solution of methyl carbonochloridate (5.336 g, 56.5 mmol) in 20 mL of THF via canula, and the reaction was stirred for 2 hours while warming up to 0° C. The reaction was quenched by addition of saturated NH$_4$Cl solution (100 mL) and extracted with EtOAc (2×200 mL). The organic layer was dried over anhydrous Na$_2$SO$_4$. The solvent was filtered and the filtrate was concentrated to provide compound Int-16b as a clear oil. $^1$H NMR (400 MHz, CDCl$_3$): δ 7.67 (d, J=6.4 Hz, 4H), 7.33-7.50 (m, 6H), 3.81 (t, J=6.8 Hz, 2H), 3.76 (s, 3H), 2.58 (t, J=6.8 Hz, 2H), 1.05 (s, 9H).

Step C—Synthesis of Compound Int-16c

To a stirred solution of copper(I) iodide (13.8 g, 72.6 mmol) in THF (10 mL) at 0° C. was added methyllithium (29.7 ml, 47.5 mmol) and stirred for 15 min at 0° C. The resulting solution was cooled to −78° C. and a solution of compound Int-16b (17.4 mg, 47.5 mmol) in THF (5 mL) was added via canula and stirred for 2 hours at that temperature. The reaction mixture was then quenched by the addition of saturated NH₄Cl (10 mL) followed by water (200 mL). The mixture was extracted with EtOAc (3×20 mL), the combined organic layer was dried over anhydrous Na₂SO₄, then filtered. The filtrate was concentrated to provide compound Int-16c as a clear oil. $^1$H NMR (400 MHz, CDCl₃): δ 7.66 (d, J=6.4 Hz, 4H), 7.35-7.42 (m, 6H), 5.72 (s, 1H), 3.83 (t, J=6.4 Hz, 2H), 3.62-3.70 (m, 3H), 2.91 (t, J=6.4 Hz, 2H), 1.92 (s, 3H), 1.03 (s, 9H).

Step D—Synthesis of Compound Int-16d

To a solution of compound Int-16c (19 g, 49.7 mmol) in dichloromethane (200 mL) cooled at −78° C. was added diisopropylaluminum hydride (109 ml, 109 mmol). The reaction was allowed to stir at −78° C. for 1 h. and warm up to 0° C. At this time, it was quenched by adding 500 mL of saturated Rochelle salt solution. The mixture was allowed to stir at 0° C. for 1 hour and the organic phase was isolated. The organic layer was washed with 50 mL of brine and dried over Na₂SO₄, then it was filtered and the filtrate was concentrated. The resulting residue was purified using silica gel column chromatography (PET:EtOAc=10:1) to provide compound Int-16d as a colorless oil.

$^1$H NMR (400 MHz, CDCl₃): δ 7.67 (d, J=6.4 Hz, 4H), 7.36-7.44 (m, 6H), 5.64 (t, J=6.8 Hz, 1H), 4.04 (d, J=6.8 Hz, 2H), 3.67 (t, J=6.4 Hz, 2H), 2.36 (t, J=6.4 Hz, 2H), 1.69 (s, 3H), 1.04 (s, 9H).

Step E—Synthesis of Compound Int-16e

To a solution of compound Int-16d (7 g, 19.74 mmol) and lithium chloride (1.7 g, 39.5 mmol) in dichloromethane (70 mL) was added N-ethyl-N-isopropylpropan-2-amine (6.4 g, 49.4 mmol) followed by methanesulfonyl chloride (3619 mg, 31.6 mmol). The reaction mixture was allowed to stir at 20° C. for 2 hours. Then it was diluted with 200 mL of dichloromethane and washed with 200 mL of 0.2 N HCl (aq.) solution and 100 mL of brine. The organic phase was concentrated to provide compound Int-16e as a colorless oil. $^1$H NMR (400 MHz, CDCl₃): δ 7.66 (d, J=6.4 Hz, 4H), 7.36-7.46 (m, 6H), 5.50 (t, J=7.6 Hz, 1H), 3.96-4.14 (m, 2H), 3.64-3.80 (m, 2H), 2.35 (t, J=6.8 Hz, 2H), 1.63-1.77 (m, 3H), 1.04 (s, 9H).

Step F—Synthesis of Compound Int-16f

To a solution of lithium diethylamide (19.17 mL, 38.3 mmol) in THF (70 mL) cooled at 0° C., was added tributylstannane (10 g, 34.9 mmol). The reaction was allowed to stir at 0° C. for 30 minutes. It was then cooled to −78° C., and a solution of compound Int-16e (6.5 g, 17.43 mmol) in 30 mL of THF was added via syringe. The reaction was allowed to stir at −78° C. for 30 minutes. It was diluted with 100 mL of 20% EtOAc/hexanes and washed with 100 mL of water. The organic phase was isolated and the aqueous phase was extracted with 100 mL of 20% EtOAc/hexanes. The combined organic were washed with water, brine and concentrated under reduce pressure. The resulting residue was purified using a silica gel column chromatography (PET:EtOAc=100:1) to provide compound Int-16f as a colorless oil. $^1$H NMR (400 MHz, CDCl₃): δ 7.63-7.75 (m, 4H), 7.32-7.45 (m, 6H), 5.30 (t, J=8.8 Hz, 1H), 3.66 (t, J=7.6 Hz, 2H), 2.18-2.33 (m, 2H), 1.54-1.63 (m, 5H), 1.39-1.50 (m, 6H), 1.21-1.33 (m, 6H), 1.03-1.08 (m, 9H), 0.74-0.92 (m, 15H). MS (M+H)⁺: 628.

Step G—Synthesis of Compound Int-16g

To a solution of compound Int-16f (7.6 g, 12.11 mmol) and compound Int-1 (3.3 g, 10.09 mmol) in acetonitrile (100 mL) stirred at 0° C. was added Tin (II) chloride (5.8 g, 30.3 mmol). The reaction was then warmed to 20° C. and stirred for 15 minutes. This color was gradually disappeared over 5 minutes. The progress of the reaction was monitored by TLC. It was found that the reaction completed when the color almost all gone. This was diluted with 100 mL of 30% EtOAc/hexane, and 100 mL of 15% (wt) NH₄F aqueous solution. The resulting mixture was allowed to stir at 20° C. for 20 min. Solid was filtered off. The organic from the mother liquor was concentrated in vacuo and the resulting residue was purified using silica gel column chromatography (PET:EtOAc=10:1) to compound Int-16g as colorless oil. $^1$H NMR (400 MHz, CDCl₃): δ 8.35 (brs, 1H), 7.66 (brs, 4H), 7.48 (d, J=5.4 Hz, 2H), 7.36 (brs, 9H), 5.61-5.81 (m, 1H), 5.15-5.27 (m, 1H), 4.90-5.14 (m, 2H), 4.77 (d, J=18.0 Hz, 2H), 3.84 (brs, 3H), 3.59-3.78 (m, 3H), 1.87 (d, J=5.4 Hz, 1H), 1.68-1.80 (m, 1H), 1.03 (brs, 9H), 0.88-0.96 (m, 3H). MS (M+H)⁺: 662.

Step H—Synthesis of Compound Int-16h

To a solution of compound Int-16g (11 g, 16.65 mmol), N,N-dimethylpyridin-4-amine (407 mg, 3.33 mmol) and N-ethyl-N-isopropylpropan-2-amine (10 g, 83 mmol) in dichloromethane (100 mL) was added chloro (methoxy) methane (6.7 g, 83 mmol). The reaction mixture was allowed to stir at 30° C. for 16 hours, LCMS showed the starting material was consumed completely. The solvent was removed in vacuo. The resulting residue was purified using silica gel column chromatography (PET:EtOAc=10:1) to provide compound Int-16h as a colorless oil. $^1$H NMR (400 MHz, CDCl₃): δ 8.43 (s, 1H), 7.64 (d, J=6.8 Hz, 4H), 7.47 (d, J=5.8 Hz, 2H), 7.30-7.43 (m, 9H), 5.75-5.85 (m, 1H), 5.18-5.25 (m, 1H), 5.11 (d, J=11.6 Hz, 1H), 4.98 (d, J=11.0 Hz, 1H), 4.84-4.90 (m, 1H), 4.71-4.79 (m, 1H), 4.54-4.60 (m, 1H), 4.37-4.44 (m, 1H), 3.85 (s, 3H), 3.62-3.72 (m, 2H), 3.12-3.31 (m, 3H), 1.94-2.03 (m, 1H), 1.59-1.68 (m, 1H), 1.02 (s, 9H), 0.82-0.96 (m, 3H). MS (M+H)⁺: 706.

Step I—Synthesis of Compound Int-16i

To a solution of compound Int-16h (10 g, 14.19 mmol) in 100 mL of THF/water (3:2), was added 4-methylmorpholine 4-oxide (3.3 g, 28.4 mmol) followed by osmium (VIII) oxide (541 mg, 2.128 mmol). The reaction was allowed to stir at 35° C. for 48 hours. To this mixture was added 10 g of solid Na₂S₂O₅. The mixture was allowed to stir at 35° C. for 1 hour. The mixture was diluted with 100 mL of 50% EtOAc/hexanes. The brown solid was filtered off and the filtrate was washed with water, brine and dried over anhydrous Na₂SO₄. The solid was filtered and the filtrate was concentrated. The resulting residue was purified using silica gel column chromatography (PET:EtOAc=1:1) to provide compound Int-16i as a white solid. $^1$H NMR (400 MHz, CDCl₃): δ 8.27-8.48 (m, 1H), 7.62-7.74 (m, 4H), 7.27-7.46 (m, 11H), 5.18-5.26 (m, 1H), 5.10-5.16 (m, 1H), 5.07 (d, J=3.6 Hz, 1H), 4.49 (t, J=7.0 Hz, 1H), 4.34 (d, J=6.8 Hz, 1H), 3.77-3.89 (m, 5H), 3.45-3.76 (m, 3H), 3.08-3.26 (m, 3H), 2.40-2.58 (m, 1H), 1.67-2.07 (m, 1H), 1.40-1.58 (m, 1H), 1.01-1.10 (m, 9H), 0.78 (s, 3H). MS (M+H)⁺: 740.

Step J—Synthesis of Compound Int-16j

A solution of 4-methylbenzene-1-sulfonyl chloride (2.8 g, 14.62 mmol) in Pyridine (10 mL) was added to a solution of compound Int-16i (6 g, 8.12 mmol) in Pyridine (50 mL). The reaction mixture was allowed to stir at 35° C. for 16 hours. LCMS showed the starting material was consumed completely. The reaction was concentrated in vacuo and the resulting residue was purified using silica gel column chromatography (PET:EtOAc=1:1 then dichloromethane: MeOH=100:1) to provide compound Int-16i as a white solid. $^1$H NMR (400 MHz, CDCl₃): δ 7.52-7.82 (m, 5H), 7.34-7.51 (m, 6H), 4.62-4.96 (m, 3H), 4.33-4.57 (m, 2H), 3.91-4.00 (m, 3H), 3.64-3.90 (m, 3H), 3.24-3.41 (m, 3H), 1.21-1.31 (m, 2H), 0.60-1.17 (m, 12H). MS (M+H)⁺: 632.

Step K—Synthesis of Compound Int-16k

To a solution of compound Int-16j (246 mg, 0.390 mmol) in 5 mL of DMF, was added allyl iodide (262 mg, 1.560 mmol), followed by sodium hydride (31.2 mg, 0.780 mmol). The reaction was allowed to stir at room temperature for 40 min. It was cooled to 0° C., and quenched by adding 1 mL of water. The mixture was diluted with 70% EtOAc/hexanes (80 mL) and washed with 80 mL of water. The organic phase was concentrated. The resulting residue was purified using a silica gel column eluting with 3% MeOH/dichloromethane to provide compound Int-16k as a colorless film. LCMS anal. calcd. for $C_{34}H_{44}BrNO_6Si$: 670.7. Found: 671.9 $(M+1)^+$.

Step L—Synthesis of Compound Int-16l

To a solution of compound Int-16k (248 mg, 0.370 mmol) in 4 mL of THF, was added 1 M TBAF in THF (387 mg, 1.479 mmol). The reaction was allowed to stir at room temperature for 1 h. The solvent was removed in vacuo. The resulting residue was purified using a silica gel column (40 g) eluting with 8% MeOH/dichloromethane to provide compound Int-16l as a colorless film. LCMS anal. calcd. for $C_{18}H_{26}BrNO_6$: 433.1. Found: 433.8 $(M+1)^+$.

Step M—Synthesis of Compound Int-16m

To a solution of compound Int-16l (152 mg, 0.352 mmol) in 4 mL of dichloromethane, was added Dess-Martin periodinate (373 mg, 0.879 mmol). The reaction was allowed to stir at room temperature for 1 h. To this was added 2 drops of water, and the resulting mixture was diluted with 20 mL of EtOAc. The solid was filtered off. The mother liquor was concentrated in vacuo. The resulting residue was purified using a silica gel column eluting with 6% MeOH/dichloromethane to provide compound Int-16m as a colorless film. LCMS anal. calcd. for $C_{18}H_{24}BrNO_6$: 429.1. Found: 429.9 $(M+1)^+$.

Step N—Synthesis of Compound Int-16n

To a mixture of bromo(methyl)triphenylphosphorane (7472 mg, 20.92 mmol) (pre-dried under house vacuum at 120° C. in a flask overnight) in 60 mL of THF cooled at 0° C., was added lithium bis(trimethylsilyl)amide (13.94 ml, 20.92 mmol). It was allowed to stir at 0° C. for 0.5 h. A solution of compound Int-16m (3000 mg, 6.97 mmol) in 20 mL of THF was then added. The reaction was warmed to room temperature and stirred for 1 h. This was diluted with 200 mL of 70% EtOAc/hexanes. The solid was filtered off. The filtrate was concentrated in vacuo. The resulting residue was purified using a silica gel column (220 g)) eluting with 70% EtOAc/hexanes to provide compound Int-16n as a colorless film. LCMS anal. calcd. for $C_{19}H_{26}BrNO_5$: 427.1. Found: 428.0 $(M+1)^+$.

Step O—Synthesis of Compound Int-16o

To a solution of compound Int-16n (28 mg, 0.065 mmol) in 5 mL of dichloromethane, was added Zhang's (1B) olefin metathesis catalyst (8 mg, 10.89 µmol). The reaction was allowed to stir at room temperature for 2 h. It was concentrated in vacuo. The resulting residue was purified using a silica gel column (25 g) eluting with 5% MeOH/dichloromethane to provide compound Int-16o as a colorless film. LCMS anal. calcd. for $C_{17}H_{22}BrNO_5$: 401.1; Found: 401.8 $(M+1)^+$.

Step P—Synthesis of Compound Int-16p

To a solution of compound Int-16o (24 mg, 0.060 mmol) in MeOH (1 mL), was added 12 N aqueous HCl (200 µl, 2.435 mmol). The reaction was allowed to stir at 60° C. for 1 h. The reaction mixture was concentrated in vacuo. The resulting residue was neutralized by adding $Et_3N$. It was purified using ISCO, normal phase HP Gold silica gel (12 g), eluting with dichloromethane/MeOH (100% DCM for 5 min; gradient to 10% MeOH in dichloromethane over 12 min, isocratic for 5 min) to provide compound Int-16p as a white solid. LCMS anal. calcd. for $C_{15}H_{18}BrNO_4$: 355.04. Found: 355.84 $(M+1)^+$.

Step Q—Synthesis of Compound Int-16q and Compound Int-16r

To a solution of compound Int-16p (190 mg, 0.533 mmol) in 8 mL of dry dichloromethane, was added Dess-Martin periodinate (339 mg, 0.800 mmol). The reaction was allowed to stir at room temperature for 1 h. To the resulting solution, was added two drops of water. White solid was formed. The mixture was diluted with 20 mL of dichloromethane and filtered. The filtrate was washed with 10 mL of sat. $Na_2CO_3$ aqueous solution. The organic phase was isolated. The aqueous was extracted with 20 mL of 10% MeOH/dichloromethane solution. The combined organics were concentrated. The resulting residue was purified using a silica gel column (80 g) eluting with EtOAc to provide the cis-fused compound Int-16q and trans-fused compound Int-16r separately as white solids. LCMS anal. calcd. for $C_{15}H_{16}BrNO_4$: 353.03. Found: 353.82 $(M+1)^+$.

Step R—Synthesis of Compound Int-16s

A mixture of compound Int-16q (25.6 mg, 0.072 mmol), N-ethyl-N-isopropylpropan-2-amine (38.6 µl, 0.217 mmol)), (3-chloro-2-fluorophenyl)methanamine (14.99 mg, 0.094 mmol) and (oxybis(2,1-phenylene))bis(diphenylphosphine) (11.68 mg, 0.022 mmol) in DMSO (1.8 mL) was degassed for 5 min before adding diacetoxypalladium (4.87 mg, 0.022 mmol). The resulting mixture was flushed with a stream of CO under a balloon of CO for 30 min. The mixture was heated at 90° C. under CO balloon for 1 h. At completion, the reaction was diluted with DMSO and was filtered. The crude was purified using preparative HPLC (reverse phase, YMC-Pack ODS C-18 100×20 mm) eluting with acetonitrile/water/0.05% TFA (20% to 90% organic in 10 min, then to 100% in 2 min, 20 mL/min). Related fractions were pooled and evaporated under reduced pressure to afford compound Int-16s as its racemic mixture. This material was resolved by chiral preparative SFC (ChiralPak OJ, 20×250 mm, 50 ml/min, 100 bar, 25% MeOH (0.2% $NH_4OH$)/$CO_2$, 35° C.) to provide enantiomer A of compound Int-16s (the first eluting compound)) and enantiomer B of compound Int-16s (the second eluting compound). LCMS anal. calcd. for $C_{23}H_{22}ClFN_2O_5$ racemate: 460.12. Found: 461.01 $(M+1)^+$.

Step S—Synthesis of Compound Int-16t

Two enantiomers of compound Int-16s were converted into enantiomers of compound Int-16t separately by following the same method described in Step K of Example 10. LCMS anal. calcd. for $C_{22}H_{20}ClFN_2O_5$: 446.10. Found: enantiomer A-446.97 $(M+1)^+$; enantiomer B-446.99 $(M+1)^+$.

Step T—Synthesis of Compound 37 and Compound 38

To a solution of enantiomer B of compound Int-16t (6 mg, 10.70 µmol) in 2 mL of MeOH, was added Pd-C (0.569 mg, 5.35 µmol). The mixture was allowed to stir at room temperature under a balloon of $H_2$ for 1 h. At the completion, the catalyst was filtered off. The filtrate was concentrated in vacuo. The resulting residue was purified using preparative HPLC (reverse phase, YMC-Pack ODS C-18 100×20 mm) eluting with acetonitrile/water/0.1% TFA (20% to 90% organic in 10 min, then to 100% in 2 min, 20 mL/min). Related fractions were pooled and evaporated under reduced pressure to afford compound 38. Under essentially the same conditions, enantiomer B of compound Int-16t was converted into compound 37. Compound 37 and compound 38 show identical NMR and LCMS spectrum. $^1$H NMR (500

MHz, CDCl₃): δ 10.48 (brs, 1H); 8.48 (s, 1H); 7.29-7.33 (m, 2H); 7.05 (t, J=7.7 Hz, 1H); 4.74 (m, 2H); 4.42-4.45 (m, 1H); 4.23-4.31 (m, 1H); 3.94-3.98 (m, 1H); 3.85 (m, 1H); 3.67-3.69 (m, 1H); 2.33-2.46 (m, 1H); 1.77-1.80 (m, 1H); 1.62-1.75 (m, 4H); 1.30 (s, 3H). LCMS anal. calcd. for $C_{22}H_{22}ClFN_2O_5$: 448.12. Found: 448.97 (M+1)⁺.

Example 26

Preparation of Compound 39-42

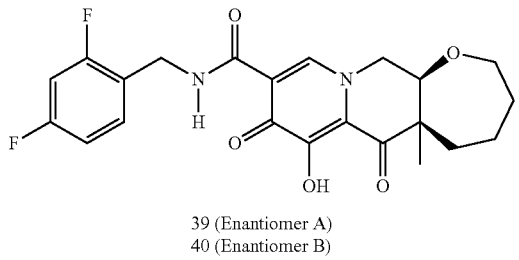

39 (Enantiomer A)
40 (Enantiomer B)

-continued

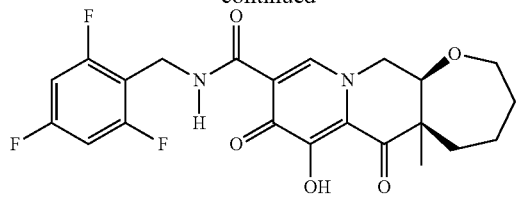

41 (Enantiomer A)
42 (Enantiomer B)

Starting from compound Int-16q, compound 39-42 were prepared by essentially the same method described from Step R to Step T of Example 25, only replacing 2,4-difluorobenzylamine with appropriate benzylamines in Step R. Compound 39 and 41 were prepared from the earlier eluting enantiomer in the chiral separation process of the corresponding intermediate in step R. Compound 40 and 42 were prepared from the later eluting enantiomer in the chiral separation process of the corresponding intermediate in step R.

| Compound # | Structure | Enantiomer | Rt (min) | M + 1 (found) |
|---|---|---|---|---|
| 39 | 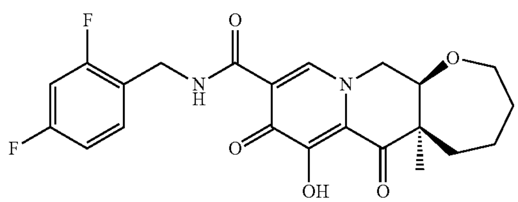 [SMILES: C[C@@]12CCCCO[C@@H]1Cn1cc(C(=O)NCc3ccc(F)cc3F)c(=O)c(O)c1C2=O] | A | 1.91 (LC3) | 433.0 |
| 40 | 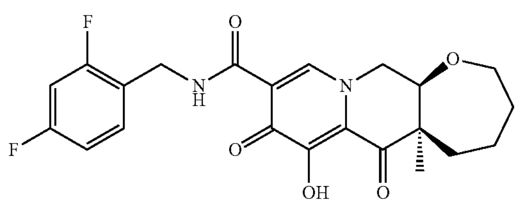 [SMILES: C[C@@]12CCCCO[C@@H]1Cn1cc(C(=O)NCc3ccc(F)cc3F)c(=O)c(O)c1C2=O] | B | 1.89 (LC3) | 433.0 |
| 41 | 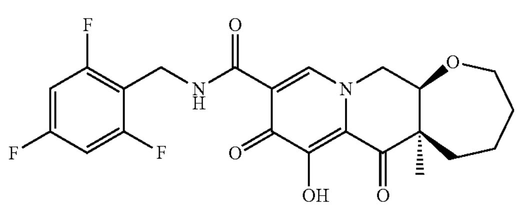 [SMILES: C[C@@]12CCCCO[C@@H]1Cn1cc(C(=O)NCc3c(F)cc(F)cc3F)c(=O)c(O)c1C2=O] | A | 1.92 (LC3) | 451.0 |
| 42 | 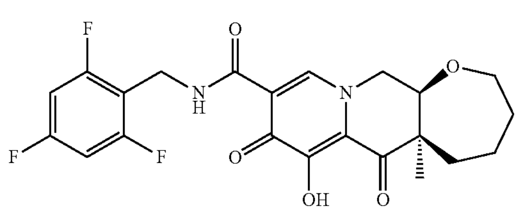 [SMILES: C[C@@]12CCCCO[C@@H]1Cn1cc(C(=O)NCc3c(F)cc(F)cc3F)c(=O)c(O)c1C2=O] | B | 1.92 (LC3) | 451.0 |

Example 27

Preparation of Compound 43-46

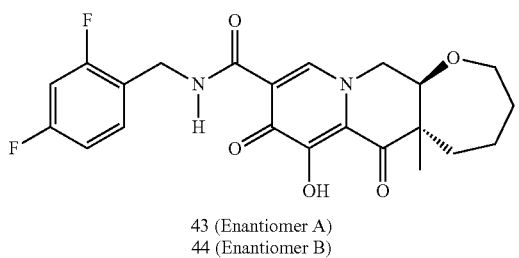

43 (Enantiomer A)
44 (Enantiomer B)

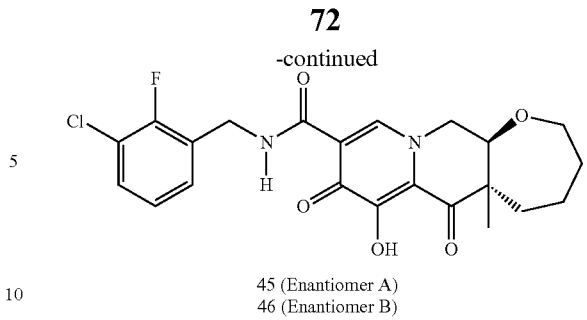

45 (Enantiomer A)
46 (Enantiomer B)

Starting from compound Int-16r, compound 43-46 were prepared by essentially the same method described from Step R to Step T of Example 25, employing appropriate benzylamines in Step R. Compound 43 and 45 were prepared from the earlier eluting enantiomer in the chiral separation process of the corresponding intermediate in step R. Compound 44 and 46 were prepared from the later eluting enantiomer in the chiral separation process of the corresponding intermediate in step R.

Compound 43: $^1$H NMR (500 MHz, CDCl$_3$): δ 10.44 (s, 2H); 8.51 (s, 1H); 7.38 (q, J=7.7 Hz, 2H); 7.29 (s, 1H); 6.81-6.86 (m, 2H); 4.68 (m, 2H); 4.05-4.20 (m, 3H); 3.88-3.92 (m, 2H); 2.26-2.29 (m, 1H); 1.92-2.01 (m, 1H); 1.85-1.91 (m, 1H); 1.72-1.83 (m, 3H); 1.32 (s, 3H). LCMS anal. calcd. for $C_{22}H_{22}F_2N_2O_5$: 432.15. Found: 433.06 (M+1)$^+$.

| Compound | Structure | Enantiomer | Rt (min) | M + 1 (found) |
|---|---|---|---|---|
| 43 | 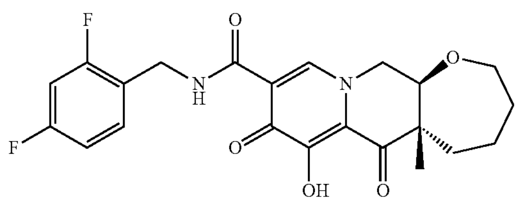 [SMILES: C[C@]12CCCCO[C@@H]1Cn1cc(C(=O)NCc3ccc(F)cc3F)c(=O)c(O)c1C2=O] | A | 1.93 (LC3) | 433.1 |
| 44 | 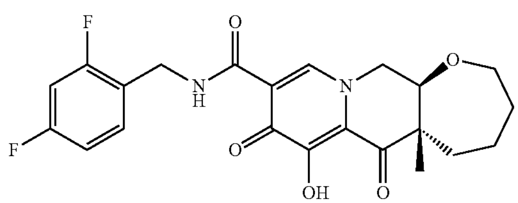 [SMILES: C[C@]12CCCCO[C@@H]1Cn1cc(C(=O)NCc3ccc(F)cc3F)c(=O)c(O)c1C2=O] | B | 1.96 (LC3) | 433.0 |
| 45 | 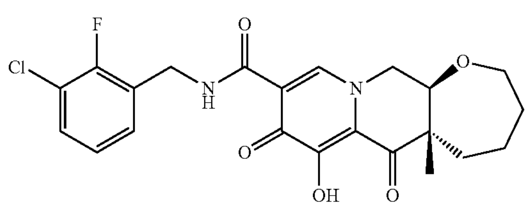 [SMILES: C[C@]12CCCCO[C@@H]1Cn1cc(C(=O)NCc3cccc(Cl)c3F)c(=O)c(O)c1C2=O] | A | 2.06 (LC3) | 449.0 |
| 46 | 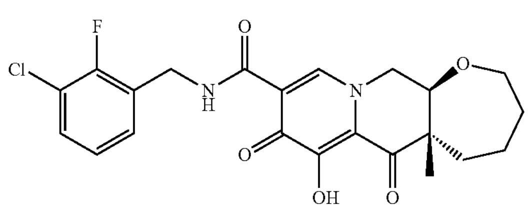 [SMILES: C[C@]12CCCCO[C@@H]1Cn1cc(C(=O)NCc3cccc(Cl)c3F)c(=O)c(O)c1C2=O] | B | 2.04 (LC3) | 449.0 |

Example 28

Preparation of Compound 47-50

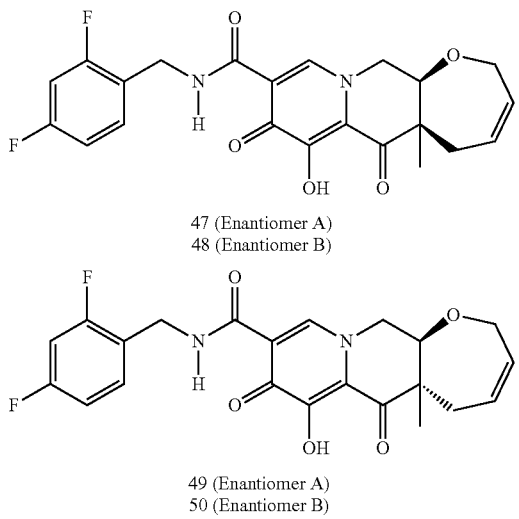

47 (Enantiomer A)
48 (Enantiomer B)

49 (Enantiomer A)
50 (Enantiomer B)

Starting from compound Int 16q, compound 47 and compound 48 were prepared by essentially the same method described from step R to step S of example 25. Compound 47 was prepared from the earlier eluting enantiomer in the chiral separation process of the corresponding intermediate in Step R. Compound 48 was prepared from the later eluting enantiomer in the chiral separation process of the corresponding intermediate in Step R. Similarly, compound 49 and compound 50 were prepared starting from compound Int 16r.

Compound 47: $^1$H NMR (500 MHz, CDCl$_3$) δ 10.42 (brs, 1H); 8.53 (s, 1H); 7.30-7.39 (m, 1H); 6.75-6.90 (m, 2H); 5.81-5.96 (m, 1H); 5.62-5.77 (m, 1H); 4.63-4.73 (m, 2H); 4.12-4.53 (m, 4H); 3.90-4.12 (m, 1H); 2.90 (dd, J=14.2, 6.6 Hz, 1H); 2.38 (dd, J=14.4, 6.7 Hz, 1H); 1.39 (s, 3H). LCMS anal. calcd. for C$_{22}$H$_{20}$F$_2$N$_2$O$_5$: 430.13. Found: 431.00 (M+1)$^+$.

Compound 48: $^1$H NMR (500 MHz, CDCl$_3$) δ 10.42 (brs, 1H); 8.53 (s, 1H); 7.30-7.39 (m, 1H); 6.75-6.90 (m, 2H); 5.81-5.96 (m, 1H); 5.62-5.77 (m, 1H); 4.63-4.73 (m, 2H); 4.12-4.53 (m, 4H); 3.90-4.12 (m, 1H); 2.90 (dd, J=14.2, 6.6 Hz, 1H); 2.38 (dd, J=14.4, 6.7 Hz, 1H); 1.39 (s, 3H). LCMS anal. calcd. for C$_{22}$H$_{20}$F$_2$N$_2$O$_5$: 430.13. Found: 431.00 (M+1)$^+$.

Compound 49: $^1$H NMR (500 MHz, CDCl$_3$): δ 10.36 (brs, 1H); 8.52 (s, 1H); 7.32-7.45 (m, 1H); 6.81-6.85 (m, 2H); 5.94 (m, 2H); 4.60-4.72 (m, 2H); 4.35-4.50 (m, 1H); 4.06-4.32 (m, 4H); 3.02-3.15 (m, 1H); 2.35-2.50 (m, 1H); 1.33 (s, 3H). LCMS anal. calcd. for C$_{22}$H$_{20}$F$_2$N$_2$O$_5$: 430.13. Found: 430.98 (M+1)$^+$.

Compound 50: $^1$H NMR (500 MHz, CDCl$_3$): δ 10.36 (brs, 1H); 8.52 (s, 1H); 7.32-7.45 (m, 1H); 6.81-6.85 (m, 2H); 5.94 (m, 2H); 4.60-4.72 (m, 2H); 4.35-4.50 (m, 1H); 4.06-4.32 (m, 4H); 3.02-3.15 (m, 1H); 2.35-2.50 (m, 1H); 1.33 (s, 3H). LCMS anal. calcd. for C$_{22}$H$_{20}$F$_2$N$_2$O$_5$: 430.13. Found: 430.98 (M+1)$^+$.

Example 29

Preparation of Compound 51-52

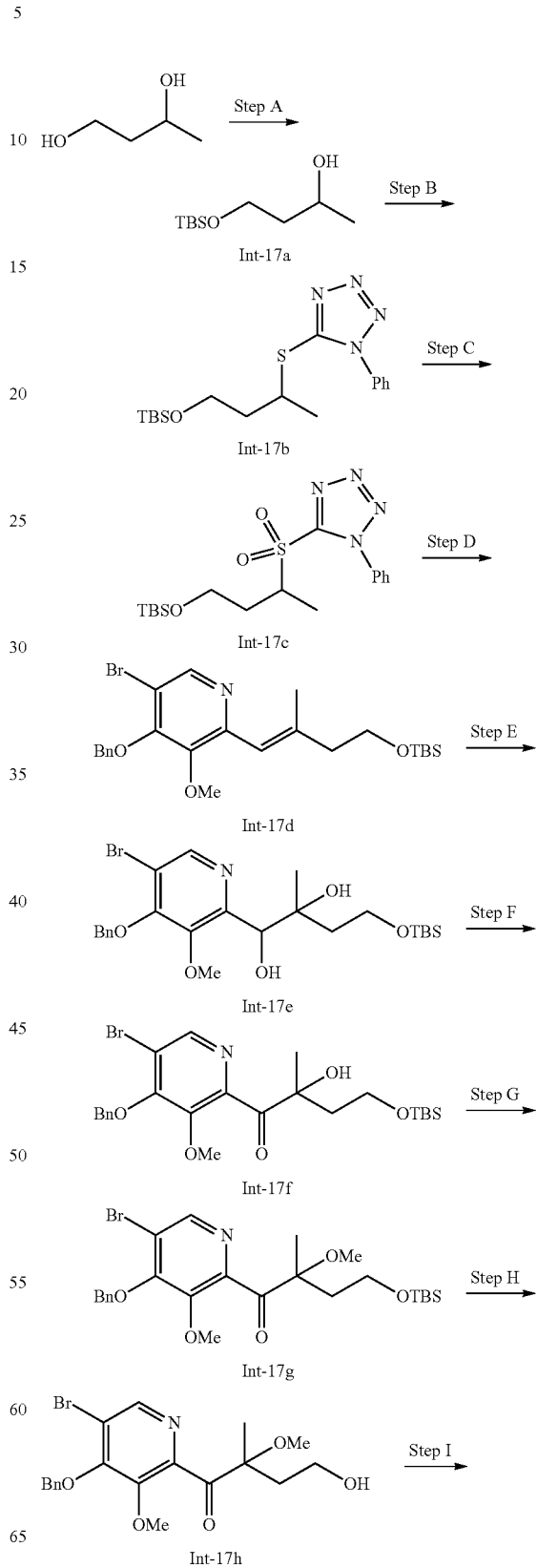

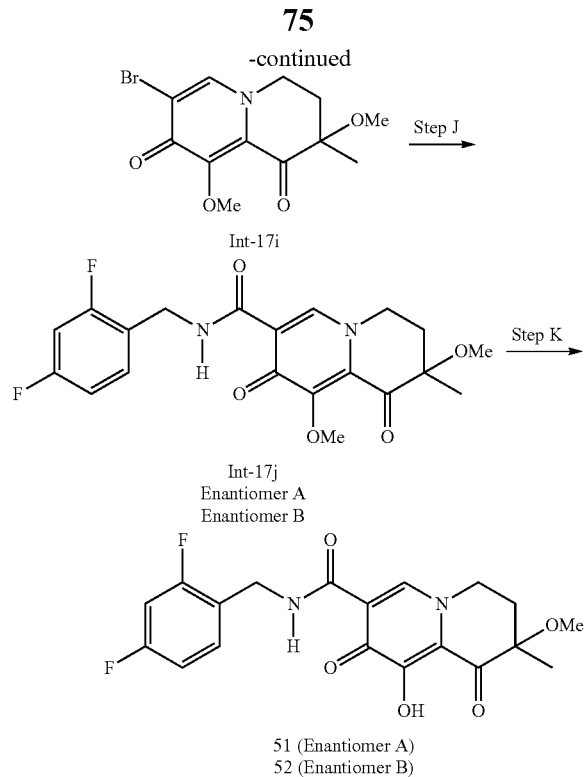

Step A—Synthesis of Compound Int-17a

To a solution of butane-1,3-diol (3.8 g, 42.2 mmol) in 30 mL of DMF, was added 1H-imidazole (5.74 g, 84 mmol). The solution was cooled to 0° C. and tert-butylchlorodimethylsilane (6.67 g, 44.3 mmol) was added. The reaction was allowed to stir at room temperature overnight. The solution was poured into 200 mL of water. The resulting mixture was extracted by 40% EtOAc/hexanes (120 mL×2). The combined organic phase was washed with 100 mL of 0.2 N HCl aqueous solution, and then 100 mL of brine. The solvent was removed in vacuo to provide compound Int-17a as a colorless oil. $^1$H NMR (400 MHz, CDCl$_3$): δ 4.00-4.08 (m, 1H), 3.80-3.94 (m, 2H), 1.55-1.72 (m, 2H), 1.21 (d, J=6.2 Hz, 3H), 0.92 (s, 9H), 0.10 (s, 6H).

Step B—Synthesis of Compound Int-17b

To a solution of compound Int-17a (1500 mg, 7.34 mmol) in 23 mL of THF, was added triphenylphosphine (4812 mg, 18.35 mmol) and 1-phenyl-1H-tetrazole-5-thiol (1962 mg, 11.01 mmol). The solution was cooled to 0° C., and diisopropyl diazene-1,2-dicarboxylate (3.61 ml, 18.35 mmol) was then added dropwise. The reaction was then warmed to room temperature and stirred for 20 h. The mixture was diluted with 100 mL of 20% EtOAc/hexanes. It was then filtered. The filtrate was concentrated. The resulting residue was purified using a silica gel column (120 g) eluting with 10% EtOAC/hexanes to provide compound Int-17b as a colorless oil. LCMS anal. calcd. for C$_{17}$H$_{28}$N$_4$OSSi: 364.2. Found: 365.1 (M+1)$^+$.

Step C—Synthesis of Compound Int-17c

To a solution of compound Int-17b (1.840 g, 5.05 mmol) in 20 mL of EtOH cooled at 0° C., was added a pre-mixed solution of NH$_4$ molybdate tetrahydrate (2.495 g, 2.019 mmol) in 10 mL of 30% H$_2$O$_2$ in water. The resulting mixture was warmed to room temperature and stirred for 3 h. To this was added 100 mL of saturated NaHCO$_3$ aq. solution. It was extracted by 50% EtOAc/hexanes (60 mL×2). The organic phase was concentrated. The resulting residue was purified using a silica gel column eluting with 20% EtOAc/hexanes to provide compound Int-17c as a colorless oil. LCMS anal. calcd. for C$_{17}$H$_{28}$N$_4$OSSi: 396.2. Found: 397.2 (M+1)$^+$.

Step D—Synthesis of Compound Int-17d

To a solution of compound Int-17c (98 mg, 0.248 mmol) in 4 mL of THF cooled at −78° C., was added sodium bis(trimethylsilyl)amide (1 M in THF) (0.497 ml, 0.497 mmol). The yellowish solution was allowed to stir at −78° C. for 30 min. A solution of compound Int-1 (80 mg, 0.248 mmol) in 1 mL of THF was then added. The reaction was allowed to stir at −78° C. for 1 h. It was warmed to 0° C. by allowing the ice bath expire. During the time, the color of the reaction changed from blue/green to yellowish. It was quenched by 10 mL of saturated aqueous NH$_4$Cl solution. The resulting mixture was extracted by 20 mL of 50% EtOAc/hexanes. The organic phase was concentrated in vacuo. The resulting residue was purified using a silica gel column (40 g) eluting with 12% EtOAc/hexanes to provide a compound Int-17d as a colorless film. LCMS anal. calcd. for C$_{24}$H$_{34}$BrNO$_3$Si: 491.2. Found: 492.0 (M+1)$^+$.

Step E—Synthesis of Compound Int-17e

To a solution of compound Int-17d (40 mg, 0.081 mmol) in 1 mL of t-BuOH/water/pyridine (5:5:1), was added methanesulfonamide (15.45 mg, 0.162 mmol), potassium ferricyanide (80 mg, 0.244 mmol), and potassium carbonate (67.3 mg, 0.487 mmol), followed by osmium(VIII) oxide (0.050 ml, 4.06 μmol). The reaction was allowed to stir at room temperature for 1 day. LCMS indicates it was less than half completed. To this was added a solution of 1 M sodium hydroxide (0.162 ml, 0.162 mmol). The reaction was stirred for additional 1 day. It was diluted with 1 mL of THF, and quenched by adding 700 mg of sodium bissulfite. The mixture was diluted with 20 mL of EtOAc, and washed with water (20 mL). The organic phase was concentrated in vacuo and the resulting residue was purified using a silica gel prep-TLC plate (1000 mm) eluting with 50% EtOAc/hexanes to provide compound Int-17e as a white film. LCMS anal. calcd. for C$_{24}$H$_{36}$BrNO$_5$Si: 527.2. Found: 528.0 (M+1)$^+$.

Step F—Synthesis of Compound Int-17f

2-Iodoxybenzoic acid (42.5 mg, 0.152 mmol) was stirred in 1 mL of DMSO for 5 min until it dissolved. The resulting solution was added into a flask containing compound Int-17e (40 mg, 0.076 mmol). The reaction was allowed to stir at room temperature for 4 h. This was diluted with 20 mL of 50% EtOAc/hexanes, and washed with water. The organic phase was concentrated in vacuo and purified using a silica gel prep-TLC plate (1000 mm) eluting with 30% EtOAc/hexanes to provide compound Int-17f as a colorless film. LCMS anal. calcd. for C$_{24}$H$_{34}$BrNO$_5$Si: 525.1. Found: 526.0 (M+1)$^+$.

Step G—Synthesis of Compound Int-17g

To a solution of compound Int-17f (28 mg, 0.053 mmol) in 1 mL of DMF, was added iodomethane (30.3 mg, 0.214 mmol). This was cooled to 0° C. and sodium hydride (6.41 mg, 0.160 mmol) was then added. The reaction was allowed to stir at 0° C. for 15 min. It was then quenched by adding 10 mL of water. This was extracted by 20 mL of 40% EtOAc/hexanes. The organic phase was concentrated. The resulting residue was purified using a silica gel prep-TLC plate (1000 mm) eluting with 10% EtOAc/hexanes to provide compound Int-17g as a colorless film. LCMS anal. calcd. for C$_{25}$H$_{36}$BrNO$_5$Si: 539.2. Found: 540.1 (M+1)$^+$.

Step H—Synthesis of Compound Int-17h

To a solution of compound Int-17g (20 mg, 0.037 mmol) in 1 mL of MeOH, was added 0.5 mL of 1.25 M HCl in MeOH. The reaction was allowed to stir at room temperature for 15 min. The solvent was removed in vacuo. The resulting residue was diluted in 2 mL of dichloromethane. To this was added 0.2 mL of NEt₃. The resulting solution was purified using a silica gel column (25 g), eluting with 80% EtOAc/hexanes to provide compound Int-17h as a colorless film. LCMS anal. calcd. for C₁₉H₂₂BrNO₅: 425.1. Found: 425.9 (M+1)⁺.

Step I—Synthesis of Compound Int-17i

To a solution of compound Int-17h (10 mg, 0.024 mmol) in 0.5 mL of pyridine, was added 4-methylbenzene-1-sulfonyl chloride (17.97 mg, 0.094 mmol). The reaction was allowed to stir at room temperature overnight. At this time, 0.5 mL of MeOH was added. It was allowed to stir at room temperature for 1 h. The reaction was diluted with 2 mL of toluene and then concentrated in vacuo. The resulting residue was purified using a silica gel prep-TLC plate eluting with EtOAc to provide compound Int-17i as a colorless film. LCMS anal. calcd. for C₁₂H₁₄BrNO₄: 317.0. Found: 318.1 (M+1)⁺.

Step J—Synthesis of Compound Int-17j

A mixture of compound Int-17i (18 mg, 0.057 mmol), N-ethyl-N-isopropylpropan-2-amine (30.4 µl, 0.171 mmol)), (2,4-difluorophenyl)methanamine (10.19 µl, 0.085 mmol) and (oxybis(2,1-phenylene))bis(diphenylphosphine) (6.13 mg, 0.011 mmol) in DMSO (569 µl) was added diacetoxypalladium (2.56 mg, 0.011 mmol). CO balloon was attached to the reaction vessel and CO gas was bubbled through a long needle to the mixture at room temperature for 20 min. The mixture was then heated under CO balloon at 80° C. for 2 h. At completion, the reaction was diluted with 1.5 mL of DMSO and was then filtered. The filtrate was purified using preparative HPLC (reverse phase, YMC-Pack ODS C-18 100×20 mm) eluting with acetonitrile/water/0.1% TFA (10% to 90% organic in 10 min, then to 100% in 2 min, 20 mL/min). Related fractions were pooled and evaporated under reduced pressure to afford compound Int-17j as a racemate. This material was further resolved by a chiral preparative SFC (ChiralPak AD, 30×250 mm, 70 mL/min, 100 bar, 40% MeOH (0.2% NH₄OH)/CO₂, 35° C.) to provide enantiomer A of compound Int-17j (first to elute) and enantiomer B of compound Int-17j (second to elute) as pure enantiomers. LCMS anal. calcd. for C₂₀H₂₀F₂N₂O₅: 406.13; Found: 407.05 (M+1)⁺.

Step K—Synthesis of Compound 51 and Compound 52

Using the method described in Step K in example 10, compound 51 was prepared from enantiomer A of compound Int-17j. Similarly, compound 52 was prepared from enantiomer B of compound Int-17j.

Compound 51: ¹H NMR (500 MHz, CDCl₃): δ 10.32 (brs, 1H); 8.46 (s, 1H); 7.35-7.42 (m, 1H); 6.78-6.88 (m, 2H); 4.56-4.71 (m, 3H); 4.01-4.15 (m, 1H); 3.30 (s, 3H); 2.26-2.47 (m, 2H); 1.51 (s, 3H). LCMS anal. calcd. for C₁₉H₁₈F₂N₂O₅: 392.12. Found: 392.94 (M+1)⁺.

Compound 52: ¹H NMR (500 MHz, CDCl₃): δ 10.32 (brs, 1H); 8.46 (s, 1H); 7.35-7.42 (m, 1H); 6.78-6.88 (m, 2H); 4.56-4.71 (m, 3H); 4.01-4.15 (m, 1H); 3.30 (s, 3H); 2.26-2.47 (m, 2H); 1.51 (s, 3H). LCMS anal. calcd. for C₁₉H₁₈F₂N₂O₅: 392.12. Found: 392.94 (M+1)⁺.

Example 30

Preparation of Compound 53

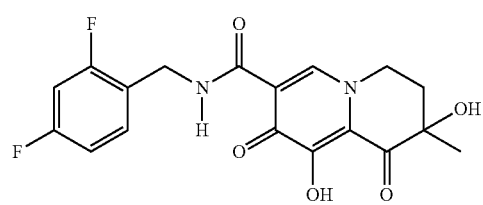

Starting from compound Int-17f, compound 53 was prepared as its racemic mixture following essentially the same procedure from Step H to Step K of example 29. ¹H NMR (500 MHz, DMSO): δ 10.29 (brs, 1H); 8.42 (s, 1H); 7.37-7.42 (m, 1H); 7.21-7.25 (m, 1H); 7.05 (m, 1H); 6.02 (s, 1H); 4.50-4.58 (m, 2H); 4.27-4.45 (m, 2H); 2.11-2.30 (m, 2H); 1.36 (s, 3H). LCMS anal. calcd. for C₁₈H₁₆F₂N₂O₅: 378.10. Found: 378.94 (M+1)⁺.

Example 31

Preparation of Compound 54-57

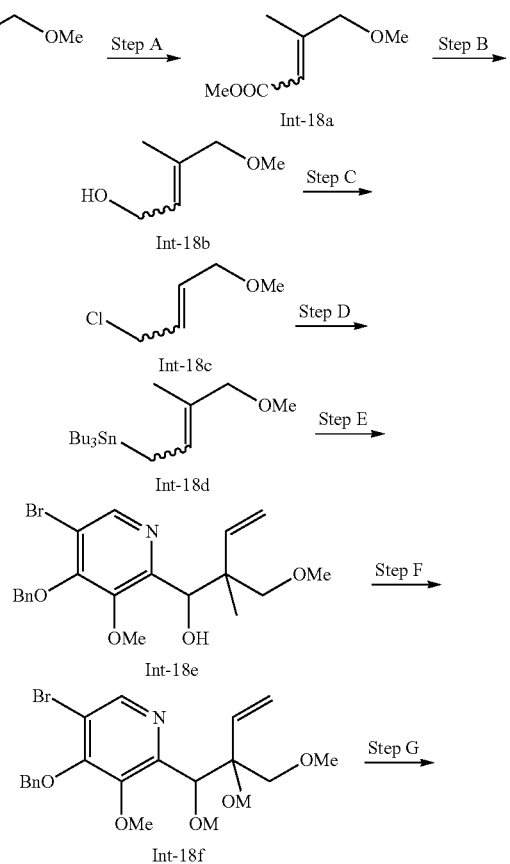

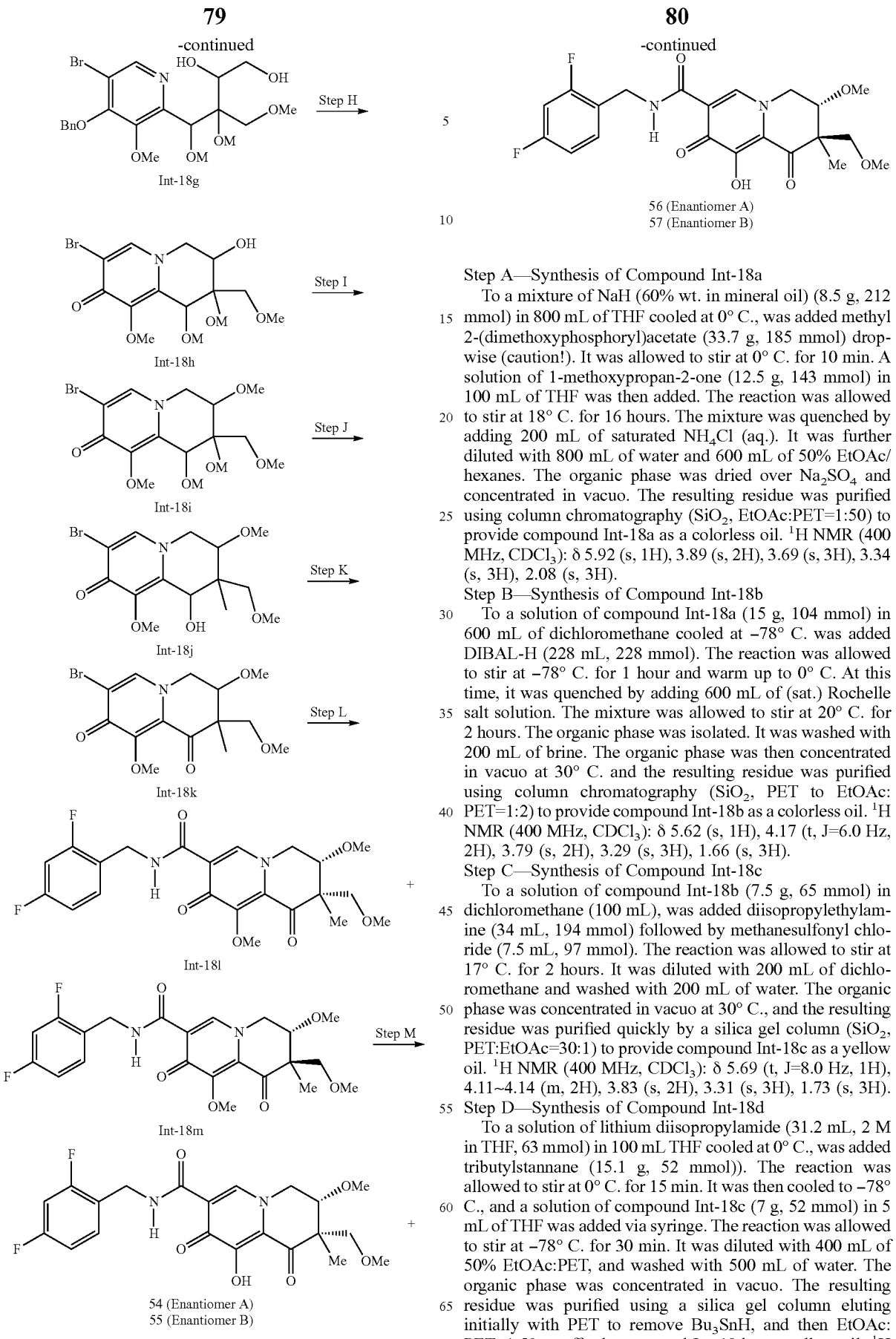

Step A—Synthesis of Compound Int-18a

To a mixture of NaH (60% wt. in mineral oil) (8.5 g, 212 mmol) in 800 mL of THF cooled at 0° C., was added methyl 2-(dimethoxyphosphoryl)acetate (33.7 g, 185 mmol) dropwise (caution!). It was allowed to stir at 0° C. for 10 min. A solution of 1-methoxypropan-2-one (12.5 g, 143 mmol) in 100 mL of THF was then added. The reaction was allowed to stir at 18° C. for 16 hours. The mixture was quenched by adding 200 mL of saturated NH$_4$Cl (aq.). It was further diluted with 800 mL of water and 600 mL of 50% EtOAc/hexanes. The organic phase was dried over Na$_2$SO$_4$ and concentrated in vacuo. The resulting residue was purified using column chromatography (SiO$_2$, EtOAc:PET=1:50) to provide compound Int-18a as a colorless oil. $^1$H NMR (400 MHz, CDCl$_3$): δ 5.92 (s, 1H), 3.89 (s, 2H), 3.69 (s, 3H), 3.34 (s, 3H), 2.08 (s, 3H).

Step B—Synthesis of Compound Int-18b

To a solution of compound Int-18a (15 g, 104 mmol) in 600 mL of dichloromethane cooled at −78° C. was added DIBAL-H (228 mL, 228 mmol). The reaction was allowed to stir at −78° C. for 1 hour and warm up to 0° C. At this time, it was quenched by adding 600 mL of (sat.) Rochelle salt solution. The mixture was allowed to stir at 20° C. for 2 hours. The organic phase was isolated. It was washed with 200 mL of brine. The organic phase was then concentrated in vacuo at 30° C. and the resulting residue was purified using column chromatography (SiO$_2$, PET to EtOAc:PET=1:2) to provide compound Int-18b as a colorless oil. $^1$H NMR (400 MHz, CDCl$_3$): δ 5.62 (s, 1H), 4.17 (t, J=6.0 Hz, 2H), 3.79 (s, 2H), 3.29 (s, 3H), 1.66 (s, 3H).

Step C—Synthesis of Compound Int-18c

To a solution of compound Int-18b (7.5 g, 65 mmol) in dichloromethane (100 mL), was added diisopropylethylamine (34 mL, 194 mmol) followed by methanesulfonyl chloride (7.5 mL, 97 mmol). The reaction was allowed to stir at 17° C. for 2 hours. It was diluted with 200 mL of dichloromethane and washed with 200 mL of water. The organic phase was concentrated in vacuo at 30° C., and the resulting residue was purified quickly by a silica gel column (SiO$_2$, PET:EtOAc=30:1) to provide compound Int-18c as a yellow oil. $^1$H NMR (400 MHz, CDCl$_3$): δ 5.69 (t, J=8.0 Hz, 1H), 4.11~4.14 (m, 2H), 3.83 (s, 2H), 3.31 (s, 3H), 1.73 (s, 3H).

Step D—Synthesis of Compound Int-18d

To a solution of lithium diisopropylamide (31.2 mL, 2 M in THF, 63 mmol) in 100 mL THF cooled at 0° C., was added tributylstannane (15.1 g, 52 mmol)). The reaction was allowed to stir at 0° C. for 15 min. It was then cooled to −78° C., and a solution of compound Int-18c (7 g, 52 mmol) in 5 mL of THF was added via syringe. The reaction was allowed to stir at −78° C. for 30 min. It was diluted with 400 mL of 50% EtOAc:PET, and washed with 500 mL of water. The organic phase was concentrated in vacuo. The resulting residue was purified using a silica gel column eluting initially with PET to remove Bu$_3$SnH, and then EtOAc:PET=1:50 to afford compound Int-18d as a yellow oil. $^1$H NMR (400 MHz, CDCl$_3$) δ 5.60~5.72 (m, 1H), 4.11~4.15 (m, 2H), 3.31 (s, 3H), 1.62~1.82 (m, 5H), 1.43~1.53 (m, 6H), 1.24~1.34 (m, 6H), 0.76~0.96 (m, 15H).

Step E—Synthesis of Compound Int-18e

To a solution of compound Int-1 (4.1 g, 12.7 mmol) and compound Int-18d (6 g, 15.27 mmol) in acetonitrile (100 mL) stirred at 0° C., was added Tin (II) chloride (3.62 g, 19.1 mmol). The reaction was then warmed to 16° C. and stirred for 2 hours. The progress of the reaction was monitored by TLC and LCMS. The mixture was diluted with 50 mL EtOAc, and 100 mL of 15% (wt) NH$_4$F aqueous solution. The resulting mixture was allowed to stir at 16° C. for 15 min. Solid was filtered off. The organic from the mother liquor was extracted EtOAc (50 mL×3) and the organic phase was dried over anhydrous Na$_2$SO$_4$, concentrated in vacuo and the resulting residue was purified using column chromatography (SiO$_2$, PET:EtOAc=3:1) to provide compound Int-18e as a colorless oil. $^1$H NMR (400 MHz, CDCl$_3$): δ 8.37 (s, 1H), 7.47 (d, J=6.0 Hz, 2H), 7.35-7.39 (m, 3H), 6.04-6.12 (m, 1H), 4.88-5.22 (m, 4H), 3.87-3.98 (m, 1H), 3.86 (s, 3H), 3.48-3.55 (m, 2H), 3.37 (s, 3H), 3.24-3.27 (m, 1H), 0.93 (s, 3H). MS (M+H)$^+$: 422.

Step F—Synthesis of Compound Int-18f

Under a nitrogen atmosphere, MOMCl (4.3 mL, 56.8 mmol) was added to a solution of compound Int-18e (4.8 g, 11.4 mmol), diisopropylethylamine (20 mL, 114 mmol) and DMAP (0.72 g, 5.76 mmol) in anhydrous dichloromethane (80 mL) at 0° C. The reaction mixture was allowed to stir at 35° C. for 16 hours and washed with saturated aqueous NaHCO$_3$ solution, extracted with dichloromethane (40 mL×3). The organic phase was dried over anhydrous Na$_2$SO$_4$, concentrated in vacuo and purified using column chromatography (SiO$_2$, dichloromethane:EtOAc=1:1) to provide compound Int-18f as a yellow oil. $^1$H NMR (400 MHz, CDCl$_3$): δ 8.42 (s, 1H), 7.47 (d, J=6.0 Hz, 2H), 7.35-7.39 (m, 3H), 6.08-6.14 (m, 1H), 5.16-5.29 (m, 4H), 4.87-5.11 (m, 2H), 4.46-4.65 (m, 2H), 3.88 (s, 3H), 3.58-3.60 (m, 1H), 3.35 (s, 3H), 3.20 (s, 3H), 1.12 (s, 3H). MS (M+H)$^+$: 466.

Step G—Synthesis of Compound Int-18g

To a solution of compound Int-18f (4.8 g, 10.3 mmol)) in 110 mL of THF/t-BuOH/water (5:5:1), was added NMO (2.4 g, 20.6 mmol), followed by osmium tetroxide (262 mg, 1 mmol) in H$_2$O. The reaction was allowed to stir at 16° C. for 16 hours. To this was added Na$_2$SO$_3$ aqueous solution. The mixture was allowed to stir at 16° C. for 1 hour and extracted with EtOAc (50 mL×3), the organic phase was dried over anhydrous Na$_2$SO$_4$ and concentrated, the resulting residue was purified using column chromatography (SiO$_2$, dichloromethane:MeOH=20:1) to afford compound Int-18g as yellow oil. $^1$H NMR (400 MHz, CDCl$_3$): δ 8.44 (s, 1H), 7.47 (d, J=6.0 Hz, 2H), 7.35-7.39 (m, 3H), 5.17-5.35 (m, 4H), 4.44-4.60 (m, 2H), 3.91 (s, 3H), 3.63-3.66 (m, 4H), 3.19-3.34 (m, 8H), 1.04 (s, 3H). MS (M+H)$^+$: 500.

Step H—Synthesis of Compound Int-18h

To a mixture of compound Int-18g (4.0 g, 8.00 mmol) in pyridine (30 mL) was added p-TsCl (2.0 g, 10.4 mmol). The reaction solution was allowed to stir at 30° C. for 16 hours. The reaction was concentrated. The resulting residue was purified using column chromatography (SiO$_2$, DCM:EtOAc=1:1) to provide compound Int-18h as a yellow oil. $^1$H NMR (400 MHz, CDCl$_3$): δ 7.68 (s, 1H), 4.38~5.00 (m, 4H), 3.75~4.25 (m, 4H), 3.18~3.47 (m, 8H), 2.96~3.03 (m, 1H), 0.85~0.88 (m, 3H). MS (M+H)$^+$: 392.

Step I—Synthesis of Compound Int-18i

To a solution of compound Int-18h (2.0 g, 5.1 mmol) in DMF (20 mL) was added NaH (60% wt. in mineral oil) (0.6 g, 15.3 mmol). The reaction mixture was allowed to stir at 15° C. for 10 min, iodomethane (3.2 mL, 51 mmol) was then added, and the reaction mixture was allowed to stir at 15° C. for 1 hour. It was quenched by water, extracted with dichloromethane (20 mL×5), the organic phase was concentrated. The resulting residue was purified using column chromatography (SiO$_2$, DCM:MeOH=30:1) to afford compound Int-18i as a yellow oil. $^1$H NMR (400 MHz, CDCl$_3$): δ 7.63 (s, 1H), 4.61-5.04 (m, 4H), 3.94-3.98 (m, 4H), 3.20-3.45 (m, 12H), 0.83-0.87 (m, 3H). MS (M+H)$^+$: 406.

Step J—Synthesis of Compound Int-18j

To a stirred solution of compound Int-18i (1.0 g, 2.46 mmol) in MeOH (20 mL) was added p-TsOH (1.873 g, 9.85 mmol). The reaction mixture was allowed to stir at 35° C. for 48 hours. The solvent was removed in vacuo. The resulting residue was washed with saturated aqueous NaHCO$_3$ solution, extracted with dichloromethane (30 mL×5), the organic phase was concentrated in vacuo and purified using column chromatography (SiO$_2$, dichloromethane:MeOH=30:1) to provide compound Int-18j as a yellow oil. $^1$H NMR (400 MHz, CDCl$_3$): δ 7.63 (s, 1H), 4.70-5.08 (m, 2H), 3.79-4.79 (m, 4H), 3.30-3.51 (m, 10H), 1.19-1.26 (m, 3H). MS (M+H)$^+$: 362.

Step K—Synthesis of Compound Int-18k

To a stirred solution of compound Int-18j (500 mg, 1.38 mmol) in 1,2-dichloroethane (15 mL) was added Dess-Martin periodinane (585 mg, 1.38 mmol). The reaction mixture was allowed to stir at 15° C. for 2 hours. The solvent was concentrated in vacuo and the resulting residue was purified using column chromatography (SiO$_2$, dichloromethane:MeOH=10:1) to provide compound Int-18k as a yellow solid. $^1$H NMR (400 MHz, CDCl$_3$): δ 7.69 (s, 1H), 3.26-4.35 (m, 14H), 1.17 (m, 3H). MS (M+H)$^+$: 360.

Step L—Synthesis of Compound Int-18l and Compound Int-18m

To a mixture of compound Int-18k (60 mg, 0.167 mmol), diisopropylethylamine (0.116 mL, 0.666 mmol) and (2,4-difluorophenyl)methanamine (47.7 mg, 0.333 mmol) in DMSO (5 mL) was added Pd (Ph$_3$P)$_4$ (96 mg, 0.083 mmol) under N$_2$. The mixture was allowed to stir at 80° C. for 4 hours under a CO balloon. The reaction mixture was diluted with EtOAc, and washed with diluted HCl. The organic phase was dried over anhydrous Na$_2$SO$_4$. It was then concentrated in vacuo and purified via prep-TLC (SiO$_2$, EtOAc:PET=1:1) to afford compound Int-18l and compound Int-18m as yellow oil.

Compound Int-18l: $^1$H NMR (400 MHz, CDCl$_3$): δ 10.39 (s, 1H), 8.37 (s, 1H), 7.26-7.32 (m, 1H), 6.70-6.78 (m, 2H), 4.56 (d, J=5.6 Hz, 2H), 4.22~4.34 (m, 2H), 3.93 (s, 3H), 3.75 (s, 1H), 3.67 (d, J=8.8 Hz, 1H), 3.54 (d, J=8.8 Hz, 1H), 3.36 (s, 3H), 3.30 (s, 3H), 1.21 (m, 3H). MS (M+H)$^+$: 451.

Compound Int-18m: $^1$H NMR (400 MHz, CDCl$_3$): δ 10.39 (s, 1H), 8.39 (s, 1H), 7.26-7.32 (m, 1H), 6.75-6.81 (m, 2H), 4.62 (d, J=5.6 Hz, 2H), 4.46-4.49 (m, 1H), 4.10-4.19 (m, 1H), 4.00 (s, 3H), 3.84 (d, J=3.2 Hz, 1H), 3.71 (d, J=8.8 Hz, 1H), 3.38-3.42 (m, 4H), 3.25 (s, 3H), 1.17 (m, 3H). MS (M+H)$^+$: 451.

Compound Int-18l was further purified using a chiral preparative SFC (Column: Chiralpak AS-H 250×4.6 mm I.D., 5 um Mobile phase: isopropanol (0.05% DEA) in CO$_2$ from 5% to 40% Flow rate: 2.5 mL/min Wavelength: 220 nm) to provide an earlier eluting component which is corresponding to the enantiomer A of compound Int-18l (MS (M+H)$^+$: 451), and a later eluting component corresponding to the enantiomer B of compound Int-18l (MS (M+H)$^+$: 451).

Compound Int-18m was further purified using a chiral preparative SFC (Column: Chiralpak AS-H 250×4.6 mm I.D., 5 um Mobile phase: isopropanol (0.05% DEA) in $CO_2$ from 5% to 40% Flow rate: 2.5 mL/min Wavelength: 220 nm) to provide an earlier eluting component which is corresponding to the enantiomer A of compound Int-18m (MS (M+H)$^+$: 451), and a later eluting component corresponding to the enantiomer B of compound Int-18m (MS (M+H)$^+$: 451).

Step M—Synthesis of Compound 54-57

Following essentially the same method described in Step K of Example 10, starting from enantiomer A of compound Int-18l, compound 54 was prepared. Similarly, compound 55 was prepared from enantiomer B of compound Int-18l.

Compound 54: $^1$H NMR (400 MHz, CDCl$_3$): δ 10.40 (s, 1H), 8.43 (s, 1H), 7.32-7.36 (m, 1H), 6.77-6.83 (m, 2H), 4.63-4.66 (m, 2H), 4.41 (d, J=4.0 Hz, 1H), 4.28-4.32 (m, 1H), 3.83 (s, 1H), 3.67-3.74 (m, 2H), 3.44 (s, 3H), 3.37 (s, 3H), 1.35 (m, 3H). MS (M+H)$^+$: 437.

Compound 55: $^1$H NMR (400 MHz, CDCl$_3$): δ 10.40 (s, 1H), 8.43 (s, 1H), 7.32-7.36 (m, 1H), 6.77-6.83 (m, 2H), 4.63-4.66 (m, 2H), 4.41 (d, J=4.0 Hz, 1H), 4.28-4.32 (m, 1H), 3.82 (s, 1H), 3.67-3.74 (m, 2H), 3.44 (s, 3H), 3.37 (s, 3H), 1.35 (m, 3H). MS (M+H)$^+$: 437.

Following essentially the same method described in Step K of Example 10, starting from enantiomer A of compound Int-18m, compound 56 was prepared. Similarly, compound 57 was prepared from enantiomer B of compound Int-18m.

Compound 56: $^1$H NMR (400 MHz, CDCl$_3$): δ 10.45 (s, 1H), 8.43 (s, 1H), 7.32-7.36 (m, 1H), 6.77-6.83 (m, 2H), 4.58-4.66 (m, 3H), 4.26-4.29 (m, 1H), 3.81 (d, J=2.4 Hz, 1H), 3.65 (d, J=9.6 Hz, 1H), 3.43-3.47 (m, 4H), 3.24 (s, 3H), 1.27 (m, 3H). MS (M+H)$^+$: 437.

Compound 57: $^1$H NMR (400 MHz, CDCl$_3$): δ 10.45 (s, 1H), 8.43 (s, 1H), 7.32~7.36 (m, 1H), 6.77~6.83 (m, 2H), 4.58~4.66 (m, 3H), 4.26~4.29 (m, 1H), 3.81 (d, J=2.4 Hz, 1H), 3.65 (d, J=9.6 Hz, 1H), 3.43~3.47 (m, 4H), 3.25 (s, 3H), 1.27 (m, 3H). MS (M+H)$^+$: 437.

Example 32

Preparation of Compound 58-61

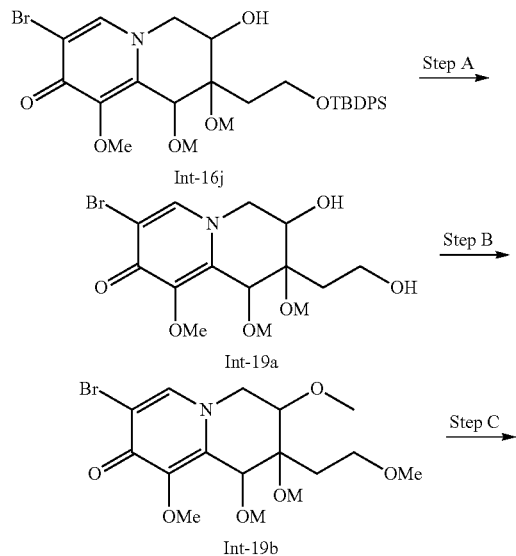

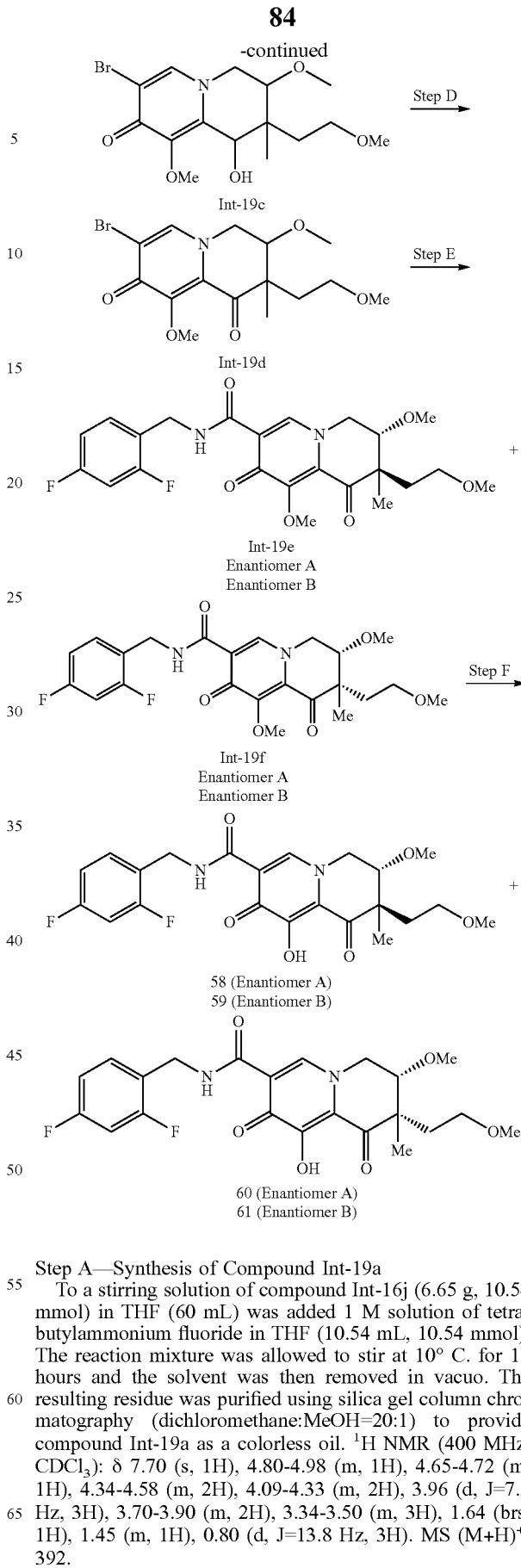

Step A—Synthesis of Compound Int-19a

To a stirring solution of compound Int-16j (6.65 g, 10.54 mmol) in THF (60 mL) was added 1 M solution of tetrabutylammonium fluoride in THF (10.54 mL, 10.54 mmol). The reaction mixture was allowed to stir at 10° C. for 18 hours and the solvent was then removed in vacuo. The resulting residue was purified using silica gel column chromatography (dichloromethane:MeOH=20:1) to provide compound Int-19a as a colorless oil. $^1$H NMR (400 MHz, CDCl$_3$): δ 7.70 (s, 1H), 4.80-4.98 (m, 1H), 4.65-4.72 (m, 1H), 4.34-4.58 (m, 2H), 4.09-4.33 (m, 2H), 3.96 (d, J=7.2 Hz, 3H), 3.70-3.90 (m, 2H), 3.34-3.50 (m, 3H), 1.64 (brs, 1H), 1.45 (m, 1H), 0.80 (d, J=13.8 Hz, 3H). MS (M+H)$^+$: 392.

Step B—Synthesis of Compound Int-19b

To a stirred mixture of compound Int-19a (3.5 g, 8.92 mmol) in THF (50 mL) cooled at 0° C., was added NaH (60% wt in mineral oil) (2.141 g, 53.5 mmol). The reaction mixture was allowed to stir at 10° C. for 20 minutes, and iodomethane (19 g, 134 mmol) was added. The reaction mixture was allowed to stir at 10° C. for 16 hours. It was quenched by water (2 mL) and the solvent was removed in vacuo. The resulting residue was purified using silica gel column chromatography (dichloromethane:MeOH=25:1) to provide compound Int-19b as a colorless oil. $^1$H NMR (400 MHz, CDCl$_3$): δ 7.60-7.69 (m, 1H), 4.89-5.05 (m, 1H), 4.36-4.76 (m, 3H), 4.07-4.23 (m, 1H), 3.93-4.05 (m, 3H), 3.69-3.85 (m, 1H), 3.55 (t, J=7.0 Hz, 1H), 3.22-3.48 (m, 10H), 1.66-1.73 (m, 1H), 1.42-1.52 (m, 1H), 0.71-1.03 (m, 3H). MS (M+H)$^+$: 420.

Step C—Synthesis of Compound Int-19c

To a stirred solution of compound Int-19b (3.4 g, 8.09 mmol) in MeOH (30 mL) was added TsOH (4616 mg, 24.27 mmol). The reaction mixture was allowed to stir at 35° C. for 20 hours. The solvent was removed in vacuo. The resulting residue was purified using silica gel column chromatography (dichloromethane:MeOH=10:1) to provide compound Int-19c as a colorless oil. $^1$H NMR (400 MHz, CDCl$_3$): δ 7.59 (s, 1H), 4.94 (brs, 1H), 4.10-4.17 (m, 2H), 4.01 (s, 3H), 3.78-3.88 (m, 1H), 3.47-3.55 (m, 2H), 3.42 (s, 3H), 3.31 (s, 3H), 1.24-1.27 (m, 2H), 1.17 (s, 3H). MS (M+H)$^+$: 376.

Step D—Synthesis of Compound Int-19d

To a stirred solution of compound Int-19c (2.5 g, 6.64 mmol) in 1,2-dichloroethane (30 mL) was added Dess-Martin periodinane (3.4 g, 7.97 mmol). The reaction mixture was allowed to stir at 15° C. for 1 hour. The solvent was removed in vacuo, the resulting residue was purified using silica gel column chromatography (dichloromethane:MeOH=10:1) to provide compound Int-19d as a colorless oil. $^1$H NMR (400 MHz, CDCl$_3$): δ 7.68 (s, 1H), 4.08-4.43 (m, 3H), 4.00 (s, 3H), 3.77-3.85 (m, 1H), 3.53 (t, J=5.6 Hz, 1H), 3.42 (d, J=8.8 Hz, 3H), 3.19-3.32 (m, 3H), 2.10-2.24 (m, 1H), 1.94-2.03 (m, 1H), 1.28 (d, J=7.8 Hz, 3H). MS (M+H)$^+$: 374.

Step E—Synthesis of Compound Int-19e and 19f

To a solution of compound Int-19d (300 mg, 0.802 mmol) in DMSO (5 mL) was added (2,4-difluorophenyl)methanamine (215 mg, 1.499 mmol), N-ethyl-N-isopropylpropan-2-amine (259 mg, 2.004 mmol) and Pd (Ph$_3$P)$_4$ (232 mg, 0.200 mmol). The reaction was stirred under a balloon of CO at 96° C. for 2 hours. It was cooled to 25° C. The reaction mixture was filtered and the filtrate was concentrated, the resulting residue was purified using prep-TLC (dichloromethane:EtOAc=1:1) to provide a crude mixture of all four stereoisomers of compound Int-19e and 19f as a colorless oil. This was further purified using SFC (M7 "Column: Chiralpak AD-H 250×4.6 mm I.D., 5 um Mobile phase: ethanol (0.05% DEA) in CO$_2$ from 5% to 40% Flow rate: 2.35 mL/min Wavelength: 220 nm") to provide each individual stereoisomer: enantiomer A of compound Int-19e (the first eluting compound), enantiomer B of compound Int-19e (the second eluting compound), enantiomer A of compound Int-19f (the third eluting compound), and enantiomer B of compound Int-19f (the fourth eluting compound). MS (M+H)$^+$: 465.

Enantiomer A of compound Int-19e: $^1$H NMR (400 MHz, CDCl$_3$): δ 10.48 (brs, 1H), 8.40 (s, 1H), 7.32-7.42 (m, 1H), 6.74-6.87 (m, 2H), 4.57-4.70 (m, 2H), 4.44 (dd, J=1.60, 13.60 Hz, 1H), 4.22 (dd, J=4.40, 13.60 Hz, 1H), 4.00 (s, 3H), 3.79 (d, J=1.20 Hz, 1H), 3.46-3.51 (m, 1H), 3.35-3.44 (m, 4H), 3.20 (s, 3H), 1.94-2.02 (m, 1H), 1.78 (m, 1H), 1.30 (s, 3H).

Enantiomer B of compound Int-19e: $^1$H NMR (400 MHz, CDCl$_3$): δ 10.49 (brs, 1H), 8.40 (s, 1H), 7.31-7.41 (m, 1H), 6.80 (d, J=8.40 Hz, 2H), 4.63 (dd, J=6.40, 8.80 Hz, 2H), 4.44 (d, J=13.60 Hz, 1H), 4.23 (dd, J=4.00, 13.60 Hz, 1H), 3.99 (s, 3H), 3.78 (brs, 1H), 3.46-3.50 (m, 1H), 3.36-3.44 (m, 4H), 3.20 (s, 3H), 1.92-2.04 (m, 1H), 1.78 (m, 1H), 1.30 (s, 3H).

Enantiomer A of compound Int-19f: $^1$H NMR (400 MHz, CDCl$_3$): δ 10.35-10.56 (m, 1H), 8.40 (s, 1H), 7.30-7.42 (m, 1H), 6.73-6.88 (m, 2H), 4.63 (d, J=5.60 Hz, 2H), 4.24-4.35 (m, 2H), 4.00 (s, 3H), 3.85 (brs, 1H), 3.49-3.59 (m, 2H), 3.39 (s, 3H), 3.30 (s, 3H), 2.14-2.23 (m, 1H), 1.95-2.03 (m, 1H), 1.27 (s, 3H).

Enantiomer B of compound Int-19f: $^1$H NMR (400 MHz, CDCl$_3$): δ 10.35-10.56 (m, 1H), 8.40 (s, 1H), 7.30-7.42 (m, 1H), 6.73-6.88 (m, 2H), 4.63 (d, J=5.60 Hz, 2H), 4.24-4.35 (m, 2H), 4.00 (s, 3H), 3.85 (brs, 1H), 3.49-3.59 (m, 2H), 3.39 (s, 3H), 3.30 (s, 3H), 2.14-2.23 (m, 1H), 1.95-2.03 (m, 1H), 1.27 (s, 3H).

Step F—Synthesis of Compound 58-61

Following essentially the same method described in Step K of Example 10, compound 58 was prepared starting from enantiomer A of compound Int-19e. Similarly, compound 59 was prepared from enantiomer B of compound Int-19e.

Compound 58: $^1$H NMR (400 MHz, CDCl$_3$): δ 10.44 (brs, 1H), 8.41 (s, 1H), 7.32-7.39 (m, 1H), 6.76-6.85 (m, 2H), 4.65 (d, J=3.60 Hz, 2H), 4.52 (d, J=13.60 Hz, 1H), 4.28 (dd, J=3.60, 13.60 Hz, 1H), 3.82 (d, J=1.60 Hz, 1H), 3.52-3.59 (m, 1H), 3.41 (s, 4H), 3.22 (s, 3H), 1.98-2.06 (m, 1H), 1.73-1.80 (m, 1H), 1.38 (s, 3H). MS (M+H)$^+$: 451.

Compound 59: $^1$H NMR (400 MHz, CDCl$_3$) δ 10.44 (brs, 1H), 8.41 (s, 1H), 7.31-7.40 (m, 1H), 6.75-6.87 (m, 2H), 4.65 (brs, 2H), 4.52 (d, J=13.60 Hz, 1H), 4.24-4.31 (m, 1H), 3.82 (brs, 1H), 3.56 (t, J=7.20 Hz, 1H), 3.42 (s, 4H), 3.22 (s, 3H), 2.02 (m, 1H), 1.76 (d, J=15.20 Hz, 1H), 1.38 (s, 3H). MS (M+H)$^+$: 451.

Following essentially the same method described in Step K of Example 10, compound 60 was prepared starting from enantiomer A of compound Int-19f. Similarly, compound 61 was prepared from enantiomer B of compound Int-19e.

Compound 60: $^1$H NMR (400 MHz, CDCl$_3$) δ 10.43 (br. s., 1H), 8.42 (s, 1H), 7.31-7.40 (m, 1H), 6.74-6.89 (m, 2H), 4.65 (t, J=5.60 Hz, 2H), 4.28-4.39 (m, 2H), 3.91 (br. s., 1H), 3.52-3.63 (m, 2H), 3.40 (s, 3H), 3.31 (s, 3H), 2.20 (dd, J=5.60, 7.60 Hz, 1H), 2.09-2.16 (m, 1H), 1.33 (s, 3H). MS (M+H)$^+$: 451.

Compound 61: $^1$H NMR (400 MHz, CDCl$_3$) δ 10.45 (brs, 1H), 8.44 (s, 1H), 7.30-7.40 (m, 1H), 6.72-6.89 (m, 2H), 4.64 (t, J=5.60 Hz, 2H), 4.28-4.40 (m, 2H), 3.91 (brs, 1H), 3.58 (m, 2H), 3.40 (s, 3H), 3.31 (s, 3H), 2.08-2.26 (m, 2H), 1.33 (s, 3H). MS (M+H)$^+$: 451.

Example 33

Preparation of Compound 62-73

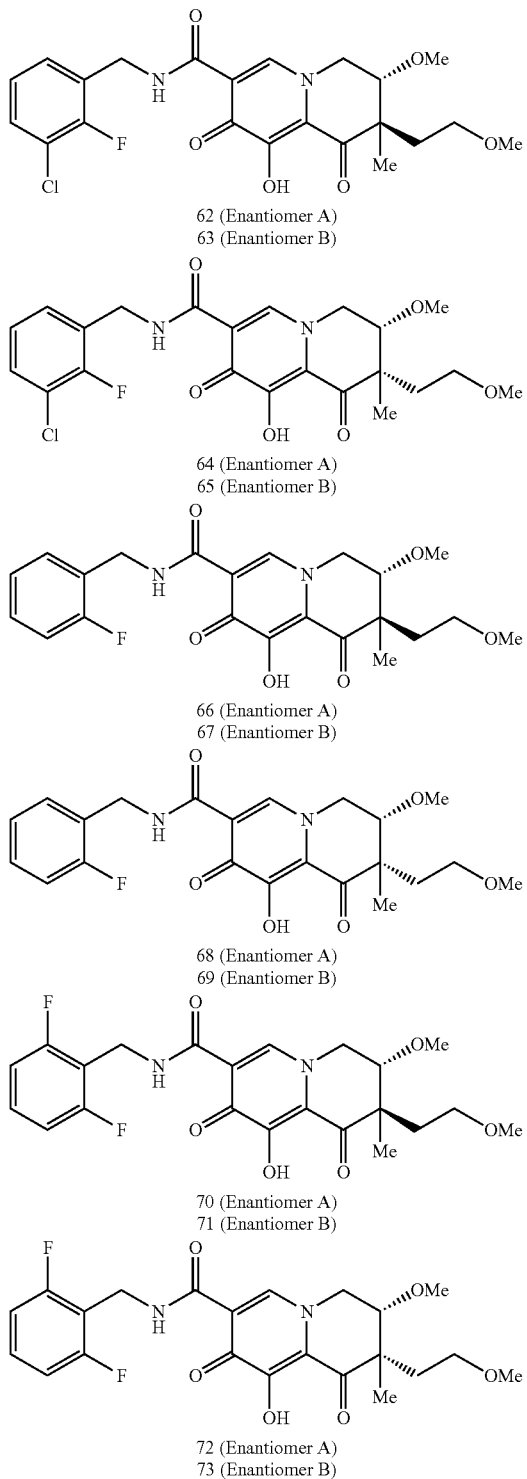

62 (Enantiomer A)
63 (Enantiomer B)

64 (Enantiomer A)
65 (Enantiomer B)

66 (Enantiomer A)
67 (Enantiomer B)

68 (Enantiomer A)
69 (Enantiomer B)

70 (Enantiomer A)
71 (Enantiomer B)

72 (Enantiomer A)
73 (Enantiomer B)

Compound 62-71 were prepared by essentially the same method described in Example 32, only substituting (2,4-difluorophenyl)methanamine in Step E with appropriate benzylamines.

Compound 62: $^1$H NMR (400 MHz, CDCl$_3$) δ 10.45 (brs, 1H), 8.38 (s, 1H), 7.27-7.31 (m, 2H), 7.02 (t, J=7.83 Hz, 1H), 4.72 (brs, 2H), 4.52 (d, J=12.72 Hz, 1H), 4.26 (dd, J=4.01, 13.99 Hz, 1H), 3.82 (brs, 1H), 3.55 (dd, J=2.93, 9.00 Hz, 1H), 3.42 (s, 4H), 3.23 (s, 3H), 1.99-2.05 (m, 1H), 1.75-1.79 (m, 1H), 1.38 (s, 3H). MS (M+H)$^+$: 467.

Compound 63: $^1$H NMR (400 MHz, CDCl$_3$) δ 10.45 (brs, 1H), 8.38 (s, 1H), 7.26-7.32 (m, 2H), 7.02 (t, J=7.83 Hz, 1H), 4.68-4.75 (m, 2H), 4.52 (d, J=13.11 Hz, 1H), 4.26 (dd, J=4.11, 13.89 Hz, 1H), 3.82 (d, J=1.76 Hz, 1H), 3.53-3.59 (m, 1H), 3.38-3.47 (m, 4H), 3.22 (s, 3H), 2.00-2.06 (m, 1H), 1.78 (brs, 1H), 1.38 (s, 3H). MS (M+H)$^+$: 467.

Compound 64: $^1$H NMR (400 MHz, CDCl$_3$) δ 10.44 (brs, 1H), 8.40 (s, 1H), 7.28 (brs, 2H), 7.02 (t, J=7.73 Hz, 1H), 4.71 (brs, 2H), 4.33 (brs, 2H), 3.91 (brs, 1H), 3.53-3.62 (m, 2H), 3.40 (s, 3H), 3.32 (s, 3H), 2.18-2.23 (m, 1H), 2.11-2.17 (m, 1H), 1.34 (s, 3H). MS (M+H)$^+$: 467.

Compound 65: $^1$H NMR (400 MHz, CDCl$_3$) δ 10.44 (brs, 1H), 8.40 (s, 1H), 7.28 (brs, 2H), 7.02 (t, J=7.63 Hz, 1H), 4.71 (brs, 2H), 4.32 (brs, 2H), 3.91 (brs, 1H), 3.53-3.62 (m, 2H), 3.40 (s, 3H), 3.32 (s, 3H), 2.18-2.24 (m, 1H), 2.14 (t, J=4.99 Hz, 1H), 1.34 (s, 3H). MS (M+H)$^+$: 467.

Compound 66: $^1$H NMR (400 MHz, CDCl$_3$) δ 10.41 (brs, 1H), 8.40 (s, 1H), 7.36-7.40 (m, 1H), 7.17~7.25 (m, 1H), 6.98-7.12 (m, 2H), 4.70 (d, J=4.50 Hz, 2H), 4.51 (d, J=13.89 Hz, 1H), 4.26 (dd, J=3.72, 13.89 Hz, 1H), 3.81 (brs, 1H), 3.38-3.60 (m, 5H), 3.22 (s, 3H), 2.00-2.05 (m, 1H), 1.74-1.78 (m, 1H), 1.37 (s, 3H). MS (M+H)$^+$: 433.

Compound 67: $^1$H NMR (400 MHz, CDCl$_3$) δ 10.41 (brs, 1H), 8.40 (s, 1H), 7.38 (t, J=6.85 Hz, 1H), 7.17-7.25 (m, 1H), 6.95-7.14 (m, 2H), 4.70 (d, J=3.91 Hz, 2H), 4.50 (d, J=13.69 Hz, 1H), 4.26 (dd, J=3.72, 13.89 Hz, 1H), 3.81 (brs, 1H), 3.52-3.58 (m, 1H), 3.41 (s, 4H), 3.22 (s, 3H), 1.99-2.05 (m, 1H), 1.73-1.79 (m, 1H), 1.37 (s, 3H). MS (M+H)$^+$: 433.

Compound 68: $^1$H NMR (400 MHz, CDCl$_3$) δ 10.39 (brs, 1H), 8.41 (s, 1H), 7.38 (t, J=7.14 Hz, 1H), 7.17-7.25 (m, 1H), 6.98-7.12 (m, 2H), 4.70 (brs, 2H), 4.25-4.39 (m, 2H), 3.89 (brs, 1H), 3.50-3.64 (m, 2H), 3.39 (s, 3H), 3.32 (s, 3H), 2.19 (dd, J=5.58, 7.73 Hz, 1H), 2.09-2.16 (m, 1H), 1.33 (s, 3H). MS (M+H)$^+$: 433.

Compound 69: $^1$H NMR (400 MHz, CDCl$_3$) δ 10.41 (brs, 1H), 8.44 (brs, 1H), 7.37 (t, J=6.75 Hz, 1H), 7.17-7.25 (m, 1H), 6.97-7.14 (m, 2H), 4.70 (brs, 2H), 4.24-4.41 (m, 2H), 3.88 (brs, 1H), 3.50~3.64 (m, 2H), 3.39 (s, 3H), 3.31 (s, 3H), 2.08-2.25 (m, 2H), 1.33 (s, 3H). MS (M+H)$^+$: 433.

Compound 70: $^1$H NMR (400 MHz, CDCl$_3$) δ 10.32 (brs, 1H), 8.37 (s, 1H), 7.16-7.25 (m, 1H), 6.87 (t, J=7.63 Hz, 2H), 4.65-4.81 (m, 2H), 4.49 (d, J=13.50 Hz, 1H), 4.23 (dd, J=3.91, 13.89 Hz, 1H), 3.81 (brs, 1H), 3.51-3.59 (m, 1H), 3.36-3.47 (m, 4H), 3.21 (s, 3H), 1.97-2.06 (m, 1H), 1.73-1.78 (m, 1H), 1.36 (s, 3H). MS (M+H)$^+$: 451.

Compound 71: $^1$H NMR (400 MHz, CDCl$_3$) δ 10.31 (brs, 1H), 8.36 (s, 1H), 7.14-7.23 (m, 1H), 6.86 (t, J=7.53 Hz, 2H), 4.64-4.79 (m, 2H), 4.47 (d, J=13.50 Hz, 1H), 4.22 (dd, J=3.72, 13.69 Hz, 1H), 3.79 (brs, 1H), 3.49-3.56 (m, 1H), 3.39 (s, 4H), 3.20 (s, 3H), 1.97-2.04 (m, 1H), 1.75 (d, J=4.30 Hz, 1H), 1.34 (s, 3H). MS (M+H)$^+$: 451.

Compound 72: $^1$H NMR (400 MHz, CDCl$_3$) δ 10.33 (brs, 1H), 8.36-8.44 (m, 1H), 7.16-7.25 (m, 1H), 6.88 (t, J=7.53 Hz, 2H), 4.73 (dq, J=5.38, 14.51 Hz, 2H), 4.26-4.36 (m, 2H), 3.89 (brs, 1H), 3.51-3.62 (m, 2H), 3.39 (s, 3H), 3.31 (s, 3H), 2.10-2.21 (m, 1H), 1.32 (s, 3H). MS (M+H)$^+$: 451.

Compound 73: $^1$H NMR (400 MHz, CDCl$_3$) δ 10.32 (brs, 1H), 8.40 (s, 1H), 7.14-7.25 (m, 1H), 6.87 (t, J=7.63 Hz, 2H), 4.66-4.80 (m, 2H), 4.31 (brs, 2H), 3.89 (brs, 1H), 3.51-3.63 (m, 2H), 3.38 (s, 3H), 3.31 (s, 3H), 2.10-2.22 (m, 2H), 1.32 (s, 3H). MS (M+H)$^+$: 451.

Example 34

Preparation of Compound 74-93

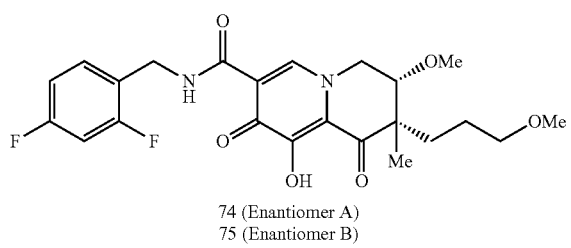

74 (Enantiomer A)
75 (Enantiomer B)

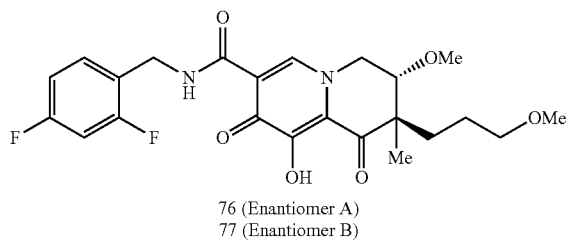

76 (Enantiomer A)
77 (Enantiomer B)

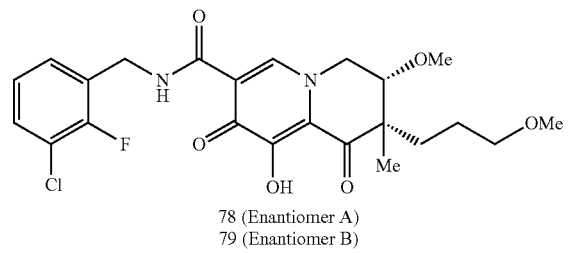

78 (Enantiomer A)
79 (Enantiomer B)

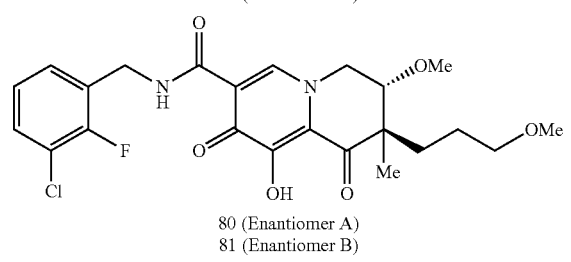

80 (Enantiomer A)
81 (Enantiomer B)

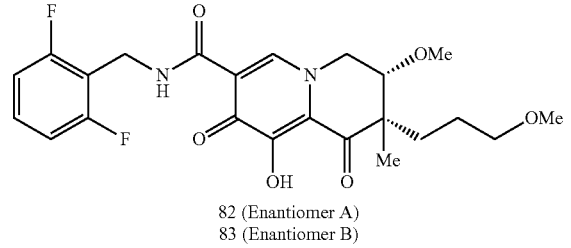

82 (Enantiomer A)
83 (Enantiomer B)

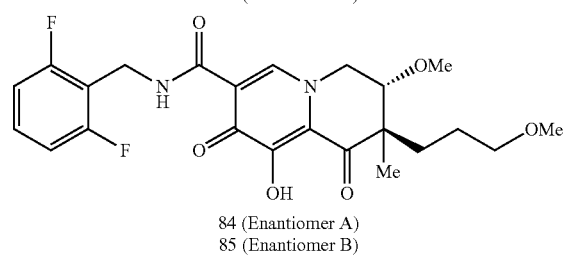

84 (Enantiomer A)
85 (Enantiomer B)

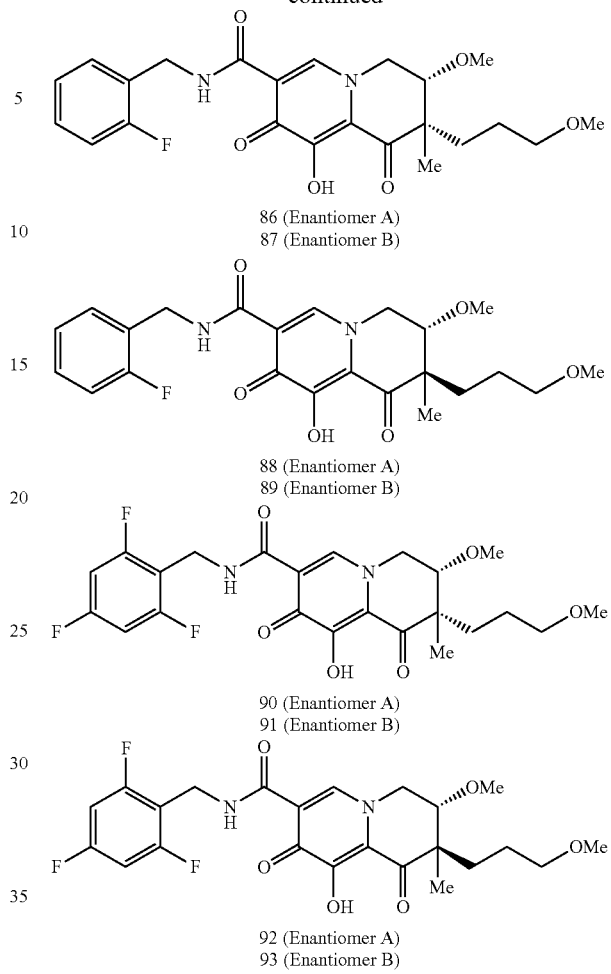

86 (Enantiomer A)
87 (Enantiomer B)

88 (Enantiomer A)
89 (Enantiomer B)

90 (Enantiomer A)
91 (Enantiomer B)

92 (Enantiomer A)
93 (Enantiomer B)

Compound 74-93 were prepared by essentially the same method described in Example 32, only replacing compound Int-16j in Step A with compound Int-20a, and substituting appropriate benzylamine in Step E.

Compound 74: $^1$H NMR (400 MHz, CDCl$_3$) δ 10.38 (br. s, 1H), 8.39 (s, 1H), 7.29-7.38 (m, 1H), 6.72-6.85 (m, 2H), 4.55-4.71 (m, 2H), 4.23-4.41 (m, 2H), 3.64 (s., 1H), 3.26-3.48 (m, 8H), 1.86-1.92 (m, 2H), 1.59-1.68 (m, 1H), 1.47-1.57 (m, 1H), 1.27 (s, 3H). MS (M+H)$^+$: 465.

Compound 75: $^1$H NMR (400 MHz, CDCl$_3$) δ 10.42 (br. s, 1H), 8.44 (s, 1H), 7.31-7.38 (m, 1H), 6.75-6.86 (m, 2H), 4.56-4.70 (m, 2H), 4.26-4.46 (m, 2H), 3.65 (s., 1H), 3.33-3.47 (m, 8H), 1.85-1.95 (m, 2H), 1.60-1.71 (m, 1H), 1.48-1.58 (m, 1H), 1.29 (s, 3H). MS (M+H)$^+$: 465.

Compound 76: $^1$H NMR (400 MHz, CDCl$_3$) δ 10.38 (br. s., 1H), 8.38 (s, 1H), 7.29-7.39 (m, 1H), 6.73-6.84 (m, 2H), 4.56-4.69 (m, 2H), 4.24-4.44 (m, 2H), 3.65 (s, 1H), 3.32-3.43 (m, 4H), 3.18-3.30 (m, 4H), 1.69-1.80 (m, 1H), 1.53-1.66 (m, 3H), 1.33 (s, 3H). MS (M+H)$^+$: 465.

Compound 77: $^1$H NMR (400 MHz, CDCl$_3$) δ 10.42 (br. s, 1H), 8.42 (s, 1H), 7.31-7.40 (m, 1H), 6.74-6.86 (m, 2H), 4.56-4.71 (m, 2H), 4.25-4.47 (m, 2H), 3.66 (s, 1H), 3.35-3.44 (m, 4H), 3.21-3.31 (m, 4H), 1.72-1.83 (m, 1H), 1.54-1.69 (m, 3H), 1.35 (s, 3H). MS (M+H)$^+$: 465.

Compound 78: $^1$H NMR (400 MHz, CDCl$_3$) δ 10.48 (br. s, 1H), 8.47 (s, 1H), 7.24-7.31 (m, 2H), 7.02 (t, J=7.6 Hz, 1H), 4.64-4.78 (m, 2H), 4.26-4.45 (m, 2H), 3.65 (s, 1H), 3.32-3.47 (m, 8H), 1.87-1.94 (m, 2H), 1.60-1.70 (m, 1H), 1.47-1.58 (m, 1H), 1.29 (s, 3H). MS (M+H)+: 481.

Compound 79: $^1$H NMR (400 MHz, CDCl$_3$) δ 10.48 (br. s, 1H), 8.46 (s, 1H), 7.23-7.32 (m, 2H), 7.02 (t, J=7.6 Hz, 1H), 4.64-4.77 (m, 2H), 4.26-4.45 (m, 2H), 3.65 (s, 1H), 3.30-3.49 (m, 8H), 1.84-1.96 (m, 2H), 1.60-1.71 (m, 1H), 1.48-1.59 (m, 1H), 1.28 (s, 3H). MS (M+H)+: 481.

Compound 80: $^1$H NMR (400 MHz, CDCl$_3$) δ 10.47 (br. s, 1H), 8.44 (s, 1H), 7.24-7.31 (m, 2H), 7.02 (t, J=7.6 Hz, 1H), 4.65-4.77 (m, 2H), 4.29-4.44 (m, 2H), 3.66 (s, 1H), 3.35-3.43 (m, 4H), 3.22-3.31 (m, 4H), 1.72-1.82 (m, 1H), 1.54-1.67 (m, 3H), 1.35 (s, 3H). MS (M+H)+: 481.

Compound 81: $^1$H NMR (400 MHz, CDCl$_3$) δ 10.48 (br. s, 1H), 8.44 (s, 1H), 7.23-7.31 (m, 2H), 7.02 (t, J=7.6 Hz, 1H), 4.65-4.77 (m, 2H), 4.29-4.45 (m, 2H), 3.66 (s, 1H), 3.34-3.45 (m, 4H), 3.21-3.31 (m, 4H), 1.72-1.82 (m, 1H), 1.54-1.68 (m, 3H), 1.35 (s, 3H). MS (M+H)+: 481.

Compound 82: $^1$H NMR (400 MHz, CDCl$_3$) δ 10.31 (br. s, 1H), 8.40 (s, 1H), 7.14-7.23 (m, 1H), 6.86 (t, J=7.6 Hz, 2H), 4.64-4.77 (m, 2H), 4.25-4.40 (m, 2H), 3.63 (s, 1H), 3.28-3.46 (m, 8H), 1.81-1.93 (m, 2H), 1.58-1.67 (m, 1H), 1.46-1.55 (m, 1H), 1.26 (s, 3H). MS (M+H)+: 465.

Compound 83: $^1$H NMR (400 MHz, CDCl$_3$) δ 10.32 (br. s, 1H), 8.41 (s, 1H), 7.16-7.23 (m, 1H), 6.86 (t, J=7.6 Hz, 2H), 4.63-4.77 (m, 2H), 4.34-4.41 (m, 1H), 4.24-4.31 (m, 1H), 3.63 (s, 1H), 3.31-3.44 (m, 8H), 1.84-1.92 (m, 2H), 1.58-1.67 (m, 1H), 1.46-1.56 (m, 1H), 1.26 (s, 3H). MS (M+H)+: 465.

Compound 84: $^1$H NMR (400 MHz, CDCl$_3$) δ 10.32 (br. s, 1H), 8.40 (s, 1H), 7.17-7.24 (m, 1H), 6.87 (t, J=7.6 Hz, 2H), 4.65-4.79 (m, 2H), 4.36-4.42 (m, 1H), 4.25-4.33 (m, 1H), 3.65 (s, 1H), 3.33-3.43 (m, 4H), 3.19-3.30 (m, 4H), 1.71-1.81 (m, 1H), 1.53-1.67 (m, 3H), 1.34 (s, 3H). MS (M+H)+: 465.

Compound 85: $^1$H NMR (400 MHz, CDCl$_3$) δ 10.35 (br. s, 1H), 8.42 (s, 1H), 7.16-7.25 (m, 1H), 6.87 (t, J=7.6 Hz, 2H), 4.65-4.79 (m, 2H), 4.36-4.43 (m, 1H), 4.25-4.34 (m, 1H), 3.65 (s, 1H), 3.34-3.43 (m, 4H), 3.20-3.30 (m, 4H), 1.70-1.81 (m, 1H), 1.54-1.66 (m, 3H), 1.34 (s, 3H). MS (M+H)+: 465.

Compound 86: $^1$H NMR (400 MHz, CDCl$_3$) (400 MHz, CDCl$_3$) δ 10.38 (s, 1H), 8.43 (s, 1H), 7.37 (t, J=7.2 Hz, 1H), 7.18-7.24 (m, 1H), 6.99-7.12 (m, 2H), 4.64-4.76 (m, 2H), 4.36-4.44 (m, 1H), 4.24-4.31 (m, 1H), 3.63 (s, 1H), 3.30-3.47 (m, 8H), 1.87-1.93 (m, 2H), 1.60-1.68 (m, 1H), 1.47-1.57 (m, 1H), 1.28 (s, 3H). MS (M+H)+: 447.

Compound 87: $^1$H NMR (400 MHz, CDCl$_3$) δ 10.40 (s, 1H), 8.45 (s, 1H), 7.37 (t, J=7.2 Hz, 1H), 7.19-7.24 (m, 1H), 7.00-7.11 (m, 2H), 4.64-4.76 (m, 2H), 4.36-4.44 (m, 1H), 4.24-4.31 (m, 1H), 3.63 (s, 1H), 3.32-3.47 (m, 8H), 1.85-1.95 (m, 2H), 1.60-1.70 (m, 1H), 1.47-1.57 (m, 1H), 1.27 (s, 3H). MS (M+H)+: 447.

Compound 88: $^1$H NMR (400 MHz, CDCl$_3$) δ 10.37 (s., 1H), 8.40 (s, 1H), 7.36 (t, J=7.2 Hz, 1H), 7.16-7.23 (m, 1H), 6.98-7.10 (m, 2H), 4.63-4.74 (m, 2H), 4.26-4.42 (m, 2H), 3.64 (s, 1H), 3.33-3.43 (m, 4H), 3.19-3.30 (m, 4H), 1.72-1.79 (m, 1H), 1.54-1.66 (m, 3H), 1.33 (s, 3H). MS (M+H)+: 447.

Compound 89: $^1$H NMR (400 MHz, CDCl$_3$) δ 10.36 (s, 1H), 8.40 (s, 1H), 7.36 (t, J=7.2 Hz, 1H), 7.16-7.23 (m, 1H), 6.98-7.09 (m, 2H), 4.63-4.74 (m, 2H), 4.26-4.40 (m, 2H), 3.63 (s, 1H), 3.32-3.42 (m, 4H), 3.20-3.29 (m, 4H), 1.72-1.78 (m, 1H), 1.54-1.64 (m, 3H), 1.33 (s, 3H). MS (M+H)+: 447.

Compound 90: $^1$H NMR (400 MHz, CDCl$_3$) δ 10.29 (br. s, 1H), 8.37 (s, 1H), 6.63 (t, J=8.0 Hz, 2H), 4.56-4.72 (m, 2H), 4.23-4.39 (m, 2H), 3.63 (s, 1H), 3.27-3.46 (m, 8H), 1.83-1.93 (m, 2H), 1.57-1.67 (m, 1H), 1.44-1.55 (m, 1H), 1.26 (s, 3H). MS (M+H)+: 483.

Compound 91: $^1$H NMR (400 MHz, CDCl$_3$) δ 10.29 (br. s, 1H), 8.37 (s, 1H), 6.63 (t, J=8.0 Hz, 2H), 4.57-4.72 (m, 2H), 4.24-4.38 (m, 2H), 3.63 (s, 1H), 3.25-3.47 (m, 8H), 1.84-1.93 (m, 2H), 1.58-1.67 (m, 1H), 1.45-1.55 (m, 1H), 1.26 (s, 3H). MS (M+H)+: 483.

Compound 92: $^1$H NMR (400 MHz, CDCl$_3$) δ 10.27 (br. s, 1H), 8.33 (s, 1H), 6.59 (t, J=8.0 Hz, 2H), 4.54-4.67 (m, 2H), 4.30-4.36 (m, 1H), 4.18-4.25 (m, 1H), 3.59 (s, 1H), 3.28-3.36 (m, 4H), 3.15-3.23 (m, 4H), 1.66-1.74 (m, 1H), 1.49-1.59 (m, 3H), 1.28 (s, 3H). MS (M+H)+: 483.

Compound 93: $^1$H NMR (400 MHz, CDCl$_3$) δ 10.20 (br. s, 1H), 8.34 (s, 1H), 6.64 (t, J=8.0 Hz, 2H), 4.59-4.73 (m, 2H), 4.23-4.46 (m, 2H), 3.64 (s, 1H), 3.33-3.41 (m, 4H), 3.19-3.28 (m, 4H), 1.66-1.74 (m, 1H), 1.49-1.59 (m, 3H), 1.32 (s, 3H). MS (M+H)+: 483.

Example 35

Preparation of Compound Int-20d

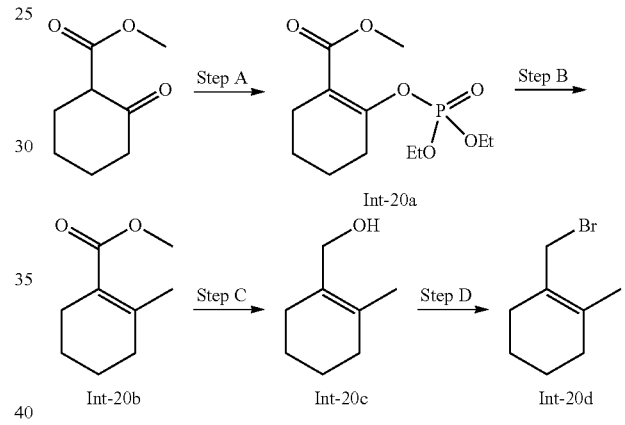

Step A—Synthesis of Compound Int-20a

To a mixture of sodium hydride (60% wt. in mineral oil) (2.56 g, 64.00 mmol) in 90 mL of THF at 0° C. was added methyl 2-oxocyclohexanecarboxylate (5.00 g, 32.00 mmol) in 50 mL of THF dropwise. The resulting mixture was allowed to stir at 0° C. for 30 min. Diethyl phosphorocyanidate (4.91 ml, 32.3 mmol) was then added to above mixture. The reaction was allowed to stir at 0° C. for another 1 h. It was slowly quenched with 200 mL of NH$_4$Cl saturated aqueous solution. The aqueous was extracted with 2×150 mL EtOAc. The combined organic phase was dried over anhydrous Na$_2$SO$_4$ and concentrated to provide the virtually pure phosphono ester derivative compound Int-20a as a colorless oil. $^1$H NMR (400 MHz, CDCl$_3$): δ 4.17-4.23 (m, 4H); 3.72 (s, 3H); 2.45-2.48 (m, 2H); 2.35-2.37 (m, 2H); 1.70-1.74 (m, 2H); 1.62-1.64 (m, 2H); 1.35-1.37 (m, 6H).

Step B—Synthesis of Compound Int-20b

In a 500 mL round bottle flask, methyllithium (40.6 ml, 65.0 mmol) was added dropwise to a suspension of copper (I) iodide (4.95 g, 26.0 mmol) in 180 mL of ether at 0° C. The resulting solution was immediately cooled to −40° C., and a solution of compound Int-20a (7.6 g, 26.0 mmol) in 10 mL Et$_2$O was added. The reaction was slowly warmed up to room temperature for overnight. Saturated NH$_4$Cl (20 mL) was added slowly to quench the reaction. Filtration followed by concentration of the filtrate gave a residue which was purified using silica gel column chromatography eluting with 10% EtOAc/hexanes to provide compound Int-20b as a colorless oil. $^1$H NMR (400 MHz, CDCl$_3$): δ 3.73 (s, 3H); 2.25-2.28 (m, 2H); 2.11-2.14 (m, 2H); 2.00 (s, 3H); 1.61-1.62 (m, 4H).

Step C—Synthesis of Compound Int-20c

1 M Diisobutylaluminium hydride in dichloromethane (20.75 ml, 20.75 mmol) was added to a solution of compound Int-20b (1.6 g, 10.38 mmol) in 100 mL of CH$_2$Cl$_2$ cooled to −78° C. The reaction was allowed to stir at this temperature for 1.5 h. It was added 10 mL MeOH and followed by 10 mL saturated Na$_2$CO$_3$ solution. The mixture was allowed to stir at room temperature for 1 h. To above mixture was added Na$_2$SO$_4$. It was filtered through celite and the cake was washed with 50 mL of CH$_2$Cl$_2$. The combined organic phase was concentrated to provide virtually pure compound Int-20c as a colorless oil. $^1$H NMR (400 MHz, CDCl$_3$): δ 4.13 (s, 2H); 2.11-2.13 (m, 2H); 1.98-2.00 (m, 2H); 1.72 (s, 3H); 1.62-1.67 (m, 4H).

Step D—Synthesis of Compound Int-20d

To a solution of compound Int-20c in 50 mL Et$_2$O was added tribromophosphine (0.452 ml, 4.75 mmol) at 0° C. The reaction was then slowly warm up to room temperature for overnight. It was quenched with 100 mL saturated NaHCO$_3$ aqueous solution at 0° C. The aqueous was extracted with 2×100 mL Et$_2$O. The combined organic phase was washed with brine, dried over Na$_2$SO$_4$ and concentrated to compound Int-20d as a colorless oil. $^1$H NMR (400 MHz, CDCl$_3$): δ 4.05 (s, 2H); 2.14-2.15 (m, 2H); 2.01-2.03 (m, 2H); 1.74 (s, 3H); 1.60-1.67 (m, 4H).

Example 36

Preparation of Compound 94 and 95

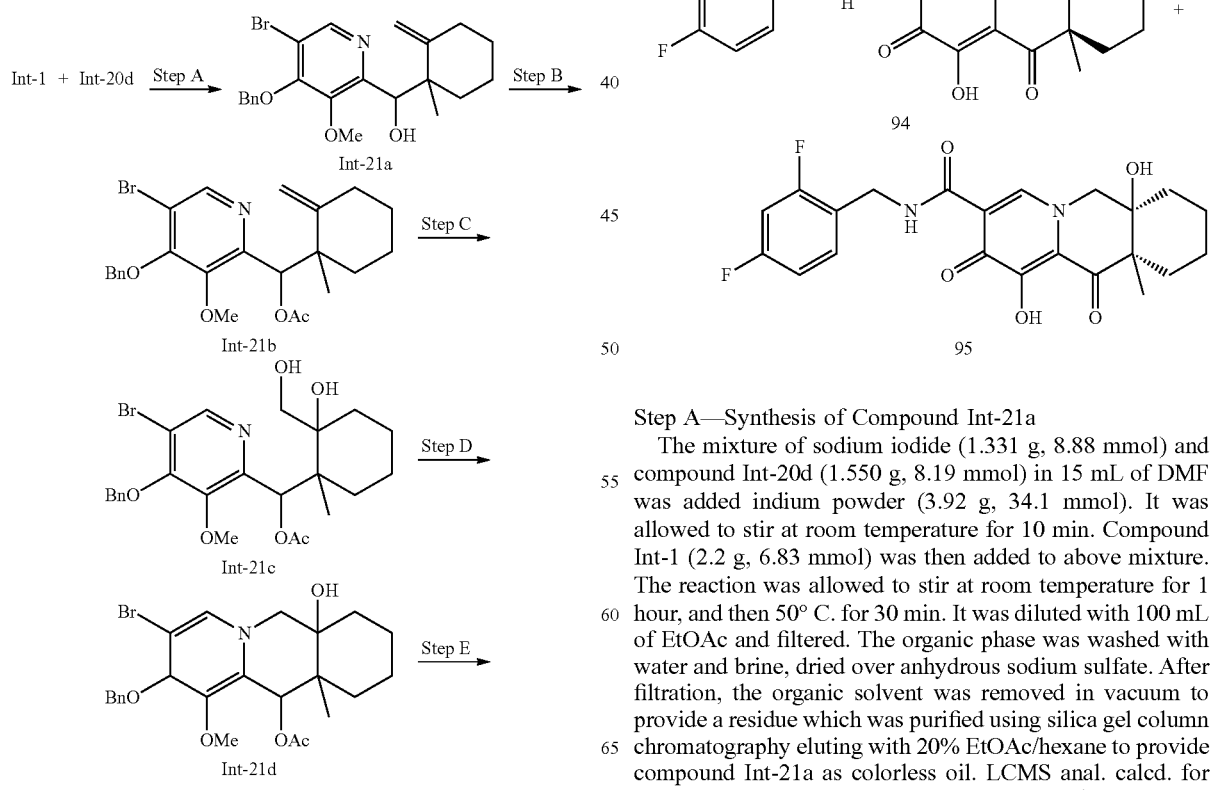

Step A—Synthesis of Compound Int-21a

The mixture of sodium iodide (1.331 g, 8.88 mmol) and compound Int-20d (1.550 g, 8.19 mmol) in 15 mL of DMF was added indium powder (3.92 g, 34.1 mmol). It was allowed to stir at room temperature for 10 min. Compound Int-1 (2.2 g, 6.83 mmol) was then added to above mixture. The reaction was allowed to stir at room temperature for 1 hour, and then 50° C. for 30 min. It was diluted with 100 mL of EtOAc and filtered. The organic phase was washed with water and brine, dried over anhydrous sodium sulfate. After filtration, the organic solvent was removed in vacuum to provide a residue which was purified using silica gel column chromatography eluting with 20% EtOAc/hexane to provide compound Int-21a as colorless oil. LCMS anal. calcd. for C$_{22}$H$_{26}$BrNO$_3$: 431.11. Found: 432.00 (M+1)$^+$.

Step B—Synthesis of Compound Int-21b

To a solution of compound Int-21a (2.10 g, 4.86 mmol) in acetic anhydride (10 ml, 106 mmol) was added triethylamine (2.45 g, 24.29 mmol) and 4-dimethylaminopyridine (0.30 g, 2.429 mmol). The reaction was allowed to stir at room temperature for 1 h. The solvent was removed in vacuo. The resulting residue was purified using silica gel column chromatography eluting with 20% EtOAc/hexanes to compound Int-21b as a colorless foam. LCMS anal. calcd. for $C_{24}H_{28}BrNO_4$: 473.12. Found: 474.03 $(M+1)^+$.

Step C—Synthesis of Compound Int-21c

The solution of compound Int-21b (2.10 g, 4.43 mmol) in 35 mL of THF/9 mL $H_2O$ was added osmium tetroxide in t-BuOH (4.50 mL, 0.443 mmol) and 4-methylmorpholine 4-oxide (1.56 g, 13.28 mmol). The mixture was allowed to stir at room temperature for overnight.

It was diluted with 100 mL of EtOAc and then added 3 g sodium metathiosulfite solid. The mixture was then stirred for 30 min. It was filtered and the filtrate was concentrated. The resulting residue was purified using silica gel column chromatography eluting with 60% EtOAc/hexanes to compound Int-21c as a white solid. LCMS anal. calcd. for $C_{24}H_{30}BrNO_6$: 507.13; Found: 508.02 $(M+1)^+$.

Step D—Synthesis of Compound Int-21d

To a stirred solution of compound Int-21c (1.9 g, 3.74 mmol) in 12 mL pyridine was added 4-methylbenzene-1-sulfonyl chloride (1.07 g, 5.61 mmol). The reaction was allowed to stir at room temperature for overnight, followed by heated at 60° C. for 2 h. The reaction was then added 5 mL MeOH and concentrated to remove most of pyridine. The resulting residue was purified using silica gel column chromatography eluting with 10% MeOH/DCM to afford compound Int-21d as a white solid. LCMS anal. calcd. for $C_{17}H_{22}BrNO_5$: 399.07. Found: 400.03 $(M+1)^+$.

Step E—Synthesis of Compound Int-21e

To a solution of compound Int-21d (0.22 g, 0.550 mmol) in 6 mL of MeOH was added potassium carbonate (380 mg, 2.75 mmol). The reaction was allowed to stir at 60° C. for 30 min. Most of the solvent was removed in vacuo. To the resulting residue was added 10 mL of 10% mL MeOH/dichloromethane. The resulting mixture was filtered. The mother liquor was concentrated in vacuo and the resulting residue was purified using silica gel column chromatography eluting with 10% MeOH/dichloromethane to afford compound Int-21e as a white solid. LCMS anal. calcd. for $C_{15}H_{20}BrNO_4$: 357.06. Found: 357.98 $(M+1)^+$.

Step F—Synthesis of Compound Int-21f

To a stirred solution of compound Int-21e (0.70 g, 1.95 mmol) in 20 mL of dichloromethane was added Dess-Martin periodinate (1.32 g, 3.13 mmol). The mixture was allowed to stir at room temperature for 2 h. It was added 1 mL of $H_2O$ and the precipitate was filtered off. The filtrate was concentrated in vacuo and the resulting residue was added 2 mL of DMSO. The mixture was purified using C18 reverse-phase column (150 g) eluting with 5% $ACN/H_2O$ to 100% $ACN/H_2O$ with 0.1% TFA to afford compound Int-21f as a white solid. LCMS anal. calcd. for $C_{15}H_{18}BrNO_4$: 355.04. Found: 356.02 $(M+1)^+$.

Step G—Synthesis of Compound Int-21g and Int-21h

To a mixture of compound Int-21f (0.50 g, 1.404 mmol), N-ethyl-N-isopropylpropan-2-amine (0.54 g, 4.21 mmol), (2,4-difluorophenyl)methanamine (0.30 g, 2.105 mmol) and (oxybis(2,1-phenylene))bis(diphenylphosphine) (0.15 mg, 0.281 mmol) in 12 mL of DMSO was added diacetoxypalladium (63.0 mg, 0.281 mmol). The above mixture was then flushed through CO for 20 min with CO balloon at room temperature, then heated at 80° C. under CO balloon for 2 h. The reaction was cooled down and directly purified using C18 reverse-phase column (150 g) eluting with 5% $ACN/H_2O$-100% $ACN/H_2O$ with 0.1% TFA to afford the desired product as its racemic mixture. The enantiomers were then separated by chiral AD column (30×250 mm) eluting with 50% $MeOH/CO_2$ at 70 mL/min to afford compound Int-21g and compound Int-21h as white solids. LCMS anal. calcd. for $C_{23}H_{24}F_2N_2O_5$: 446.17. Found: 446.99 $(M+1)^+$.

Step H—Synthesis of Compound 94 and 95

To a stirred solution of compound Int-21g (0.13 g, 0.291 mmol) in 3 mL of DMF was added lithium chloride (0.25 g, 5.82 mmol). The mixture was allowed to stir at 100° C. for 30 min. It was cooled down and added 0.2 mL $H_2O$. The mixture was purified directly by C18 reverse-phase column (40 g) eluting with 5% $ACN/H_2O$ to 100% $ACN/H_2O$ with 0.1% TFA. The fraction was collected and dried by lypholizer to afford compound 94 (0.11g, 0.250 mmol) as white solid. $^1H$ NMR (400 MHz, $CDCl_3$): δ 10.46 (s, 1H); 8.40 (s, 1H); 7.33-7.37 (m, 1H); 6.81-6.86 (m, 2H); 4.63 (d, 2H); 4.21-4.33 (2H); 1.52-2.01 (8H); 1.39 (s, 3H). LCMS anal. calcd. for $C_{22}H_{22}F_2N_2O_5$: 432.15. Found: 433.06 $(M+1)^+$.

Compound 95 was prepared using the method described in Step H of Example 36, and replacing compound Int-21g with compound Int-21h. $^1H$ NMR (400 MHz, $CDCl_3$): δ 10.47 (s, 1H); 8.43 (s, 1H); 7.35-7.38 (m, 1H); 6.81-6.86 (m, 2H); 4.65 (d, 2H); 4.21-4.33 (2H); 1.52-2.03 (8H); 1.39 (s, 3H). LCMS anal. calcd. for $C_{22}H_{22}F_2N_2O_5$: 432.15. Found: 433.06 $(M+1)^+$.

Example 37

Preparation of Compound 96, and 97

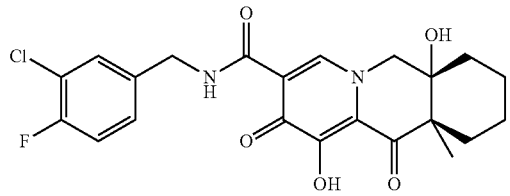

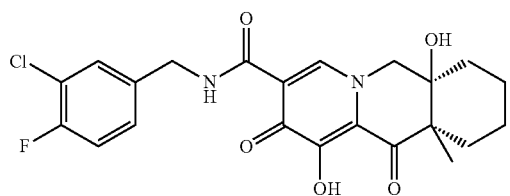

Compound 96 was prepared using the method described in Step G to Step H of Example 36, and replacing compound (2,4-difluorophenyl)methanamine with (3-chloro-4-fluorophenyl)methanamine in Step G. The stereoisomer mixture was separated by chiral OD column instead of chiral AD column in Step G. $^1H$ NMR (400 MHz, $CDCl_3$): δ 10.52 (s, 1H); 8.42 (s, 1H); 7.38 (d, J=5.2 Hz, 1H); 7.22 (d, J=1.6 Hz, 1H); 7.10 (dd, J=6.8, 1.6 Hz, 1H); 4.55-4.62 (m, 2H); 4.18-4.32 (2H); 2.02-2.03 (m, 2H); 1.51-1.84 (6H); 1.40 (s, 3H). LCMS anal. calcd. for $C_{22}H_{22}ClFN_2O_5$: 448.87. Found: 449.05 $(M+1)^+$.

Compound 97 was prepared by following essentially the same method described for compound 96. $^1H$ NMR (400

MHz, CDCl$_3$): δ 10.52 (s, 1H); 8.44 (s, 1H); 7.39 (d, J=5.2 Hz, 1H); 7.22 (d, J=1.6 Hz, 1H); 7.10 (dd, J=6.8, 1.6 Hz, 1H); 4.54-4.60 (m, 2H); 4.18-4.32 (2H); 2.02-2.03 (m, 2H); 1.51-1.84 (6H); 1.40 (s, 3H). LCMS anal. calcd. for C$_{22}$H$_{22}$ClFN$_2$O$_5$: 448.87. Found: 449.05 (M+1)$^+$.

Example 38

Preparation of Compound Int-22

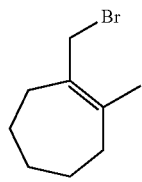

Int-22

Compound Int-22 was prepared using the method described in Step A to Step D of Example 35, and replacing methyl 2-oxocyclohexanecarboxylate with methyl 2-oxocycloheptanecarboxylate in Step A. $^1$H NMR (400 MHz, CDCl$_3$): δ 4.10 (s, 2H); 2.28-2.29 (m, 2H); 2.19-2.21 (m, 2H); 1.82 (s, 3H); 1.72-1.77 (m, 2H); 1.54-1.58 (m, 2H); 1.46-1.50 (m, 2H).

Example 39

Preparation of Compound Int-23

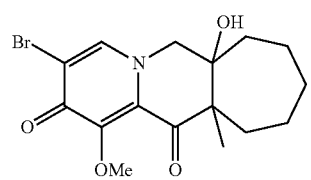

Int-23

Compound Int-23 was prepared using the method described in Step A to Step F of Example 36, and replacing compound Int-20d with compound Int-22 in Step A. LCMS anal. calcd. for C$_{16}$H$_2$BrNO$_4$: 369.06. Found: 370.95 (M+1)$^+$.

Example 40

Preparation of Compound 98-101

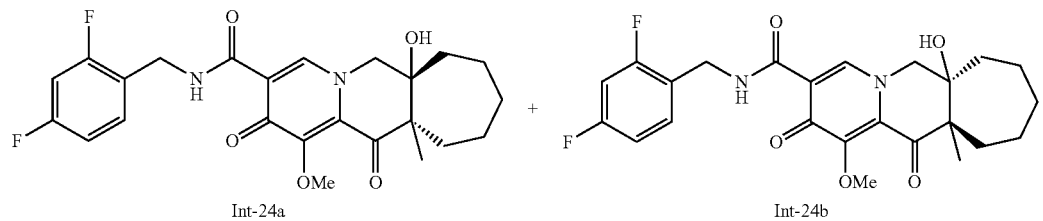

Int-24a + Int-24b

Int-23 Step A

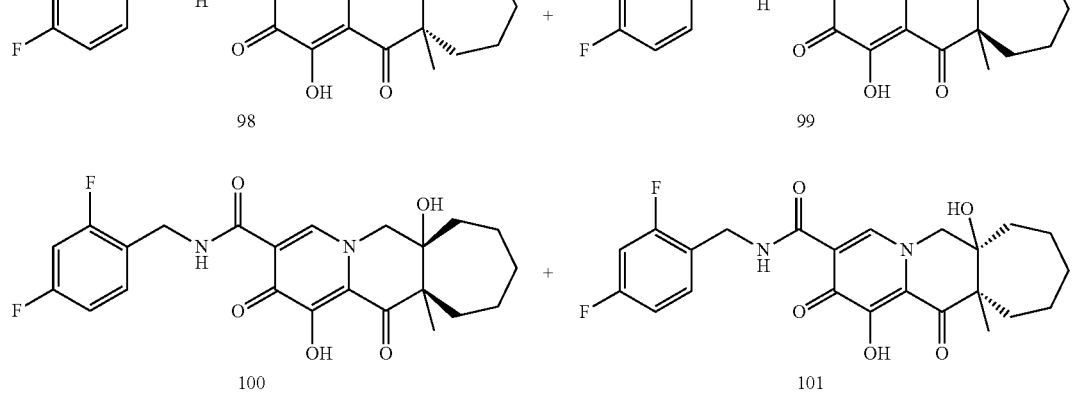

Int-24c + Int-24d

98 + 99

Step B

100 + 101

Step A—Synthesis of Compound Int-24a, Int-24b, Int-24c and Int-24d

To a mixture of compound Int-23 (0.12 g, 0.32 mmol), N-ethyl-N-isopropylpropan-2-amine (0.13 g, 0.97 mmol), (2,4-difluorophenyl)methanamine (0.07 g, 0.48 mmol) and (oxybis(2,1-phenylene))bis(diphenylphosphine) (0.03 mg, 0.05 mmol) in 3 mL of DMSO was added diacetoxypalladium (11.0 mg, 0.049 mmol). The resulting mixture was then flushed through CO for 20 min with CO balloon at room temperature, then heated at 80° C. under CO balloon for 2 h. The reaction was cooled down and directly purified using a C18 reverse-phase column (40 g) eluting with 5% ACN/H$_2$O to 100% ACN/H$_2$O with 0.1% TFA to afford stereoisomer mixture (104 mg, 0.226 mmol) as yellow solid. The stereoisomer mixture was then separated by chiral IC column (30×250 mm) eluting with 30% MeOH/CO$_2$ at 70 mL/min to afford compound Int-24a, compound Int-24b, compound Int-24c, compound Int-24d individually as a white solid. LCMS anal. calcd. for C$_{24}$H$_{26}$F$_2$N$_2$O$_5$: 460.18. Found: 461.15 (M+1)$^+$.

Step B—Synthesis of Compound 98-101

To a stirred solution of compound Int-24a (15.0 mg, 0.032 mmol) in 3 mL of DMF was added lithium chloride (0.27 g, 6.52 mmol). The mixture was allowed to stir at 100° C. for 30 min. It was cooled down and added 0.2 mL H$_2$O. The mixture was purified directly by a C18 reverse-phase column (40 g) eluting with 5% ACN/H$_2$O to 100% ACN/H$_2$O with 0.1% TFA. The fraction was collected and dried by lypholizer to afford compound 98 as a white solid. $^1$H NMR (400 MHz, CDCl$_3$): δ 10.49 (s, 1H); 8.69 (s, 1H); 7.35-7.38 (m, 1H); 6.83-6.87 (m, 2H); 4.54-4.59 (m, 2H); 3.86 (d, J=9.6 Hz, 1H); 3.77 (d, J=9.6 Hz, 1H); 2.34-2.37 (m, 2H); 2.13-2.19 (m, 2H); 1.53-1.90 (6H); 1.46 (s, 3H). LCMS anal. calcd. for C$_{23}$H$_{24}$F$_2$N$_2$O$_5$: 446.44; Found: 446.99 (M+1)$^+$.

Compound 99 was prepared using the method described in Step B of Example 40, and replacing compound Int-24a with compound Int-24b. LCMS anal. calcd. for C$_{23}$H$_{24}$F$_2$N$_2$O$_5$: 446.44. Found: 446.99 (M+1)$^+$. $^1$H NMR (400 MHz, CDCl$_3$): δ 10.39 (s, 1H); 8.79 (s, 1H); 7.39-7.42 (m, 1H); 6.81-6.86 (m, 2H); 4.54-4.62 (m, 2H); 3.88 (d, J=9.2 Hz, 1H); 3.87 (d, J=9.2 Hz, 1H); 2.34-2.39 (m, 2H); 2.15-2.19 (m, 2H); 1.53-1.90 (6H); 1.45 (s, 3H).

Compound 100 was prepared using the method described in Step B of Example 40, and replacing compound Int-24a with compound Int-24c. $^1$H NMR (400 MHz, CDCl$_3$): δ 10.51 (s, 1H); 8.32 (s, 1H); 7.33-7.37 (m, 1H); 6.81-6.84 (m, 2H); 4.63-4.65 (m, 2H); 4.48 (d, J=9.6 Hz, 1H); 4.16 (d, J=9.6 Hz, 1H); 2.24-2.27 (m, 1H); 2.03-2.11 (m, 2H); 1.49-1.82 (7H); 1.44 (s, 3H). LCMS anal. calcd. for C$_{23}$H$_{24}$F$_2$N$_2$O$_5$: 446.44. Found: 446.99 (M+1)$^+$.

Compound 101 was prepared using the method described in Step B of Example 40, and replacing compound Int-24a with compound Int-24d. $^1$H NMR (400 MHz, CDCl$_3$): δ 10.45 (s, 1H); 8.32 (s, 1H); 7.30-7.33 (m, 1H); 6.82-6.84 (m, 2H); 4.61-4.63 (m, 2H); 4.48 (d, J=9.6 Hz, 1H); 4.16 (d, J=9.6 Hz, 1H); 2.24-2.27 (m, 1H); 2.03-2.11 (m, 2H); 1.49-1.82 (7H); 1.44 (s, 3H). LCMS anal. calcd. for C$_{23}$H$_{24}$F$_2$N$_2$O$_5$: 446.44. Found: 446.99 (M+1)$^+$.

Example 41

Preparation of Compound 102, 103

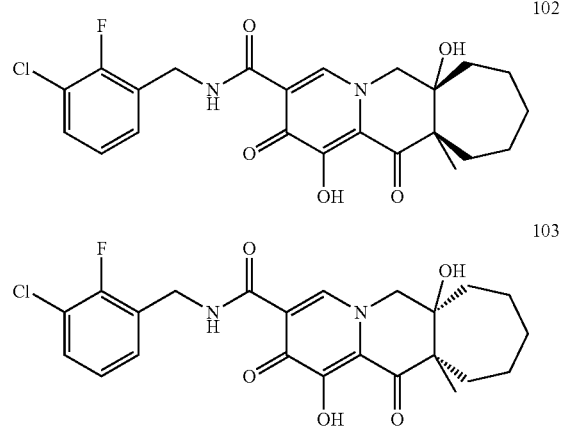

Compound 102 was prepared using the method described in Step A to Step B of Example 40, and replacing compound (2,4-difluorophenyl)methanamine with compound (3-chloro-2-fluorophenyl)methanamine in Step A. $^1$H NMR (400 MHz, CDCl$_3$): δ 10.55 (s, 1H); 8.38 (s, 1H); 7.32 (m, 1H); 7.22 (m, 1H); 7.05 (m, 1H); 4.65 (m, 2H); 4.51 (d, J=9.2 Hz, 1H); 4.37 (d, J=9.2 Hz, 1H); 3.05 (m, 1H); 1.28-2.18 (9H); 1.43 (s, 3H). LCMS anal. calcd. for C$_{23}$H$_{24}$ClFN$_2$O$_5$: 462.14. Found: 462.79 (M+1)$^+$.

Compound 103 was prepared using the method described in Step A to Step B of Example 40, and replacing (2,4-difluorophenyl)methanamine with (3-chloro-2-fluorophenyl)methanamine in Step A. $^1$H NMR (400 MHz, CD$_3$OD): δ 8.45 (s, 1H); 7.38 (m, 1H); 7.34 (m, 1H); 7.12 (m, 1H); 4.68 (m, 2H); 4.51 (d, J=9.2 Hz, 1H); 4.18 (d, J=9.2 Hz, 1H); 1.59-2.20 (10H); 1.40 (s, 3H). LCMS anal. calcd. for C$_{23}$H$_{24}$ClFN$_2$O$_5$: 462.14. Found: 462.79 (M+1)$^+$.

Example 42

Preparation of Compound Int-25

Compound Int-25 was prepared using the method described in Step A to Step D of Example 35, and replacing methyl 2-oxocyclohexanecarboxylate with methyl 2-oxocyclopentanecarboxylate in Step A. $^1$H NMR (400 MHz, CDCl$_3$): δ 4.12 (s, 2H); 2.48-2.51 (m, 2H); 2.35-2.38 (m, 2H); 1.83-1.88 (m, 2H); 1.73 (s, 3H).

Example 43

Preparation of Compound 104

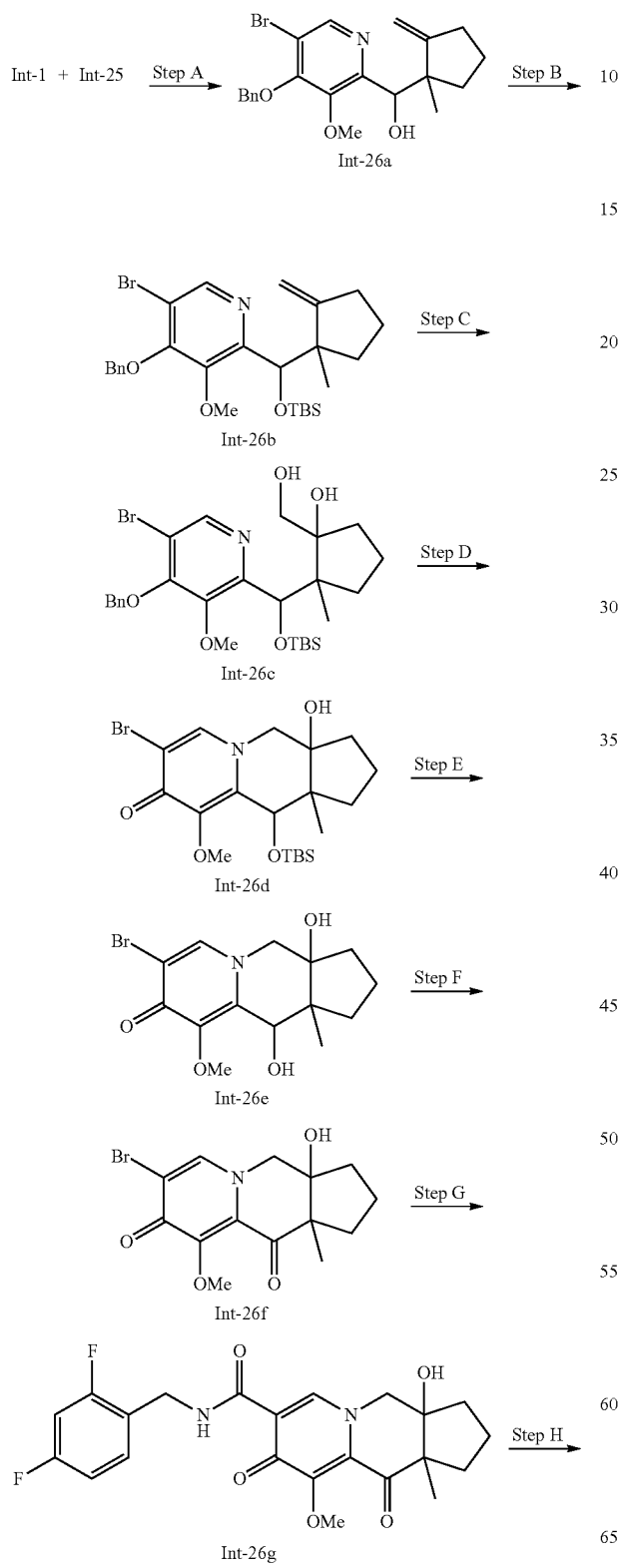

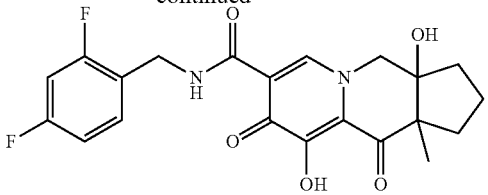

Step A—Synthesis of Compound Int-26a

The mixture of sodium iodide (0.907 g, 6.05 mmol) and compound Int-25 (1.06 g, 6.05 mmol) in 10 mL of DMF was added indium (2.67 g, 23.28 mmol). It was allowed to stir at room temperature for 10 min. Compound Int-1 (1.5 g, 4.66 mmol) was then added to the above mixture. The reaction was allowed to stir at room temperature for 1 hour, and then 50° C. for 30 min. It was diluted with 100 mL EtOAc and filtered. The organic phase was washed with water and brine, dried over anhydrous sodium sulfate. After filtration, the organic solvent was removed in vacuo to provide a residue which was purified using silica gel column chromatography eluting with 20% EtOAc/hexane to provide compound Int-26a as a colorless oil. LCMS anal. calcd. for $C_{21}H_{24}BrNO_3$: 417.09. Found: 417.93 $(M+1)^+$.

Step B—Synthesis of Compound Int-26b

The solution of compound Int-26a (1.30 g, 3.11 mmol) in 6 mL of DMF was added tert-butylchlorodimethylsilane (0.94 g, 6.22 mmol) and imidazole (0.64 g, 9.32 mmol). The mixture was allowed to stir at 60° C. for overnight. It was added 50 mL of EtOAc. The organic phase was washed with $H_2O$ and brine, dried over $Na_2SO_4$ and concentrated. The resulting residue was purified using silica gel column chromatography eluting with 5% EtOAc/hexane to provide compound Int-26b as colorless oil. LCMS anal. calcd. for $C_{27}H_{38}BrNO_3Si$: 531.18. Found: 532.03 $(M+1)^+$.

Step C—Synthesis of Compound Int-26c

A solution of compound Int-26b (1.40 g, 2.63 mmol) in 21 mL of THF and 5 mL of water was added osmium tetroxide (1.67 mL, 0.263 mmol) and 4-methylmorpholine 4-oxide (0.92 g, 7.89 mmol). The mixture was allowed to stir at room temperature for overnight. It was added 20 mL EtOAc. The organic phase was added 2 g of sodium metathiosulfite solid and stirred for 30 min. It was filtered and the filtrate was concentrated. The resulting residue was purified using silica gel column chromatography eluting with 30% EtOAc/hexane to afford compound Int-26c as light green oil. LCMS anal. calcd. for $C_{27}H_{40}BrNO_5$: 565.19. Found: 566.04 $(M+1)^+$.

Step D—Synthesis of Compound Int-26d

To a stirred solution of compound Int-26c (0.50 g, 0.88 mmol) in 4 mL of pyridine was added 4-methylbenzene-1-sulfonyl chloride (022 g, 1.15 mmol). The reaction was allowed to stir at room temperature for overnight, followed by heated at 60° C. for 2 h. The reaction was then added 5 mL MeOH and concentrated to remove most of pyridine. The resulting residue was purified using silica gel column chromatography eluting with 5% MeOH/dichloromethane to afford compound Int-26d as a white solid. LCMS anal. calcd. for $C_{20}H_{32}BrNO_4$: 457.13. Found: 457.98 $(M+1)^+$.

Step E—Synthesis of Compound Int-26e

A solution of compound Int-26d (0.12 g, 0.26 mmol) in 2 mL of THF at room temperature was added a solution of 1 N tetrabutylammonium fluoride in THF (0.52 mL, 0.524 mmol). The mixture was allowed to stir at room temperature for 3 h. The reaction was then directly purified using silica gel column chromatography eluting with 10% MeOH/dichloromethane to afford compound Int-26e as a white solid. LCMS anal. calcd. for $C_{14}H_{18}BrNO_4$: 343.03. Found: 344.01 $(M+1)^+$.

Step F—Synthesis of Compound Int-26f

To a stirred solution of compound Int-26e (86 mg, 0.25 mmol) in 3 mL of dichloromethane was added Dess-Martin periodinate (0.15 g, 0.38 mmol). The mixture was allowed to stir at room temperature for 1 h. It was added 1 mL $H_2O$ and the precipitate was filtered off. The filtrate was concentrated in vacuo and the resulting residue was added 2 mL DMSO. The mixture was purified using C18 reverse-phase column (40 g) eluting with 5% $ACN/H_2O$ to 100% $ACN/H_2O$ with 0.1% TFA to afford compound Int-26f as white solid. LCMS anal. calcd. for $C_{14}H_{16}BrNO_4$: 341.03. Found: 341.97 $(M+1)^+$.

Step G—Synthesis of Compound Int-26g

A mixture of compound Int-26f (12 mg, 0.035 mmol), N-ethyl-N-isopropylpropan-2-amine (14 mg, 0.105 mmol), (2,4-difluorophenyl)methanamine (7.5 mg, 0.053 mmol) and (oxybis(2,1-phenylene))bis(diphenylphosphine) (4.7 mg, 0.008 mmol) in 2 mL of DMSO was added diacetoxypalladium (2.0 mg, 0.008 mmol). The above mixture was then flushed through CO for 20 min with CO balloon at room temperature, then heated at 80° C. with CO balloon for 2 h. The reaction was cooled down and directly purified using C18 reverse-phase column (25 g) eluting with 5% $ACN/H_2O$ to 100% $ACN/H_2O$ with 0.1% TFA to afford stereoisomer mixture of compound Int-26g as yellow solid. LCMS anal. calcd. for $C_{22}H_{22}F_2N_2O_5$: 432.15. Found: 433.10 $(M+1)^+$.

Step H—Synthesis of Compound 104

To a stirred solution of compound Int-26g (8.0 mg, 0.019 mmol) in 1 mL of DMF was added lithium chloride (16 mg, 0.37 mmol). The mixture was allowed to stir at 100° C. for 30 min. It was cooled down and added 0.2 mL $H_2O$. The mixture was purified directly by a C18 reverse-phase column (40 g) eluting with 5% $ACN/H_2O$ to 100% ACN/H2O with 0.1% TFA. The fraction was collected and dried by lypholizer to afford compound 104 as white solid. $^1H$ NMR (400 MHz, $CD_3OD$): δ 10.52 (m, 1H); 8.45 (s, 1H); 7.39-7.44 (m, 1H); 6.91-6.98 (m, 2H); 4.59-4.77 (m, 2H); 4.36 (d, J=10.8, 1H); 4.20 (d, J=10.8, 1H); 3.30 (s, 3H); 2.26-2.31 (m, 1H); 1.83-2.04 (m, 4H); 1.64-1.69 (m, 1H); 1.34 (s, 3H). LCMS anal. calcd. for $C_{21}H_{20}F_2N_2O_5$: 418.13. Found: 418.98 $(M+1)^+$.

Example 44

Preparation of Compound 105

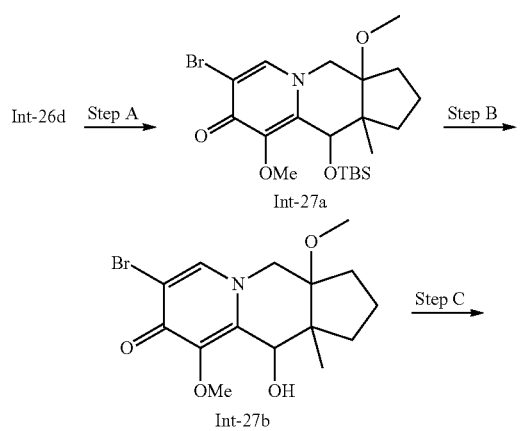

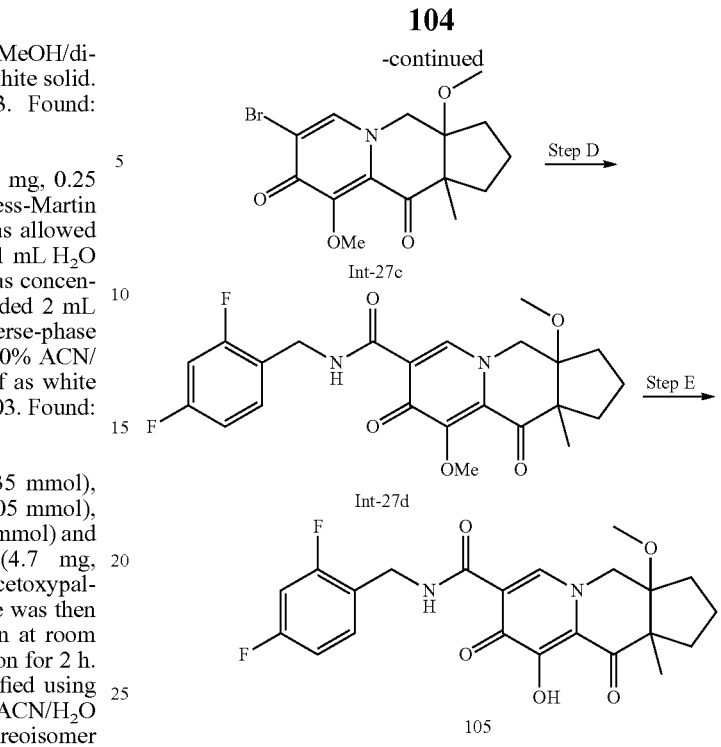

Step A—Synthesis of Compound Int-27a

A solution of compound Int-26d (145 mg, 0.316 mmol) in 2 mL of THF at room temperature was added iodomethane (135 mg, 0.949 mmol) and followed by adding sodium hydride (22.77 mg, 0.949 mmol)). The mixture was allowed to stir at room temperature for 5 h. The reaction was then quenched by 1 mL $H_2O$. The reaction was then directly purified using silica gel column chromatography eluting with 30% EtOAc/hexane to afford compound Int-27a as light yellow solid. LCMS anal. calcd. for $C_{21}H_{34}BrNO_4Si$: 471.14. Found: 472.28 $(M+1)^+$.

Step B—Synthesis of Compound Int-27b

To a solution of compound Int-27a (90 mg, 0.19 mmol) in 2 mL of THF at room temperature was added a solution of 1 N tetrabutylammonium fluoride in THF (0.40 mL, 0.40 mmol). The mixture was allowed to stir at room temperature for 3 h. The reaction was then directly purified using silica gel column chromatography eluting with 10% MeOH/dichloromethane to afford compound Int-27b as white solid. LCMS anal. calcd. for $C_{15}H_{20}BrNO_4$: 357.06. Found: 358.01 $(M+1)^+$.

Step C—Synthesis of Compound Int-27c

To a stirred solution of compound Int-27b (60 mg, 0.17 mmol) in 2 mL of dichloromethane was added Dess-Martin periodinate (71 mg, 0.17 mmol). The mixture was allowed to stir at room temperature for 1 h. It was added 1 mL of $H_2O$ and the precipitate was filtered off. The filtrate was concentrated in vacuo and the resulting residue was added 2 mL of DMSO. The mixture was purified using C18 reverse-phase column (40 g) eluting with 5% $ACN/H_2O$ to 100% $ACN/H_2O$ with 0.1% TFA to afford compound Int-27c as a white solid. LCMS anal. calcd. for $C_{15}H_{18}BrNO_4$: 355.04. Found: 356.04 $(M+1)^+$.

Step D—Synthesis of Compound Int-27d

To a mixture of compound Int-27c (20 mg, 0.056 mmol), N-ethyl-N-isopropylpropan-2-amine (21 mg, 0.168 mmol), (2,4-difluorophenyl)methanamine (12 mg, 0.084 mmol) and (oxybis(2,1-phenylene))bis(diphenylphosphine) (7.6 mg, 0.014 mmol) in 2 mL of DMSO was added diacetoxypalladium (3.0 mg, 0.014 mmol). The above mixture was then flushed through CO for 20 min with CO balloon at room temperature, then heated at 80° C. under a CO balloon for 2 h. The reaction was cooled down and directly purified using C18 reverse-phase column (25 g) eluting with 5% ACN/H$_2$O to 100% ACN/H$_2$O with 0.1% TFA to afford stereoisomer mixture of compound Int-27d as a yellow solid. LCMS anal. calcd. for C$_{23}$H$_{24}$F$_2$N$_2$O$_5$: 446.17. Found: 447.18 (M+1)$^+$.

Step E—Synthesis of Compound 105

To a stirred solution of compound Int-27d (12.0 mg, 0.027 mmol) in 1 mL of DMF was added lithium chloride (23 mg, 0.54 mmol). The mixture was allowed to stir at 100° C. for 30 min. It was cooled down and added 0.2 mL of H$_2$O. The mixture was purified directly by a C18 reverse-phase column (40 g) eluting with 5% ACN/H$_2$O to 100% ACN/H$_2$O with 0.1% TFA. The fraction was collected and dried by lypholizer to afford compound 105 as a white solid. $^1$H NMR (400 MHz, CD$_3$OD): δ 8.54 (s, 1H); 7.43-7.45 (m, 1H); 6.90-6.97 (m, 2H); 4.61-4.64 (2H); 4.34-4.36 (2H); 3.31 (s, 3H); 2.26-2.32 (m, 1H); 2.13-2.19 (m, 1H); 1.97-2.00 (m, 1H); 1.84-1.91 (m, 2H); 1.73-1.79 (m, 1H); 1.34 (s, 3H). LCMS anal. calcd. for C$_{22}$H$_{22}$F$_2$N$_2$O$_5$: 432.15. Found: 433.17 (M+1)$^+$.

Example 45

Preparation of Compound 106 and 107

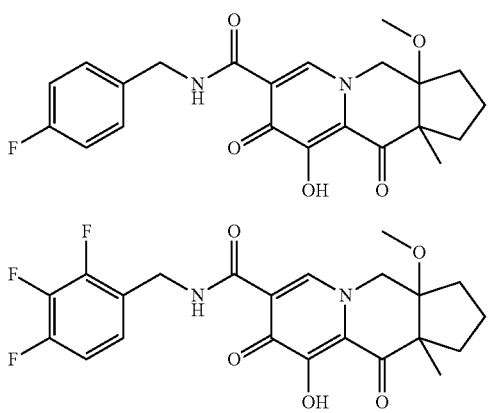

Compound 106 was prepared by following essentially the same method as described in Example 44 for compound 105, and replacing (2,4-difluorophenyl)methanamine with (4-fluorophenyl)methanamine in Step D. $^1$H NMR (400 MHz, CD$_3$OD): δ 8.56 (s, 1H); 7.36-7.39 (m, 2H); 7.05-7.08 (m, 2H); 4.60-4.65 (2H); 4.31-4.37 (2H); 3.31 (s, 3H); 2.26-2.32 (m, 1H); 2.14-2.20 (m, 1H); 1.97-2.01 (m, 1H); 1.84-1.91 (m, 2H); 1.73-1.79 (m, 1H); 1.34 (s, 3H). LCMS anal. calcd. for C$_{22}$H$_{23}$FN$_2$O$_5$: 414.16. Found: 415.16 (M+1)$^+$.

Compound 107 was prepared by following essentially the same method as described in Example 44 for compound 105, and replacing (2,4-difluorophenyl)methanamine with (2,3,4-trifluorophenyl)methanamine in Step D. $^1$H NMR (400 MHz, CD$_3$OD): δ 8.53 (s, 1H); 7.04-7.21 (m, 2H); 4.60-4.67 (2H); 4.33-4.36 (2H); 3.31 (s, 3H); 2.26-2.31 (m, 1H); 2.14-2.20 (m, 1H); 1.97-2.01 (m, 1H); 1.84-1.90 (m, 2H); 1.73-1.79 (m, 1H); 1.34 (s, 3H). LCMS anal. calcd. for C$_{22}$H$_{21}$F$_3$N$_2$O$_5$: 450.14. Found: 450.97 (M+1)$^+$.

Example 46

Preparation of Compound Int-28b

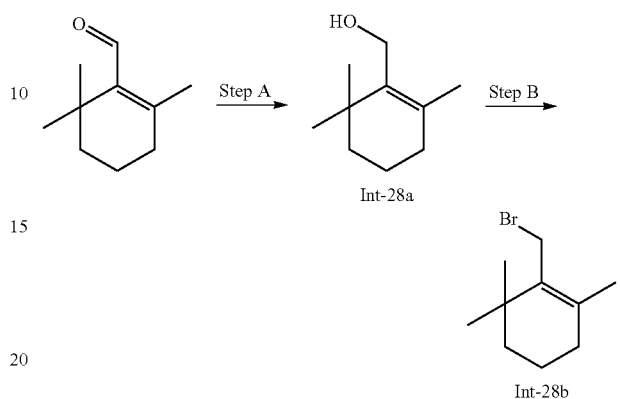

Step A—Synthesis of Compound Int-28a

Diisobutylaluminium hydride (35.50 ml, 35.50 mmol) was added to a solution of 2,6,6-trimethylcyclohex-1-enecarbaldehyde (4.50 g, 29.60 mmol) in 200 mL of CH$_2$Cl$_2$ cooled to −40° C. The resulting mixture was allowed to stir at this temperature for 1.5 h. It was added 10 mL MeOH and followed by 200 mL of saturated Rochelle solution. The mixture was allowed to stir at room temperature for 1 h. The organic phase was separated and the aqueous was extracted with 2×50 mL of EtOAc. The combined organic phase was dried over anhydrous Na$_2$SO$_4$, filtered and concentrated to provide compound Int-28a as a colorless oil. $^1$H NMR (400 MHz, CDCl$_3$): δ 4.15 (s, 2H); 1.99 (t, J=4.8 Hz, 2H); 1.77 (s, 3H); 1.59-1.64 (m, 2H); 1.45-1.48 (m, 2H); 1.06 (s, 6H).

Step B—Synthesis of Compound Int-28b

To a solution of compound Int-28a (3.70 g, 23.99 mmol) in 200 mL of Et$_2$O was added tribromophosphine (1.14 ml, 11.99 mmol) at 0° C. The reaction was then slowly warmed up to room temperature overnight. It was quenched with 200 mL of saturated NaHCO$_3$ aqueous solution at 0° C. The aqueous was extracted with 2×200 mL Et$_2$O. The combined organic phase was washed with brine, dried over anhydrous Na$_2$SO$_4$ and concentrated to compound Int-28b as a colorless oil. $^1$H NMR (400 MHz, CDCl$_3$): δ 4.11 (s, 2H); 2.05 (t, J=4.8 Hz, 2H); 1.77 (s, 3H); 1.57-1.64 (m, 2H); 1.45-1.49 (m, 2H); 1.13 (s, 6H).

Example 47

Preparation of Compound 108 and 109

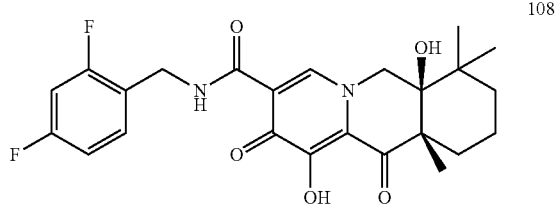

-continued

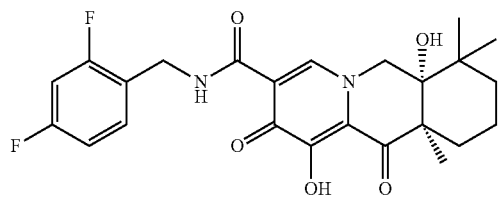

Compound 108 was prepared by following essentially the same method as described in Example 36 for compound 94, and replacing compound Int-20d with compound Int-28b in Step A. $^1$H NMR (400 MHz, CDCl$_3$): δ 10.51 (s, 1H); 8.52 (s, 1H); 7.36-7.41 (m, 1H); 6.81-6.87 (m, 2H); 4.64-4.73 (m, 2H); 4.37 (d, J=10.4, 1H); 4.23 (d, J=10.4, 1H); 2.32-2.34 (m, 1H); 1.57-1.72 (m, 3H); 1.37 (s, 3H); 1.29-1.34 (m, 2H); 1.24 (s, 3H); 0.73 (s, 3H). LCMS anal. calcd. for C$_{24}$H$_{26}$F$_2$N$_2$O$_5$: 460.18. Found: 461.18 (M+1)$^+$.

Compound 109 was prepared by following essentially the same method as described in Example 36 for compound 95, and replacing compound Int-20d with compound Int-28b in Step A. $^1$H NMR (400 MHz, CDCl$_3$): δ 10.46 (s, 1H); 8.49 (s, 1H); 7.37-7.40 (m, 1H); 6.84-6.89 (m, 2H); 4.66-4.69 (m, 2H); 4.34 (d, J=10.4, 1H); 4.22 (d, J=10.4, 1H); 2.33-2.35 (m, 1H); 1.61-1.72 (m, 3H); 1.37 (s, 3H); 1.29-1.34 (m, 2H); 1.14 (s, 3H); 0.73 (s, 3H). LCMS anal. calcd. for C$_{24}$H$_{26}$F$_2$N$_2$O$_5$: 460.18. Found: 461.18 (M+1)$^+$.

Example 48

Preparation of Compound 110 and 111

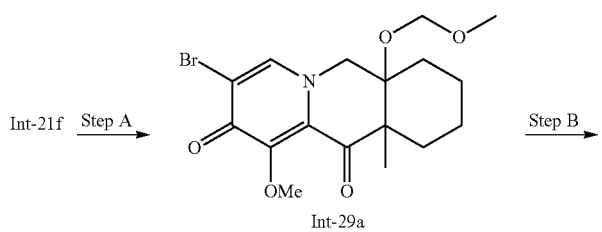

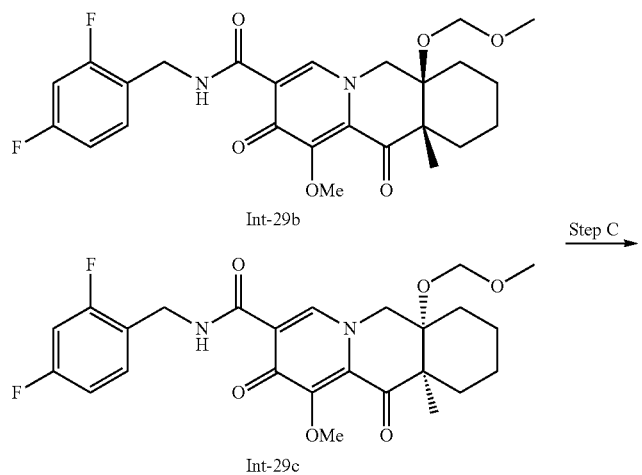

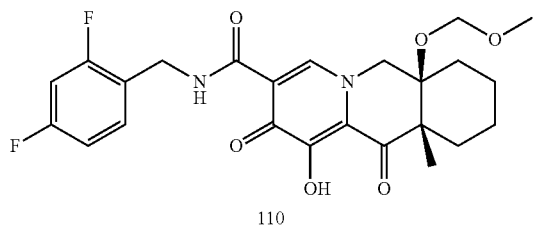

110

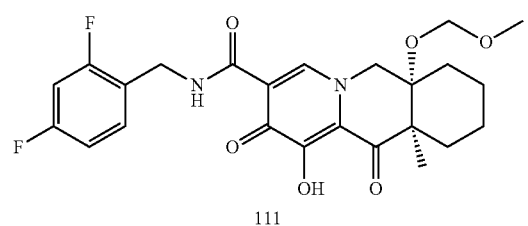

111

Step A—Synthesis of Compound Int-29a

To a stirred solution of compound Int-21f (70 mg, 0.197 mmol) in 2 mL of $CH_2Cl_2$ was added chloro(methoxy)methane (15.82 mg, 0.197 mmol), N-ethyl-N-isopropylpropan-2-amine (25.4 mg, 0.197 mmol) and N,N-dimethylpyridin-4-amine (24.01 mg, 0.197 mmol). The mixture was allowed to stir at 60° C. for 4 h. The reaction was concentrated in vacuo and the resulting residue was added 2 mL of DMSO. It was purified using Gilson eluting with 10% ACN (0.1% TFA)/$H_2O$ to 90% ACN (0.1% TFA)/$H_2O$ for 12 min to afford compound Int-29a as light yellow solid. LCMS anal. calcd. for $C_{17}H_{22}BrNO_5$: 399.07. Found: 400.07 $(M+1)^+$.

Step B—Synthesis of Compound Int-29b and Int-29c

To a mixture of compound Int-29a (50 mg, 0.125 mmol)), N-ethyl-N-isopropylpropan-2-amine (48.4 mg, 0.375 mmol)), (2,4-difluorophenyl)methanamine (26.8 mg, 0.187 mmol) and (oxybis(2,1-phenylene))bis(diphenylphosphine) (10.09 mg, 0.019 mmol) in 2 mL of DMSO was added diacetoxypalladium (4.21 mg, 0.019 mmol). The above mixture was flushed through CO for 20 min with CO balloon at room temperature, then heated at 80° C. under a CO balloon for 2 h. The reaction was cooled down and directly purified using a C18 reverse-phase column (40 g) eluting with 5% ACN/$H_2O$ to 100% ACN/$H_2O$ with 0.1% TFA to afford stereoisomer mixture of the desired product which was then separated by chiral AD column (30×250 mm) eluting with 45% MeOH/$CO_2$ at 70 mL/min to afford compound Int-29b and compound Int-29c individually as a white solid. LCMS anal. calcd. for $C_{25}H_{228}F_2N_2O_6$: 490.19. Found: 491.15 $(M+1)^+$.

Step C—Synthesis of Compound 110 and 111

Compound 110 was prepared by following essentially the same method as described in Example 36 for compound 94, and replacing compound Int-21g with compound Int-29b in Step H. $^1$H NMR (400 MHz, $CDCl_3$): δ 10.48 (s, 1H); 8.47 (s, 1H); 7.36-7.40 (m, 1H); 6.81-6.87 (m, 2H); 4.98 (d, J=6.4 Hz, 1H); 4.64-4.67 (m, 2H); 4.58 (d, J=6.4 Hz, 1H); 4.54 (1H); 4.35 (d, J=11.2, 1H); 3.20 (s, 3H); 1.66-1.96 (6H); 1.49-1.51 (2H); 1.42 (s, 3H). LCMS anal. calcd. for $C_{24}H_{26}F_2N_2O_5$: 476.18. Found: 477.16 $(M+1)^+$.

Compound 111 was prepared by following essentially the same method as described in Example 36 for compound 95, and replacing compound Int-21h with compound Int-29c in Step H. $^1$H NMR (400 MHz, $CDCl_3$): δ 10.46 (s, 1H); 8.45 (s, 1H); 7.36-7.40 (m, 1H); 6.80-6.86 (m, 2H); 4.97 (d, J=6.4 Hz, 1H); 4.64-4.67 (m, 2H); 4.57 (d, J=6.4 Hz, 1H); 4.35 (d, J=11.2, 1H); 3.20 (s, 3H); 1.66-1.95 (6H); 1.48-1.49 (2H); 1.41 (s, 3H). LCMS anal. calcd. for $C_{24}H_{26}F_2N_2O_5$: 476.18. Found: 477.16 $(M+1)^+$.

Example 49

Preparation of Compound 112 and 113

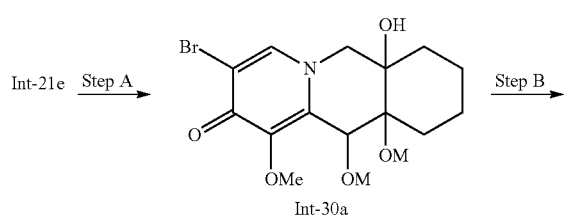

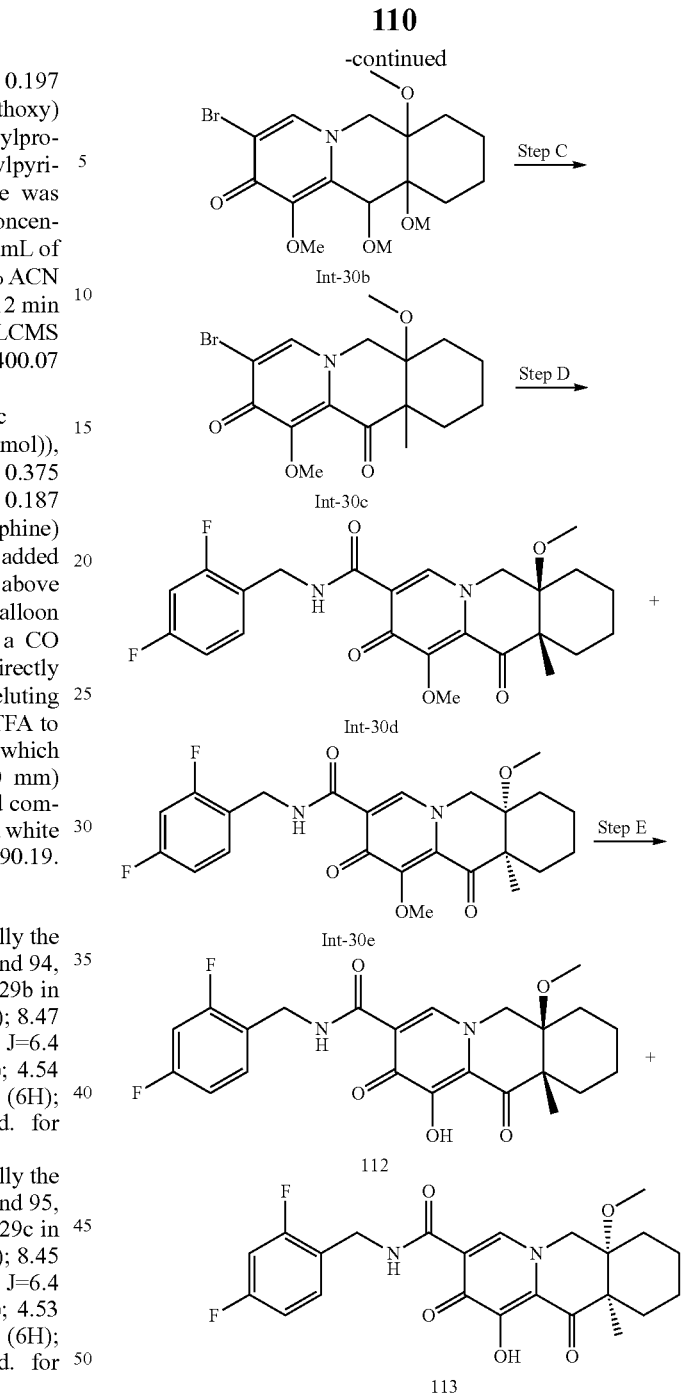

Step A—Synthesis of Compound Int-30a

To a solution of compound Int-21e (0.25 g, 0.698 mmol) in 7 mL of $CH_2Cl_2$ was added N-ethyl-N-isopropylpropan-2-amine (0.45 g, 3.49 mmol), N,N-dimethylpyridin-4-amine (17.05 mg, 0.140 mmol) and chloro(methoxy)methane (281 mg, 3.49 mmol). The mixture was allowed to stir at 50° C. for 1 h. It was cooled down and concentrated. The resulting residue was dissolved in 5 mL of DMSO and purified using Gilson (10% ACN (0.1% TFA)/$H_2O$-90% ACN (0.1% TFA)/$H_2O$, 12 min) to afford compound Int-30a as a light yellow solid. LCMS anal. calcd. for $C_{17}H_{24}BrNO_5$: 401.08. Found: 402.07 $(M+1)^+$.

Step B—Synthesis of Compound Int-30b

To a solution of compound Int-30a (85 mg, 0.211 mmol) in 2 mL of DMF was added iodomethane (90 mg, 0.634 mmol) and followed by sodium hydride (15.21 mg, 0.634 mmol). The mixture was allowed to stir at 0° C. for 30 min. It was quenched with 0.5 mL of saturated NH$_4$Cl aqueous solution. The mixture was diluted by 3 mL of DMF and purified using Gilson (10% ACN (0.1% TFA)/H$_2$O-90% ACN (0.1% TFA)/H$_2$O, 12 min) to provide compound Int-30b as a light yellow solid. LCMS anal. calcd. for C$_{18}$H$_{26}$BrNO$_5$: 415.10. Found: 415.98 (M+1)$^+$.

Step C—Synthesis of Compound Int-30c

To a stirred solution of compound Int-30b (50 mg, 0.120 mmol) in 2 mL of MeOH was added hydrogen chloride (1201 µl, 1.201 mmol). The mixture was allowed to stir at 50° C. for 30 min. It was concentrated. To the crude product was added 2 mL of CH$_2$Cl$_2$, followed by Dess-Martin periodinane (102 mg, 0.240 mmol). The reaction was allowed to stir at room temperature for 30 min. It was concentrated in vacuo and the resulting residue was dissolved in 3 mL of DMSO. The mixture was purified using Gilson (10% ACN (0.1% TFA)/H$_2$O-90% ACN (0.1% TFA)/H$_2$O, 12 min) to provide compound Int-30c as a white solid. LCMS anal. calcd. for C$_{16}$H$_{20}$BrNO$_4$: 369.06. Found: 370.05 (M+1)$^+$.

Step D—Synthesis of Compound Int-30d and Int-30e

Compound Int-30d and compound Int-30e were prepared by following essentially the same method as compound Int-29b and compound Int-29c described in Example 48, and replacing compound Int-29a with compound Int-30c in Step B. LCMS anal. calcd. for C$_{24}$H$_{26}$F$_2$N$_2$O$_5$: 460.18. Found: 461.08 (M+1)$^+$.

Step F—Synthesis of Compound 112 and 113

Compound 112 was prepared by following essentially the same method as described in Example 36 for compound 94, and replacing compound Int-21g with compound Int-30d in Step H. $^1$H NMR (400 MHz, CDCl$_3$): δ 10.56 (s, 1H); 8.52 (s, 1H); 7.36-7.40 (m, 1H); 6.82-6.87 (m, 2H); 4.64-4.67 (m, 2H); 4.40 (1H); 4.25 (d, J=10.8, 1H); 3.26 (s, 3H); 1.47-1.97 (8H); 1.37 (s, 3H). LCMS anal. calcd. for C$_{24}$H$_{26}$F$_2$N$_2$O$_5$: 446.16. Found: 447.07 (M+1)$^+$.

Compound 113 was prepared by following essentially the same method as described in Example 36 for compound 95, and replacing compound Int-21h with compound Int-30e in Step H. $^1$H NMR (400 MHz, CDCl$_3$): δ 10.56 (s, 1H); 8.47 (s, 1H); 7.32-7.40 (m, 1H); 6.81-6.86 (m, 2H); 4.67-4.69 (m, 2H); 4.37 (1H); 4.22 (d, J=10.8, 1H); 3.27 (s, 3H); 1.47-1.97 (8H); 1.37 (s, 3H). LCMS anal. calcd. for C$_{24}$H$_{26}$F$_2$N$_2$O$_5$: 446.16. Found: 447.07 (M+1)$^+$.

Example 50

Preparation of Compound 114-117

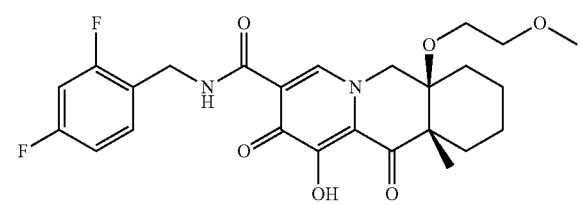

114

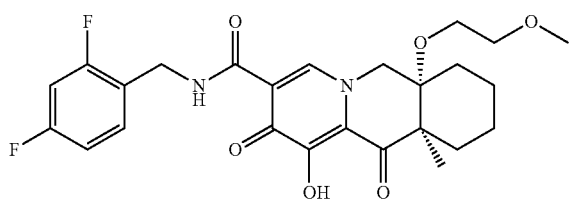

115

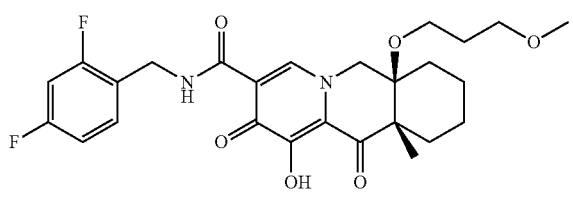

116

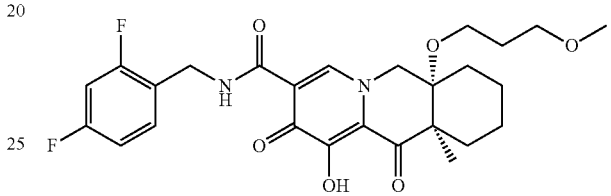

117

Compound 114 was prepared by following essentially the same method as described in Example 49 for compound 112, and replacing iodomethane with 1-bromo-2-methoxyethane in Step B. $^1$H NMR (400 MHz, CDCl$_3$): δ 10.42 (s, 1H); 8.37 (s, 1H); 7.36-7.40 (m, 1H); 6.82-6.87 (m, 2H); 4.67 (d, J=4.8, 2H); 4.35 (1H); 4.22 (d, J=11.2, 1H); 3.63-3.65 (m, 2H); 3.49-3.53 (m, 2H); 3.42 (s, 3H); 3.28 (s, 3H); 1.43-1.97 (8H); 1.39 (s, 3H). LCMS anal. calcd. for C$_{25}$H$_{28}$F$_2$N$_2$O$_6$: 490.19. Found: 491.06 (M+1)$^+$.

Compound 115 was prepared by following essentially the same method as described in Example 49 for compound 113, and replacing iodomethane with 1-bromo-2-methoxyethane in Step B. $^1$H NMR (400 MHz, CDCl$_3$): δ 10.42 (s, 1H); 8.39 (s, 1H); 7.34-7.40 (m, 1H); 6.79-6.86 (m, 2H); 4.67 (d, J=4.4, 2H); 4.40 (1H); 4.23 (d, J=10.8, 1H); 3.62-3.66 (m, 2H); 3.49-3.53 (m, 2H); 3.42 (s, 3H); 3.27 (s, 3H); 1.43-1.97 (8H); 1.39 (s, 3H). LCMS anal. calcd. for C$_{25}$H$_{28}$F$_2$N$_2$O$_6$: 490.19. Found: 491.06 (M+1)$^+$.

Compound 116 was prepared by following essentially the same method as described in Example 49 for compound 112, and replacing iodomethane with 1-bromo-3-methoxypropane in Step B. $^1$H NMR (400 MHz, CDCl$_3$): δ 10.46 (s, 1H); 8.44 (s, 1H); 7.36-7.39 (m, 1H); 6.81-6.86 (m, 2H); 4.67 (d, J=4.4, 2H); 4.38 (1H); 4.22 (d, J=10.8, 1H); 3.58-3.62 (m, 2H); 3.29-3.41 (4H); 3.25 (6H); 1.43-1.97 (8H); 1.38 (s, 3H). LCMS anal. calcd. for C$_{25}$H$_{28}$F$_2$N$_2$O$_6$: 504.21. Found: 505.11 (M+1)$^+$.

Compound 117 was prepared by following essentially the same method as described in Example 49 for compound 113, and replacing iodomethane with 1-bromo-3-methoxypropane in Step B. $^1$H NMR (400 MHz, CDCl$_3$): δ 10.46 (s, 1H); 8.44 (s, 1H); 7.36-7.41 (m, 1H); 6.81-6.86 (m, 2H); 4.67 (d, J=4.4, 2H); 4.38 (1H); 4.22 (d, J=10.8, 1H); 3.58-3.62 (m, 2H); 3.29-3.41 (4H); 3.25 (6H); 1.43-1.97 (8H); 1.38 (s, 3H). LCMS anal. calcd. for C$_{25}$H$_{28}$F$_2$N$_2$O$_6$: 504.21. Found: 505.11 (M+1)$^+$.

Example 51

Preparation of Compound Int-31

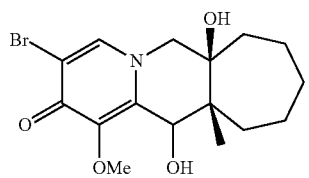

Int-31

Compound Int-31 was prepared using the method described in Step A to Step E of Example 36, and replacing compound Int-20d with compound Int-22 in Step A. LCMS anal. calcd. for $C_{16}H_{22}BrNO_4$: 371.06. Found: 372.95 $(M+1)^+$.

Example 52

Preparation of Compound 118 and compound 119

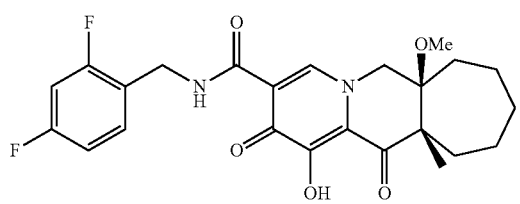

118

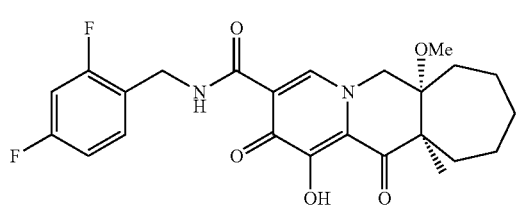

119

Compound 118 was prepared by following essentially the same method as described in Example 49 for compound 112, and replacing compound Int-21e with compound Int-31 in Step A. $^1$H NMR (400 MHz, CDCl$_3$): δ 10.60 (s, 1H); 8.54 (s, 1H); 7.36-7.40 (m, 1H); 6.82-6.87 (m, 2H); 4.65-4.73 (m, 2H); 4.52 (d, J=11.2, 1H); 4.30 (d, J=10.8, 1H); 3.17 (s, 3H); 1.48-2.02 (10H); 1.43 (s, 3H). LCMS anal. calcd. for $C_{24}H_{26}F_2N_2O_5$: 460.18. Found: 461.16 $(M+1)^+$.

Compound 119 was prepared by following essentially the same method as described in Example 49 for compound 113, and replacing compound Int-21e with compound Int-31 in Step A. $^1$H NMR (400 MHz, CDCl$_3$): δ 10.60 (s, 1H); 8.55 (s, 1H); 7.36-7.40 (m, 1H); 6.82-6.87 (m, 2H); 4.64-4.73 (m, 2H); 4.52 (d, J=11.2, 1H); 4.30 (d, J=10.8, 1H); 3.16 (s, 3H); 1.48-2.02 (10H); 1.43 (s, 3H). LCMS anal. calcd. for $C_{24}H_{26}F_2N_2O_5$: 460.18. Found: 461.16 $(M+1)^+$.

Example 53

Preparation of Compound Int-32h

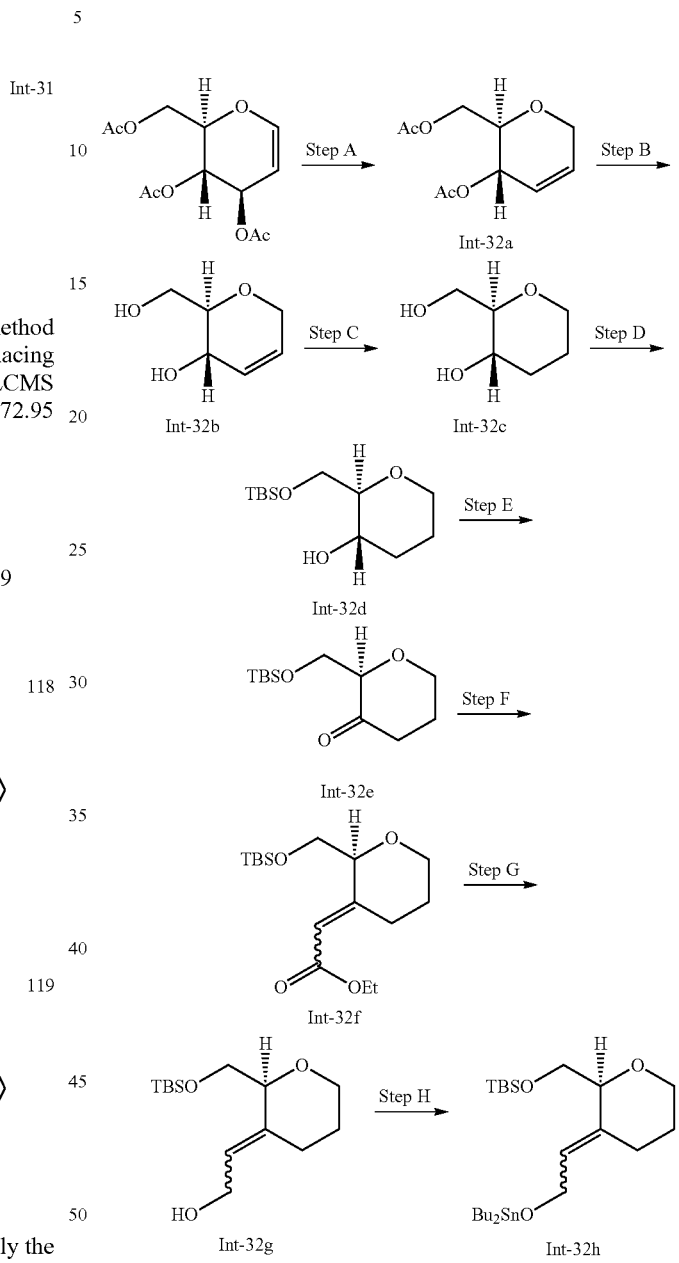

Step A—Synthesis of Compound Int-32a

To a stirred solution of tri-O-acetyl-D-glucal (10.0 g, 36.7 mmol) in 100 mL of CH$_2$Cl$_2$ was added triethylsilane (5.13 g, 44.1 mmol) and boron trifluoride etharate (5.21 g, 36.7 mmol) at 0° C. The mixture was allowed to stir at this temperature for 2 h. It was quenched by adding 100 mL of 0.2 N HCl aqueous solution and 200 mL of CH$_2$Cl$_2$. The organic phase was separated and dried over anhydrous Na$_2$SO$_4$. It was concentrated in vacuo and the resulting residue was purified using silica gel column chromatography eluting with 40% EtOAc/hexane to provide compound Int-32a as a colorless oil. LCMS anal. calcd. for $C_{10}H_{14}O_5$: 214.08. Found: 237.07 $(M+Na)^+$.

Step B—Synthesis of Compound Int-32b

To a solution of compound Int-32a (6.8 g, 31.7 mmol) in 100 mL of MeOH was added sodium methanolate (0.686 g, 3.17 mmol). The reaction was allowed to stir at room temperature overnight. It was concentrated. The resulting residue was purified using silica gel column chromatography eluting with 80% EtOAc/hexane to provide compound Int-32b as a colorless oil. $^1$H NMR (400 MHz, CDCl$_3$): δ 5.81-5.89 (2H); 4.16-4.24 (3H); 3.89 (dd, J=3.2, 5.6 Hz, 1H); 3.83 (dd, J=3.2, 5.6 Hz, 1H); 3.34-3.38 (m, 1H), 2.67 (2H).

Step C—Synthesis of Compound Int-32c

The solution of compound Int-32b (3.5 g, 26.9 mmol) in 120 mL of MeOH was added 10% wt. palladium on carbon (2.86 g, 2.69 mmol). The mixture was stirred under H$_2$ balloon overnight. It was filtered through celite. The filtrate was concentrated to provide compound Int-32c as a colorless oil. $^1$H NMR (400 MHz, CDCl$_3$): δ 3.93 (dd, J=0.8, 9.6 Hz, 1H); 3.84 (dd, J=2.4, 9.2 Hz, 1H); 3.78 (dd, J=4.0, 5.6 Hz, 1H); 3.54-3.59 (m, 1H); 3.36-3.43 (m, 1H); 3.13-3.16 (m, 1H); 2.84 (broad, 1H); 2.12-2.15 (m, 1H); 1.67-1.74 (m, 2H); 1.41-1.49 (m, 1H).

Step D—Synthesis of Compound Int-32d

The solution of compound Int-32c (3.0 g, 22.70 mmol) in 40 mL of DMF was added imidazole (4.64 g, 68.10 mmol) and tert-butyldimethychlorosilane (4.45 g, 29.50 mmol). The mixture was allowed to stir at room temperature for 3 h. It was added 200 mL of H$_2$O. The aqueous was extracted with 2×200 mL of EtOAc. The combined organic phase was dried over Na$_2$SO$_4$ and concentrated. The resulting residue was purified using silica gel column chromatography eluting with 15% EtOAc/hexane to provide compound Int-32d as a colorless oil. LCMS anal. calcd. for C$_{12}$H$_{26}$O$_3$Si: 246.17. Found: 247.17 (M+H)$^+$.

Step E—Synthesis of Compound Int-32e

To a solution of compound Int-32d (5.0 g, 20.29 mmol) in 150 mL of CH$_2$Cl$_2$ and 30 mL of DMSO was added triethylamine (6.16 g, 60.9 mmol)) and PySO$_3$ complex (6.46 g, 40.6 mmol) at 0° C. After 10 min, the ice bath was removed and the mixture was allowed to stir at room temperature for 2 h. The resulting mixture was added 100 mL of H$_2$O and 100 mL of CH$_2$Cl$_2$. The organic phase was separated and the aqueous was extracted with 2×50 mL of CH$_2$Cl$_2$. The combined organic phase was dried over Na$_2$SO$_4$ and concentrated. The resulting residue was purified using silica gel column chromatography eluting with 10% EtOAc/hexane to provide compound Int-32e as a colorless oil. LCMS anal. calcd. for C$_{12}$H$_{26}$O$_3$Si: 244.40. Found: 245.33 (M+H)$^+$.

Step F—Synthesis of Compound Int-32f

To a solution of ethyl 2-(trimethylsilyl)acetate (4.98 g, 31.1 mmol) in 150 mL of THF at −78° C. was added a solution of 2 N lithium diisopropylamide in THF (17.10 ml, 34.2 mmol) dropwise. The reaction mixture was stirred for 15 minutes, then compound Int-32e (3.8 g, 15.55 mmol) was added. The reaction mixture was allowed to warm up to 40° C. over 3 h, and was quenched by adding 100 mL of saturated aqueous NH$_4$Cl solution. The mixture was extracted with 2×150 mL of ethyl acetate and the combined organic extracts were washed with 150 mL of brine. After drying over MgSO$_4$ and filtration, the solvent was removed under reduced pressure. The resulting residue was purified using silica gel column chromatography eluting with 15% EtOAc/hexane to afford compound Int-32f as a colorless oil. LCMS anal. calcd. for C$_{16}$H$_{30}$O$_4$Si: 314.19. Found: 315.12 (M+H)$^+$.

Step G—Synthesis of Compound Int-32g

To a solution of compound Int-32f (4.0 g, 12.72 mmol) in 120 mL of CH$_2$Cl$_2$ cooled at −78° C. was added 1 N diisobutylaluminum hydride in toluene (28.0 ml, 28.0 mmol). The reaction was allowed to stir at −78° C. for 1 h and then warmed up to 0° C. At this time, it was quenched by adding 100 mL of saturated Rochelle salt solution. The mixture was allowed to stir at room temperature for 1 h. The organic phase was separated. It was washed with 50 mL of brine and concentrated to provide compound Int-32g as a colorless oil. LCMS anal. calcd. for C$_{14}$H$_{28}$O$_3$Si: 272.18. Found: 255.05 (M−H$_2$O)$^+$.

Step H—Synthesis of Compound Int-32h

To a solution of compound Int-32g (1.0 g, 3.67 mmol) in 36 mL of THF was added triethylamine (1.11 g, 11.01 mmol), followed by methanesulfonyl chloride (0.84 g, 7.34 mmol) at 0° C. The reaction was allowed to stir at 0° C. for 1 h. It was diluted with 100 mL of EtOAc and washed with 100 mL of 0.2 N aqueous HCl solution 3 times, then with 100 mL of brine. The organic phase was concentrated in vacuo. The resulting crude mesylate was dissolved in 10 mL of THF and used in the next reaction without further purification.

In a separate reaction vessel, a solution of 2 N lithium diisobutylamide in THF (3.77 ml, 7.53 mmol) solution was cooled at 0° C. To this was added tributylstannane (1.993 g, 6.85 mmol). The reaction was allowed to stir at 0° C. for 15 min. It was then cooled to −78° C., and the above mentioned mesylate solution was added via syringe. The reaction was allowed to stir at −78° C. for 30 min. It was diluted with 150 mL of 20% EtOAc/hexanes, and washed 150 mL of water. The organic phase was concentrated in vacuo. The resulting residue was purified using silica gel column chromatography eluting initially with hexanes to removed Bu$_3$SnH, and then with 10% EtOAc/hexanes to provide compound Int-32h as a colorless oil. $^1$H NMR (400 MHz, CDCl$_3$): δ 5.40-5.43 (m, 1H); 4.52-4.54 (m, 1H); 3.91-3.98 (2H); 3.76-3.90 (m, 2H); 3.62-3.68 (m, 2H); 2.31-2.37 (m, 2H); 2.11-2.18 (m, 2H); 1.58-1.70 (m, 6H); 1.44 (m, 6H); 1.30-1.37 (m, 6H); 0.86-1.00 (19H); 0.09-0.11 (6H).

Example 54

Preparation of Compound 120

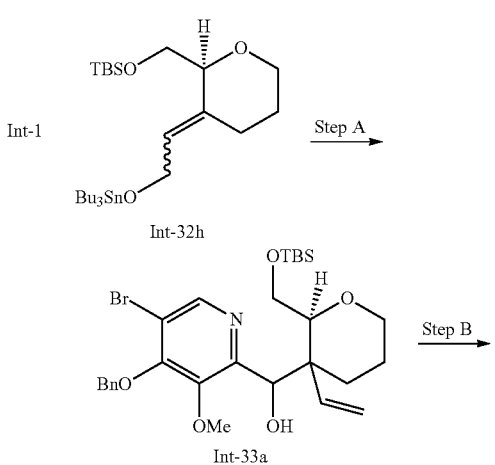

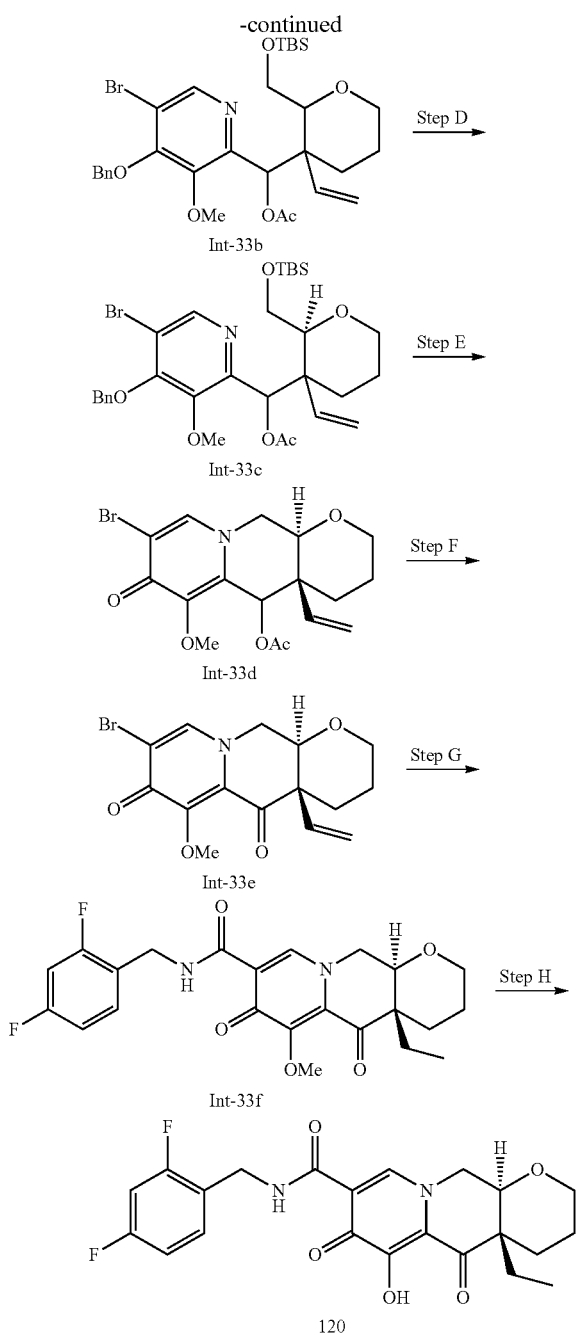

Step B—Synthesis of Compound Int-33b

A solution of compound Int-33a (755 mg, 1.305 mmol) in acetic anhydride (6 ml, 63.5 mmol) was added triethylamine (660 mg, 6.52 mmol) and N,N-dimethylpyridin-4-amine (80 mg, 0.652 mmol). The reaction was allowed to stir at room temperature for 1 h. The solvent was removed in vacuo. The resulting residue was purified using silica gel column chromatography eluting with 20% EtOAc/hexanes to provide compound Int-33b as a colorless film. LCMS anal. calcd. for $C_{30}H_{42}BrNO_6Si$: 619.20. Found: 620.16 $(M+H)^+$.

Step C—Synthesis of Compound Int-33c

To a stirred solution compound Int-33b (800 mg, 1.289 mmol) in 12 mL of THF was added 1 N tetrabutylammonium fluoride in THF (2578 μl, 2.58 mmol). The mixture was allowed to stir at room temperature for 3 h. It was concentrated to remove most of THF. The resulting residue was purified using silica gel column chromatography eluting with 50% EtOAc/hexane to compound Int-33c as a colorless foam. LCMS anal. calcd. for $C_{30}H_{42}BrNO_6$: 505.11. Found: 505.96 $(M+H)^+$.

Step D—Synthesis of Compound Int-33d

To a solution of compound Int-33c (70 mg, 0.138 mmol) in 10 mL of THF at 0° C. was added triethylamine (42.0 mg, 0.415 mmol) and methanesulfonyl chloride (31.7 mg, 0.276 mmol). The mixture was allowed to stir at this temperature for 15 min. It was diluted with 20 mL of EtOAc. The organic phase was washed with 20 mL of 0.5 N HCl, dried over $Na_2SO_4$. After filtration, it was concentrated. The resulting residue was dissolved in 2 mL of DMF and then added sodium iodide (207 mg, 1.382 mmol). The reaction was allowed to stir at 70° C. for 30 min. After cooled to room temperature, it was then purified using Gilson (10% ACN (0.1% TFA)/$H_2O$-90% ACN (0.1% TFA)/$H_2O$, 12 min) to afford the desired iodo intermediate. This intermediate was then dissolved in 2 mL of DMF, followed by adding cesium carbonate (225 mg, 0.691 mmol). The reaction mixture was allowed to stir at 70° C. for 30 min. It was cooled to room temperature and purified using Gilson (10% ACN (0.1% TFA)/$H_2O$-90% ACN (0.1% TFA)/$H_2O$, 12 min) to afford compound Int-33d as a white solid. LCMS anal. calcd. for $C_{12}H_{20}NO_5$: 397.05. Found: 398.02 $(M+H)^+$.

Step D—Synthesis of Compound Int-33e

To a stirred mixture of compound Int-33d (40 mg, 0.101 mmol) in 2 mL of MeOH was added potassium carbonate (45 mg, 0.303 mmol). The mixture was allowed to stir at room temperature for 1 h. It was concentrated in vacuo and the resulting residue was dissolved in 3 mL of DMSO. This was purified using Gilson (10% ACN (0.1% TFA)/$H_2O$-90% ACN (0.1% TFA)/$H_2O$, 12 min) to provide the desired alcohol intermediate, which was then dissolved in 3 mL of $CH_2Cl_2$. Dess-Martin periodinane (79 mg, 0.187 mmol) was then added. The reaction was allowed to stir at room temperature for 30 min. It was added 1 drop of water and the resulting reaction mixture was filtered. The filtrate was concentrated in vacuo and the resulting residue was dissolved in 3 mL of DMSO. It was purified using Gilson (10% ACN (0.1% TFA)/$H_2O$—90% ACN (0.1% TFA)/$H_2O$, 12 min) to afford compound Int-33e as a white solid. LCMS anal. calcd. for $C_{15}H_{16}BrNO_4$: 353.03. Found: 353.97 $(M+H)^+$.

Step E—Synthesis of Compound Int-33f

To a mixture of compound Int-33e (20 mg, 0.056 mmol), N-ethyl-N-isopropylpropan-2-amine (21.89 mg, 0.169 mmol), (2,4-difluorophenyl)methanamine (12.12 mg, 0.085 mmol) and (oxybis(2,1-phenylene))bis(diphenylphosphine) (6.08 mg, 0.011 mmol) in 1 mL of DMSO was added diacetoxypalladium (2.54 mg, 0.011 mmol). The above Step A—Synthesis of Compound Int-33a To a solution of compound Int-1 (810 mg, 2.51 mmol)) and compound Int-32h (1.50 g, 2.75 mmol) in 25 mL of ACN at 0° C. was added stannous chloride (763 mg, 4.02 mmol). The reaction was then warm to room temperature and stirred for 30 min. It was added 20 mL of saturated $NH_4Cl$ aqueous solution. The resulting mixture was allowed to stir at room temperature for 5 min. This was diluted with 100 mL of 30% EtOAc/hexanes, and washed with 100 mL of water. The organic phase was separated and filtered. The mother liquor was concentrated in vacuo and the resulting residue was purified using silica gel column chromatography eluting with 10% EtOAc/hexane to compound Int-33a as colorless oil. LCMS anal. calcd. for $C_{28}H_{40}BrNO_5Si$: 577.19. Found: 578.12 $(M+H)^+$.

mixture was then flushed through CO for 20 min with CO balloon at room temperature, then heated at 80° C. under CO balloon for 2 h. The reaction was cooled down to room temperature and directly purified using Gilson (10% ACN (0.1% TFA)/H$_2$O-90% ACN (0.1% TFA)/H$_2$O, 12 min) to afford the carbonylation product, which was then dissolved in 2 mL of MeOH. To this was added 10 mg 10% Pd on carbon. The reaction was allowed to stir at room temperature under a H$_2$ balloon for 3 h. It was filtered. The filtrate was concentrated in vacuo and the resulting residue was purified using silica gel column chromatography eluting with 20% EtOAc/CH$_2$Cl$_2$ to provide compound Int-33f as a white solid. LCMS anal. calcd. for C$_{23}$H$_{24}$F$_2$N$_2$O$_5$: 446.17. Found: 447.12 (M+H)$^+$.

Step F—Synthesis of Compound 120

Compound 120 was prepared by following essentially the same method as compound 94 described in Example 36, and replacing compound Int-21g with compound Int-33f in Step H. $^1$H NMR (400 MHz, CDCl$_3$): δ 10.36 (s, 1H); 8.47 (s, 1H); 7.36-7.40 (m, 1H); 6.81-6.87 (m, 2H); 4.68 (d, J=8.4 Hz, 2H); 4.20 (m, 2H); 4.13 (dd, J=4.8, 9.2 Hz, 1H); 3.99 (dd, J=4.8, 9.2 Hz, 1H); 3.56 (m, 1H); 2.45-2.48 (m, 1H); 2.27 (m, 1H); 1.85 (m, 1H); 1.65 (m, 1H); 1.54 (m, 1H); 0.91 (t, J=5.6, 3H). LCMS anal. calcd. for C$_{22}$H$_{22}$F$_2$N$_2$O$_5$: 432.15. Found: 433.07 (M+1)$^+$.

Example 55

Preparation of Compound 121 and Compound 122

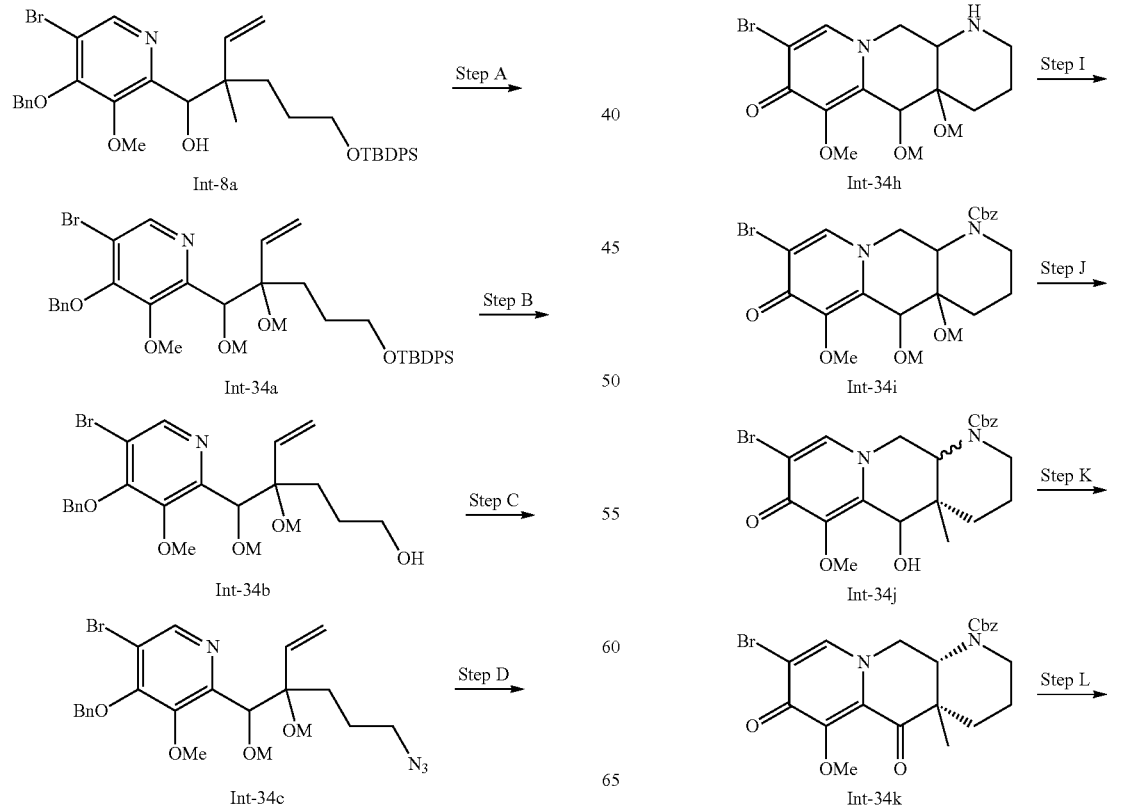

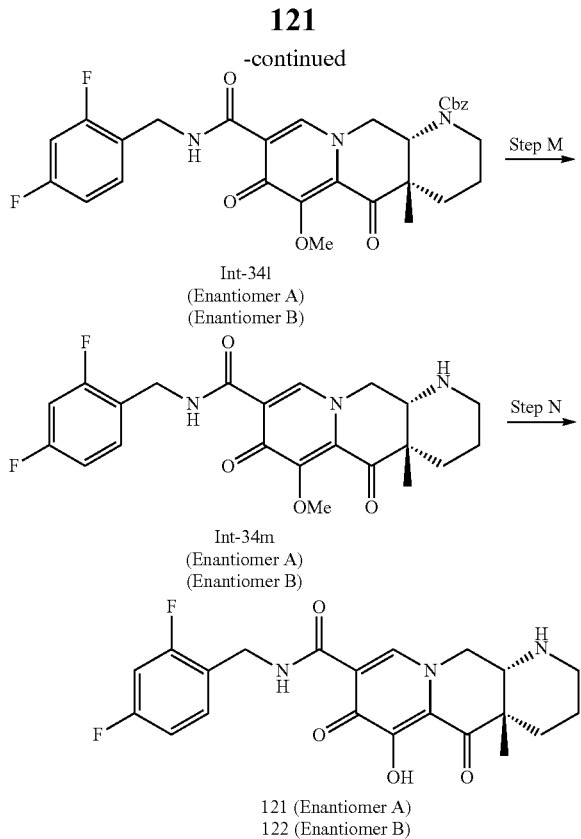

Int-34l
(Enantiomer A)
(Enantiomer B)

Int-34m
(Enantiomer A)
(Enantiomer B)

121 (Enantiomer A)
122 (Enantiomer B)

Step A—Synthesis of Compound Int-34a

To a solution of compound Int-8a (4.85 g, 7.19 mmol) in CH$_2$Cl$_2$ (71.9 ml) was added Hunig's Base (6.28 ml, 35.9 mmol) followed by chloromethyl methyl ether (2.457 ml, 32.3 mmol) and DMAP (0.044 g, 0.359 mmol). The reaction was allowed to stir at room temperature for 72 h. At the completion, the volatiles were removed under vacuo. The resulting residue was purified using ISCO, normal phase HP Gold silica gel (120 g), eluting with hexanes/EtOAc (100% hexanes for 5 min; gradient to 30% EtOAc in hexanes over 30 min, isocratic for 5 min) to afford compound Int-34a as a colorless oil. LCMS anal. calcd. for C$_{39}$H$_{48}$BrNO$_5$Si: 717.25. Found: 717.81 (M+1)$^+$.

Step B—Synthesis of Compound Int-34b

To a solution of compound Int-34a (4.35 g, 6.05 mmol) in THF (30.3 ml) was added TBAF (1M in THF) (18.16 ml, 18.16 mmol). The reaction was allowed to stir at room temperature for 2 h. At the completion, the volatiles were removed under vacuo. The resulting residue was purified using ISCO, normal phase HP Gold silica gel (80 g), eluting with hexanes/EtOAc (100% hexanes for 5 min; gradient to 100% EtOAc in hexanes over 25 min, isocratic for 10 min) to afford compound Int-34b as a colorless oil. LCMS anal. calcd. for C$_{23}$H$_{30}$BrNO$_5$: 479.13. Found: 480.01 (M+1)$^+$.

Step C—Synthesis of Compound Int-34c

To a solution of compound Int-34b (3 g, 6.24 mmol) in THF (62.4 ml), was added Hunig's Base (3.27 ml, 18.73 mmol). It was cooled to 0° C., and methanesulfonyl chloride (0.888 ml, 11.24 mmol) was then added. The reaction was allowed to stir at 0° C. for 30 min. It was diluted with 60 mL of hexanes and then filtered. The filtrate was concentrated in vacuo. The resulting residue was mixed with sodium azide (4.06 g, 62.4 mmol) and then added DMF (62.4 ml). The resulting mixture was heated at 60° C. for 1 h. The reaction was allowed to cool to room temperature. It was diluted with 500 mL of 50% EtOAc/hexanes and washed with 300 mL of water. The organic layer was dried over anhydrous Na$_2$SO$_4$, filtered and concentrated in vacuo. The resulting residue was purified using a silica gel column (120 g) eluting with EtOAc/hexanes 0-35% in 35 min to provide compound Int-34c. LCMS anal. calcd. for C$_{23}$H$_{29}$BrN$_4$O$_4$: 504.14; Found: 505.08 (M+1)$^+$.

Step D—Synthesis of Compound Int-34d

To a solution of compound Int-34c (2.4 g, 4.75 mmol) in 47.3 mL of THF/t-BuOH/water (5:5:1), was added 4-methylmorpholine n-oxide (0.612 g, 5.22 mmol) followed by 4% wt. osmium tetroxide in water (8.93 ml, 0.712 mmol). The reaction was allowed to stir at room temperature for 24 h. To this was added 30 g of solid Na$_2$S$_2$O$_5$. The mixture was allowed to stir at room temperature for 1 h. The content was diluted with 300 mL of 50% EtOAc/hexanes. The brown solid was filtered off. The filtrated was washed with water and concentrated. The resulting residue was purified using a silica gel column (120 g) eluting with 0-100% EtOAc/hexanes over 30 min, 100% for 5 min to provide compound Int-34d as a colorless oil. LCMS anal. calcd. for C$_{23}$H$_{31}$BrN$_4$O$_6$: 538.14. Found: 539.09 (M+1)$^+$.

Step E—Synthesis of Compound Int-34e

To a mixture of compound Int-34d (2.2 g, 4.08 mmol) and 4-methylbenzene-1-sulfonyl chloride (1.555 g, 8.16 mmol), was added pyridine (20.39 ml). The reaction solution was allowed to stir at room temperature for 7 h. To this was added 20 mL of MeOH. It was allowed to stir at room temperature for 20 min. The volatile was removed in vacuo. The resulting residue was diluted with 200 mL of CH$_2$Cl$_2$, and washed with 100 mL of 0.5 N HCl (aq.) twice. The organic layer was dried over anhydrous Na$_2$SO$_4$ and then concentrated. The resulting residue was purified using ISCO, normal phase HP Gold silica gel (120 g), eluting with hexanes/EtOAc (100% hexanes for 5 min; gradient to 100% EtOAc in hexanes over 25 min, isocratic for 5 min) to provide compound Int-34e. LCMS anal. calcd. for C$_{16}$H$_{23}$BrN$_4$O$_5$: 430.09. Found: 431.00 (M+1)$^+$.

Step F—Synthesis of Compound Int-34f

To a solution of compound Int-34e (1.55 g, 3.59 mmol) in CH$_2$Cl$_2$ (71.9 ml) at room temperature under N$_2$, was added Dess-Martin Periodinane (3.05 g, 7.19 mmol) portionwise. The reaction was allowed to stir at room temperature for 1 h. To the reaction mixture was added 1 ml of water and stirred for a while. Then reaction was diluted with 50 mL of EtOAc. The solid was filtered off. The filtrate was concentrated in vacuo. The resulting residue was purified using ISCO, normal phase HP Gold silica gel (120 g), eluting with hexanes/EtOAc (100% hexanes for 5 min; gradient to 100% EtOAc over 15 min, isocratic for 10 min) to provide compound Int-34f. LCMS anal. calcd. for C$_{16}$H$_{21}$BrN$_4$O$_5$: 428.07. Found: 429.00 (M+1)$^+$.

Step G—Synthesis of Compound Int-34g

To a solution of compound Int-34f (1.4 g, 3.26 mmol) and Et$_3$N (2.273 ml, 16.31 mmol) in THF (26.1 ml) and Water (6.52 ml) was added Ph$_3$P (1.711 g, 6.52 mmol). The reaction was allowed to stir at room temperature overnight. The volatile was removed under vacuo. The resulting residue was purified using ISCO, reverse phase HP Gold C18 (100 g), eluting with acetonitrile (with 0.1% TFA)/water (0% water for 2 min; gradient to 100% ACN in water over 30 min, isocratic for 5 min). Related fractions were pooled and evaporated under reduced pressure to afford compound Int-34g. LCMS anal. calcd. for C$_{16}$H$_{23}$BrN$_2$O$_5$: 402.08. Found: 402.98 (M+1)$^+$.

Step H—Synthesis of Compound Int-34h

To a mixture of compound Int-34g TFA salt form (1.641 g, 3.29 mmol) in $CH_2Cl_2$ (49.8 ml) and MeOH (9.96 ml) was added sodium cyanoborohydride (0.413 g, 6.57 mmol). The mixture was allowed to stir at room temperature for 2 h. The mixture was quenched by adding dropwise 1 mL of HOAc, and then concentrated in vacuo. The resulting residue was purified using ISCO, reverse phase HP Gold C18 (275 g), eluting with acetonitrile (with 0.1% TFA)/water (0% water for 4 min; gradient to 40% ACN in water over 30 min, isocratic for 5 min). Related fractions were pooled and evaporated under reduced pressure to provide compound Int-34h as a colorless oil. LCMS anal. calcd. for $C_{16}H_{23}BrN_2O_4$: 386.08. Found: 387.00 $(M+1)^+$.

Step I—Synthesis of Compound Int-34i

To a mixture of compound Int-34h TFA salt form (600 mg, 1.197 mmol) in 12 mL of $CH_2Cl_2$ was added triethylamine (1001 µl, 7.18 mmol) followed by benzyl chloroformate (342 µl, 2.394 mmol) dropwise. The mixture was allowed to stir at room temperature for 2 h. The mixture was diluted with water and extracted with ethyl acetate twice. The combined organic fractions were washed with brine, dried ($Na_2SO_4$), filtered and the solvent was evaporated under reduced pressure. The resulting residue was purified using ISCO, normal phase HP Gold silica gel (40 g), eluting with hexanes/EtOAc (100% hexanes for 5 min; gradient to 100% EtOAc over 20 min, isocratic for 10 min) to provide compound Int-34i. LCMS anal. calcd. for $C_{24}H_{29}BrN_2O_6$: 520.12. Found: 521.03 $(M+1)^+$.

Step J—Synthesis of Compound Int-34j

To a solution of compound Int-34i (527 mg, 1.011 mmol) in 10 mL of MeOH, was added 2 ml of 12 N aqueous HCl. The reaction was allowed to stir at 60° C. for 5 h. The volatile was removed under vacuo. The resulting residue was dissolved in EtOAc and neutralized by adding $Et_3N$ dropwise. The resulting mixture was washed with water followed by brine. The organic phase was dried over anhydrous $Na_2SO_4$, filtered and concentrated in vacuo. The resulting residue was purified using ISCO, normal phase HP Gold silica gel (80 g), eluting with $CH_2Cl_2$/MeOH (100% $CH_2Cl_2$ for 5 min; gradient to 10% MeOH in $CH_2Cl_2$ over 24 min, isocratic for 5 min) to provide compound Int-34j. LCMS anal. calcd. for $C_{22}H_{25}BrN_2O_5$: 476.09; Found: 477.05 $(M+1)^+$.

Step K—Synthesis of Compound Int-34k

To a solution of compound Int-34j (482 mg, 1.010 mmol) in 20 mL of $CH_2Cl_2$ at room temperature under $N_2$, was added Dess-MartinPeriodinane (557 mg, 1.313 mmol). The reaction was allowed to stir at room temperature for 2 h. The reaction was diluted with EtOAc and washed with saturated $Na_2CO_3$ aqueous solution. The organic suspension was concentrated in vacuo. To the resulting residue was added 10 mL of $CH_2Cl_2$. The solid was collected by filtration to provide compound Int-34k. The filtrate was purified using by ISCO, normal phase HP Gold silica gel (80 g) column and eluting with hexanes/EtOAc (100% hexanes for 5 min; gradient to 100% EtOAc over 35 min, isocratic for 6 min) to provide additional compound Int-34k as a white solid. LCMS anal. calcd. for $C_{22}H_{23}BrN_2O_5$: 474.08. Found: 475.03 $(M+1)^+$.

Step L—Synthesis of Compound Int-34l

To a mixture of compound Int-34k (93.7 mg, 0.197 mmol), N-ethyl-N-isopropylpropan-2-amine (105 µl, 0.591 mmol)), (2,4-difluorophenyl)methanamine (42.3 µl, 0.355 mmol) and (oxybis(2,1-phenylene))bis(diphenylphosphine) (42.5 mg, 0.079 mmol) in 5 mL of DMSO was added diacetoxypalladium (17.70 mg, 0.079 mmol). The mixture was flushed with CO balloon for 30 min. Then the mixture was heated at 90° C. for 1 h under CO balloon. The reaction mixture was purified using preparative HPLC (reverse phase, YMC-Pack ODS C-18 100×20 mm) eluting with acetonitrile/water/0.05% TFA (20% to 90% organic in 10 min, then to 100% in 2 min, 20 mL/min). Related fractions were pooled and evaporated under reduced pressure to afford compound Int-34l as its racemic mixture. This material was resolved by a chiral preparative SFC (ChiralPak AS, 30×250 mm, 70 mL/min, 100 bar, 50% MeOH (0.2% $NH_4OH$)/$CO_2$, 35° C.) to provide enantiomer A of compound Int-34l (first to elute) and enantiomer B of compound Int-34l (second to elute). LCMS anal. calcd. for $C_{30}H_{29}F_2N_3O_6$: 565.20. Found: 566.16 $(M+1)^+$.

Step M—Synthesis of Compound Int-34m

To a solution of enantiomer A of compound Int-34l (8.8 mg, 0.016 mmol) in MeOH (2 ml), was added 10% wt. Pd-C (2.484 mg, 2.334 µmol). The mixture was stirred under $H_2$ balloon for 1 h. At the completion, the catalyst was filtered off. The filtrate was concentrated in vacuo to afford enantiomer A of compound Int-34m as a pale yellow solid. LCMS anal. calcd. for $C_{22}H_{23}F_2N_3O_4$: 431.17. Found: 432.11 $(M+1)^+$.

Step N—Synthesis of Compound 121 and 122

A mixture of enantiomer A of compound Int-34m (7.5 mg, 0.017 mmol) and lithium chloride (7.37 mg, 0.174 mmol) in DMF (435 µl) was heated at 100° C. for 2 h. At completion, it was cooled down and diluted with 1 mL of DMSO. The crude was purified using preparative HPLC (reverse phase, YMC-Pack ODS C-18 100×20 mm) eluting with acetonitrile/water/0.1% TFA (0% to 70% organic in 10 min, then to 100% in 2 min, 20 mL/min). Related fractions were pooled and evaporated under reduced pressure to afford compound 121 as a pale yellow solid. $^1H$ NMR (500 MHz, $CD_3OD$): δ 10.3 (brs, 1H); 8.50 (s, 1H); 7.41-7.45 (m, 1H); 6.93-6.99 (m, 2H); 4.93-5.02 (m, 1H); 4.51-4.67 (m, 3H); 4.02-4.07 (m, 1H); 3.36-3.45 (m, 1H); 3.13-3.24 (m, 1H); 2.60-2.75 (m, 1H); 1.83-1.93 (m, 1H); 1.52-1.68 (m, 2H); 1.48 (s, 3H). LCMS anal. calcd. for $C_{21}H_{21}F_2N_3O_4$: 417.15. Found: 418.11 $(M+1)^+$.

Compound 122 was prepared from enantiomer B of compound Int-34l, using essentially the same method described in Step M and Step N of example 55 for making compound 121. $^1H$ NMR (500 MHz, $CD_3OD$): δ 10.3 (brs, 1H); 8.50 (s, 1H); 7.41-7.45 (m, 1H); 6.93-6.99 (m, 2H); 4.93-5.02 (m, 1H); 4.51-4.67 (m, 3H); 4.02-4.07 (m, 1H); 3.36-3.45 (m, 1H); 3.13-3.24 (m, 1H); 2.60-2.75 (m, 1H); 1.83-1.93 (m, 1H); 1.52-1.68 (m, 2H); 1.48 (s, 3H). LCMS anal. calcd. for $C_{21}H_{21}F_2N_3O_4$: 417.15. Found: 418.11 $(M+1)^+$.

Example 56

Preparation of Compound 123 and Compound 124

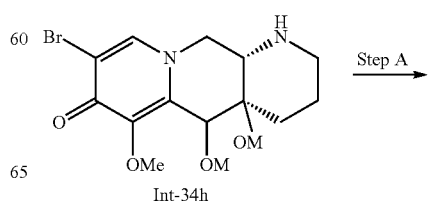

Int-34h

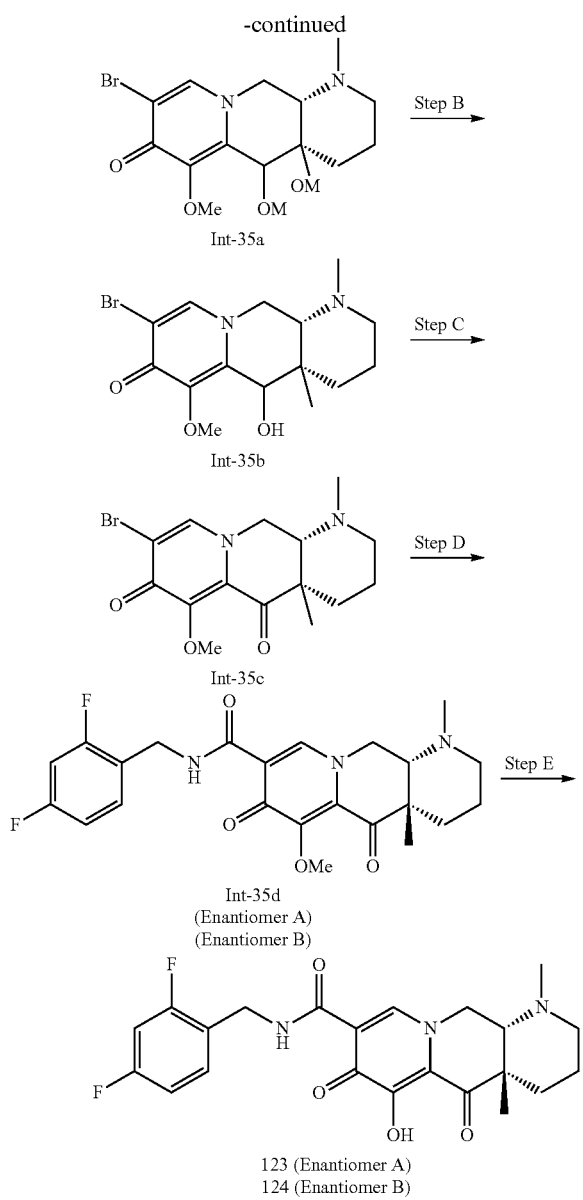

Int-35a

Int-35b

Int-35c

Int-35d
(Enantiomer A)
(Enantiomer B)

123 (Enantiomer A)
124 (Enantiomer B)

Step A—Synthesis of Compound Int-35a

To a mixture of compound Int-34h (724 mg, 1.870 mmol) in 15 mL of CH$_2$Cl$_2$ and 3 mL of MeOH was added formaldehyde (696 μl, 9.35 mmol) followed by sodium cyanoborohydride (235 mg, 3.74 mmol). The mixture was allowed to stir at room temperature for 1 h. At the completion, acetic acid (642 μl, 11.22 mmol) was added to the mixture slowly to quench the reaction. The mixture was concentrated in vacuo. The resulting residue was purified using ISCO, reverse phase HP Gold C18 (150 g), eluting with acetonitrile (0.05% TFA)/water (0.05% TFA) (0% water for 4 min; gradient to 60% ACN in water over 10 min, isocratic for 5 min). Related fractions were pooled and evaporated under reduced pressure to provide compound Int-35a as a colorless oil. LCMS anal. calcd. for C$_{17}$H$_{25}$BrN$_2$O$_4$: 400.10. Found: 401.01 (M+1)$^+$.

Step B—Synthesis of Compound Int-35b

To a solution of compound Int-35a TFA salt form (680 mg, 1.320 mmol) in MeOH (10 ml), was added HCl (concentrated) (2 ml, 24.35 mmol). The reaction was allowed to stir at 60° C. for 5 h. The volatile was removed under vacuo. The resulting residue was redissolved in CH$_2$Cl$_2$ and neutralized by adding Et$_3$N dropwise. The resulting residue was purified using ISCO, reverse phase HP Gold C18 (150 g), eluting with acetonitrile (0.05% TFA)/water (0.05% TFA) (0% water for 4 min; gradient to 50% ACN in water over 10 min, isocratic for 5 min) Related fractions were pooled and evaporated under reduced pressure to provide compound Int-35b as a colorless oil. LCMS anal. calcd. for C$_{21}$H$_{21}$F$_2$N$_3$O$_4$: 356.07. Found: 357.01 (M+1)+.

Step C—Synthesis of Compound Int-35c

To a solution of compound Int-35b TFA salt form (520 mg, 1.103 mmol) in 22 mL of CH$_2$Cl$_2$ stirred at room temperature under N$_2$, was added Dess-Martin Periodinane (608 mg, 1.434 mmol). The reaction was allowed to stir at room temperature for 2 h. The mixture was added 1 drop of water and stir for 5 min. The solid was filtered off. The filtrate was concentrated in vacuo. The resulting residue was purified using ISCO, normal phase HP Gold silica gel (80 g), eluting with CH$_2$Cl$_2$/MeOH (gradient from 5% to 10% MeOH in CH$_2$Cl$_2$ over 25 min, isocratic for 5 min) to provide compound Int-35c as a white solid. LCMS anal. calcd. for C$_{15}$H$_{19}$BrN$_2$O$_3$: 354.06. Found: 355.01 (M+1)$^+$.

Step D—Synthesis of Compound Int-35d

To a mixture of compound Int-35c (20 mg, 0.056 mmol), N-ethyl-N-isopropylpropan-2-amine (30.1 μl, 0.169 mmol)), (2,4-difluorophenyl)methanamine (8.06 μl, 0.068 mmol) and (oxybis(2,1-phenylene))bis(diphenylphosphine) (18.19 mg, 0.034 mmol) in DMSO (1408 μl) was added diacetoxypalladium (7.58 mg, 0.034 mmol). The above reaction was flushed with CO balloon through a long needle to the solution for 30 min. Then the mixture was heated at 90° C. under a balloon of CO for 1 h. The reaction was diluted with 2 mL of DMSO and filtered through a filter disc. The filtrate was purified using preparative HPLC (reverse phase, YMC-Pack ODS C-18 100×20 mm) eluting with acetonitrile (0.05% TFA)/water (0.05% TFA) (0% to 70% organic in 10 min, then to 100% in 2 min, 20 mL/min). Related fractions were pooled and evaporated under reduced pressure to afford compound Int-35d as its racemic mixture. This material was resolved by a chiral preparative SFC (ChiralPak OJ, 20×250 mm, 50 mL/min, 100 bar, 40% MeOH (0.2% NH4OH)/CO2, 35° C.) to provide enantiomer A of compound Int-35d (first to elute) and enantiomer B of compound Int-35d (second to elute). LCMS anal. calcd. for C$_{21}$H$_{21}$F$_2$N$_3$O$_4$: 445.18. Found: 446.14 (M+1)$^+$.

Step D—Synthesis of Compound 123 and 124

A mixture of enantiomer A of compound Int-35d (3.9 mg, 8.76 μmol) and lithium chloride (7.42 mg, 0.175 mmol) in DMF (292 μl) was heated at 100° C. for 2 h. At completion, it was cooled down and diluted with 1 mL of DMSO. The crude was purified using preparative HPLC (reverse phase, YMC-Pack ODS C-18 100×20 mm) eluting with acetonitrile (0.05% TFA)/water (0.05% TFA) (0% to 70% organic in 10 min, then to 100% in 2 min, 20 mL/min) Related fractions were pooled and evaporated under reduced pressure to afford compound 123 as a pale yellow solid. $^1$H NMR (500 MHz, CD$_3$OD): δ 8.63 (s, 1H); 7.43 (m, 1H); 6.92-6.99 (m, 2H); 4.81-5.16 (m, 2H); 4.57-4.69 (m, 2H); 3.93-4.04 (m, 1H); 3.47-3.57 (m, 1H); 3.15-3.26 (m, 1H); 3.07 (s, 3H); 2.64-2.75 (m, 1H); 1.80-1.92 (m, 1H); 1.60-1.73 (m, 2H); 1.52 (s, 3H). LCMS anal. calcd. for C$_{21}$H$_{21}$F$_2$N$_3$O$_4$: 431.17. Found: 432.12 (M+1)$^+$.

A mixture of enantiomer B of compound Int-35d and lithium chloride (7.42 mg, 0.175 mmol) in DMF (88 μl) was heated at 100° C. for 2 h. At completion, it was cooled down and diluted with 1 mL of DMSO. The crude was purified using preparative HPLC (reverse phase, YMC-Pack ODS C-18 100×20 mm) eluting with acetonitrile (0.05% TFA)/water (0.05% TFA) (0% to 70% organic in 10 min, then to 100% in 2 min, 20 mL/min). Related fractions were pooled and evaporated under reduced pressure to afford compound 124 as a pale yellow solid. $^1$H NMR (500 MHz, CD$_3$OD): δ 8.63 (s, 1H); 7.43 (m, 1H); 6.92-6.99 (m, 2H); 4.81-5.16 (m, 2H); 4.57-4.69 (m, 2H); 3.93-4.04 (m, 1H); 3.47-3.57 (m, 1H); 3.15-3.26 (m, 1H); 3.07 (s, 3H); 2.64-2.75 (m, 1H); 1.80-1.92 (m, 1H); 1.60-1.73 (m, 2H); 1.52 (s, 3H). LCMS anal. calcd. for $C_{21}H_{21}F_2N_3O_4$: 431.17. Found: 432.12 (M+1)$^+$.

Example 57

Assay for Inhibition of HIV Replication

This assay is a kinetic assay that employs a reporter cell line (MT4-gag-GFP) to quantify the number of new cells infected in each round of replication.

MT4-GFP cells (250,000 cells/ml) were bulk-infected with HIV-1 (NL4-3 strain) at low multiplicity of infection (MOI) in RPMI+10% FBS for 24 hours. Cells were then washed once in RPMI+10% FBS and resuspended in RPMI+0% or 10% or 100% normal human serum (NHS). Test compounds were serial-diluted in DMSO on ECHO. The infected MT4-GFP cells were added to a 384-well poly-D-lysine coated black plate with clear bottom in which the diluted test compounds were placed. The cells were seeded at 8,000 cells per well and the final DMSO concentration was 0.4%. The infected cells (Green GFP cells) were quantified at both 24 and 48 hours post incubation using Acumen eX3. Viral reproductive ratio (R$_0$) was determined using the number of infected cells at 48 hours divided by the number of infected cells at 24 hours. Percent viral growth inhibition was calculated by [1-(R-R$_{tripledrug}$)/(R$_{DMSO}$-R$_{tripledrug}$)]*100. Compound potency IP or IC$_{50}$ was determined by a 4-parameter dose response curve analysis.

Illustrative compounds of the present invention were tested using this assay protocol and results are presented in the Table below.

| Compound No. | WILD TYPE CELL ASSAY Viking IP (0% NHS) (nM) | WILD TYPE CELL ASSAY Viking IP (100% NHS) (nM) |
|---|---|---|
| 1 | 5.5 | NA |
| 2 | 27 | NA |
| 3 | 6.5 | NA |
| 4 | 74 | 1852 |
| 5 | 2.6 | 102 |
| 6 | 10 | NA |
| 7 | 2.2 | 154 |
| 8 | 1.8 | 500 |
| 9 | 2.6 | 235 |
| 10 | 66 | NA |
| 11 | 3.2 | 484 |
| 12 | 2.6 | 595 |
| 13 | 3.8 | 124 |
| 14 | 0.7 | 26 |
| 15 | 0.5 | 73 |
| 16 | 4.1 | 257 |
| 17 | 2.9 | 117 |
| 18 | 8.7 | 315 |
| 19 | 4.6 | 709 |
| 20 | 3.5 | 839 |
| 21 | 2.4 | 385 |
| 22 | 2.7 | 251 |
| 23 | 1.5 | 1260 |
| 24 | 4.3 | >8400 |
| 25 | 4.2 | >8400 |
| 26 | 1.1 | 2554 |
| 27 | 2.0 | >8400 |
| 28 | 4.4 | >8400 |
| 29 | 17 | >8400 |
| 30 | 2.8 | >8400 |
| 31 | 48 | >8400 |
| 32 | 8.2 | >8400 |
| 33 | 0.5 | 281 |
| 34 | 1.7 | 1500 |
| 35 | 0.4 | 337 |
| 36 | 0.6 | 1400 |
| 37 | 1.5 | 80 |
| 38 | 1.8 | 1600 |
| 39 | 0.8 | 33 |
| 40 | 1.5 | 442 |
| 41 | 2.0 | 34 |
| 42 | 2.1 | 517 |
| 43 | 3.2 | 1999 |
| 44 | 1.9 | 316 |
| 45 | 2.3 | 4748 |
| 46 | 1.3 | 459 |
| 47 | 1.3 | 70 |
| 48 | 1.7 | 913 |
| 49 | 3.2 | 4066 |
| 50 | 1.6 | 293 |
| 51 | 3.6 | 2200 |
| 52 | 3.4 | >8400 |
| 53 | 64 | >8400 |
| 54 | 1.8 | 55 |
| 55 | 8.1 | >8400 |
| 56 | 3.4 | 342 |
| 57 | 4.7 | 3501 |
| 58 | 2.6 | 99 |
| 59 | 2.0 | 110 |
| 60 | 2.9 | 2228 |
| 61 | 1.3 | 32 |
| 62 | 0.9 | 481 |
| 63 | 0.9 | 249 |
| 64 | 0.9 | 2957 |
| 65 | 0.8 | 34 |
| 66 | 2.5 | 126 |
| 67 | 1.7 | 154 |
| 68 | 1.8 | 604 |
| 69 | 1.2 | 24 |
| 70 | 1.9 | 80 |
| 71 | 2.2 | 89 |
| 72 | 2.2 | 467 |
| 73 | 1.0 | 22 |
| 74 | 4.0 | 262 |
| 75 | 0.5 | 13 |
| 76 | 0.9 | 35 |
| 77 | 1.2 | 60 |
| 78 | 0.8 | 15 |
| 79 | 1.0 | 662 |
| 80 | 1.1 | 101 |
| 81 | 1.0 | 296 |
| 82 | 4.1 | 160 |
| 83 | 0.9 | 19 |
| 84 | 1.8 | 31 |
| 85 | 2.2 | 53 |
| 86 | 1.3 | 18 |
| 87 | 8.0 | 269 |
| 88 | 2.3 | 63 |
| 89 | 2.1 | 73 |
| 90 | 0.8 | 13 |
| 91 | 3.8 | 273 |
| 92 | 1.3 | 59 |
| 93 | 1.2 | 52 |
| 94 | 1.8 | 282 |
| 95 | 2.2 | 41 |

-continued

| Compound No. | WILD TYPE CELL ASSAY Viking IP (0% NHS) (nM) | WILD TYPE CELL ASSAY Viking IP (100% NHS) (nM) |
|---|---|---|
| 96 | 6.2 | >8400 |
| 97 | 2.4 | 151 |
| 98 | 28 | 1114 |
| 99 | 3.7 | 616 |
| 100 | 1.9 | 60 |
| 101 | 2.1 | 105 |
| 102 | 0.5 | 365 |
| 103 | 0.8 | 46 |
| 104 | 3.6 | 343 |
| 105 | 3.5 | 2292 |
| 106 | 3.3 | 3336 |
| 107 | 5.7 | 4933 |
| 108 | 2.0 | 105 |
| 109 | 3.2 | 714 |
| 110 | 2.1 | 140 |
| 111 | 3.0 | 858 |
| 112 | 0.65 | 4114 |
| 113 | 1.3 | >8000 |
| 114 | 1.9 | 137 |
| 115 | 1.4 | 225 |
| 116 | 2.3 | 256 |
| 117 | 2.5 | 1443 |
| 118 | 1.4 | 873 |
| 119 | 2.1 | 2059 |
| 120 | 0.8 | 116 |
| 121 | 2.6 | 62 |
| 122 | 3.3 | 35 |
| 123 | NA | NA |
| 124 | 3.2 | 53 |

Treatment or Prevention of HIV Infection

The Substituted Quinolizine Derivatives are useful in the inhibition of HIV, the inhibition of HIV integrase, the treatment of HIV infection and/or reduction of the likelihood or severity of symptoms of HIV infection and the inhibition of HIV viral replication and/or HIV viral production in a cell-based system. For example, the Substituted Quinolizine Derivatives are useful in treating infection by HIV after suspected past exposure to HIV by such means as blood transfusion, exchange of body fluids, bites, accidental needle stick, or exposure to subject blood during surgery or other medical procedures.

Accordingly, in one embodiment, the invention provides methods for treating HIV infection in a subject, the methods comprising administering to the subject an effective amount of at least one Substituted Quinolizine Derivative or a pharmaceutically acceptable salt or prodrug thereof. In a specific embodiment, the amount administered is effective to treat or prevent infection by HIV in the subject. In another specific embodiment, the amount administered is effective to inhibit HIV viral replication and/or viral production in the subject. In one embodiment, the HIV infection has progressed to AIDS.

The Substituted Quinolizine Derivatives are also useful in the preparation and execution of screening assays for antiviral compounds. For example the Substituted Quinolizine Derivatives are useful for identifying resistant HIV cell lines harboring mutations, which are excellent screening tools for more powerful antiviral compounds. Furthermore, the Substituted Quinolizine Derivatives are useful in establishing or determining the binding site of other antivirals to the HIV Integrase.

The compositions and combinations of the present invention can be useful for treating a subject suffering from infection related to any HIV genotype.

Combination Therapy

In another embodiment, the present methods for treating or preventing HIV infection can further comprise the administration of one or more additional therapeutic agents which are not Substituted Quinolizine Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: (i) at least one Substituted Quinolizine Derivative (which may include two or more different Substituted Quinolizine Derivatives), or a pharmaceutically acceptable salt or prodrug thereof, and (ii) at least one additional therapeutic agent that is other than a Substituted Quinolizine Derivative, wherein the amounts administered are together effective to treat or prevent a viral infection.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Substituted Quinolizine Derivative and an additional therapeutic agent may be present in fixed amounts (dosage amounts) in a single dosage unit (e.g., a capsule, a tablet and the like).

In one embodiment, at least one Substituted Quinolizine Derivative is administered during a time when the additional therapeutic agent(s) exert their prophylactic or therapeutic effect, or vice versa.

In another embodiment, at least one Substituted Quinolizine Derivative and the additional therapeutic agent(s) are administered in doses commonly employed when such agents are used as monotherapy for treating a viral infection.

In another embodiment, at least one Substituted Quinolizine Derivative and the additional therapeutic agent(s) are administered in doses lower than the doses commonly employed when such agents are used as monotherapy for treating a viral infection.

In still another embodiment, at least one Substituted Quinolizine Derivative and the additional therapeutic agent(s) act synergistically and are administered in doses lower than the doses commonly employed when such agents are used as monotherapy for treating a viral infection.

In one embodiment, at least one Substituted Quinolizine Derivative and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HIV infection.

In another embodiment, the viral infection is AIDS.

The at least one Substituted Quinolizine Derivative and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Substituted Quinolizine Derivative and the additional therapeutic agent(s) may inhibit the resistance of a viral infection to these agents.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS. Suitable HIV antivirals for use in combination with the compounds of the present invention include, for example, those listed in Table A as follows:

TABLE A

| Name | Type |
| --- | --- |
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| dolutegravir, Tivicay ® | II |
| efavirenz, EFV, Sustiva ®, Stocrin ® | nnRTI |
| efavirenz + emtricitabine + tenofovir DF, Atripla ® | nnRTI + nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |

TABLE A-continued

| Name | Type |
| --- | --- |
| nevirapine, NVP, Viramune ® | nnRTI |
| rilpivirine, TMC-278 | nnRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor;
FI = fusion inhibitor;
PI = protease inhibitor;
nRTI = nucleoside reverse transcriptase inhibitor;
II = integrase inhibitor;
nnRTI = non-nucleoside reverse transcriptase inhibitor.
Some of the drugs listed in the table are used in a salt form; e.g., abacavir sulfate, indinavir sulfate, atazanavir sulfate, nelfinavir mesylate.

In one embodiment, one or more anti-HIV drugs are selected from, lamivudine, abacavir, ritonavir, darunavir, atazanavir, emtricitabine, tenofovir, rilpivirine and lopinavir.

In another embodiment, the compound of formula (I) is used in combination with lamivudine.

In still another embodiment, the compound of formula (I) is used in combination atazanavir.

In another embodiment, the compound of formula (I) is used in combination with darunavir.

In another embodiment, the compound of formula (I) is used in combination with rilpivirine.

In one embodiment, the compound of formula (I) is used in combination with lamivudine and abacavir.

In another embodiment, the compound of formula (I) is used in combination with darunavir.

In another embodiment, the compound of formula (I) is used in combination with emtricitabine and tenofovir.

In still another embodiment, the compound of formula (I) is used in combination atazanavir.

In another embodiment, the compound of formula (I) is used in combination with ritonavir and lopinavir.

In another embodiment, the compound of formula (I) is used in combination with lamivudine.

In one embodiment, the compound of formula (I) is used in combination with abacavir and lamivudine.

In another embodiment, the compound of formula (I) is used in combination with lopinavir and ritonavir.

In one embodiment, the present invention provides pharmaceutical compositions comprising (i) a compound of formula (I) or a pharmaceutically acceptable salt or prodrug thereof; (ii) a pharmaceutically acceptable carrier; and (iii) one or more additional anti-HIV agents selected from lamivudine, abacavir, ritonavir and lopinavir, or a pharmaceutically acceptable salt or prodrug thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula (I) or a pharmaceutically acceptable salt or prodrug thereof and (ii) one or more additional anti-HIV agents selected from lamivudine, abacavir, ritonavir and lopinavir, or a pharmaceutically acceptable salt or prodrug thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson P D R, Thomson P D R, 57$^{th}$ edition (2003), the 58$^{th}$ edition (2004), the 59$^{th}$ edition (2005), and the like. The dosage ranges for a compound of the invention in these combinations are the same as those set forth above.

The doses and dosage regimen of the other agents used in the combination therapies of the present invention for the treatment or prevention of HIV infection can be determined by the attending clinician, taking into consideration the approved doses and dosage regimen in the package insert; the age, sex and general health of the subject; and the type and severity of the viral infection or related disease or disorder. When administered in combination, the Substituted Quinolizine Derivative(s) and the other agent(s) can be administered simultaneously (i.e., in the same composition or in separate compositions one right after the other) or sequentially. This is particularly useful when the components of the combination are given on different dosing schedules, e.g., one component is administered once daily and another component is administered every six hours, or when the pharmaceutical compositions are different, e.g., one is a tablet and one is a capsule. A kit comprising the separate dosage forms is therefore advantageous.

Compositions and Administration

When administered to a subject, the Substituted Quinolizine Derivatives can be administered as a component of a composition that comprises a pharmaceutically acceptable carrier or vehicle. The present invention provides pharmaceutical compositions comprising an effective amount of at least one Substituted Quinolizine Derivative and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Substituted Quinolizine Derivatives are administered orally.

In another embodiment, the one or more Substituted Quinolizine Derivatives are administered intravenously.

In one embodiment, a pharmaceutical preparation comprising at least one Substituted Quinolizine Derivative is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Substituted Quinolizine Derivative(s) by weight or volume. In various embodiments, the present compositions can contain, in one embodiment, from about 1% to about 70% or from about 5% to about 60% of the Substituted Quinolizine Derivative(s) by weight or volume.

The compounds of Formula I can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The unit dosages of the Substituted Quinolizine Derivatives may be administered at varying frequencies. In one embodiment, a unit dosage of a Substituted Quinolizine Derivative can be administered once daily. In another embodiment, a unit dosage of a Substituted Quinolizine Derivative can be administered twice weekly. In another embodiment, a unit dosage of a Substituted Quinolizine Derivative can be administered once weekly. In still another embodiment, a unit dosage of a Substituted Quinolizine Derivative can be administered once biweekly. In another embodiment, a unit dosage of a Substituted Quinolizine Derivative can be administered once monthly. In yet another embodiment, a unit dosage of a Substituted Quinolizine Derivative can be administered once bimonthly. In another embodiment, a unit dosage of a Substituted Quinolizine Derivative can be administered once every 3 months. In a further embodiment, a unit dosage of a Substituted Quinolizine Derivative can be administered once every 6 months. In another embodiment, a unit dosage of a Substituted Quinolizine Derivative can be administered once yearly.

The amount and frequency of administration of the Substituted Quinolizine Derivatives will be regulated according to the judgment of the attending clinician considering such factors as age, condition and size of the subject as well as severity of the symptoms being treated. The compositions of the invention can further comprise one or more additional therapeutic agents, selected from those listed above herein.

Kits

In one aspect, the present invention provides a kit comprising a therapeutically effective amount of at least one Substituted Quinolizine Derivative, or a pharmaceutically acceptable salt or prodrug of said compound and a pharmaceutically acceptable carrier, vehicle or diluent.

In another aspect the present invention provides a kit comprising an amount of at least one Substituted Quinolizine Derivative, or a pharmaceutically acceptable salt or prodrug of said compound and an amount of at least one additional therapeutic agent listed above, wherein the amounts of the two or more active ingredients result in a desired therapeutic effect. In one embodiment, the one or more Substituted Quinolizine Derivatives and the one or more additional therapeutic agents are provided in the same container. In one embodiment, the one or more Substituted Quinolizine Derivatives and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:
1. A compound having the formula:

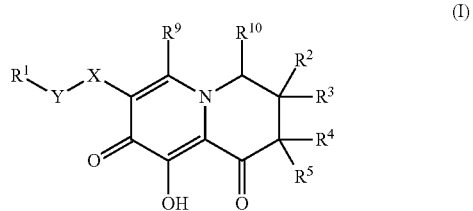

or a pharmaceutically acceptable salt thereof,
wherein:
X is selected from a 5-membered monocyclic heteroaryl and —N(R$^6$)C(O)—;
Y is C$_1$-C$_3$ alkylene;
R$^1$ is selected from phenyl, 5 or 6-membered monocyclic heteroaryl and 9-membered bicyclic heteroaryl, wherein said phenyl group, said 5 or 6-membered monocyclic heteroaryl group and said 9-membered bicyclic heteroaryl group can each be optionally substituted with up to three R$^8$ groups;
R$^2$ is H, methyl, or —OR$^7$ or R$^2$ and R$^4$, together with the carbon atoms to which they are attached, can join to form a 5 to 7-membered monocyclic cycloalkyl group, 5 to 7-membered monocyclic heterocycloalkyl group, or a 5 to 7-membered monocyclic heterocycloalkenyl group, wherein said 5 to 7-membered monocyclic cycloalkyl group, said 5 to 7-membered monocyclic heterocycloalkyl group, and said 5 to 7-membered monocyclic heterocycloalkenyl group can be optionally substituted with up to three R$^8$ groups, which can be the same or different;
R$^3$ is H, methyl, or —OR$^7$;
R$^4$ is selected from methyl, ethyl, —(C$_1$-C$_6$ alkylene)-O—(C$_1$-C$_6$ alkyl), and —OR$^7$;
R$^5$ is selected from methyl, ethyl, —(C$_1$-C$_6$ alkylene)-O—(C$_1$-C$_6$ alkyl), and —OR$^7$;
each occurrence of R$^6$ is independently H or C$_1$-C$_6$ alkyl;
each occurrence of R$^7$ is independently selected from H, C$_1$-C$_6$ alkyl, (C$_1$-C$_6$ alkylene)-O—(C$_1$-C$_6$ alkyl) and C$_3$-C$_7$ cycloalkyl;
each occurrence of R$^8$ is independently selected from C$_1$-C$_6$ alkyl, halo and —OR$^6$;
R$^9$ is H; and
R$^{10}$ is H.

2. The compound of claim 1, wherein X is —NHC(O)—, or a pharmaceutically acceptable salt thereof.

3. The compound of claim 1, wherein X is 5-membered monocyclic heteroaryl, or a pharmaceutically acceptable salt thereof.

4. The compound of claim 1, wherein Y is CH$_2$, or a pharmaceutically acceptable salt thereof.

5. The compound of claim 1, wherein R$^1$ is phenyl or 9-membered bicyclic heteroaryl, wherein said phenyl and said 9-membered bicyclic heteroaryl groups can each be optionally substituted with up to three R⁸ groups, or a pharmaceutically acceptable salt thereof.

6. The compound of claim 5, wherein R¹ is phenyl, which is substituted by 1 to 3 halo groups, which can be the same or different, or a pharmaceutically acceptable salt thereof.

7. The compound of claim 5, wherein R¹ is 2,4-difluorophenyl or 3-chloro-2-fluorophenyl, or a pharmaceutically acceptable salt thereof.

8. The compound of claim 1, wherein R² and R³ are each independently selected from H, —OH and —O—(C₁-C₆ alkyl), or a pharmaceutically acceptable salt thereof.

9. The compound of claim 1, wherein one of R² is H and R³ is —OH or —O—(C₁-C₆ alkyl), or a pharmaceutically acceptable salt thereof.

10. The compound of claim 1, wherein R⁴ and R⁵ are each independently selected from methyl, ethyl, and —(C₁-C₆ alkylene)-O—(C₁-C₆ alkyl), or a pharmaceutically acceptable salt thereof.

11. The compound of claim 10, wherein R⁴ and R⁵ are each independently selected from methyl and —CH₂CH₂OCH₃, or a pharmaceutically acceptable salt thereof.

12. The compound of claim 1, wherein R² and R⁴, together with the carbon atoms to which they are attached, join to form a 5 to 7-membered monocyclic heterocycloalkyl group, or a pharmaceutically acceptable salt thereof.

13. The compound of claim 12, wherein R⁵ is methyl, or a pharmaceutically acceptable salt thereof.

14. The compound of claim 5 wherein R³ is H; R⁵ is methyl; and R² and R⁴, together with the carbon atoms to which they are attached, join to form a group selected from:

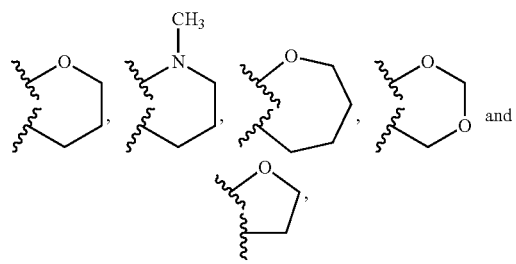

pharmaceutically acceptable salt thereof.

15. The compound of claim 14, wherein R² and R⁴, together with the carbon atoms to which they are attached, join to form:

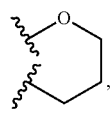

or a pharmaceutically acceptable salt thereof.

16. A compound selected from

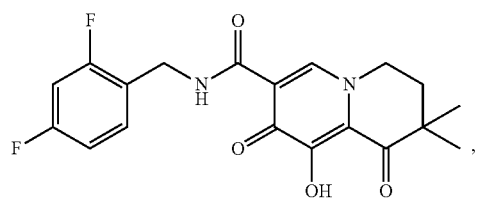

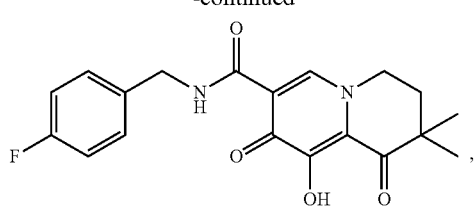

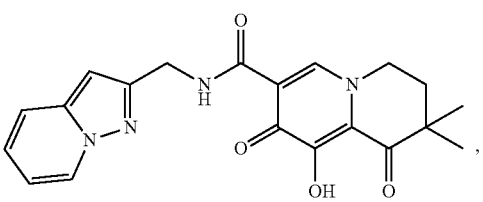

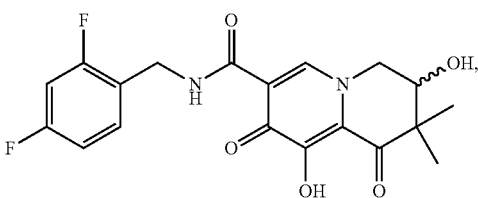

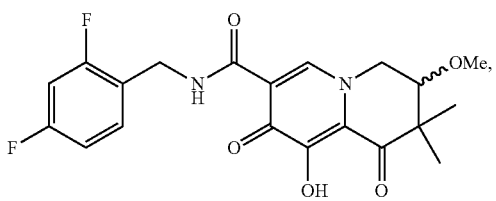

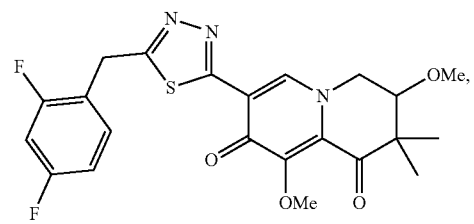

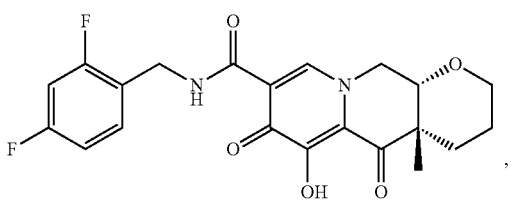

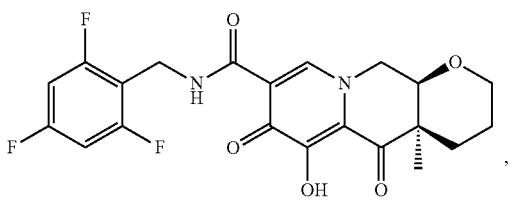

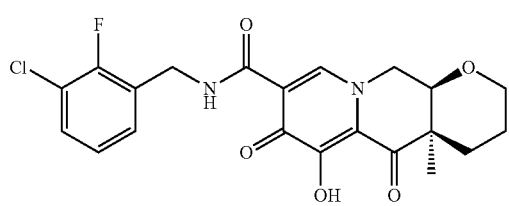

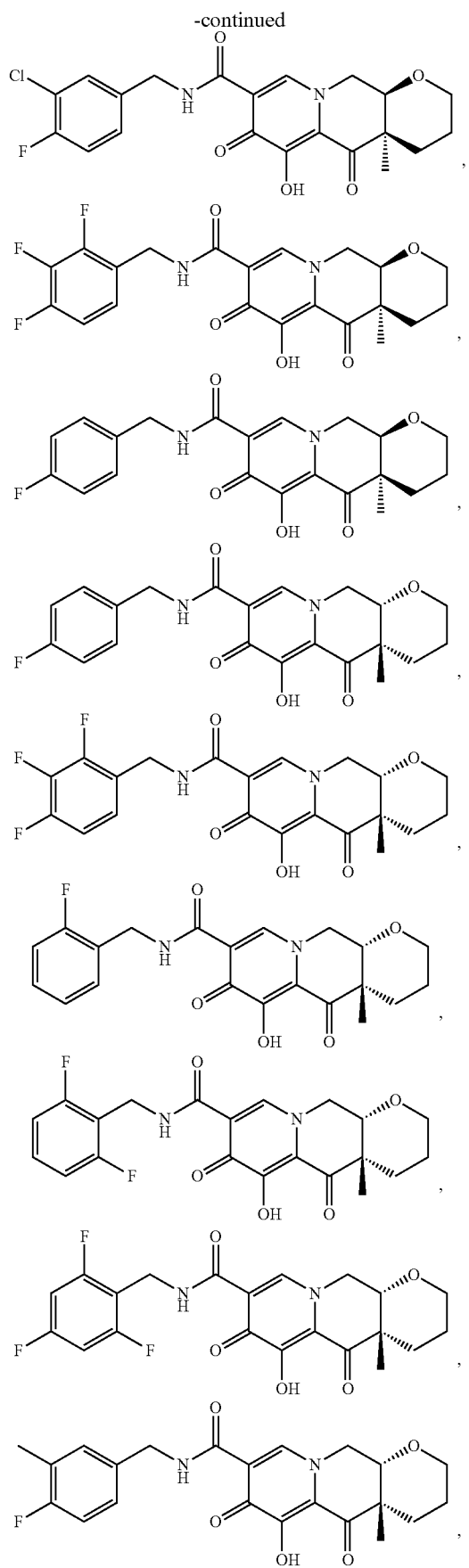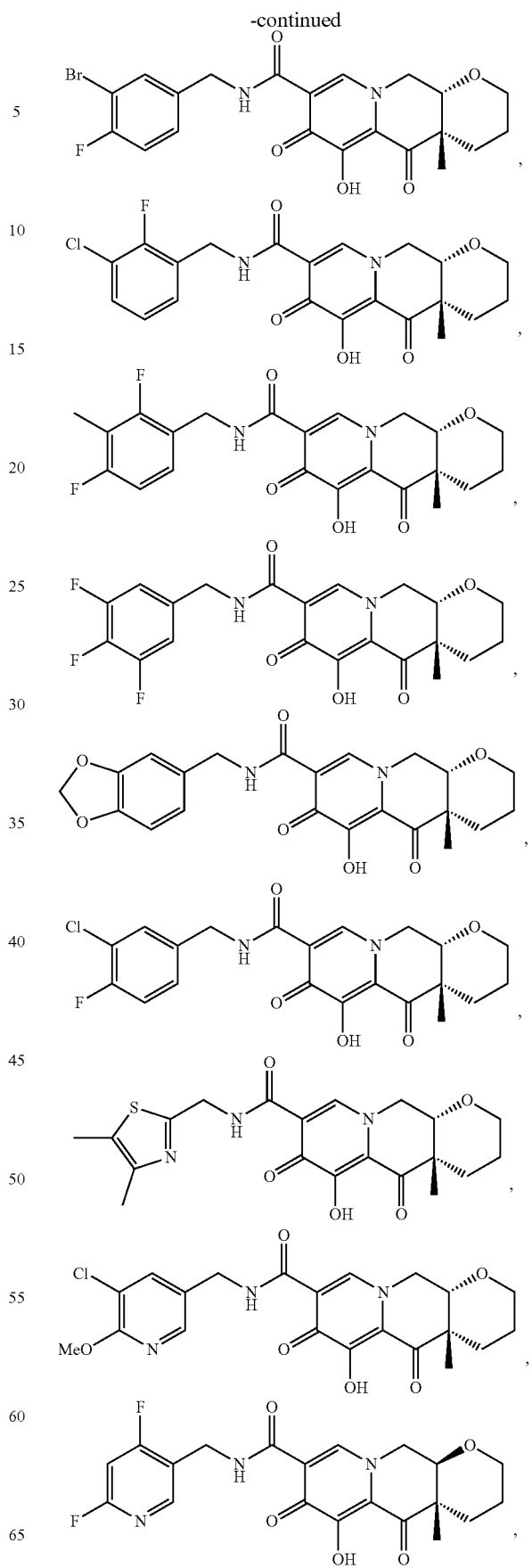

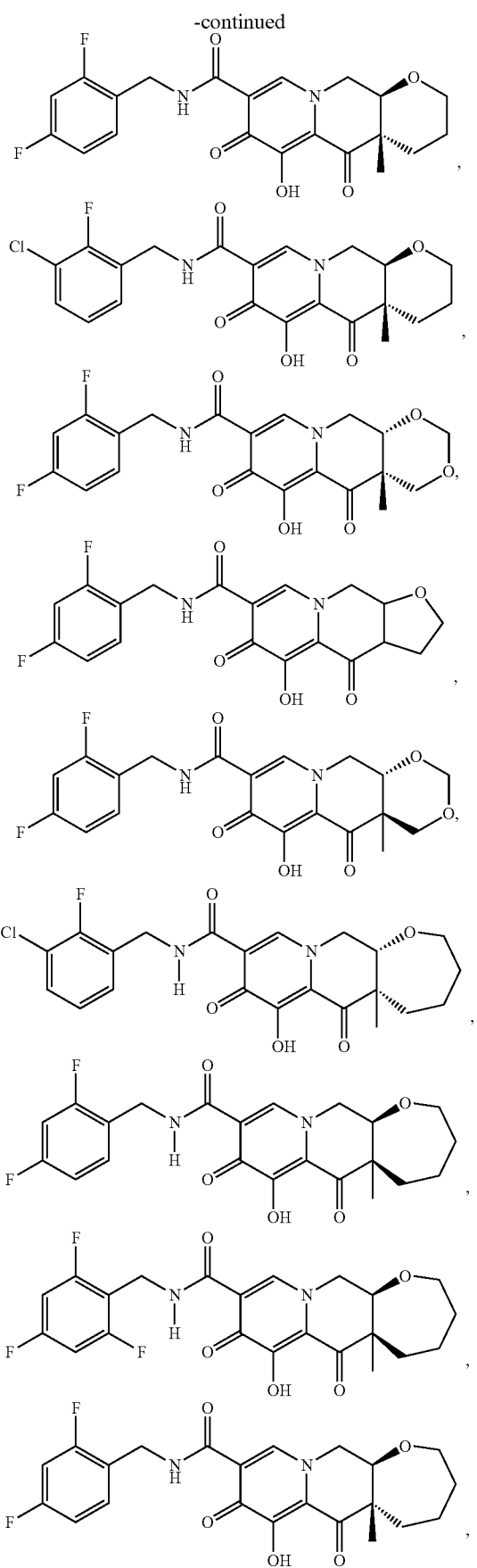
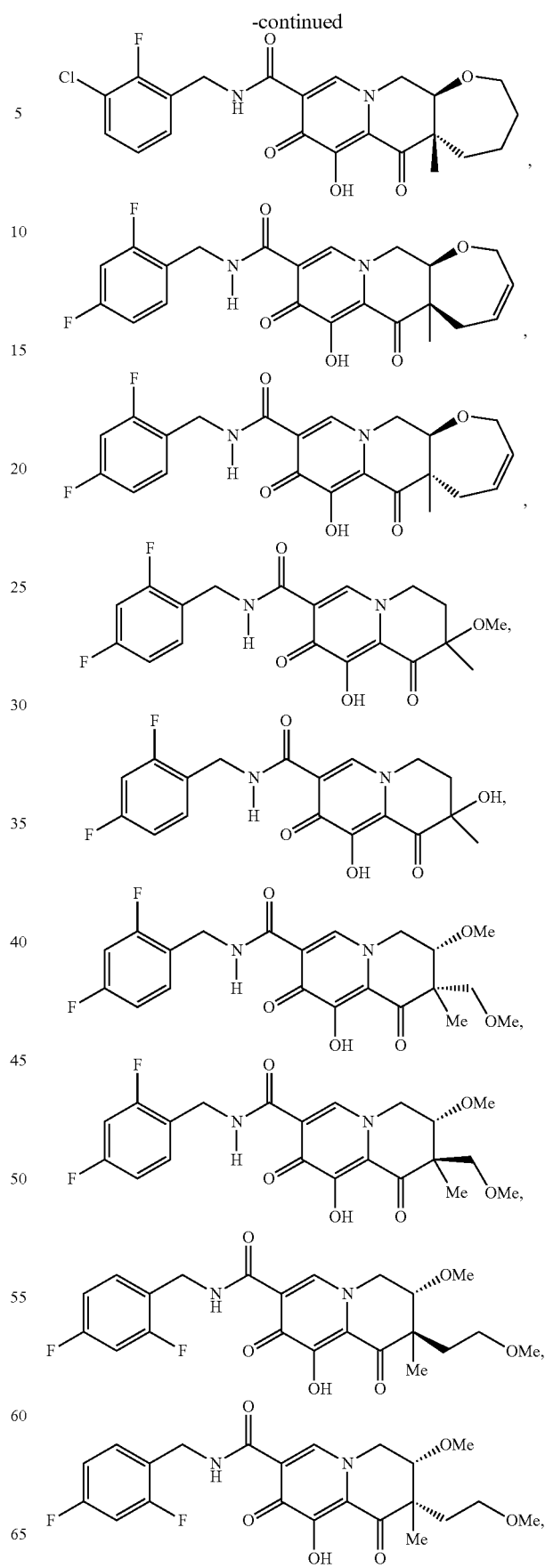

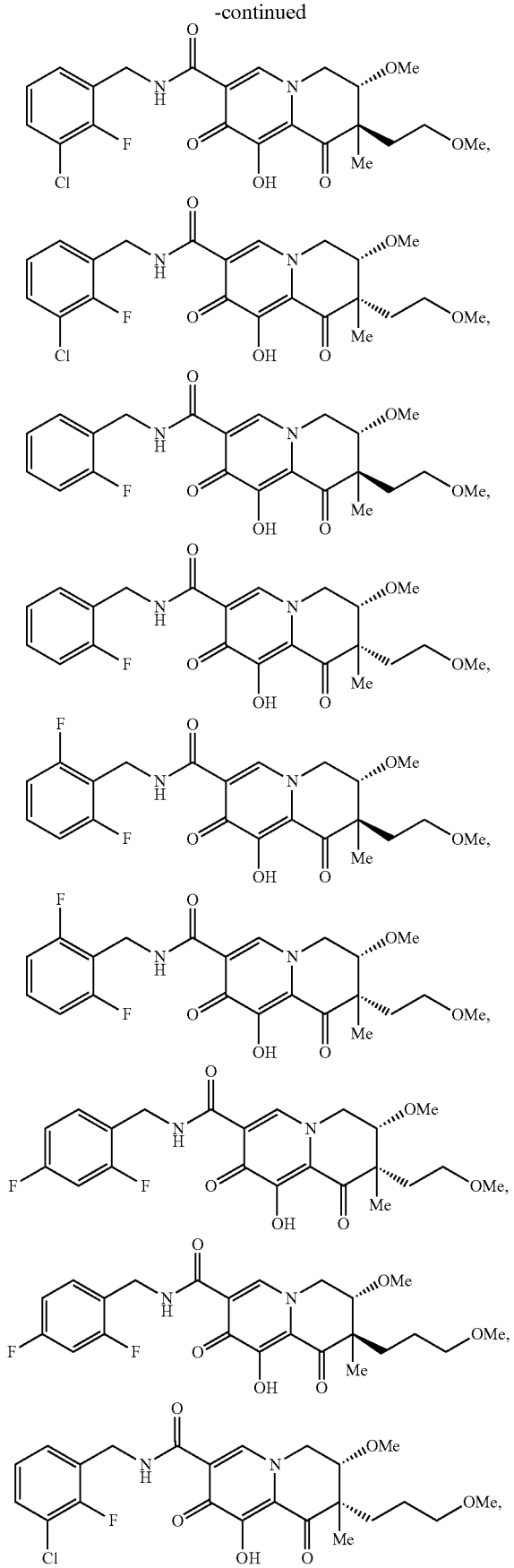
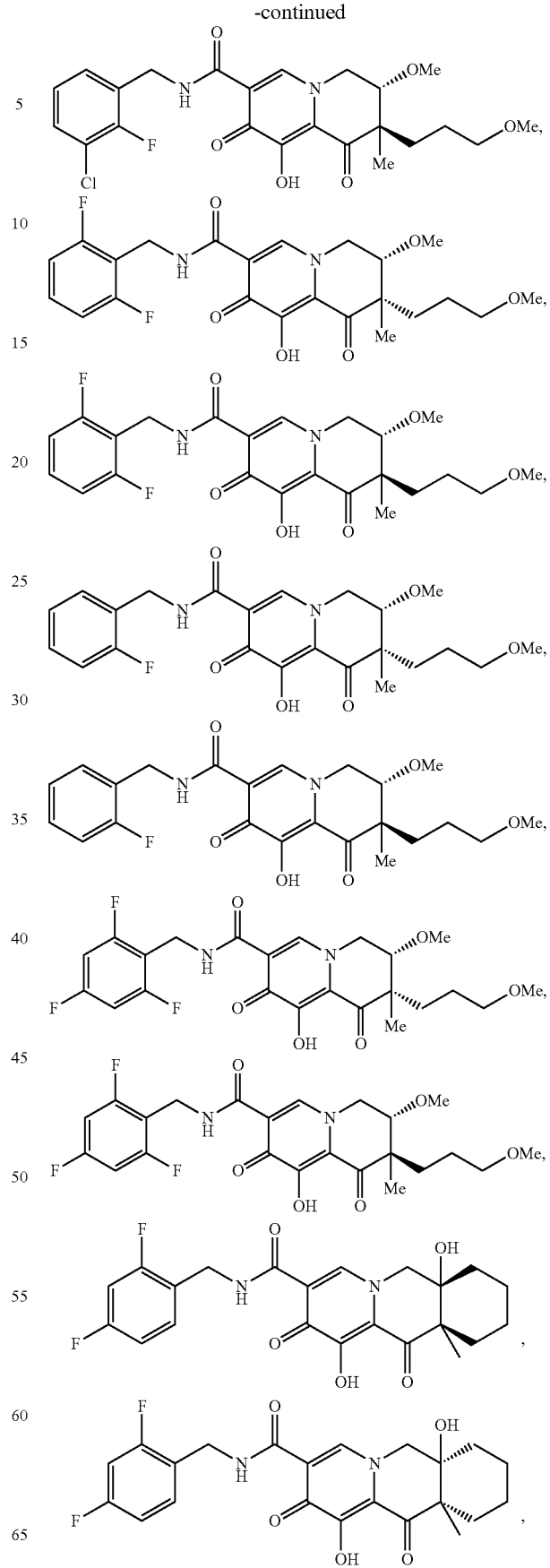

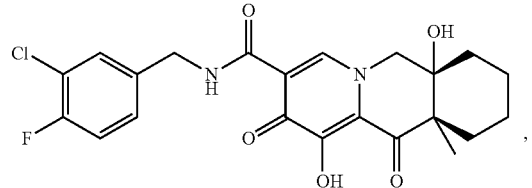
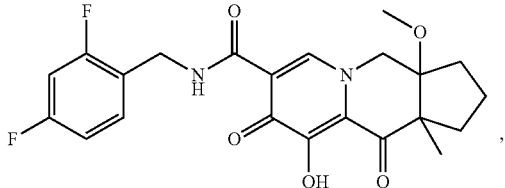
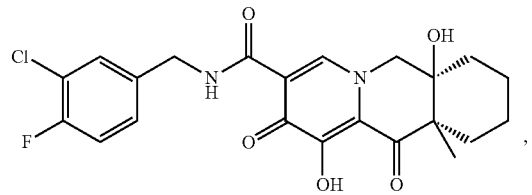
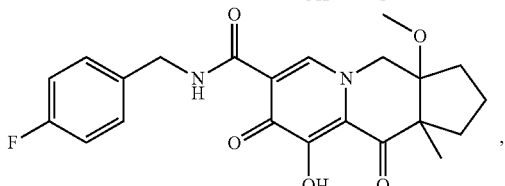
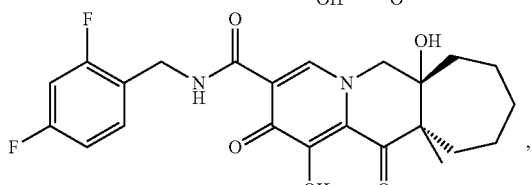
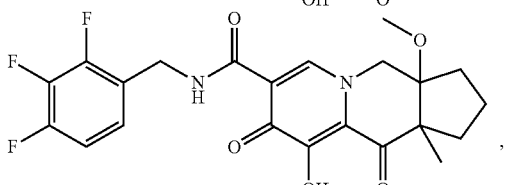
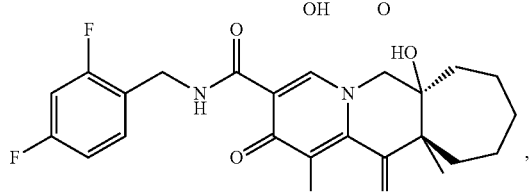
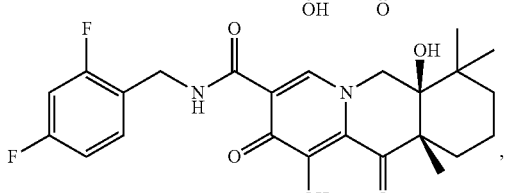
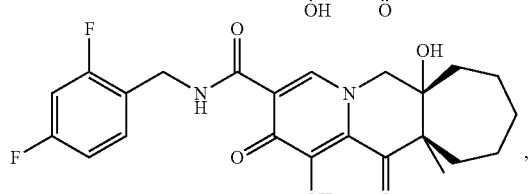
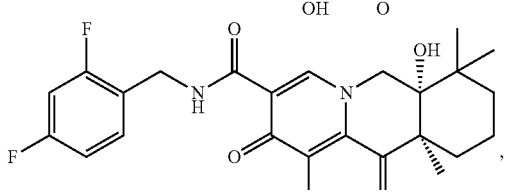
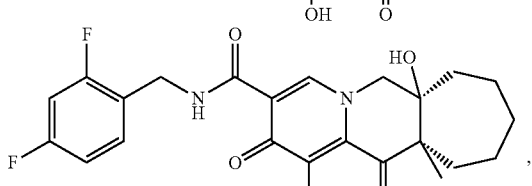
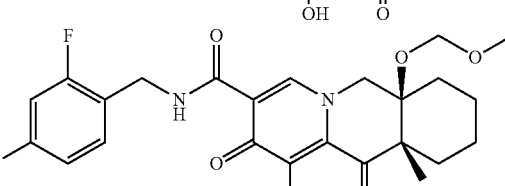
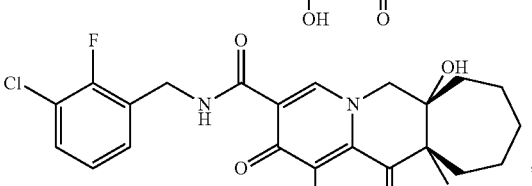
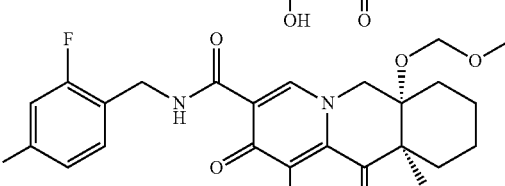
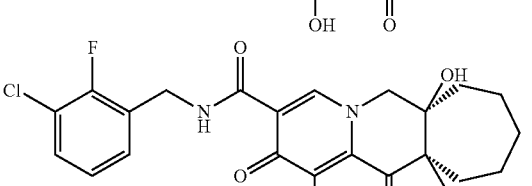
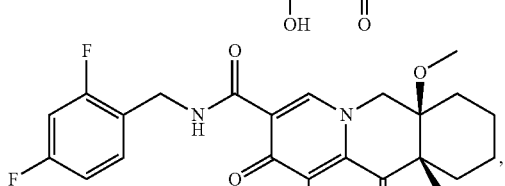
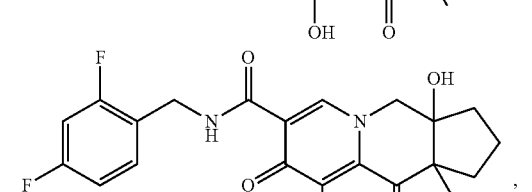
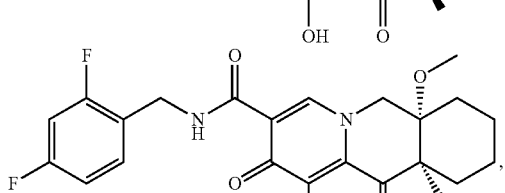

-continued
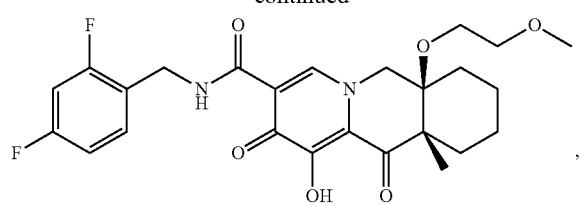
,
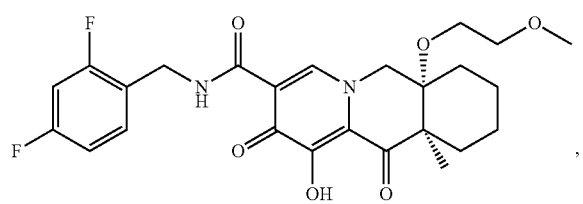
,
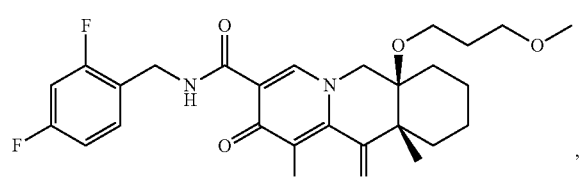
,
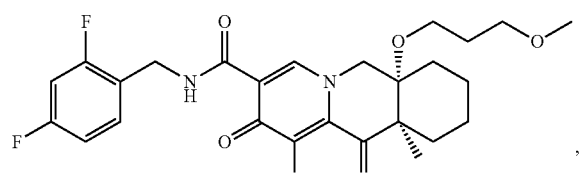
,
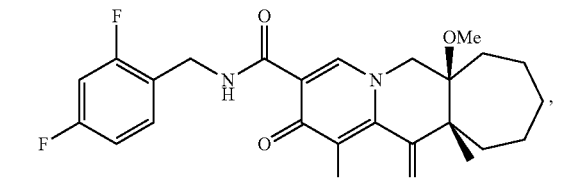
,
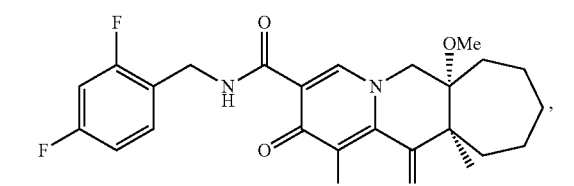
,
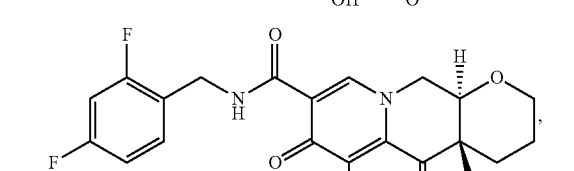
,
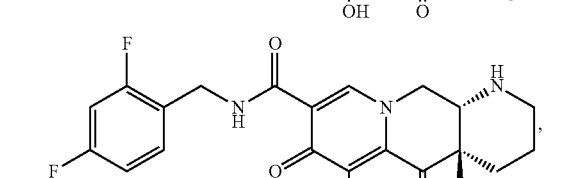
-continued
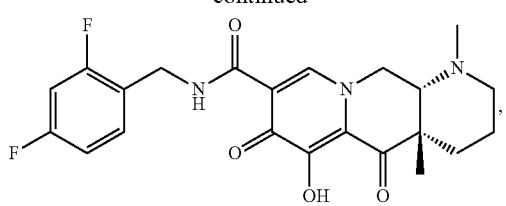
,
or a pharmaceutically acceptable salt thereof.
17. A compound of the formula
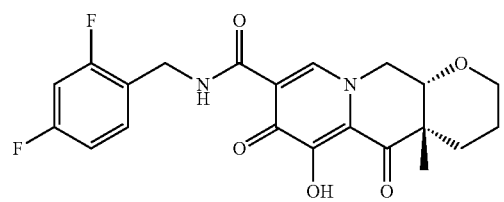 [SMILES: C[C@]12CCCO[C@H]1Cn1cc(C(=O)NCc3ccc(F)cc3F)c(=O)c(O)c1C2=O]
or a pharmaceutically acceptable salt thereof.
18. A compound of the formula
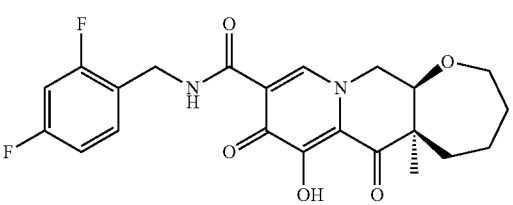 [SMILES: C[C@@]12CCCCO[C@@H]1Cn1cc(C(=O)NCc3ccc(F)cc3F)c(=O)c(O)c1C2=O]
or a pharmaceutically acceptable salt thereof.
19. A compound of the formula
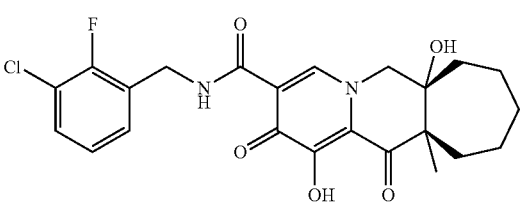 [SMILES: C[C@@]12CCCCC[C@]1(O)Cn1cc(C(=O)NCc3cccc(Cl)c3F)c(=O)c(O)c1C2=O]
or a pharmaceutically acceptable salt thereof.
20. A compund of the formula
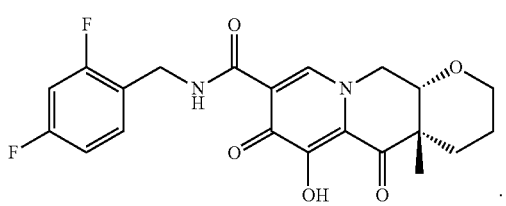 [SMILES: C[C@]12CCCO[C@H]1Cn1cc(C(=O)NCc3ccc(F)cc3F)c(=O)c(O)c1C2=O]

21. A compound of the formula

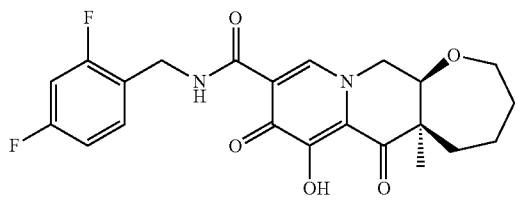

22. A compound of formula

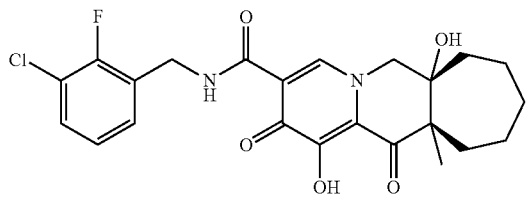

23. A pharmaceutical composition comprising an effective amount of a compound according to claim 1, or a pharmaceutically acceptable salt thereof, and a pharmaceutically acceptable carrier.

24. The pharmaceutical composition of claim 23, further comprising one or more additional therapeutic agents selected from, lamivudine, abacavir, ritonavir, darunavir, atazanavir, emtricitabine, tenofovir, rilpivirine and lopinavir.

25. A method for the inhibition of HIV integrase in a subject in need thereof which comprises administering to the subject an effective amount of the compound according to claim 1, or a pharmaceutically acceptable salt thereof.

26. A method for the treatment of infection by HIV or for the treatment of AIDS in a subject in need thereof, which comprises administering to the subject an effective amount of the compound according to claim 1, or a pharmaceutically acceptable salt thereof.

27. The method of claim 26, further comprising administering to the subject one or more additional therapeutic agents selected from, abacavir, lamivudine, ritonavir and lopinavir, wherein the amounts administered of the compound of claim 1 and the one or more additional therapeutic agents, are together effective to treat infection by HIV or to treat the progression of AIDS.

* * * * *